United States Patent
Frost et al.

(10) Patent No.: US 7,560,481 B2
(45) Date of Patent: Jul. 14, 2009

(54) INDOLES ARE CANNABINOID RECEPTOR LIGANDS

(75) Inventors: Jennifer M. Frost, Grayslake, IL (US); Karin R. Tietje, Mundelein, IL (US); Michael J. Dart, Highland Park, IL (US); Michael D. Meyer, Lake Villa, IL (US)

(73) Assignee: Abbott Laboratories, Abbott Park, IL (US)

( * ) Notice: Subject to any disclaimer, the term of this patent is extended or adjusted under 35 U.S.C. 154(b) by 157 days.

(21) Appl. No.: 11/315,862

(22) Filed: Dec. 21, 2005

(65) Prior Publication Data

US 2007/0037801 A1 Feb. 15, 2007

Related U.S. Application Data

(60) Provisional application No. 60/637,987, filed on Dec. 21, 2004.

(51) Int. Cl.
- *A61K 31/55* (2006.01)
- *A61K 31/5377* (2006.01)
- *A61K 31/454* (2006.01)
- *A61K 31/4439* (2006.01)
- *A61K 31/404* (2006.01)
- *C07D 403/06* (2006.01)
- *C07D 413/06* (2006.01)
- *C07D 401/06* (2006.01)
- *C07D 209/12* (2006.01)

(52) U.S. Cl. ............. 514/419; 514/217.08; 514/235.2; 514/323; 514/414; 540/602; 544/143; 544/373; 546/201; 546/278.1; 548/465; 548/193

(58) Field of Classification Search ............. 514/217.8, 514/235.2, 323, 414, 419; 540/602; 544/143, 544/373; 546/201, 278.1; 548/465, 493
See application file for complete search history.

(56) References Cited

U.S. PATENT DOCUMENTS

| | | | |
|---|---|---|---|
| 3,843,683 A | 10/1974 | Bell | |
| 4,885,295 A | 12/1989 | Bell | |
| 4,973,587 A | 11/1990 | Ward et al. | |
| 4,978,664 A | 12/1990 | Bell | |
| 5,013,837 A | 5/1991 | Ward et al. | |
| 5,530,019 A | 6/1996 | Okada et al. | |
| 6,358,992 B1 * | 3/2002 | Pamukcu et al. | 514/414 |
| 2004/0034090 A1 | 2/2004 | Barth et al. | |

FOREIGN PATENT DOCUMENTS

| WO | 9601591 | 1/1996 |
|---|---|---|
| WO | 97/00860 | 1/1997 |
| WO | 01/28557 | 4/2001 |
| WO | 01/83422 | 11/2001 |
| WO | 02/42269 | 5/2002 |
| WO | 02/060447 | 8/2002 |
| WO | 2004/050086 | 6/2004 |

OTHER PUBLICATIONS

Arevalo-Martin, A., et al., J. Neurosci., vol. 23(7), pp. 2511-2516 (2003).
Benito, C., et al., J. Neurosci., vol. 23(35), pp. 11136-11141 (2003).
Benito, C., et al., J. Neurosci., vol. 25(10), pp. 2530-2536 (2005).
Bouchard, J.F., et al., Life Sci., vol. 72, pp. 1859-1870 (2003).
Boyle, W.J., et al., Nature, vol. 423, pp. 337-342 (2003).
Buckley, N.E., et al., Eur. J. Pharmacol., vol. 396, pp. 141-149 (2000).
Carlisle, S.J., et al., Int. Immunopharmacol., vol. 2, p. 69 (2002).
Carrier, E.J., et al., Current Drug Targets-CNS & Neurological Disorders, vol. 4, pp. 657-665 (2005).
Casanova, M.L., et al., J. Clin. Invest., vol. 111, pp. 43-50 (2003).
Cichewicz, D.L., Life Sci., vol. 74, pp. 1317-1324 (2004).
Clayton, N., et al., Pain, vol. 96, pp. 253-260 (2002).
Filippo, C.D., et al., J. Leukoc. Biol., vol. 75, pp. 453-459 (2004).
Galiegue, et al., Eur. J. Biochem., vol. 232, pp. 54-61 (1995).
Golech, S.A., et al., Mol. Brain Res., vol. 132, pp. 87-92 (2004).
Grotenhermen, F. and Muller-Vahl, K., Expert Opin. Pharmacother., vol. 4(12), pp. 2367-2371 (2003).
Hanus, L., et al., Proc. Nat. Acad. Sci., vol. 96, pp. 14228-14233 (1999).
Hohmann, A.G., et a., J. Pharmacol. Exp. Ther., vol. 308, pp. 446-453 (2004).
Ibrahim, M.M., et al., Proc. Nat. Acad. Sci., vol. 100, pp. 10529-10533 (2003).
Ibrahim, M.M., et al., Proc. Nat. Acad. Sci., vol. 102(8), pp. 3093-3098 (2005).
Ihenetu, K., et al., Eur. J. Pharmacol., vol. 458, pp. 207-215 (2003).
Julien, B., et al., Gastroenterology, vol. 128, pp. 742-755 (2005).
Karsak, M., et al., Human Molecular Genetics, vol. 14(22), pp. 3389-3396 (2005).
Kreutzberg, G.W., Trends in Neurosci., vol. 19, pp. 312-318 (1996).
Lepicier, P., et al., Brit. J. Pharm., vol. 139, pp. 805-815 (2003).
Lotersztajn, S., Annu. Rev. Pharmacol. Toxicol., vol. 45, pp. 605-628 (2005).
Malan, T.P., et al., Pain, vol. 93, pp. 239-245 (2001).
Maresz, K., et al., J. Neurochem., vol. 95, pp. 437-445 (2005).

(Continued)

*Primary Examiner*—Rebecca L Anderson
*Assistant Examiner*—Jason Nolan
(74) *Attorney, Agent, or Firm*—Sonali S. Srivastava

(57) ABSTRACT

The present invention provides novel compounds of Formula (I)

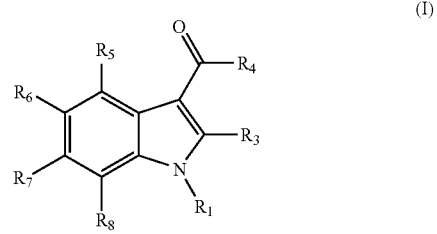

which are $CB_2$ selective ligands useful for the treatment of pain.

14 Claims, No Drawings

OTHER PUBLICATIONS

Mathison, R., et al., Br. J. Pharmacol., vol. 142, pp. 1247-1254 (2004).
McKallip, R.J., et al., Blood, vol. 100, pp. 637-634 (2002).
Molina-Holgado, F., et al., J. Neurosci., vol. 23 (16), pp. 6470-6474 (2003).
Nackley, A.G., et al., Neuroscience, vol. 119, pp. 747-757 (2003).
Ni, X., et al., Multiple Sclerosis, vol. 10, pp. 158-164 (2004).
Nunez, E., et al., Synapse, vol. 53, pp. 208-213 (2004).
Patel, H.J., et al., Brit. J. Pharmacol., vol. 140, pp. 261-268 (2003).
Pertwee, R.G., Pharmacol. Ther., vol. 95, pp. 165-174 (2002).
Quartilho, A., et al., Anesthesiology, vol. 99, pp. 955-960 (2003).
Ralston, S.H., Curr. Opin. Pharmacol., vol. 3, pp. 286-290 (2003).
Ralston, S.H., Nature Medicine, vol. 11, pp. 774-779 (2005).
Ramirez, B.G., J. Neurosci., vol. 25(8), pp. 1904-1913 (2005).
Sanchez, C., et al., Cancer Res., vol. 61, pp. 5784-5789 (2001).
Steffens, S., et al., Nature, vol. 434, pp. 782-786 (2005).
Valenzano, K.J., Neuropharmacology, vol. 48. pp. 658-672 (2005).
Walter, L., Stella, N., Br. J. Pharmacol., vol. 141, pp. 775-785 (2004).
Warhurst, A.C., et al., Gut, vol. 42, pp. 208-213 (1998).
Watkins, L.R., et al., Trends in Neuroscience, vol. 24(8), p. 450(2001).
Williams, K., et al., Glia, vol. 36, pp. 156-164 (2001).
Wright, K., et al., Gastroenterology, vol. 129, pp. 437-453 (2005).
Yoshihara, S., et al., Am. J. Respir. Crit. Care Med., vol. 170, pp. 941-946 (2004).
Yoshihara, S., et al., Allergy and Immunology, vol. 138, pp. 80-87 (2005).
Yoshihara, S., et al., J. Pharmacol. Sci., vol. 98(1), pp. 77-82 (2005).
Zimmer, A., et al., Proc. Nat. Acad. Sci., vol. 96, pp. 5780-5785 (1999).
International Search Report for application No. PCT/US2005/0046480, Mailed on Apr. 18, 2006, 5 pages.

* cited by examiner

INDOLES ARE CANNABINOID RECEPTOR LIGANDS

This application claims priority from U.S. Provisional Patent Application Ser. No. 60/637,987 filed Dec. 21, 2004, incorporated herein by reference.

TECHNICAL FIELD

The present invention relates to indole derivatives, compositions comprising such compounds, and methods of treating conditions and disorders using such compounds and compositions.

BACKGROUND OF THE INVENTION $(-)$-$\Delta^9$-Tetrahydrocannabinol ($\Delta^9$-THC), the major psychoactive constituent of marijuana, exerts a broad range of therapeutic effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic side effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$-selective modulators are analgesic in preclinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that selectively interact with $CB_2$ receptors offer a unique pharmacotherapy for the treatment of immune and inflammatory disorders.

SUMMARY OF THE PRESENT INVENTION

In the principle embodiment, the present invention provides compounds of Formula (I)

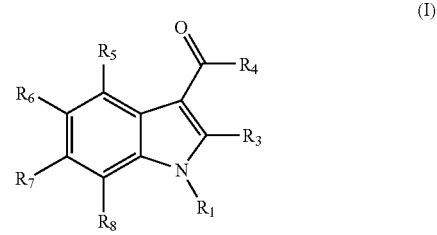

(I)

or a pharmaceutically acceptable salt or prodrug thereof, wherein $R_1$ is selected from the group consisting of alkoxyalkyl, alkylcarbonyl, alkylcarbonylalkyl, alkylthioalkyl, arylalkyl, arylalkylcarbonyl, azidoalkyl, cycloalkylalkyl, cycloalkylalkylcarbonyl, haloalkyl, heteroarylalkyl, heteroarylalkylcarbonyl, heterocyclealkyl, heterocyclealkylcarbonyl, hydroxyalkyl, mercaptoalkyl, $(NR_AR_B)$carbonylalkyl, $(NR_AR_B)$sulfonylalkyl, $(NR_CR_D)$alkyl, -$LOR_2$, -$LSR_2$, -$LS(O)R_2$, and -$LS(O)_2R_2$;

L is alkylene;

$R_2$ is selected from the group consisting of alkyl, alkylcarbonyl, aryl, arylalkyl, carboxyalkenylcarbonyl, carboxyalkyl, carboxyalkylcarbonyl, cycloalkyl, cycloalkylalkyl, haloalkyl, heteroaryl, heteroarylalkyl, heterocycle, heterocyclealkyl, $(NR_AR_B)$carbonylalkenylcarbonyl, $(NR_AR_B)$carbonylalkyl, and $(NR_AR_B)$carbonylalkylcarbonyl;

$R_3$ is selected from the group consisting of hydrogen, alkoxyalkyl, alkyl, and haloalkyl;

$R_4$ is selected from the group consisting of cyclopropyl, cyclobutyl, cyclopentyl, cycloheptyl, and cyclooctyl, wherein the cyclopropyl, cyclobutyl, and cyclopentyl are substituted with 1, 2, 3, 4, 5, or 6 substituents selected from the group consisting of alkenyl, alkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, haloalkoxy, haloalkyl, halogen, hydroxy, hydroxyalkyl, mercapto, mercaptoalkyl, oxo, —$NR_ER_F$, (NR$_E$R$_F$)alkyl, (NR$_G$R$_H$)carbonyl, (NR$_G$R$_H$)carbonylalkyl, (NR$_G$R$_H$)sulfonyl, and (NR$_G$R$_H$)sulfonylalkyl, wherein the cycloheptyl and cyclooctyl are optionally substituted with 1, 2, 3, 4, 5, or 6 substituents selected from the group consisting of alkenyl, alkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, haloalkoxy, haloalkyl, halogen, hydroxy, hydroxyalkyl, mercapto, mercaptoalkyl, oxo, —NR$_E$R$_F$, (NR$_E$R$_F$)alkyl, (NR$_G$R$_H$)carbonyl, (NR$_G$R$_H$)carbonylalkyl, (NR$_G$R$_H$)sulfonyl, and (NR$_G$R$_H$)sulfonylalkyl;

R$_5$, R$_6$, R$_7$, and R$_8$ are independently selected from the group consisting of hydrogen, alkenyl, alkoxy, alkoxyalkyl, alkoxycarbonyl, alkoxycarbonylalkoxy, alkoxycarbonylalkyl, alkoxysulfonyl, alkyl, alkylcarbonyl, alkylcarbonylalkyl, alkylcarbonyloxy, alkylsulfinyl, alkylsulfinylalkyl, alkylsulfonyl, alkylsulfonylalkyl, alkylsulfonyloxy, alkylthio, alkylthioalkyl, alkynyl, aryl, arylalkoxy, arylalkyl, arylalkylthio, arylcarbonyl, aryloxy, aryloxyalkyl, arylthio, arylthioalkyl, carboxy, carboxyalkenyl, carboxyalkenylcarbonyl, carboxyalkenylcarbonyloxy, carboxy, carboxyalkyl, carboxyalkylcarbonyl, carboxyalkylcarbonyloxy, cyano, cyanoalkyl, cycloalkyl, cycloalkylalkoxy, cycloalkylalkyl, cycloalkylcarbonyl, cycloalkyloxy, cycloalkyloxyalkyl, haloalkoxy, haloalkyl, halogen, heteroaryl, heteroarylalkoxy, heteroarylalkyl, heteroaryloxy, heteroaryloxyalkyl, heterocycle, heterocyclealkoxy, heterocyclealkoxycarbonyl, heterocyclealkyl, heterocycleoxy, heterocycleoxyalkyl, hydroxy, hydroxyalkoxy, hydroxyalkyl, mercapto, mercaptoalkyl, nitro, —NR$_J$R$_K$, (NR$_J$R$_K$)alkoxy, (NR$_J$R$_K$)alkyl, (NR$_M$R$_N$)carbonyl, (NR$_M$R$_N$)carbonylalkyl, (NR$_M$R$_N$)sulfonyl, and (NR$_M$R$_N$)sulfonylalkyl;

R$_A$, R$_B$, R$_G$, R$_H$, R$_M$, and R$_N$ are independently selected from the group consisting of hydrogen, alkenyl, alkoxyalkyl, alkoxycarbonylalkyl, alkyl, alkynyl, aryl, arylalkyl, cycloalkyl, cycloalkylalkyl, heteroaryl, heteroarylalkyl, heterocycle, heterocyclealkyl, and hydroxyalkyl; and R$_C$, R$_D$, R$_E$, R$_F$, R$_J$, R$_K$, are independently selected from the group consisting of hydrogen, alkenyl, alkoxyalkyl, alkoxycarbonyl, alkoxycarbonylalkyl, alkyl, alkylcarbonyl, alkylsulfonyl, alkynyl, aryl, arylalkyl, arylsulfonyl, arylalkylsulfonyl, cycloalkyl, cycloalkylalkyl, cycloalkylsulfonyl, cycloalkylalkylsulfonyl, heteroaryl, heteroarylalkyl, heteroarylsulfonyl, heteroarylalkylsulfonyl, heterocycle, heterocyclealkyl, heterocyclesulfonyl, and heterocyclealkylsulfonyl.

In another embodiment, the present invention provides a pharmaceutical composition comprising a therapeutically effective amount of a compound of Formula (I) or a pharmaceutically acceptable salt thereof in combination with a pharmaceutically acceptable carrier.

In another embodiment, the present invention provides a method of treating pain in a mammal in need of such treatment comprising administering to the mammal a therapeutically effective amount of a compound of Formula (I) or a pharmaceutically acceptable salt thereof.

In another embodiment, the present invention provides a method of treating neuropathic pain in a mammal in need of such treatment comprising administering to the mammal a therapeutically effective amount of a compound of Formula (I) or a pharmaceutically acceptable salt thereof.

In another embodiment, the present invention provides a method of treating nociceptive pain in a mammal in need of such treatment comprising administering to the mammal a therapeutically effective amount of a compound of Formula (I) or a pharmaceutically acceptable salt thereof.

In another embodiment, the present invention provides a method of treating a disorder selected from the group consisting of inflammatory disorders, immune disorders, neurological disorders, cancers of the immune system, respiratory disorders, and cardiovascular disorders in a mammal in need of such treatment comprising administering to the mammal a therapeutically effective amount of a compound of Formula (I) or a pharmaceutically acceptable salt thereof.

In another embodiment, the present invention provides a method of neuroprotection in a mammal in need of such treatment comprising administering to the mammal a therapeutically effective amount of a compound of Formula (I) or a pharmaceutically acceptable salt thereof.

The present invention contemplates the use of a therapeutically effective amount of a compound of Formula (I), or a therapeutically acceptable salt thereof, to prepare a medicament for treating nociceptive pain in a patient.

The present invention contemplates the use of a therapeutically effective amount of a compound of Formula (I), or a therapeutically acceptable salt thereof, to prepare a medicament for treating neuropathic pain in a patient.

The present invention contemplates the use of a therapeutically effective amount of a compound of Formula (I), or a therapeutically acceptable salt thereof, to prepare a medicament for treating inflammatory disorders, immune disorders, neurological disorders, cancers of the immune system, respiratory disorders, or cardiovascular disorders in a patient.

The present invention contemplates the use of a therapeutically effective amount of a compound of Formula (I), or a therapeutically acceptable salt thereof, to prepare a medicament for providing neuroprotection in a patient.

DETAILED DESCRIPTION OF THE PRESENT INVENTION

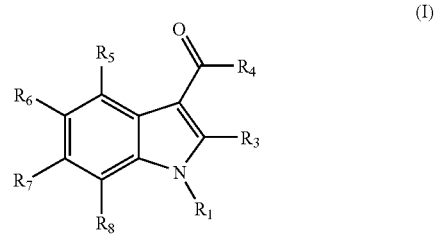

(I)

In one embodiment, the present invention provides compounds of Formula (I) wherein R$_1$ is selected from the group consisting of alkoxyalkyl, alkylcarbonylalkyl, alkylthioalkyl, arylalkyl, azidoalkyl, cycloalkylalkyl, haloalkyl, heteroarylalkyl, heterocyclealkyl, heterocyclealkylcarbonyl, hydroxyalkyl, mercaptoalkyl, (NR$_A$R$_B$)carbonylalkyl, (NR$_A$R$_B$)sulfonylalkyl, (NR$_C$R$_D$)alkyl, and -LOR$_2$; L is alkylene; R$_2$ is selected from the group consisting of alkylcarbonyl, arylalkyl, and carboxyalkenylcarbonyl; R$_3$ is selected from the group consisting of hydrogen and alkyl wherein the alkyl is methyl; R$_4$ is selected from the group consisting of cyclopropyl, cyclobutyl, cyclopentyl, and cycloheptyl, wherein the cyclopropyl, cyclobutyl, and cyclopentyl are substituted with 1, 2, 3, 4, 5, or 6 substituents selected from the group consisting of alkyl and halogen; R$_5$, R$_6$, R$_7$, and R$_8$ are independently selected from the group consisting of hydrogen, alkoxy, alkoxyalkyl, alkoxycarbonyl, alkoxycarbonylalkoxy, alkyl, alkylsulfonyl, arylalkoxy, carboxy, carboxyalkenylcarbonyloxy, carboxy, carboxyalkylcarbonyloxy, cyano, haloalkoxy, haloalkyl, halogen, heterocyclealkoxycarbonyl, hydroxy, hydroxyalkoxy, hydroxyalkyl, nitro, —$NR_JR_K$, $(NR_JR_K)$alkoxy, $(NR_JR_K)$alkyl, and $(NR_MR_N)$carbonyl; $R_A$, $R_B$, $R_M$, and $R_N$ are independently selected from the group consisting of hydrogen, alkoxycarbonylalkyl, alkyl, and hydroxyalkyl; and $R_C$, $R_D$, $R_J$, $R_K$, are independently selected from the group consisting of hydrogen, alkoxycarbonyl, alkyl, and alkylsulfonyl.

In another embodiment, the present invention provides compounds of Formula (I) wherein $R_3$ is selected from the group consisting of hydrogen and alkyl wherein the alkyl is methyl; $R_4$ is 2,2,3,3-tetramethylcyclopropyl and $R_1$, $R_5$, $R_6$, $R_7$, and $R_8$ are as defined in Formula (I).

In another embodiment, the present invention provides compounds of Formula (I) wherein $R_1$ is heterocyclealkyl; $R_3$ is selected from the group consisting of hydrogen and alkyl wherein the alkyl is methyl; $R_4$ is 2,2,3,3-tetramethylcyclopropyl; and $R_5$, $R_6$, $R_7$, and $R_8$ are as defined in Formula (I).

In another embodiment, the present invention provides compounds of Formula (I) wherein $R_1$ is heterocyclealkyl wherein the heterocyclealkyl is selected from the group consisting of 2-(azepan-1-yl)ethyl, 2-(2,2,-dimethyl-1,3-dioxolan-4-yl)ethyl, (1,3-dioxolan-4-yl)methyl, (tetrahydrofuran-3-yl)methyl, (2R)-(tetrahydrofuran-2-yl)methyl, (2S)-(tetrahydrofuran -2-yl)methyl, 2-(morpholin-4-yl)ethyl, 3-(morpholin-4-yl)propyl, 2-(2-oxo -1,3-oxazolidin-3-yl)ethyl, (1-methylpiperidin-2-yl)methyl, (piperidin-2-yl)methyl, 2-(piperidin-1-yl)ethyl, 2-(pyrrolidin-1-yl)ethyl, 2-(2-oxopyrrolidin-1-yl)ethyl, 2-(2,5-dioxopyrrolidin-1-yl)ethyl, 2-(tetrahydro-2H-pyran-4-yl)ethyl, (tetrahydro-2H-pyran-4-yl)methyl, (tetrahydro-2H-pyran-4-yl)methyl, carboxy(tetrahydro-2H-pyran-4-yl)methyl, 2-ethoxy-2-oxo-1-tetrahydro-2H-pyran-4-ylethyl, 2-piperazin-1-ylethyl, and 4-methyl-2-piperazin-1-ylethyl; $R_3$ is selected from the group consisting of hydrogen and alkyl wherein the alkyl is methyl; $R_4$ is 2,2,3,3-tetramethylcyclopropyl; $R_5$, $R_6$, $R_7$, and $R_8$ are independently selected from the group consisting of hydrogen, alkoxy, alkoxyalkyl, alkoxycarbonyl, alkoxycarbonylalkoxy, alkylsulfonyl, arylalkoxy, carboxy, carboxyalkenylcarbonyloxy, carboxyalkylcarbonyloxy, cyano, haloalkoxy, haloalkyl, halogen, heterocyclealkoxycarbonyl, hydroxy, hydroxyalkoxy, hydroxyalkyl, nitro, —$NR_JR_K$, $(NR_JR_K)$alkoxy, $(NR_JR_K)$alkyl, and $(NR_MR_N)$carbonyl; $R_J$ and $R_K$ are independently selected from the group consisting of hydrogen, alkoxycarbonyl, alkyl, and alkylsulfonyl; and $R_M$ and $R_N$ are independently selected from the group consisting of hydrogen, alkoxycarbonylalkyl, alkyl, and hydroxyalkyl.

In another embodiment, the present invention provides compounds of Formula (I) wherein $R_1$ is heterocyclealkyl wherein the heterocyclealkyl is selected from the group consisting of 2-(azepan-1-yl)ethyl, 2-(2,2,-dimethyl-1,3-dioxolan-4-yl)ethyl, (1,3-dioxolan-4-yl)methyl, (tetrahydrofuran-3-yl)methyl, (2R)-(tetrahydrofuran-2-yl)methyl, (2S)-(tetrahydrofuran-2-yl)methyl, 2-(morpholin-4-yl)ethyl, 3-(morpholin-4-yl)propyl, 2-(2-oxo -1,3-oxazolidin-3-yl)ethyl, (1-methylpiperidin-2-yl)methyl, (piperidin-2-yl)methyl, 2-(piperidin-1-yl)ethyl, 2-(pyrrolidin-1-yl)ethyl, 2-(2-oxopyrrolidin-1-yl)ethyl, 2-(2,5-dioxopyrrolidin-1-yl)ethyl, 2-(tetrahydro-2H-pyran-4-yl)ethyl, (tetrahydro-2H-pyran-4-yl)methyl, (tetrahydro-2H-pyran-4-yl)methyl, carboxy(tetrahydro-2H-pyran-4-yl)methyl, 2-ethoxy-2-oxo-1-tetrahydro-2H-pyran-4-ylethyl, 2-piperazin-1-ylethyl, and 4-methyl-2-piperazin-1-ylethyl; $R_3$ is selected from the group consisting of hydrogen and alkyl wherein the alkyl is methyl; $R_4$ is 2,2,3,3-tetramethylcyclopropyl; and $R_5$, $R_6$, $R_7$, and $R_8$ are each hydrogen.

In another embodiment, the present invention provides compounds of Formula (I) wherein $R_1$ is heteroarylalkyl; $R_3$ is selected from the group consisting of hydrogen and alkyl wherein the alkyl is methyl; $R_4$ is 2,2,3,3-tetramethylcyclopropyl, $R_5$, $R_6$, $R_7$, and $R_8$ are as defined in Formula (I).

In another embodiment, the present invention provides compounds of Formula (I) wherein $R_1$ is heteroarylalkyl wherein the heteroarylalkyl is selected from the group consisting of (1,3-benzothiazol-2-yl)methyl, (1H-imidazolyl-2-yl)methyl, (1-methyl-1H-imidazolyl-2-yl)methyl, 2-pyridin-2-ylethyl, 2-pyridin-3-ylethyl, 2-pyridin-4-ylethyl, 2-(1H-pyrrol-1-yl)ethyl, (5-chloro-1,2,4-thiadiazol-3-yl)methyl, (1,2,4-thiadiazol-3-yl)methyl, 2-(4-methyl-1,3-thiazol-5-yl)ethyl, 2-(1,3-thiazol-5-yl)ethyl, 2-thien-2-ylethyl, and 2-thien-3-ylethyl; $R_3$ is selected from the group consisting of hydrogen and alkyl wherein the alkyl is methyl; $R_4$ is 2,2,3,3-tetramethylcyclopropyl; $R_5$, $R_6$, $R_7$, and $R_8$ are independently selected from the group consisting of hydrogen, alkoxy, alkoxyalkyl, alkoxycarbonyl, alkoxycarbonylalkoxy, alkylsulfonyl, arylalkoxy, carboxy, carboxyalkenylcarbonyloxy, carboxyalkylcarbonyloxy, cyano, haloalkoxy, haloalkyl, halogen, heterocyclealkoxycarbonyl, hydroxy, hydroxyalkoxy, hydroxyalkyl, nitro, —$NR_JR_K$, $(NR_JR_K)$alkoxy, $(NR_JR_K)$alkyl, and $(NR_MR_N)$carbonyl; $R_J$ and $R_K$ are independently selected from the group consisting of hydrogen, alkoxycarbonyl, alkyl, and alkylsulfonyl; and $R_M$ and $R_N$ are independently selected from the group consisting of hydrogen, alkoxycarbonylalkyl, alkyl, and hydroxyalkyl.

In another embodiment, the present invention provides compounds of Formula (I) wherein $R_1$ is heteroarylalkyl wherein the heteroarylalkyl is selected from the group consisting of (1,3-benzothiazol-2-yl)methyl, (1H-imidazolyl-2-yl)methyl, (1-methyl-1H-imidazolyl-2-yl)methyl, 2-pyridin-2-ylethyl, 2-pyridin-3-ylethyl, 2-pyridin-4-ylethyl, 2-(1H-pyrrol-1-yl)ethyl, (5-chloro-1,2,4-thiadiazol-3-yl)methyl, (1,2,4-thiadiazol-3-yl)methyl, 2-(4-methyl-1,3-thiazol-5-yl)ethyl, 2-(1,3-thiazol-5-yl)ethyl, 2-thien-2-ylethyl, and 2-thien-3-ylethyl; $R_3$ is selected from the group consisting of hydrogen and alkyl wherein the alkyl is methyl; $R_4$ is 2,2,3,3-tetramethylcyclopropyl; and $R_5$, $R_6$, $R_7$, and $R_8$ are each hydrogen.

In another embodiment, the present invention provides compounds of Formula (I) wherein $R_1$ is arylalkyl; $R_3$ is selected from the group consisting of hydrogen and alkyl wherein the alkyl is methyl; $R_4$ is 2,2,3,3-tetramethylcyclopropyl; and $R_5$, $R_6$, $R_7$, and $R_8$ are as defined in Formula (I).

In another embodiment, the present invention provides compounds of Formula (I) wherein $R_1$ is arylalkyl wherein the arylalkyl is selected from the group consisting of (1,3-benzodioxol-5-yl)methyl, (2,3-dihydro-1,4-benzodioxin-6-yl)methyl, 4-(acetyloxy)benzyl, benzyl, 2-phenylethyl, 3-phenylpropyl, 3-methoxybenzyl, 4-methoxybenzyl, and 4-hydroxybenzyl; $R_3$ is selected from the group consisting of hydrogen and alkyl wherein the alkyl is methyl; $R_4$ is 2,2,3,3-tetramethylcyclopropyl; $R_5$, $R_6$, $R_7$, and $R_8$ are independently selected from the group consisting of hydrogen, alkoxy, alkoxyalkyl, alkoxycarbonyl, alkoxycarbonylalkoxy, alkylsulfonyl, arylalkoxy, carboxy, carboxyalkenylcarbonyloxy, carboxyalkylcarbonyloxy, cyano, haloalkoxy, haloalkyl, halogen, heterocyclealkoxycarbonyl, hydroxy, hydroxyalkoxy, hydroxyalkyl, nitro, —$NR_JR_K$, $(NR_JR_K)$alkoxy, $(NR_JR_K)$alkyl, and $(NR_MR_N)$carbonyl; $R_J$ and $R_K$ are independently selected from the group consisting of hydrogen, alkoxycarbonyl, alkyl, and alkylsulfonyl; and $R_M$ and $R_N$ are independently selected from the group consisting of hydrogen, alkoxycarbonylalkyl, alkyl, and hydroxyalkyl.

In another embodiment, the present invention provides compounds of Formula (I) wherein $R_1$ is arylalkyl wherein the arylalkyl is selected from the group consisting of (1,3-benzodioxol-5-yl)methyl, (2,3-dihydro-1,4-benzodioxin-6-yl)methyl, 4-(acetyloxy)benzyl, benzyl, 2-phenylethyl, 3-phenylpropyl, 3-methoxybenzyl, 4-methoxybenzyl, and 4-hydroxybenzyl; $R_3$ is selected from the group consisting of hydrogen and alkyl wherein the alkyl is methyl; $R_4$ is 2,2,3,3-tetramethylcyclopropyl; and $R_5$, $R_6$, $R_7$, and $R_8$ are each hydrogen.

In another embodiment, the present invention provides compounds of Formula (I) wherein $R_1$ is selected from the group consisting of alkoxyalkyl, alkylcarbonylalkyl, alkylthioalkyl, azidoalkyl, cycloalkylalkyl, haloalkyl, heterocyclealkylcarbonyl, mercaptoalkyl, $(NR_AR_B)$carbonylalkyl, $(NR_AR_B)$sulfonylalkyl, $(NR_AR_B)$sulfonylalkyl, and $(NR_CR_D)$alkyl; $R_3$ is selected from the group consisting of hydrogen and alkyl wherein the alkyl is methyl; $R_4$ is 2,2,3,3-tetramethylcyclopropyl; $R_A$ and $R_B$ are independently selected from the group consisting of hydrogen, alkoxycarbonylalkyl, alkyl, and hydroxyalkyl; $R_C$ and $R_D$ are independently selected from the group consisting of hydrogen, alkoxycarbonyl, alkyl, and alkylsulfonyl; and $R_5$, $R_6$, $R_7$, and $R_8$ are as defined in Formula (I).

In another embodiment, the present invention provides compounds of Formula (I) wherein $R_1$ is selected from the group consisting of alkoxyalkyl, alkylcarbonylalkyl, alkylthioalkyl, azidoalkyl, cycloalkylalkyl, haloalkyl, heterocyclealkylcarbonyl, mercaptoalkyl, $(NR_AR_B)$carbonylalkyl, $(NR_AR_B)$sulfonylalkyl, $(NR_AR_B)$sulfonylalkyl, and $(NR_CR_D)$alkyl; $R_3$ is selected from the group consisting of hydrogen and alkyl wherein the alkyl is methyl; $R_4$ is 2,2,3,3-tetramethylcyclopropyl; $R_A$ and $R_B$ are independently selected from the group consisting of hydrogen, alkoxycarbonylalkyl, alkyl, and hydroxyalkyl; $R_C$ and $R_D$ are independently selected from the group consisting of hydrogen, alkoxycarbonyl, alkyl, and alkylsulfonyl; $R_5$, $R_6$, $R_7$, and $R_8$ are independently selected from the group consisting of hydrogen, alkoxy, alkoxyalkyl, alkoxycarbonyl, alkoxycarbonylalkoxy, alkylsulfonyl, arylalkoxy, carboxy, carboxyalkenylcarbonyloxy, carboxyalkylcarbonyloxy, cyano, haloalkoxy, haloalkyl, halogen, heterocyclealkoxycarbonyl, hydroxy, hydroxyalkoxy, hydroxyalkyl, nitro, $—NR_JR_K$, $(NR_JR_K)$alkoxy, $(NR_JR_K)$alkyl, and $(NR_MR_N)$carbonyl; $R_J$ and $R_K$ are independently selected from the group consisting of hydrogen, alkoxycarbonyl, alkyl, and alkylsulfonyl; and $R_M$ and $R_N$ are independently selected from the group consisting of hydrogen, alkoxycarbonylalkyl, alkyl, and hydroxyalkyl.

In another embodiment, the present invention provides compounds of Formula (I) wherein $R_1$ is selected from the group consisting of alkoxyalkyl, alkylcarbonylalkyl, alkylthioalkyl, azidoalkyl, cycloalkylalkyl, haloalkyl, heterocyclealkylcarbonyl, mercaptoalkyl, $(NR_AR_B)$carbonylalkyl, $(NR_AR_B)$sulfonylalkyl, $(NR_AR_B)$sulfonylalkyl, and $(NR_CR_D)$alkyl; $R_3$ is selected from the group consisting of hydrogen and alkyl wherein the alkyl is methyl; $R_4$ is 2,2,3,3-tetramethylcyclopropyl; $R_A$ and $R_B$ are independently selected from the group consisting of hydrogen, alkoxycarbonylalkyl, alkyl, and hydroxyalkyl; and $R_C$ and $R_D$ are independently selected from the group consisting of hydrogen, alkoxycarbonyl, alkyl, and alkylsulfonyl.

In another embodiment, the present invention provides compounds of Formula (I) wherein $R_1$ is -$LOR_2$; L is alkylene; $R_2$ is selected from the group consisting of alkylcarbonyl, arylalkyl, and carboxyalkenylcarbonyl; $R_3$ is selected from the group consisting of hydrogen and alkyl wherein the alkyl is methyl; $R_4$ is 2,2,3,3-tetramethylcyclopropyl; and $R_5$, $R_6$, $R_7$, and $R_8$ are as defined in Formula (I).

In another embodiment, the present invention provides compounds of Formula (I) wherein $R_1$ is -$LOR_2$; L is alkylene; $R_2$ is selected from the group consisting of alkylcarbonyl, arylalkyl, and carboxyalkenylcarbonyl; $R_3$ is selected from the group consisting of hydrogen and alkyl wherein the alkyl is methyl; $R_4$ is 2,2,3,3-tetramethylcyclopropyl; $R_5$, $R_6$, $R_7$, and $R_8$ are independently selected from the group consisting of hydrogen, alkoxy, alkoxyalkyl, alkoxycarbonyl, alkoxycarbonylalkoxy, alkylsulfonyl, arylalkoxy, carboxy, carboxyalkenylcarbonyloxy, carboxyalkylcarbonyloxy, cyano, haloalkoxy, haloalkyl, halogen, heterocyclealkoxycarbonyl, hydroxy, hydroxyalkoxy, hydroxyalkyl, nitro, $—NR_JR_K$, $(NR_JR_K)$alkoxy, $(NR_JR_K)$alkyl, and $(NR_MR_N)$carbonyl; $R_J$ and $R_K$ are independently selected from the group consisting of hydrogen, alkoxycarbonyl, alkyl, and alkylsulfonyl; and $R_M$ and $R_N$ are independently selected from the group consisting of hydrogen, alkoxycarbonylalkyl, alkyl, and hydroxyalkyl.

In another embodiment, the present invention provides compounds of Formula (I) wherein $R_1$ is -$LOR_2$; L is alkylene; $R_2$ is selected from the group consisting of alkylcarbonyl, arylalkyl, and carboxyalkenylcarbonyl; $R_3$ is selected from the group consisting of hydrogen and alkyl wherein the alkyl is methyl; $R_4$ is 2,2,3,3-tetramethylcyclopropyl; and $R_5$, $R_6$, $R_7$, and $R_8$ are each hydrogen.

In another embodiment, the present invention provides compounds of Formula (I) wherein $R_1$ is hydroxyalkyl; $R_3$ is selected from the group consisting of hydrogen and alkyl wherein the alkyl is methyl; $R_4$ is 2,2,3,3-tetramethylcyclopropyl; and $R_5$, $R_6$, $R_7$, and $R_8$ are as defined in Formula (I).

In another embodiment, the present invention provides compounds of Formula (I) wherein $R_1$ is hydroxyalkyl; $R_3$ is selected from the group consisting of hydrogen and alkyl wherein the alkyl is methyl; $R_4$ is 2,2,3,3-tetramethylcyclopropyl; $R_5$, $R_6$, $R_7$, and $R_8$ are independently selected from the group consisting of hydrogen, alkoxy, alkoxyalkyl, alkoxycarbonyl, alkoxycarbonylalkoxy, alkylsulfonyl, arylalkoxy, carboxy, carboxyalkenylcarbonyloxy, carboxyalkylcarbonyloxy, cyano, haloalkoxy, haloalkyl, halogen, heterocyclealkoxycarbonyl, hydroxy, hydroxyalkoxy, hydroxyalkyl, nitro, $—NR_JR_K$, $(NR_JR_K)$alkoxy, $(NR_JR_K)$alkyl, and $(NR_MR_N)$carbonyl; $R_J$ and $R_K$ are independently selected from the group consisting of hydrogen, alkoxycarbonyl, alkyl, and alkylsulfonyl; and $R_M$ and $R_N$ are independently selected from the group consisting of hydrogen, alkoxycarbonylalkyl, alkyl, and hydroxyalkyl.

In another embodiment, the present invention provides compounds of Formula (I) wherein $R_1$ is hydroxyalkyl; $R_3$ is selected from the group consisting of hydrogen and alkyl wherein the alkyl is methyl; $R_4$ is 2,2,3,3-tetramethylcyclopropyl; and $R_5$, $R_6$, $R_7$, and $R_8$ are each hydrogen.

In another embodiment, the present invention provides compounds of Formula (I) wherein $R_1$ is alkylthioalkyl; $R_3$ is selected from the group consisting of hydrogen and alkyl wherein the alkyl is methyl; $R_4$ is 2,2,3,3-tetramethylcyclopropyl; and $R_5$, $R_6$, $R_7$, and $R_8$ are as defined in Formula (I).

In another embodiment, the present invention provides compounds of Formula (I) wherein $R_1$ is alkylthioalkyl; $R_3$ is selected from the group consisting of hydrogen and alkyl wherein the alkyl is methyl; $R_4$ is 2,2,3,3-tetramethylcyclopropyl; $R_5$, $R_6$, $R_7$, and $R_8$ are independently selected from the group consisting of hydrogen, alkoxy, alkoxyalkyl, alkoxycarbonyl, alkoxycarbonylalkoxy, alkylsulfonyl, arylalkoxy, carboxy, carboxyalkenylcarbonyloxy, carboxyalkylcarbonyloxy, cyano, haloalkoxy, haloalkyl, halogen, heterocyclealkoxycarbonyl, hydroxy, hydroxyalkoxy, hydroxyalkyl, nitro, —NR$_J$R$_K$, (NR$_J$R$_K$)alkoxy, (NR$_J$R$_K$) alkyl, and (NR$_M$R$_N$)carbonyl; R$_J$ and R$_K$ are independently selected from the group consisting of hydrogen, alkoxycarbonyl, alkyl, and alkylsulfonyl; and R$_M$ and R$_N$ are independently selected from the group consisting of hydrogen, alkoxycarbonylalkyl, alkyl, and hydroxyalkyl.

In another embodiment, the present invention provides compounds of Formula (I) wherein R$_1$ is alkylthioalkyl; R$_3$ is selected from the group consisting of hydrogen and alkyl wherein the alkyl is methyl; R$_4$ is 2,2,3,3-tetramethylcyclopropyl; and R$_5$, R$_6$, R$_7$, and R$_8$ are each hydrogen.

In another embodiment, the present invention provides compounds of Formula (I) wherein R$_1$ is heterocyclealkyl; R$_3$ is selected from the group consisting of hydrogen and alkyl wherein the alkyl is methyl; R$_4$ is 2,2,3,3-tetrafluoro-1-methylcyclobutyl; and R$_5$, R$_6$, R$_7$, and R$_8$ are as defined in Formula (I).

In another embodiment, the present invention provides compounds of Formula (I) wherein R$_1$ is heterocyclealkyl wherein the heterocyclealkyl is selected from the group consisting of 2-(azepan-1-yl)ethyl, 2-(2,2,-dimethyl-1,3-dioxolan-4-yl)ethyl, (1,3-dioxolan-4-yl)methyl, (tetrahydrofuran-3-yl)methyl, (2R)-(tetrahydrofuran-2-yl)methyl, (2S)-(tetrahydrofuran-2-yl)methyl, 2-(morpholin-4-yl)ethyl, 3-(morpholin-4-yl)propyl, 2-(2-oxo -1,3-oxazolidin-3-yl) ethyl, (1-methylpiperidin-2-yl)methyl, (piperidin-2-yl)methyl, 2-(piperidin-1-yl)ethyl, 2-(pyrrolidin-1-yl)ethyl, 2-(2-oxopyrrolidin-1-yl)ethyl, 2-(2,5-dioxopyrrolidin-1-yl)ethyl, 2-(tetrahydro-2H-pyran-4-yl)ethyl, (tetrahydro-2H-pyran-4-yl)methyl, (tetrahydro-2H-pyran-4-yl)methyl, carboxy(tetrahydro-2H-pyran-4-yl)methyl, 2-ethoxy-2-oxo-1-tetrahydro-2H-pyran-4-ylethyl, 2-piperazin-1-ylethyl, and 4-methyl-2-piperazin-1-ylethyl; R$_3$ is selected from the group consisting of hydrogen and alkyl wherein the alkyl is methyl; R$_4$ is 2,2,3,3-tetrafluoro-1-methylcyclobutyl; R$_5$, R$_6$, R$_7$, and R$_8$ are independently selected from the group consisting of hydrogen, alkoxy, alkoxyalkyl, alkoxycarbonyl, alkoxycarbonylalkoxy, alkylsulfonyl, arylalkoxy, carboxy, carboxyalkenylcarbonyloxy, carboxyalkylcarbonyloxy, cyano, haloalkoxy, haloalkyl, halogen, heterocyclealkoxycarbonyl, hydroxy, hydroxyalkoxy, hydroxyalkyl, nitro, —NR$_J$R$_K$, (NR$_J$R$_K$)alkoxy, (NR$_J$R$_K$)alkyl, and (NR$_M$R$_N$)carbonyl; R$_J$ and R$_K$ are independently selected from the group consisting of hydrogen, alkoxycarbonyl, alkyl, and alkylsulfonyl; and R$_M$ and R$_N$ are independently selected from the group consisting of hydrogen, alkoxycarbonylalkyl, alkyl, and hydroxyalkyl.

In another embodiment, the present invention provides compounds of Formula (I) wherein R$_1$ is heterocyclealkyl wherein the heterocyclealkyl is selected from the group consisting of 2-(azepan-1-yl)ethyl, 2-(2,2,-dimethyl-1,3-dioxolan-4-yl)ethyl, (1,3-dioxolan-4-yl)methyl, (tetrahydrofuran-3-yl)methyl, (2R)-(tetrahydrofuran-2-yl)methyl, (2S)-(tetrahydrofuran -2-yl)methyl, 2-(morpholin-4-yl)ethyl, 3-(morpholin-4-yl)propyl, 2-(2-oxo -1,3-oxazolidin-3-yl) ethyl, (1-methylpiperidin-2-yl)methyl, (piperidin-2-yl)methyl, 2-(piperidin-1-yl)ethyl, 2-(pyrrolidin-1-yl)ethyl, 2-(2-oxopyrrolidin-1-yl)ethyl, 2-(2,5-dioxopyrrolidin-1-yl)ethyl, 2-(tetrahydro-2H-pyran-4-yl)ethyl, (tetrahydro-2H-pyran-4-yl)methyl, (tetrahydro-2H-pyran-4-yl)methyl, carboxy(tetrahydro-2H-pyran-4-yl)methyl, 2-ethoxy-2-oxo-1-tetrahydro-2H-pyran-4-ylethyl, 2-piperazin-1-ylethyl, and 4-methyl-2-piperazin-1-ylethyl; R$_3$ is selected from the group consisting of hydrogen and alkyl wherein the alkyl is methyl; R$_4$ is 2,2,3,3-tetrafluoro-1-methylcyclobutyl; and R$_5$, R$_6$, R$_7$, and R$_8$ are each hydrogen.

In another embodiment, the present invention provides compounds of Formula (I) wherein R$_1$ is heterocyclealkyl; R$_3$ is selected from the group consisting of hydrogen and alkyl wherein the alkyl is methyl; R$_4$ is cycloheptyl; and R$_5$, R$_6$, R$_7$, and R$_8$ are as defined in Formula (I).

In another embodiment, the present invention provides compounds of Formula (I) wherein R$_1$ is heterocyclealkyl wherein the heterocyclealkyl is selected from the group consisting of 2-(azepan-1-yl)ethyl, 2-(2,2,-dimethyl-1,3-dioxolan-4-yl)ethyl, (1,3-dioxolan-4-yl)methyl, (tetrahydrofuran-3-yl)methyl, (2R)-(tetrahydrofuran-2-yl)methyl, (2S)-(tetrahydrofuran -2-yl)methyl, 2-(morpholin-4-yl)ethyl, 3-(morpholin-4-yl)propyl, 2-(2-oxo-1,3-oxazolidin-3-yl) ethyl, (1-methylpiperidin-2-yl)methyl, (piperidin-2-yl)methyl, 2-(piperidin-1-yl)ethyl, 2-(pyrrolidin-1-yl)ethyl, 2-(2-oxopyrrolidin-1-yl)ethyl, 2-(2,5-dioxopyrrolidin-1-yl)ethyl, 2-(tetrahydro-2H-pyran-4-yl)ethyl, (tetrahydro-2H-pyran-4-yl)methyl, (tetrahydro-2H-pyran-4-yl)methyl, carboxy(tetrahydro-2H-pyran-4-yl)methyl, 2-ethoxy-2-oxo-1-tetrahydro-2H-pyran-4-ylethyl, 2-piperazin-1-ylethyl, and 4-methyl-2-piperazin-1-ylethyl; R$_3$ is selected from the group consisting of hydrogen and alkyl wherein the alkyl is methyl; R$_4$ is cycloheptyl; R$_5$, R$_6$, R$_7$, and R$_8$ are independently selected from the group consisting of hydrogen, alkoxy, alkoxyalkyl, alkoxycarbonyl, alkoxycarbonylalkoxy, alkylsulfonyl, arylalkoxy, carboxy, carboxyalkenylcarbonyloxy, carboxyalkylcarbonyloxy, cyano, haloalkoxy, haloalkyl, halogen, heterocyclealkoxycarbonyl, hydroxy, hydroxyalkoxy, hydroxyalkyl, nitro, —NR$_J$R$_K$, (NR$_J$R$_K$)alkoxy, (NR$_J$R$_K$)alkyl, and (NR$_M$R$_N$)carbonyl; R$_J$ and R$_K$ are independently selected from the group consisting of hydrogen, alkoxycarbonyl, alkyl, and alkylsulfonyl; and R$_M$ and R$_N$ are independently selected from the group consisting of hydrogen, alkoxycarbonylalkyl, alkyl, and hydroxyalkyl.

In another embodiment, the present invention provides compounds of Formula (I) wherein R$_1$ is heterocyclealkyl wherein the heterocyclealkyl is selected from the group consisting of 2-(azepan-1-yl)ethyl, 2-(2,2,-dimethyl-1,3-dioxolan-4-yl)ethyl, (1,3-dioxolan-4-yl)methyl, (tetrahydrofuran-3-yl)methyl, (2R)-(tetrahydrofuran-2-yl)methyl, (2S)-(tetrahydrofuran-2-yl)methyl, 2-(morpholin-4-yl)ethyl, 3-(morpholin-4-yl)propyl, 2-(2-oxo -1,3-oxazolidin-3-yl) ethyl, (1-methylpiperidin-2-yl)methyl, (piperidin-2-yl)methyl, 2-(piperidin-1-yl)ethyl, 2-(pyrrolidin-1-yl)ethyl, 2-(2-oxopyrrolidin-1-yl)ethyl, 2-(2,5-dioxopyrrolidin-1-yl)ethyl, 2-(tetrahydro-2H-pyran-4-yl)ethyl, (tetrahydro-2H-pyran-4-yl)methyl, (tetrahydro-2H-pyran-4-yl)methyl, carboxy(tetrahydro-2H-pyran-4-yl)methyl, 2-ethoxy-2-oxo-1-tetrahydro-2H-pyran-4-ylethyl, 2-piperazin-1-ylethyl, and 4-methyl-2-piperazin-1-ylethyl; R$_3$ is selected from the group consisting of hydrogen and alkyl wherein the alkyl is methyl; R$_4$ is cycloheptyl; and R$_5$, R$_6$, R$_7$, and R$_8$ are each hydrogen.

Definition of Terms

All patents, patent applications, and literature references cited in the specification are herein incorporated by reference in their entirety. In the case of inconsistencies, the present disclosure, including definitions, will prevail.

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein, means an alkoxy group, as defined herein, appended to the parent molecular moiety through an alkyl group, as defined herein except for $R_1$ in Formula (I) wherein the alkoxy group is at least two carbons from the indole nitrogen. Representative examples of alkoxyalkyl include, but are not limited to, tert-butoxymethyl, 2-ethoxyethyl, 2-methoxyethyl, methoxymethyl, 3-methoxypropyl, 4-methoxybutyl, and 5-methoxypentyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkoxy" as used herein, means an alkoxycarbonyl group, as defined herein, appended to the parent molecular moiety through an alkoxy group, as defined herein. Representative examples of alkoxycarbonylalkoxy include, but are not limited to, 3-ethoxy-3-oxopropoxy, 3-methoxy-3-oxopropoxy, 4-ethoxy-4-oxobutoxy, 5-methoxy-5-oxopentyloxy, 5-ethoxy-5-oxopentyloxy, 6-ethoxy-6-oxohexyloxy.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-ethoxy-3-oxopropyl, 3-methoxy-3-oxopropyl, 4-ethoxy-4-oxobutyl, 5-methoxy-5-oxopentyl, 5-ethoxy-5-oxopentyl, 6-ethoxy-6-oxohexyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, 3-oxopentyl, and 5-oxohexyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent alkyl group derived from a straight or branched chain hydrocarbon of from 2 to 10 carbon atoms. Representative examples of alkylene include, but are not limited to, —CH$_2$CH$_2$—, —CH$_2$CH$_2$CH$_2$—, —CH$_2$CH(-)CH$_3$, —CH$_2$CH$_2$CH$_2$CH$_2$—, —CH$_2$CH(CH$_3$)CH$_2$—, —CH$_2$C(CH$_3$)$_2$CH$_2$—, —CH$_2$CH$_2$CH$_2$CH$_2$CH$_2$—, —CH$_2$CH$_2$CH(-)CH$_2$CH$_3$, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH(-)CH$_2$CH$_2$CH$_3$—, —CH$_2$CH(CH$_2$CH$_3$)CH$_2$—, and —CH$_2$CH(CH$_2$CH$_2$—)CH$_3$.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkyl group, as defined herein. Representative examples of alkylsulfinylalkyl include, but are not limited to, methylsulfinylmethyl and ethylsulfinylmethyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkyl group, as defined herein. Representative examples of alkylsulfonylalkyl include, but are not limited to, methylsulfonylmethyl and ethylsulfonylmethyl.

The term "alkylsulfonyloxy" as used herein, means an alkylsulfonyl group, as defined herein, appended to the parent molecular moiety through an oxygen atom, as defined herein.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkyl group, as defined herein except for $R_1$ in Formula (I) wherein the alkylthio group is at least two carbons from the indole nitrogen. Representative examples of alkylthioalkyl include, but are not limited, methylthiomethyl, 2-(ethylthio)ethyl, and 4-(methylthio)butyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl group or a naphthyl group.

The aryl groups of the present invention can be optionally substituted with one, two, three, four, or five substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, ethylenedioxy, formyl, haloalkoxy, haloalkyl, halogen, hydroxy, hydroxyalkyl, mercapto, methylenedioxy, nitro, —$NZ_1Z_2$, ($NZ_1Z_2$)alkyl, ($NZ_1Z_2$)carbonyl, and ($NZ_1Z_2$)sulfonyl. Representative examples of substituted aryl include, but are not limited to, 3-(acetyloxy)phenyl, 4-(acetyloxy)phenyl, 3-(dimethylamino)phenyl, 4-(dimethylamino)phenyl, 3-hydroxyphenyl, 4-hydroxyphenyl, 3-methoxyphenyl, and 4-methoxyphenyl.

The term "arylalkoxy" as used herein, means an aryl group, as defined herein, appended to the parent molecular moiety through an alkoxy group, as defined herein. Representative examples of arylalkoxy include, but are not limited to, benzyloxy, 2-phenylethoxy, and 3-phenylpropoxy.

The term "arylalkoxyalkyl" as used herein, means an arylalkoxy group, as defined herein, appended to the parent molecular moiety through an alkyl group, as defined herein. Representative examples of arylalkoxyalkyl include, but are not limited to, 4-(benzyloxy)butyl, 3-(benzyloxy)propyl, 2-(benzyloxy)ethyl, and 5-(benzyloxy)pentyl.

The term "arylalkyl" as used herein, means an aryl group, as defined herein, appended to the parent molecular moiety through an alkyl group, as defined herein. Representative examples of arylalkyl include, but are not limited to, (1,3-benzodioxol-5-yl)methyl, (2,3-dihydro-1,4-benzodioxin-6-yl)methyl, 4-(acetyloxy)benzyl, benzyl, 2-phenylethyl, 3-phenylpropyl, 2-(4-dimethylaminophenyl)ethyl, 2-naphth-2-ylethyl, 3-methoxybenzyl, 4-methoxybenzyl, and 4-hydroxybenzyl.

The term "arylalkylcarbonyl" as used herein, means an arylalkyl group, as defined herein, appended to the parent molecular moiety through a carbonyl group, as defined herein. Representative examples of arylalkyl include, but are not limited to, 2-phenylacetyl and 3-phenylpropanoyl.

The term "arylalkylsulfonyl" as used herein, means an arylalkyl group, as defined herein, appended to the parent molecular moiety through a sulfonyl group, as defined herein. Representative examples of "arylalkylsulfonyl" include, but are not limited to, benzylsulfonyl and 2-phenylethylsulfonyl.

The term "arylalkylthio" as used herein, means an arylalkyl group, as defined herein, appended to the parent molecular moiety through a sulfur atom. Representative examples of arylalkylthio include, but are not limited to, 2-phenylethylthio, 3-naphth-2-ylpropylthio, and 5-phenylpentylthio.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl" as used herein, means an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl and 3-bromophenoxymethyl.

The term "arylsulfonyl" as used herein, means an aryl group, as defined herein, appended to the parent molecular moiety through a sulfonyl group, as defined herein.

The term "arylthio" as used herein, means an aryl group, as defined herein, appended to the parent molecular moiety through a sulfur atom. Representative examples of arylthio include, but are not limited to, phenylthio and 2-naphthylthio.

The term "arylthioalkyl" as used herein, means an arylthio group, as defined herein, appended to the parent molecular moiety through an alkyl group, as defined herein. Representative examples of arylthioalkyl include, but are not limited to, phenylthiomethyl, 2-naphth-2-ylthioethyl, and 2-(phenylthio)ethyl.

The term "azide" as used herein, means a —$N_3$ group.

The term "azidoalkyl" as used herein, means an azide group, as defined herein, appended to the parent molecular moiety through an alkyl group, as defined herein except for $R_1$ in Formula (I) wherein the azide group is at least two carbons from the indole nitrogen. Representative examples of azidoalkyl include, but are not limited to, 2-azidoethyl, 3-azidopropyl, and 4-azidobutyl.

The term "carbonyl" as used herein, means a —C(O)— group.

The term "carboxy" as used herein, means a —$CO_2H$ group.

The term "carboxyalkenyl" as used herein, means a carboxy group, as defined herein, appended to the parent molecular moiety through an alkenyl group, as defined herein. Representative examples of carboxyalkenyl include, but are not limited to, 3-ethoxy-3-oxoprop-1-enyl.

The term "carboxyalkenylcarbonyl" as used herein, means a carboxyalkenyl group, as defined herein, appended to the parent molecular moiety through a carbonyl group, as defined herein. Representative examples of carboxyalkenylcarbonyl include, but are not limited to, 4-ethoxy-4-oxobut-2-enoyl.

The term "carboxyalkenylcarbonyloxy" as used herein, means a carboxyalkenylcarbonyl group, as defined herein, appended to the parent molecular moiety through an oxygen atom, as defined herein. Representative examples of carboxyalkenylcarbonyloxy include, but are not limited to, (3-carboxyprop-2-enoyl)oxy.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, 3-carboxypropyl, 4-carboxybutyl, 5-carboxypentyl, and 6-carboxyhexyl.

The term "carboxyalkylcarbonyl" as used herein, means a carboxyalkyl group, as defined herein, appended to the parent molecular moiety through a carbonyl group, as defined herein. Representative examples of carboxyalkylcarbonyl include, but are not limited to, 3-carboxypropanoyl and 4-carboxybutanoyl.

The term "carboxyalkylcarbonyloxy" as used herein, means a carboxyalkylcarbonyl group, as defined herein, appended to the parent molecular moiety through a oxygen atom, as defined herein. Representative examples of carboxyalkylcarbonyloxy include, but are not limited to, (3-carboxypropanoyl)oxy and (4-carboxybutanoyl)oxy.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkenyl" as used herein, means a cyclic hydrocarbon containing from 3 to 8 carbons and containing at least one carbon-carbon double bond formed by the removal of two hydrogens. Representative examples of cycloalkenyl include, but are not limited to, 2-cyclohexen-1-yl, 3-cyclohexen-1-yl, 2,4-cyclohexadien-1-yl and 3-cyclopenten-1-yl.

The term "cycloalkyl" as used herein, means a saturated cyclic hydrocarbon group containing from 3 to 8 carbons, examples of cycloalkyl include cyclopropyl, cyclobutyl, cyclopentyl, cyclohexyl, cycloheptyl, and cyclooctyl.

The cycoalkyl groups of the present invention are optionally substituted with 1, 2, 3, 4, 5, or 6 substituents selected from the group consisting of alkenyl, alkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, haloalkoxy, haloalkyl, halogen, hydroxy, hydroxyalkyl, mercapto, mercaptoalkyl, oxo, —$NZ_1Z_2$, ($NZ_1Z_2$)alkyl, ($NZ_1Z_2$)carbonyl, and ($NZ_1Z_2$)sulfonyl.

The term "cycloalkylalkoxy" as used herein, means a cycloalkyl group, as defined herein, appended to the parent molecular moiety through an alkoxy group, as defined herein. Representative examples of cycloalkylalkoxy include, but are not limited to, cyclopropylmethoxy, 2-cyclobutylethoxy, cyclopentylmethoxy, cyclohexylmethoxy, and 4-cycloheptylbutoxy.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, 4-cycloheptylbutyl, and (4-methoxycarbonylcyclohexyl)methyl.

The term "cycloalkylalkylcarbonyl" as used herein, means a cycloalkylalkyl group, as defined herein, appended to the parent molecular moiety through a carbonyl group, as defined herein. Representative examples of cycloalkylalkylcarbonyl include, but are not limited to, 4-cyclopentylbutanoyl and 3-cyclopentylpropanoyl.

The term "cycloalkylalkylsulfonyl" as used herein, means a cycloalkylalkyl group, as defined herein, appended to the parent molecular moiety through a sulfonyl group, as defined herein. Representative examples of cycloalkylalkylsulfonyl include, but are not limited to, (2-cyclopentylethyl)sulfonyl and (2-cyclopropylethyl)sulfonyl.

The term "cycloalkylcarbonyl" as used herein, means cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, and cyclohexylcarbonyl.

The term "cycloalkyloxy" as used herein, means cycloalkyl group, as defined herein, appended to the parent molecular moiety through an oxygen atom, as defined herein. Representative examples of cycloalkyloxy include, but are not limited to, cyclopropyloxy, cyclobutyloxy, cyclopentyloxy, cyclohexyloxy, cycloheptyloxy, and cyclooctyloxy.

The term "cycloalkyloxyalkyl" as used herein, means cycloalkyloxy group, as defined herein, appended to the parent molecular moiety through an alkyl group, as defined herein. Representative examples of cycloalkyloxyalkyl include, but are not limited to, 2-(cyclopropyloxy)ethyl, 4-(cyclobutyloxy)pentyl, cyclopentyloxymethyl, 3-(cyclohexyloxy)propyl, cycloheptyloxymethyl, and 2-(cyclooctyloxy)ethyl.

The term "cycloalkylsulfonyl" as used herein, means a cycloalkyl group, as defined herein, appended to the parent molecular moiety through a sulfonyl group, as defined herein. Representative examples of cyclalkylsulfonyl include, but are not limited to, cyclopentylsulfonyl and cyclopropylsulfonyl.

The term "ethylenedioxy" as used herein, means a —$O(CH_2)_2O$— group wherein the oxygen atoms of the ethylenedioxy group are attached to the parent molecular moiety through two adjacent carbon atoms forming a six membered ring.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and 4,4,4,-trifluorobutyl.

The term "heteroaryl," as used herein, means a monocyclic heteroaryl ring or a bicyclic heteroaryl ring. The monocyclic heteroaryl ring is a 5 or 6 membered ring. The 5 membered ring has two double bonds and contains one, two, three or four heteroatoms independently selected from the group consisting of N, O, and S. The 6 membered ring has three double bonds and contains one, two, three or four heteroatoms independently selected from the group consisting of N, O, and S. The bicyclic heteroaryl ring consists of the 5 or 6 membered heteroaryl ring fused to a phenyl group or the 5 or 6 membered heteroaryl ring fused to another 5 or 6 membered heteroaryl ring. Nitrogen heteroatoms contained within the heteroaryl may be optionally oxidized to the N-oxide or optionally protected with a nitrogen protecting group known to those of skill in the art. The heteroaryl is connected to the parent molecular moiety through any carbon atom contained within the heteroaryl. Representative examples of heteroaryl include, but are not limited to, benzothiazolyl, benzothienyl, benzoxadiazolyl, cinnolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, pyridinium N-oxide, quinolinyl, tetrazolyl, thiadiazolyl, thiazolyl, thienopyridinyl, thienyl, triazolyl, and triazinyl.

The heteroaryl groups of the present invention are optionally substituted with 1, 2, 3, or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, nitro, —$NZ_1Z_2$, ($NZ_1Z_2$)alkyl, ($NZ_1Z_2$)carbonyl, and ($NZ_1Z_2$)sulfonyl. Representative examples of substituted heteroaryls include, but are not limited to, 1-methyl-1H-imidazolyl, 5-chloro-1,2,4-thiadiazolyl, and 4-methyl-1,3-thiazolyl. Heteroaryl groups of the present invention that are substituted may be present as tautomers. The present invention encompasses all tautomers including non-aromatic tautomers.

The term "heteroarylalkoxy" as used herein, means a heteroaryl group, as defined herein, appended to the parent molecular moiety through an alkoxy group, as defined herein. Representative examples of heteroarylalkoxy include, but are not limited to, fur-3-ylmethoxy, 1H-imidazol-2-ylmethoxy, 1H-imidazol-4-ylmethoxy, 1-(pyridin-4-yl)ethoxy, pyridin-3-ylmethoxy, 6-chloropyridin-3-ylmethoxy, pyridin-4-ylmethoxy, (6-(trifluoromethyl)pyridin -3-yl)methoxy, (6-(cyano)pyridin-3-yl)methoxy, (2-(cyano)pyridin-4-yl)methoxy, (5-(cyano)pyridin-2-yl)methoxy, (2-(chloro)pyridin-4-yl) methoxy, pyrimidin-5-ylmethoxy, 2-(pyrimidin-2-yl)propoxy, thien-2-ylmethoxy, and thien-3-ylmethoxy.

The term "heteroarylalkyl" as used herein, means a heteroaryl, as defined herein, appended to the parent molecular moiety through an alkyl group, as defined herein. Representative examples of heteroarylalkyl include, but are not limited to, (1H-imidazolyl-2-yl)methyl, (1-methyl-1H-imidazolyl-2-yl)methyl, 2-pyridin-2-ylethyl, 2-pyridin-3-ylethyl, 2-pyridin-4-ylethyl, 2-(1H-pyrrol-1-yl)ethyl, (5-chloro-1,2,4-thiadiazol-3-yl)methyl, (1,2,4-thiadiazol-3-yl)methyl, 2-(4-methyl-1,3-thiazol-5-yl)ethyl, 2-(1,3-thiazol-5-yl)ethyl, 2-thien-2-ylethyl, and 2-thien-3-ylethyl.

The term "heteroarylalkylcarbonyl" as used herein, means a heteroarylalkyl, as defined herein, appended to the parent molecular moiety through a carbonyl group, as defined herein. Representative example of heteroarylalkylcarbonyl include, but are not limited to, (3-pyridin-3-ylpropyl)carbonyl and (2-pyrimidin-5-ylethyl)carbonyl.

The term "heteroaryloxy" as used herein, means a heteroaryl group, as defined herein, appended to the parent molecular moiety through an oxygen atom. Representative examples of heteroaryloxy include, but are not limited to, pyrimidinyloxy and pyridinyloxy.

The term "heteroaryloxyalkyl" as used herein, means a heteroaryloxy group, as defined herein, appended to the parent molecular moiety through an alkyl group, as defined herein. Representative examples of heteroaryloxyalkyl include, but are not limited to, pyridinyloxymethyl and 2-quinolinyloxyethyl.

The term "heteroarylalkylsulfonyl" as used herein, means a heteroarylalkyl, as defined herein, appended to the parent molecular moiety through a sulfonyl group, as defined herein.

The term "heteroarylsulfonyl" as used herein, means a heteroaryl, as defined herein, appended to the parent molecular moiety through a sulfonyl group, as defined herein.

The term "heterocycle" or "heterocyclic" as used herein, means a monocyclic or a bicyclic heterocyclic ring. The monocyclic heterocyclic ring consists of a 3, 4, 5, 6 or 7 membered ring containing at least one heteroatom independently selected from O, N and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. Representative examples of the monocyclic heterocyclic ring include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocyclic ring consists of the monocyclic heterocyclic ring fused to a cycloalkyl group or the monocyclic heterocyclic ring fused to a cycloalkenyl group or the monocyclic heterocyclic ring fused to another monocyclic heterocyclic ring or the monocyclic heterocyclic ring fused to an aryl group wherein the aryl group is an optionally substituted phenyl group. The bicyclic heterocyclic ring can be appended to the parent molecular moiety via any carbon or nitrogen atom within the bicyclic heterocyclic ring while maintaining the proper valence. Representative examples of the bicyclic heterocyclic ring include, but are not limited to, 1,3-benzodioxolyl, 2,3-dihydro-1,4-benzodioxinyl, 1,2,3,4-tetrahydroquinoxalinyl, decahydroquinoxalinyl, and octahydro-1,4-benzodioxinyl.

The heterocycles of this invention are optionally substituted with 1, 2, 3, or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, nitro, oxo, —$NZ_1Z_2$, ($NZ_1Z_2$)alkyl, ($NZ_1Z_2$)carbonyl, ($NZ_1Z_2$)sulfonyl. Representative examples of substituted heterocycle include, but not limited to, 2,2-dimethyl-1,3-dioxolanyl, 4-methylpiperazinyl, 1-methylpiperidinyl, 1-methylpyrrolidinyl, 2,5-dioxopyrrolidinyl, 2-oxopyrrolidinyl, 2-oxo-1,3-oxazolidinyl, and 1-(tert-butoxycarbonyl)piperidinyl.

The term "heterocyclealkoxy" as used herein, means a heterocycle group, as defined herein, appended to the parent molecular moiety through an alkoxy group, as defined herein. Representative examples of heterocyclealkoxy include, but are not limited to, 2-morpholin-1-ylethoxy and 2-piperidin-1-ylethoxy.

The term "heterocyclealkoxycarbonyl" as used herein, means a heterocyclealkoxy group, as defined herein, appended to the parent molecular moiety through a carbonyl group. Representative examples of heterocyclealkoxycarbonyl include, but are not limited to, (2-morpholin-4-ylethoxy) carbonyl.

The term "heterocyclealkyl" as used-herein, means a heterocycle, as defined herein, appended to the parent molecular moiety through an alkyl group, as defined herein, wherein the alkyl group of the heterocyclealkyl at $R_1$ of Formula (I) may be optionally substituted with 1 substituent selected from the group consisting of alkoxycarbonyl and carboxy. Representative examples of heterocyclealkyl include, but are not limited to, 2-(azepan-1-yl)ethyl, 2-(2,2,-dimethyl-1,3-dioxolan-4-yl)ethyl, (1,3-dioxolan-4-yl)methyl, (tetrahydrofuran-3-yl)methyl, (2R)-(tetrahydrofuran-2-yl)methyl, (2S)-(tetrahydrofuran-2-yl)methyl, 2-(morpholin-4-yl)ethyl, 3-(morpholin-4-yl)propyl, 2-(2-oxo-1,3-oxazolidin-3-yl) ethyl, 2-(piperazin-1-yl)ethyl, 2-(4-methylpiperazin-1-yl) ethyl, 2-(1-methylpiperidin-4-yl)ethyl, (1-methylpiperidin-2-yl)methyl, 2-(piperidin-4-yl)ethyl, 2-(1-tert-butoxycarbonylpiperidin-4-yl)ethyl, (piperidin-2-yl)methyl, 2-(piperidin-1-yl)ethyl, 2-(pyrrolidin-1-yl)ethyl, 2-(1-methylpyrrolidin-2-yl)ethyl, 2-(2-oxopyrrolidin-1-yl)ethyl, 2-(2,5-dioxopyrrolidin-1-yl)ethyl, 2-(tetrahydro-2H-pyran-4-yl) ethyl, (tetrahydro-2H-pyran-4-yl)methyl, (tetrahydro-2H-pyran-4-yl)methyl, carboxy(tetrahydro-2H-pyran-4-yl) methyl, and 2-ethoxy-2-oxo-1-tetrahydro-2H-pyran-4-ylethyl.

The term "heterocyclealkylcarbonyl" as used herein, means a heterocyclealkyl, as defined herein, appended to the parent molecular moiety through a carbonyl group, as defined herein. Representative examples of heterocyclealkylcarbonyl include, but are not limited to, tetrahydro-2H-pyran-4-ylacetyl.

The term "heterocyclealkylsulfonyl" as used herein, means a heterocyclealkyl, as defined herein, appended to the parent molecular moiety through a sulfonyl group, as defined herein. Representative example of "heterocyclealkylsulfonyl" include, but are not limited to, (3-pyrrolidin-3-ylpropyl)sulfonyl and (3-piperidin-4-ylpropyl)sulfonyl.

The term "heterocyclealkylthio" as used herein, means a heterocyclealkyl group, as defined herein, appended to the parent molecular moiety through a sulfur atom. Representative examples of heterocyclealkylthio include, but are not limited to, (3-pyrrolidin-3-ylpropyl)thio and (3-piperidin-4-ylpropyl)thio.

The term "heterocycleoxy" as used herein, means a heterocycle group, as defined herein, appended to the parent molecular moiety through an oxygen atom. Representative examples of heterocycleoxy include, but are not limited to, piperidin-4-yloxy and pyrrolidin-3-yloxy.

The term "heterocycleoxyalkyl" as used herein, means a heterocycleoxy group, as defined herein, appended to the parent molecular moiety through an alkyl group, as defined herein. Representative examples of heterocycleoxyalkyl include, but are not limited to, 2-(piperidin-4-yloxy)ethyl and 3-(piperidin-4-yloxy)propyl.

The term "heterocyclesulfonyl" as used herein, means a heterocycle, as defined herein, appended to the parent molecular moiety through a sulfonyl group, as defined herein. Representative examples of "heterocyclesulfonyl" include, but are not limited to, piperidin-4-ylsulfonyl and pyrrolidin-3-ylsulfonyl.

The term "hydroxy" as used herein, means an —OH group.

The term "hydroxyalkoxy" as used herein, means at least one hydroxy group, as defined herein, is appended to the parent molecular moiety through an alkoxy group, as defined herein. Representative examples of hydroxyalkoxy include, but are not limited to, hydroxymethyl, 2-hydroxyethoxy, 3-hydroxypropoxy, 2,3-dihydroxypropoxy, (2S) 2,3-dihydroxypropoxy, (2R) 2,3-dihydroxypropoxy, 2,3-dihydroxypentyloxy, 4-hydroxybutoxy, 2-ethyl-4-hydroxyheptyloxy, 3,4-dihydroxybutoxy, and 5-hydroxypentyloxy.

The term "hydroxyalkyl" as used herein, means at least one hydroxy group, as defined herein, is appended to the parent molecular moiety through an alkyl group, as defined herein except for $R_1$ in Formula (I) wherein the hydroxy group is at least two carbons from the indole nitrogen. Representative examples of hydroxyalkyl include, but are not limited to, hydroxymethyl, 2-hydroxyethyl, 3-hydroxypropyl, 2,3-dihydroxypropyl, (2S) 2,3-dihydroxypropyl, (2R) 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

The term "mercapto" as used herein, means a —SH group.

The term "mercaptoalkyl" as used herein, means a mercapto group, as defined herein, appended to the parent molecular moiety through an alkyl group, as defined herein except for $R_1$ in Formula (I) wherein the mercapto group is at least two carbons from the indole nitrogen. Representative examples of mercaptoalkyl include, but are not limited to, 2-mercaptoethyl and 3-mercaptopropyl.

The term "methylenedioxy" as used herein, means a —OCH$_2$O— group wherein the oxygen atoms of the methylenedioxy are attached to the parent molecular moiety through two adjacent carbon atoms.

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The term "nitro" as used herein, means a —NO$_2$ group.

The term "NR$_A$R$_B$" as used herein, means two groups, $R_A$ and $R_B$, which are appended to the parent molecular moiety through a nitrogen atom. $R_A$ and $R_B$ are each independently selected from the group consisting of hydrogen, alkenyl, alkoxyalkyl, alkoxycarbonyl, alkoxycarbonylalkyl, alkyl, alkynyl, aryl, arylalkyl, cycloalkyl, cycloalkylalkyl, heteroaryl, heteroarylalkyl, heterocycle, heterocyclealkyl, and hydroxyalkyl.

The term "(NR$_A$R$_B$)carbonyl" as used herein, means a NR$_A$R$_B$ group, as defined herein, appended to the parent molecular moiety through a carbonyl group, as defined herein. Representative examples of (NR$_A$R$_B$)carbonyl include, but are not limited to, aminocarbonyl, (methylamino)carbonyl, (dimethylamino)carbonyl, and (ethylmethylamino)carbonyl.

The term "(NR$_A$R$_B$)carbonylalkenyl" as used herein, means a (NR$_A$R$_B$)carbonyl group, as defined herein, appended to the parent molecular moiety through an alkenyl group, as defined herein. Representative examples of "(NR$_A$R$_B$)carbonylalkenyl" includes, but is not limited to, 4-amino-4-oxobut-1-enyl and 4-dimethylamino-4-oxobut-1-enyl.

The term "(NR$_A$R$_B$)carbonylalkenylcarbonyl" as used herein, means a (NR$_A$R$_B$)carbonylalkenyl group, as defined herein, appended to the parent molecular moiety through a carbonyl group, as defined herein. Representative examples (NR$_A$R$_B$)carbonylalkenylcarbonyl includes, but is not limited to 6-(dimethylamino)-6-oxohex-3-enoyl and 6-(amino)-6-oxohex-3-enoyl.

The term "(NR$_A$R$_B$)carbonylalkyl" as used herein, means a (NR$_A$R$_B$)carbonyl group, as defined herein, appended to the parent molecular moiety through an alkyl group, as defined herein. Representative examples of (NR$_A$R$_B$)carbonylalkyl include, but are not limited to, 2-amino-2-oxoethyl, 3-amino-3-oxopropyl, and 4-amino-4-oxobutyl.

The term "(NR$_A$R$_B$)carbonylalkylcarbonyl" as used herein, means a (NR$_A$R$_B$)carbonylalkyl group, as defined herein, appended to the parent molecular moiety through a carbonyl group, as defined herein. Representative examples (NR$_A$R$_B$)carbonylalkylcarbonyl includes, but is not limited to, 6-(dimethylamino)-6-oxohexanoyl and 6-amino-6-oxohexanoyl.

The term "(NR$_A$R$_B$)sulfonyl" as used herein, means a NR$_A$R$_B$ group, as defined herein, appended to the parent molecular moiety through a sulfonyl group, as defined herein.

The term "(NR$_A$R$_B$)sulfonylalkyl" as used herein, means a (NR$_A$R$_B$)sulfonyl group, as defined herein, appended to the parent molecular moiety through an alkyl group, as defined herein except for $R_1$ in Formula (I) wherein the (NR$_A$R$_B$) sulfonyl group is at least two carbons from the indole nitrogen.

The term "NR$_C$R$_D$" as used herein, means two groups, $R_C$ and $R_D$, which are appended to the parent molecular moiety through a nitrogen atom. $R_C$ and $R_D$ are each independently selected from the group consisting of hydrogen, alkenyl, alkoxyalkyl, alkoxycarbonyl, alkoxycarbonylalkyl, alkyl, alkylcarbonyl, alkylsulfonyl, alkynyl, aryl, arylalkyl, arylsulfonyl, arylalkylsulfonyl, cycloalkyl, cycloalkylalkyl, cycloalkylsulfonyl, cycloalkylalkylsulfonyl, heteroaryl, heteroarylalkyl, heteroarylsulfonyl, heteroarylalkylsulfonyl, heterocycle, heterocyclealkyl, heterocyclesulfonyl, and heterocyclealkylsulfonyl.

The term "(NR$_C$R$_D$)alkyl" as used herein, means a NR$_C$R$_D$ group, as defined herein, appended to the parent molecular moiety through an alkyl group, as defined herein except for $R_1$ in Formula (I) wherein the NR$_C$R$_D$ group is at least two carbons from the indole nitrogen.

The term "NR$_E$R$_F$" as used herein, means two groups, $R_E$ and $R_F$, which are appended to the parent molecular moiety through a nitrogen atom. $R_E$ and $R_F$ are each independently selected from the group consisting of hydrogen, alkenyl, alkoxyalkyl, alkoxycarbonyl, alkoxycarbonylalkyl, alkyl, alkylcarbonyl, alkylsulfonyl, alkynyl, aryl, arylalkyl, arylsulfonyl, arylalkylsulfonyl, cycloalkyl, cycloalkylalkyl, cycloalkylsulfonyl, cycloalkylalkylsulfonyl, heteroaryl, heteroarylalkyl, heteroarylsulfonyl, heteroarylalkylsulfonyl, heterocycle, heterocyclealkyl, heterocyclesulfonyl, and heterocyclealkylsulfonyl.

The term "($NR_E R_F$)alkyl" as used herein, means a $NR_E R_F$ group, as defined herein, appended to the parent molecular moiety through an alkyl group, as defined herein.

The term "$NR_G R_H$" as used herein, means two groups, $R_G$ and $R_H$, which are appended to the parent molecular moiety through a nitrogen atom. $R_G$ and $R_H$ are each independently selected from the group consisting of hydrogen, alkenyl, alkoxyalkyl, alkoxycarbonylalkyl, alkyl, alkynyl, aryl, arylalkyl, cycloalkyl, cycloalkylalkyl, heteroaryl, heteroarylalkyl, heterocycle, heterocyclealkyl, and hydroxyalkyl.

The term "($NR_G R_H$)carbonyl" as used herein, means a $NR_G R_H$ group, as defined herein, appended to the parent molecular moiety through a carbonyl group, as defined herein.

The term "($NR_G R_H$)carbonylalkyl" as used herein, means a ($NR_G R_H$)carbonyl group, as defined herein, appended to the parent molecular moiety through an alkyl group, as defined herein.

The term "($NR_G R_H$)sulfonyl" as used herein, means a $NR_G R_H$ group, as defined herein, appended to the parent molecular moiety through a sulfonyl group, as defined herein.

The term "($NR_G R_H$)sulfonylalkyl" as used herein, means a ($NR_G R_H$)sulfonyl group, as defined herein, appended to the parent molecular moiety through an alkyl group, as defined herein.

The term "$NR_J R_K$" as used herein, means two groups, $R_J$ and $R_K$, which are appended to the parent molecular moiety through a nitrogen atom. $R_J$ and $R_K$ are each independently selected from the group consisting of hydrogen, alkenyl, alkoxyalkyl, alkoxycarbonyl, alkoxycarbonylalkyl, alkyl, alkylcarbonyl, alkylsulfonyl, alkynyl, aryl, arylalkyl, arylsulfonyl, arylalkylsulfonyl, cycloalkyl, cycloalkylalkyl, cycloalkylsulfonyl, cycloalkylalkylsulfonyl, heteroaryl, heteroarylalkyl, heteroarylsulfonyl, heteroarylalkylsulfonyl, heterocycle, heterocyclealkyl, heterocyclesulfonyl, and heterocyclealkylsulfonyl.

The term "($NR_J R_K$)alkoxy" as used herein, means a $NR_J R_K$ group, as defined herein, appended to the parent molecular moiety through an alkoxy group, as defined herein.

The term "($NR_J R_K$)alkyl" as used herein, means a $NR_J R_K$ group, as defined herein, appended to the parent molecular moiety through an alkyl group, as defined herein.

The term "$NR_M R_N$" as used herein, means two groups, $R_M$ and $R_N$, which are appended to the parent molecular moiety through a nitrogen atom. $R_M$ and $R_N$ are each independently selected from the group consisting of hydrogen, alkenyl, alkoxyalkyl, alkoxycarbonylalkyl, alkyl, alkynyl, aryl, arylalkyl, cycloalkyl, cycloalkylalkyl, heteroaryl, heteroarylalkyl, heterocycle, heterocyclealkyl, and hydroxyalkyl.

The term "($NR_M R_N$)carbonyl" as used herein, means a $NR_M R_N$ group, as defined herein, appended to the parent molecular moiety through a carbonyl group, as defined herein.

The term "($NR_M R_N$)carbonylalkyl" as used herein, means a ($NR_M R_N$)carbonyl group, as defined herein, appended to the parent molecular moiety through an alkyl group, as defined herein.

The term "($NR_M R_N$)sulfonyl" as used herein, means a $NR_M R_N$ group, as defined herein, appended to the parent molecular moiety through a sulfonyl group, as defined herein.

The term "($NR_M R_N$)sulfonylalkyl" as used herein, means a ($NR_M R_N$)sulfonyl group, as defined herein, appended to the parent molecular moiety through an alkyl group, as defined herein.

The term "$NZ_1 Z_2$" as used herein, means two groups, $Z_1$ and $Z_2$, which are appended to the parent molecular moiety through a nitrogen atom. $Z_1$ and $Z_2$ are each independently selected from the group consisting of hydrogen, alkenyl, alkyl, alkylcarbonyl, alkylsulfonyl, alkynyl, aryl, arylalkyl, formyl, heteroaryl, heteroarylalkyl, heterocycle, and heterocyclealkyl. Representative examples of $NZ_1 Z_2$ include, but are not limited to, amino, methylamino, acetylamino, and acetylmethylamino.

The term "($NZ_1 Z_2$)alkyl" as used herein, means a $NZ_1 Z_2$ group, as defined herein, appended to the parent molecular moiety through an alkyl group, as defined herein. Representative examples of ($NZ_1 Z_2$)alkyl include, but are not limited to, aminocarbonyl, (methylamino)carbonyl, (dimethylamino)carbonyl, and (ethylmethylamino)carbonyl.

The term "($NZ_1 Z_2$)carbonyl" as used herein, means a $NZ_1 Z_2$ group, as defined herein, appended to the parent molecular moiety through a carbonyl group, as defined herein. Representative examples of ($NZ_1 Z_2$)carbonyl include, but are not limited to, aminocarbonyl, (methylamino)carbonyl, (dimethylamino)carbonyl, and (ethylmethylamino)carbonyl.

The term "($NZ_1 Z_2$)sulfonyl" as used herein, means a $NZ_1 Z_2$ group, as defined herein, appended to the parent molecular moiety through a sulfonyl group, as defined herein. Representative examples of ($NZ_1 Z_2$)sulfonyl include, but are not limited to, aminosulfonyl, (methylamino)sulfonyl, (dimethylamino)sulfonyl, and (ethylmethylamino)sulfonyl.

The term "oxo" as used herein, means a =O moiety.

The term "sulfinyl" as used herein, means a —S(O)— group.

The term "sulfonyl" as used herein, means a —S(O)$_2$— group.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The present invention contemplates various stereoisomers and mixtures thereof and are specifically included within the scope of this invention. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Compounds of the present invention were named by ACD/ChemSketch version 5.06 (developed by Advanced Chemistry Development, Inc., Toronto, ON, Canada) or were given names which appeared to be consistent with ACD nomenclature.

Abbreviations

Abbreviations which have been used in the descriptions of the Schemes and the Examples that follow are: DMF for N,N-dimethylformamide; DMSO for dimethylsulfoxide; Et for ethyl; Me for methyl; Ms for $CH_3S(O)_2O—$; Ph for phenyl; THF for tetrahydrofuran; Ts for p-$CH_3PhS(O)_2O—$; and Tf for $CF_3S(O)_2O—$;

Preparation of Compounds of the Present Invention

The compounds and processes of the present invention will be better understood in connection with the following synthetic Schemes and Examples which illustrate a means by which the compounds of the present invention can be prepared.

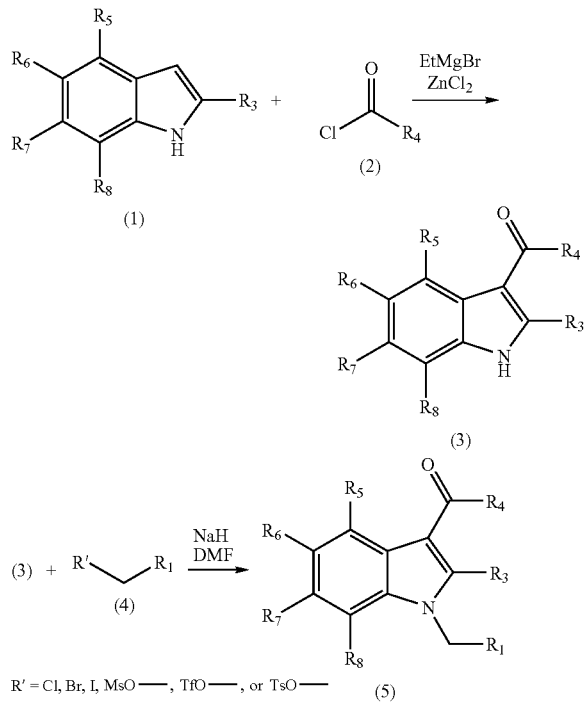

Indoles of formula (5), wherein $R_1$, $R_3$, $R_4$, $R_5$, $R_6$, $R_7$, and $R_8$ are as defined in Formula (I), can be prepared using the method described in Scheme 1 or by methods known to those of skill in the art. Indoles of formula (1), purchased or prepared using methodology known to those of skill in the art, can be treated with acid chlorides of formula (2), a grignard reagent such as ethylgrignard (EtMgBr), and $ZnCl_2$ in a solvent such as methylene chloride to provide indoles of formula (3). Indoles of formula (3) can be treated with a compound of formula (4) and a base such as sodium hydride in a solvent such as N,N-dimethylformamide to provide indoles of formula (5).

It is to be understood that substituents at the $R_1$, $R_5$, $R_6$, $R_7$, or $R_8$ positions of formula (1) (3), or (5), can be further subjected to methods known to those of skill in the art to provide compounds of the present invention.

EXAMPLE 1

{1-[(1-methylpiperidin-2-yl)methyl]-1H-indol-3-yl}(2,2,3,3-tetramethylcyclopropyl)methanone

EXAMPLE 1A 2,2,3,3-tetramethylcyclopropanecarbonyl chloride

To a flask containing 2,2,3,3-tetramethylcyclopropane carboxylic acid (Aldrich, 13.5 g, 95 mmol) was added 30 mL of thionyl chloride (410 mmol, excess). This solution was warmed to reflux and stirred for 2 h. The mixture was then cooled to ambient temperature and concentrated under reduced pressure. The residue was azeotroped three times with 10 mL of benzene to remove any remaining thionyl chloride, and used without further purification.

EXAMPLE 1B 1H-indol-3-yl(2,2,3,3-tetramethylcyclopropyl)methanone

To a solution of indole (Aldrich, 11 g, 95 mmol) in 30 mL dichloromethane at ambient temperature was added 105 mL of a 1 M solution of ethyl magnesium bromide in tetrahydrofuran (THF) (105 mmol) dropwise via syringe pump. After the addition was complete, the solution was stirred for 15 min at which time $ZnCl_2$ (14 g, 105 mmol) was added. The mixture stirred for an additional 30 min then the product of Example 1A (95 mmol) in 50 mL dichloromethane was added via cannula. The mixture was stirred for 6 h then was quenched with 50 mL saturated aqueous $NH_4Cl$ and diluted with 50 mL dichloromethane. The layers were separated and the aqueous layer was extracted with 3×30 mL dichloromethane. The combined organics were washed with 1×20 mL $H_2O$ then were dried over anhydrous $Na_2SO_4$, filtered and concentrated under reduced pressure. The crude material was purified via column chromatography ($SiO_2$, 50% ethyl acetate:hexanes) to give 9.7 g of the major regioisomer 1H-indol-3-yl(2,2,3,3-tetramethylcyclopropyl)methanone (40 mmol, 42% yield) and 6.1 g of the minor regioisomer of 1-[(2,2,3,3-tetramethylcyclopropyl)carbonyl]-1H-indole (25 mmol, 27% yield). MS (major and minor regioisomers) (DCI/$NH_3$) m/z 242 $(M+H)^+$.

EXAMPLE 1C (1-methylpiperidin-2-yl)methyl methanesulfonate

To a solution of 1-methyl-2-piperidine-methanol (Aldrich, 0.27 mL, 2.1 mmol) in 10 mL tetrahydrofuran (THF) at 0° C. was added triethylamine (0.87 mL, 6.22 mmol) followed by methanesulfonyl chloride (0.24 mL, 3.1 mmol). The mixture was stirred at 0° C. for 10 min then the ice-bath was removed and the reaction mixture was stirred at 23° C. for an additional 1.5 h. The reaction mixture was filtered though Celite with THF and concentrated under reduced pressure. This crude material was used directly in the next reaction.

EXAMPLE 1D

{1-[(1-methylpiperidin-2-yl)methyl]-1H-indol-3-yl}(2,2,3,3-tetramethylcyclopropyl)methanone To a solution of the major product of Example 1B (0.25 g, 1.0 mmol) in 5 mL DMF at 0° C. was added NaH (60% dispersal in mineral oil, 0.10 g, 2.6 mmol). This mixture was stirred at 0° C. for 10 min then was warmed to ambient temperature and allowed to stir for 30 min. The solution was again cooled to 0° C. and the product of Example 1C (2.1 mmol) in 5 mL DMF was added via cannula. The ice-bath was removed after the addition was complete and the reaction mixture was warmed to 50° C. at which temperature it was stirred for 2 h. The mixture was cooled to ambient temperature, diluted with 10 mL ethyl acetate and quenched with 10 mL saturated, aqueous $NH_4Cl$ and 5 mL $H_2O$. The layers were separated and the aqueous layer was extracted with 3×5 mL ethyl acetate and the combined organics were dried over anhydrous $Na_2SO_4$, filtered, concentrated and purified via column chromatography ($SiO_2$, 1% $NH_4OH$:9% $CH_3OH$:

EXAMPLE 1E

{1-[(1-methylpiperidin-2-ylmethyl]-1H-indol-3-yl}(2,2,3,3-tetramethylcyclopropyl)methanone p-toluenesulfonic acid To the product of Example 1D (0.18 g, 0.51 mmol) in 5 mL of 10% EtOH in ethyl acetate, was added p-toluenesulfonic acid monohydrate (97 mg, 0.51 mmol). The resulting precipitate was isolated via filtration resulting in 0.21 g of the title compound (0.40 mmol, 78% yield). $^1$H NMR (MeOH-$d_4$, 300 MHz) δ 1.33 (s, 12H), 1.57 (m, 2H), 1.79 (m, 2H), 1.93 (m, 1H), 2.17 (s, 1H), 2.36 (s, 3H), 3.08 (s, 3H), 3.18 (m, 1H), 3.60 and 3.75 (m, rotamers 1H), 4.37 and 4.95 (m, rotamers 1H), 7.23 (br d, J=7.8 Hz, 2H), 7.26 (m, 1H), 7.34 (ddd, J=7.1, 7.1, 1.4 Hz, 1H), 7.55 (m, 1H), 7.71 (br d, J=8.1 Hz, 2H) 8.12 (br s, 1H), 8.30 (d, J=7.8 Hz, 1H); MS (DCI/NH$_3$) m/z 353 (M+H)$^+$; Anal. Calculated for $C_{23}H_{32}N_2O.C_7H_8O_3S.0.1H_2O$: C, 68.44; H, 7.70; N, 5.32. Found: C, 68.19; H, 7.61; N, 5.13.

EXAMPLE 2

[1-(2-morpholin-4-ylethyl)-1H-indol-3-yl](2,2,3,3-tetramethylcyclopropyl)methanone p-toluenesulfonic acid

EXAMPLE 2A 2-morpholin-4-ylethyl methanesulfonate

A solution of 4-(2-hydroxylethyl)-morpholine (Aldrich, 5.1 mL, 42 mmol), triethylamine (17 mL, 124 mmol), and methanesulfonyl chloride (4.8 mL, 62 mmol) in 100 mL THF were processed as described in Example 1C to give the crude material which was used directly in the next reaction.

EXAMPLE 2B

[1-(2-morpholin-4-ylethyl)-1H-indol-3-yl](2,2,3,3-tetramethylcyclopropyl)methanone The major product of Example 1B (5.0 g, 21 mmol), the product of Example 2A (42 mmol) and NaH (60% dispersal in mineral oil, 4.2 g, 104 mmol) in 40 mL dimethylformamide were processed as in Example 1D. Purification via column chromatography (SiO$_2$, 10% CH$_3$OH:90% EtOAc) gave 6.6 g of the title compound (18.6 mmol, 90% yield). MS (DCI/NH$_3$) m/z 355 (M+H)$^+$.

EXAMPLE 2C

[1-(2-morpholin-4-ylethyl)-1H-indol-3-yl](2,2,3,3-tetramethylcyclopropyl)methanone p-toluenesulfonic acid p-Toluenesulfonic acid monohydrate (3.5 g, 19 mmol) and of the product of Example 2B (6.6 g, 19 mmol) were processed as in Example 1E. The crude material was concentrated under reduced pressure and dried under reduced pressure to give 9.4 g of the title compound (18 mmol, 96% yield). $^1$H NMR (MeOH-$d_4$, 300 MHz) δ 1.33 (s, 6H), 1.34 (s, 6H), 2.15 (s, 1H), 2.36 (s, 3H), 3.40 (m, 4H), 3.68 (dd, J=7.1, 7.1 Hz, 2H), 3.90 (m, 4H), 4.73 (dd, J=7.1, 7.1 Hz, 2H), 7.23 (br d, J=7.8 Hz, 2H), 7.26 (ddd, J=8.1, 8.1, 1.4 Hz, 1H), 7.33 (ddd, J=7.1, 7.1, 1.0 Hz, 1H), 7.56 (br d, J=8.1 Hz, 1H), 7.72 (br d, J=8.5 Hz, 2H), 8.15 (s, 1H), 8.29 (dt, J=7.8, 1.0 Hz, 1H); MS (DCI/NH$_3$) m/z 355 (M+H)$^+$; Anal. Calculated for $C_{22}H_{30}N_2O_2.C_7H_8O_3S$: C, 66.13; H, 7.27; N, 5.32. Found: C, 66.24; H, 7.23; N, 5.19.

EXAMPLE 3

[1-(2-pyridin-2-ylethyl)-1H-indol-3-yl](2,2,3,3-tetramethylcyclopropyl)methanone p-toluenesulfonic acid

EXAMPLE 3A 2-pyridin-2-ylethyl methanesulfonate

A solution of 2-pyridin-2-yl-ethanol (Aldrich, 0.11 mL, 0.99 mmol), triethylamine (0.42 mL, 3.0 mmol), and methanesulfonyl chloride (0.12 mL, 1.5 mmol) in 5 mL THF were processed as described in Example 1C to give the crude title compound which was used directly in the next reaction.

EXAMPLE 3B

[1-(2-pyridin-2-ylethyl)-1H-indol-3-yl](2,2,3,3-tetramethylcyclopropyl)methanone The major product of Example 1B (0.12 g, 0.50 mmol), the product of Example 3A (0.99 mmol), and NaH (60% dispersal in mineral oil, 0.1 g, 2.5 mmol) in 10 mL dimethylformamide were processed as in Example 1D. Purification via column chromatography (SiO$_2$, 50% hexanes:50% EtOAc) provided 78 mg of the title compound (0.23 mmol, 45% yield). MS (DCI/NH$_3$) m/z 347 (M+H)$^+$.

EXAMPLE 3C

[1-(2-pyridin-2-ylethyl)-1H-indol-3-yl](2,2,3,3-tetramethylcyclopropyl)methanone p-toluenesulfonic acid p-Toluenesulfonic acid monohydrate (44 mg, 0.23 mmol) and of the product of Example 3B (78 mg, 0.23 mmol) were processed as in Example 1E. Recrystallization with CH$_3$OH and EtOAc gave 51 mg of the title compound (0.10 mmol, 43% yield). $^1$H NMR (MeOH-$d_4$, 300 MHz) δ 1.29 (s, 6H), 1.30 (s, 6H), 2.01 (s, 1H), 2.36 (s, 3H), 3.58 (t, J=6.8 Hz, 2H), 4.75 (t, J=6.5 Hz, 2H), 7.22 (m, 4H), 7.37 (m, 1H), 7.71 (br d, J=8.5 Hz, 2H), 7.76 (br d, J=7.8 Hz, 1H), 7.84 (m, 1H), 7.88 (s, 1H), 8.24 (m, 1H), 8.39 (ddd, J=7.8, 7.8, 1.7 Hz, 1H), 8.65 (br d, 5.1 Hz, 1H); MS (DCI/NH$_3$) m/z 347 (M+H)$^+$; Anal. Calculated for $C_{23}H_{26}N_2O.C_7H_8O_3S$: C, 69.47; H, 6.61; N, 5.40. Found: C, 69.13; H, 6.60; N, 5.28.

EXAMPLE 4

{-[(1-methyl-1H-imidazol-2-yl)methyl]-1H-indol-3-yl}(2,2,3,3-tetramethylcyclopropyl)methanone p-toluenesulfonic acid

EXAMPLE 4A (1-methyl-1H-imidazol-2-yl methyl methanesulfonate

A solution of (1-methyl-1H-imidazol-2-yl)-methanol (Bionet Research, 66 mg, 0.59 mmol), triethylamine (0.25 mL, 0.89 mmol), and methanesulfonyl chloride (69 µL, 0.89 mmol) in 5 mL THF were processed as described in Example 1C to give the crude material which was used directly in the next reaction.

EXAMPLE 4B

{1-[(1-methyl-1H-imidazol-2-yl)methyl]-1H-indol-3-yl}(2,2,3,3-tetramethylcyclopropyl)methanone The major product of Example 1B (0.10 g, 0.42 mmol), the product of Example 4A (0.59 mmol) and NaH (60% dispersal in mineral oil, 60 mg, 1.5 mmol) in 5 mL dimethylformamide were processed as in Example 1D. Purification via column chromatography ($SiO_2$, 100% EtOAc) afforded 25 mg of the title compound (0.075 mmol, 18% yield). MS ($DCI/NH_3$) m/z 336 $(M+H)^+$.

EXAMPLE 4C

{1-[(1-methyl-1H-imidazol-2-yl)methyl]-1H-indol-3-yl}(2,2,3,3-tetramethylcyclopropyl)methanone p-toluenesulfonic acid p-Toluenesulfonic acid monohydrate (14 mg, 0.075 mmol) and the product of Example 4B (25 mg, 0.075 mmol) were processed as in Example 1E. Recrystallization with $CH_3OH$ gave 16 mg of the title compound (0.028 mmol, 37% yield). $^1$H NMR ($CDCl_3$, 300 MHz) δ 1.24 (s, 6H), 1.31 (s, 6H), 1.99 (s, 1H), 2.35 (s, 3H), 3.58 (s, 3H), 6.12 (br s, 2H), 6.96 (br s, 1H), 7.18 (br d, J=8.1 Hz, 2H), 7.24 (m, 2H), 7.34 (m, 2H), 7.79 (br d, J=8.1 Hz, 2H), 8.09 (br s, 1H), 8.41 (dd, J=7.5, 1.4 Hz, 1H); MS ($DCI/NH_3$) m/z 336 $(M+H)^+$; Anal. Calculated for $C_{21}H_{25}N_3O \cdot C_7H_8O_3S$: C, 62.62; H, 6.53; N, 7.28. Found: C, 62.37; H, 6.68; N, 7.26.

EXAMPLE 5 tert-butyl 4-(2-{3-[(2,2,3,3-tetramethylcyclopropyl)carbonyl]-1H-indol-1-yl}ethyl)piperidine-1-carboxylate

EXAMPLE 5A tert-butyl 4-{[(methylsulfonyl)oxy]ethyl}piperidine-1-carboxylate A solution of 4-(2-hydroxyethyl)-piperidine-1-carboxylic acid tert-butyl ester (Aldrich, 0.50 g, 2.2 mmol), triethylamine (0.91 mL, 6.5 mmol), and methanesulfonyl chloride (0.25 mL, 3.3 mmol) in 10 mL THF were processed as described in Example 1C to give the crude title compound which was used directly in the next reaction.

EXAMPLE 5B tert-butyl 4-(2-{3-[(2,2,3,3-tetramethylcyclopropyl)carbonyl]-1H-indol-1-yl}ethyl)piperidine-1-carboxylate The major product of Example 1B (0.26 g, 1.1 mmol), the product of Example 5A (2.2 mmol), and NaH (60% dispersal in mineral oil, 0.22 g, 5.5 mmol) in 10 mL dimethylformamide were processed as in Example 1D. Purification via column chromatography ($SiO_2$, 1% $NH_4OH$, 9% $CH_3OH$: 90% $CH_2Cl_2$) provided 0.50 g of the title compound (1.1 mmol, 98% yield). $^1$H NMR ($CDCl_3$, 300 MHz) δ 1.24 (m, 3H), 1.31 (s, 6H), 1.35 (s, 6H), 1.46 (s, 9H), 1.72 (m, 2H), 1.86 (dd, J=14.9, 6.8 Hz, 2H), 1.93 (s, 1H), 2.67 (dd, J=14.9, 13.6 Hz, 2H), 4.11 (br d, J=12.9 Hz, 2H), 4.20 (dd, J=7.5, 7.5 Hz, 2H), 7.28 (m, 3H), 7.64 (s, 1H), 8.41 (ddd, J=7.5, 3.1, 2.0 Hz, 1H); MS ($DCI/NH_3$) m/z 452 $(M+H)^+$; Anal. Calculated for $C_{28}H_{40}N_2O_3 \cdot 0.5CH_3OH$: C, 73.04; H, 9.03; N, 5.98. Found: C, 73.00; H, 9.37; N, 6.06.

EXAMPLE 6

[1-(2-Piperidin-4-yl-ethyl)-1H-indol-3-yl]-(2,2,3,3-tetramethyl-cyclopropyl)-methanone p-toluenesulfonic acid

EXAMPLE 6A

[1-(2-piperidin-4-ylethyl)-1H-indol-3-yl](2,2,3,3-tetramethylcyclopropyl)methanone To the product of Example 5B (0.42 g, 0.93 mmol) in 5 mL dichloromethane at 0° C. was added trifluoroacetic acid (TFA, 3 mL, excess). The ice-bath was removed and the mixture stirred at 23° C. for 2 h then the mixture was concentrated and purified via flash column chromatography ($SiO_2$, 1% $NH_4OH$:9% $CH_3OH$:90% dichloromethane) to give 0.30 g of the title compound (0.85 mmol, 92% yield). MS ($DCI/NH_3$) m/z 352 $(M+H)^+$.

EXAMPLE 6B

[1-(2-piperidin-4-ylethyl)-1H-indol-3-yl](2,2,3,3-tetramethylcyclopropyl)methanone p-toluenesulfonic acid p-Toluenesulfonic acid monohydrate (81 mg, 43 mmol) and the product of Example 6A (0.15 g, 0.43 mmol) were processed as in Example 1E. Recrystallization with $CH_3OH$ and EtOAc gave 0.16 g of the title compound (0.28 mmol, 66% yield). $^1$H NMR (MeOH-$d_4$, 300 MHz) δ 1.33 (s, 12H), 1.46 (m, 2H), 1.64 (m, 1H), 1.90 (dd, J=6.8, 6.8 Hz, 2H), 1.99 (br d, J=13.9 Hz, 2H), 2.15 (s, 1H), 2.35 (s, 3H), 2.93 (ddd, J=12.9, 12.9, 2.7 Hz, 2H), 3.36 (m, 2H), 4.33 (dd, J=7.1, 7.1 Hz, 2H), 7.20 (m, 1H), 7.23 (br d, J=8.5 Hz, 2H), 7.26 (ddd, J=7.1, 7.1, 1.4 Hz, 1H), 7.48 (dt, J=7.8, 1.0 Hz, 1H), 7.70 (br d, J=8.5 Hz, 2H), 8.08(s, 1H), 8.25 (ddd, J=7.8, 1.4, 1.0 Hz, 1H); MS ($DCI/NH_3$) m/z 353 $(M+H)^+$; Anal. Calculated for $C_{23}H_{32}N_2O \cdot 1.25C_7H_8O_3S$: C, 66.64; H, 7.49; N, 4.90. Found: C, 66.53; H, 7.86; N, 4.77.

EXAMPLE 7

{1-[2-(1-methylpiperidin-4-yl)ethyl]-1H-indol-3-yl}(2,2,3,3-tetramethylcyclopropyl)methanone p-toluenesulfonic acid

EXAMPLE 7A

{1-[2-(1-methylpiperidin-4-yl)ethyl]-1H-indol-3-yl}(2,2,3,3-tetramethylcyclopropyl)methanone To the product of Example 6A (0.15 g, 0.43 mmol) in 5 mL of 36% aqueous formaldehyde was added $NaBH(OAc)_3$ (0.17 g, 0.80 mmol). This mixture stirred at 23° C. for 16 h then it was diluted with 5 mL dichloromethane and was quenched with 3 mL aqueous saturated $NH_4Cl$ and 3 mL $H_2O$. The layers were separated and the aqueous layer was extracted with 3×5 mL dichloromethane. The combined organics were dried over Na$_2$SO$_4$, filtered, concentrated and purified via column chromatography (SiO$_2$, 1% NH$_4$OH:9% CH$_3$OH: 90% dichloromethane) to give 0.15 g of the title compounds (0.41 mol, 95% yield).

MS (DCI/NH$_3$) m/z 367 (M+H)$^+$.

EXAMPLE 7B

{1-[2-(1-methylpiperidin-4-yl)ethyl]-1H-indol-3-yl} (2,2,3,3-tetramethylcyclopropyl)methanone p-toluenesulfonic acid p-Toluenesulfonic acid monohydrate (78 mg, 0.41 mmol) and the product of Example 7A (0.15 g, 0.41 mmol) were processed as in Example 1E. Recrystallization with CH$_3$OH and EtOAc provided 25 mg of the title compound (0.050 mmol, 12% yield). $^1$H NMR (MeOH-d$_4$, 300 MHz) δ 1.33 (s, 12H), 1.54 (m, 3H), 1.91 (br q, J=7.1 Hz, 2H), 2.03 (m, 2H), 2.15 (s, 1H), 2.81 (s, 3H), 2.93 (m, 2H), 3.26 (m, 1H), 3.45 (m, 2H), 4.34 (t, J=7.1 Hz, 2H), 6.70 (s, 2H), 7.21 (dd, J=7.8, 1.0 Hz, 1H), 7.27 (dd, J=7.1, 1.4 Hz, 1H), 7.49 (br d, J=8.1 Hz, 1H), 8.09 (s, 1H), 8.25 (br d, J=7.1 Hz, 1H); MS (DCI/NH$_3$) m/z 367 (M+H)$^+$; Anal. Calculated for C$_{24}$H$_{34}$N$_2$O.C$_4$H$_4$O$_4$.0.5CH$_4$O: C, 68.65; H, 8.09; N, 5.62. Found: C, 68.68; H, 8.49; N, 5.82.

EXAMPLE 8

[1-(2-tetrahydro-2H-pyran-4-ylethyl)-1H-indol-3-yl] (2,2,3,3-tetramethylcyclopropyl)methanone

EXAMPLE 8A 2-tetrahydro-2H-pyran-4-ylethanol

To 15 mL of tetrahydrofuran (THF) at 0° C. was added LiAlH$_4$ (0.28 g, 7.3 mmol). This mixture was stirred for 10 min then the ethyl tetrahydropyran-4-yl-acetate (Combi-Blocks Inc., 0.50 g, 2.9 mmol) was added. The reaction was stirred for 5 min at 0° C. then was allowed to warm to ambient temperature and was stirred for 90 min. The reaction was quenched with excess NaHSO$_4$.10H$_2$O and was stirred for 60 min. The mixture was filtered through Celite. The filtrate was concentrated to give the title compound which was carried on without further purification. MS (DCI/NH$_3$) m/z 131 (M+H)$^+$.

EXAMPLE 8B 2-tetrahydro-2H-pyran-4-ylethyl methanesulfonate

The product of Example 8A (2.9 mmol), triethylamine (1.2 mL, 8.7 mmol) and methanesulfonyl chloride (0.34 mL, 4.4 mmol) in 10 mL tetrahydrofuran (THF) were reacted and the product isolated as in Example 1C to give the title compound that was used directly in the next reaction.

EXAMPLE 8C

[1-(2-tetrahydro-2H-pyran-4-ylethyl)-1H-indol-3-yl] (2,2,3,3-tetramethylcyclopropyl)methanone The major product of Example 1B (0.35 g, 1.5 mmol), the product of Example 8B (2.9 mmol) and NaH (60% dispersal in mineral oil, 0.29 g, 7.3 mmol) in 15 mL dimethylformamide (DMF) were processed as in Example 1D. Purification via column chromatography (SiO$_2$, 50% hexanes:50% EtOAc) gave 0.36 g of the title compound in 70% three-step yield (1.0 mmol). $^1$H NMR (CDCl$_3$, 300 MHz) δ 1.31 (s, 6H), 1.35 (s, 6H), 1.42 (dt, J=12.4, 4.7 Hz, 2H), 1.60 (m, 2H), 1.69 (m, 1H), 1.86 (q, J=6.4 Hz, 2H), 1.94 (s, 1H), 3.37 (dt, J=11.5, 1.7 Hz, 2H), 3.98 (dd, J=11.5, 4.8 Hz, 2H), 4.20 (dd, J=7.5, 7.5 Hz, 2H), 7.29 (m, 3H), 7.65 (s, 1H), 8.40 (m, 1H); MS (DCI/NH$_3$) m/z 354 (M+H)$^+$; Anal. Calculated for C$_{23}$H$_{31}$NO$_2$: C, 78.15; H, 8.84; N, 3.96. Found: C, 77.88; H, 8.89; N, 3.91.

EXAMPLE 9

[1-(2-pyrrolidin-1-ylethyl)-1H-indol-3-yl](2,2,3,3-tetramethylcyclopropyl)methanone p-toluenesulfonic acid

EXAMPLE 9A 2-pyrrolidin-1-ylethyl methanesulfonate

The 1-(2-hydroxyethyl)-pyrrolidine (Aldrich, 0.14 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 9B

[1-(2-pyrrolidin-1-ylethyl)-1H-indol-3-yl](2,2,3,3-tetramethylcyclopropyl)methanone The major product of Example 1B (0.15 g, 0.62 mmol), the product of Example 9A (1.2 mmol) and NaH (60% dispersion in mineral oil, 62 mg, 1.6 mmol) in 8 mL DMF were processed as in Example 1D. Purification via column chromatography (SiO$_2$, 2% CH$_3$OH:98% EtOAc) afforded 45 mg of the title compound (0.13 mmol, 21% yield. MS (DCI/NH$_3$) m/z 338 (M+H)$^+$.

EXAMPLE 9C

[1-(2-pyrrolidin-1-ylethyl)-1H-indol-3-yl](2,2,3,3-tetramethylcyclopropyl)methanone p-toluenesulfonic acid p-Toluenesulfonic acid monohydrate (24 mg, 0.12 mmol) and the product of Example 9B (41 mg, 0.12 mmol) were processed as in Example 1E. Recrystallization with CH$_3$OH, EtOAc and Et$_2$O provided 44 mg of the title compound (0.086 mmol, 14% yield). $^1$H NMR (MeOH-d$_4$, 300 MHz) δ 1.33 (s, 6H), 1.34 (s, 6H), 2.06 (m, 4H), 2.17 (s, 1H), 2.36 (s, 3H), 3.16 (m, 2H), 3.59 (m, 2H), 3.75 (t, J=6.8 Hz, 2H), 4.67 (t, J=6.8 Hz, 2H), 7.23 (br d, J=8.1 Hz, 2H), 7.30 (m, 2H), 7.56 (m, 1H), 7.71 (br d, J=8.1 Hz, 2H) 8.16 (s, 1H), 8.30 (m, 1H); MS (DCI/NH$_3$) m/z 339 (M+H)$^+$; Anal. Calculated for C$_{22}$H$_{30}$N$_2$O.C$_7$H$_8$O$_3$S: C, 68.20; H, 7.50; N, 5.49. Found: C, 68.14; H, 7.51; N, 5.35.

EXAMPLE 10

(2,2,3,3-tetramethylcyclopropyl)[1-(2-thien-2-yl-ethyl)-1H-indol-3-yl]methanone

EXAMPLE 10A 2-thien-2-ylethyl methanesulfonate

The 2-(2-thienyl)ethanol (Aldrich, 0.16 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 10B (2,2,3,3-tetramethylcyclopropyl)[1-(2-thien-2-yl-ethyl)-1H-indol-3-yl]methanone The major product of Example 1B (0.15 g, 0.62 mmol), the product of Example 10A (1.2 mmol) and NaH (60% dispersion in mineral oil, 0.12 g, 3.1 mmol) in 8 mL DMF were processed as in Example 1D. Purification via column chromatography ($SiO_2$, 10% EtOAc:90% hexanes) afforded 0.12 g of the title compound (0.33 mmol, 53% yield). $^1$H NMR ($CDCl_3$, 300 MHz) δ 1.26 (s, 6H), 1.31 (s, 6H), 1.81 (s, 1H), 3.37 (t, J=6.8 Hz, 2H), 4.42 (t, J=7.1 Hz, 2H), 6.66 (m, 1H), 6.91 (dd, J=5.1, 3.4 Hz, 1H), 7.19 (dd, J=5.1, 1.4 Hz, 1H), 7.29 (m, 2H), 7.33 (m, 1H), 7.43 (s, 1H), 8.42 (m, 1H); MS ($DCI/NH_3$) m/z 352 $(M+H)^+$; Anal. Calculated for $C_{22}H_{25}NOS$: C, 75.17; H, 7.17; N, 3.98. Found: C, 74.99; H, 7.34; N, 3.91.

EXAMPLE 11

[1-(2-methoxyethyl)-1H-indol-3-yl](2,2,3,3-tetramethylcyclopropyl)methanone

EXAMPLE 11A 2-methoxyethyl methanesulfonate

The 2-methoxyethanol (Aldrich, 94 mg, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 11B

[1-(2-methoxyethyl)-1H-indol-3-yl](2,2,3,3-tetramethylcyclopropyl)methanone

The major product of Example 1B (0.15 g, 0.62 mmol), the product of Example 11A (1.2 mmol) and NaH (60% dispersion in mineral oil, 0.12 g, 3.1 mmol) in 8 mL DMF were processed as in Example 1D. Purification via column chromatography ($SiO_2$, 90% hexanes:10% EtOAc) gave 0.122 g of the title compound (0.41 mmol, 66% yield). $^1$H NMR (MeOH-$d_4$, 300 MHz) δ 1.32 (s, 6H), 1.33 (s, 6H), 2.11 (s, 1H), 3.31 (s, 3H), 3.76 (dd, J=5.4, 5.4 Hz, 2H), 4.41 (dd, J=5.1, 5.1 Hz, 2H), 7.22 (m, 2H), 7.48 (m, 1H), 8.03 (s, 1H), 8.24 (m, 1H); MS ($DCI/NH_3$) m/z 300 $(M+H)^+$; Anal. Calculated for $C_{19}H_{25}NO_2$: C, 76.22; H, 8.42; N, 4.68. Found: C, 76.18; H, 8.73; N, 4.35.

EXAMPLE 12

1-(2-{3-[(2,2,3,3-tetramethylcyclopropyl)carbonyl]-1H-indol-1-yl}ethyl)pyrrolidin-2-one

EXAMPLE 12A 2-(2-oxopyrrolidin-1-yl)ethyl methanesulfonate

The 1-(2-hydroxyethyl)-2-pyrrolidinone (Aldrich, 0.16 g, 1.2 mmol), triethylamine (0.56 mL, 4.1 mmol), and methane-sulfonyl chloride (0.15 mL, 1.9 mmol) in 10 mL THF were processed as described in Example 1C to give the title compound that was used directly in the next reaction.

EXAMPLE 12B 1-(2-{3-[(2,2,3,3-tetramethylcyclopropyl)carbonyl]-1H-indol-1-yl}ethyl)pyrrolidin-2-one The major product of Example 1B (0.15 g, 0.62 mmol), the product of Example 12A (1.2 mmol) and NaH (60% dispersion in mineral oil, 0.12 g, 3.1 mmol) in 8 mL DMF were processed as in Example 1D. Purification via column chromatography ($SiO_2$, 90% hexanes:10% EtOAc) provided 0.12 g of the title compound (0.33 mmol, 53% yield). $^1$H NMR (MeOH-$d_4$, 300 MHz) δ 1.33 (s, 12H), 1.79 (m, 2H), 2.15 (s, 1H), 2.23 (dd, J=7.8, 7.8 Hz, 2H), 3.04 (dd, J=6.8, 6.8 Hz, 2H), 3.70 (dd, J=6.1, 6.1 Hz, 2H), 4.45 (dd, J=5.8, 5.8 Hz, 2H), 7.21 (td, J=8.1, 1.4 Hz, 1H), 7.28 (td, J=7.1, 1.4 Hz, 1H), 7.50 (td, J=8.1, 1.0 Hz, 1H), 8.07 (s, 1H), 8.26 (ddd, J=7.8, 1.4, 0.7 Hz, 1H); MS ($DCI/NH_3$) m/z 353 $(M+H)^+$; Anal. calculated for $C_{22}H_{28}N_2O_2$: C, 74.97; H, 8.01; N, 7.95. Found: C, 74.62; H, 8.12; N, 7.88.

EXAMPLE 13

1-(2-{3-[(2,2,3,3-tetramethylcyclopropyl)carbonyl]-1H-indol-1-yl}ethyl)pyrrolidine-2,5-dione

EXAMPLE 13A 2-(2,5-dioxopyrrolidin-1-yl)ethyl methanesulfonate

The N-(2-hydroxyethyl)succinimide (Aldrich, 0.19 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 13B 1-(2-{3-[(2,2,3,3-tetramethylcyclopropyl)carbonyl]-1H-indol-1-yl}ethyl)pyrrolidine-2,5-dione The major product of Example 1B (0.15 g, 0.62 mmol), the product of Example 13A (1.2 mmol) and NaH (60% dispersion in mineral oil, 0.12 g, 3.1 mmol) in 8 mL DMF were processed as in Example 1D. Purification via column chromatography ($SiO_2$, 50% hexanes:50% EtOAc) afforded 43 mg of the title compound (0.12 mmol, 18% yield). $^1$H NMR ($CDCl_3$, 300 MHz) δ 1.32 (s, 6H), 1.35 (s, 6H), 1.94 (s, 1H), 2.57 (s, 4H), 3.98 (t=7.1 Hz, 2H), 4.38 (t=7.2 Hz, 2H), 7.25 (td, J=7.1, 1.4 Hz, H), 7.29 (td, J=7.1, 1.7 Hz, 1H), 7.39 (m, 1H), 7.67 (s, 1H), 8.40 (m, 1H); MS ($DCI/NH_3$) m/z 366 $(M+H)^+$; Anal. Calculated for $C_{22}H_{26}N_2O_3 \cdot 0.5H_2O$: C, 70.38; H, 7.25; N, 7.46. Found: C, 70.41; H, 6.94; N, 7.25.

EXAMPLE 14

{1-[2-(4-methyl-1,3-thiazol-5-yl)ethyl]-1H-indol-3-yl}(2,2,3,3-tetramethylcyclopropyl)methanone

EXAMPLE 14A 2-(4-methyl-1,3-thiazol-5-yl)ethyl methanesulfonate

The 4-methyl-5-thiazole ethanol (Aldrich, 0.18 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 14B

{1-[2-(4-methyl-1,3-thiazol-5-yl)ethyl]-1H-indol-3-yl}(2,2,3,3-tetramethylcyclopropyl)methanone The major product of Example 1B (0.15 g, 0.62 mmol), the product of Example 14A (1.2 mmol) and NaH (60% dispersion in mineral oil, 0.12 g, 3.1 mmol) in 8 mL DMF were processed as in Example 1D. Purification via column chromatography ($SiO_2$, 50% hexanes:50% EtOAc) provided 73 mg of the title compound (0.20 mmol, 32% yield). $^1$H NMR ($CDCl_3$, 300 MHz) δ 1.26 (s, 6H), 1.32 (s, 6H), 1.81 (s, 1H), 2.15 (s, 3H), 3.33 (t, J=5.8 Hz, 2H), 4.39 (t, J=6.1 Hz, 2H), 7.28 (m, 2H), 7.29 (s, 1H), 7.39 (m, 1H), 8.41 (m, 1H), 8.64 (m, 1H); MS ($DCI/NH_3$) m/z 366 $(M+H)^+$; Anal. Calculated for $C_{22}H_{26}N_2OS \cdot 0.5H_2O$: C, 72.09; H, 7.15; N, 7.64. Found: C, 71.79; H, 7.29; N, 7.56.

EXAMPLE 15

{1-[2-(dimethylamino)ethyl]-1H-indol-3-yl}(2,2,3,3-tetramethylcyclopropyl)methanone p-toluenesulfonic acid

EXAMPLE 15A 2-(dimethylamino)ethyl methanesulfonate

The N,N-dimethylethanolamine (Aldrich, 0.11 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 15B

{1-[2-(dimethylamino)ethyl]-1H-indol-3-yl}(2,2,3,3-tetramethylcyclopropyl)methanone The major product of Example 1B (0.15 g, 0.62 mmol), the product of Example 15A (1.2 mmol) and NaH (60% dispersion in mineral oil, 0.12 g, 3.1 mmol) in 8 mL DMF were processed as in Example 1D. Purification via column chromatography ($SiO_2$, 2% $CH_3OH$:98% EtOAc) afforded 0.12 g of the title compound (0.37 mmol, 60% yield). MS (DCI/$NH_3$) m/z 313 $(M+H)^+$.

EXAMPLE 15C

{1-[2-(dimethylamino)ethyl]-1H-indol-3-yl}(2,2,3,3-tetramethylcyclopropyl)methanone p-toluenesulfonic acid p-Toluenesulfonic acid monohydrate (71 mg, 0.37 mmol) and the product of Example 15B (0.12 g, 0.37 mmol) were processed as in Example 1E. Recrystallization with $CH_3OH$, EtOAc and $Et_2O$ gave 0.12 g of the title compound (0.3 mmol, 81% yield). $^1$H NMR (MeOH-$d_4$, 300 MHz) δ 1.33 (s, 6H), 1.34 (s, 6H), 2.16 (s, 1H), 2.36 (s, 3H), 2.98 (s, 6H), 3.68 (t, J=6.8 Hz, 2H), 4.70 (t, J=7.1 Hz, 2H), 7.22 (br d, J=8.1 Hz, 2H), 7.26 (m, 1H), 7.33 (ddd, J=8.1, 7.1, 1.4 Hz, 1H), 7.57 (br d, J=8.1 Hz, 1H), 7.70 (br d, J=8.1 Hz, 2H), 8.17 (s, 1H), 8.30 (ddd, J=7.8, 1.4, 0.7 Hz, 1H); MS ($DCI/NH_3$) m/z 313 $(M+H)^+$; Anal. Calculated for $C_{20}H_{28}N_2O \cdot C_7H_8O_3S$: C, 66.91; H, 7.49; N, 5.70. Found: C, 66.78; H, 7.39; N, 5.60.

EXAMPLE 16

(2,2,3,3-tetramethylcyclopropyl)[1-(2-thien-3-yl-ethyl)-1H-indol-3-yl]methanone

EXAMPLE 16A 2-thien-3-ylethyl methanesulfonate

The 2-(3-thienyl)ethanol (Aldrich, 0.16 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 16B (2,2,3,3-tetramethylcyclopropyl)[1-(2-thien-3-yl-ethyl)-1H-indol-3-yl]methanone The major product of Example 1B (0.15 g, 0.62 mmol), the product of Example 16A (1.2 mmol) and NaH (60% dispersion in mineral oil, 0.12 g, 3.1 mmol) in 8 mL DMF were processed as in Example 1D. Purification via column chromatography ($SiO_2$, 90% hexanes:10% EtOAc) provided 0.15 g of the title compound (0.43 mmol, 69% yield). $^1$H NMR ($CDCl_3$, 300 MHz) δ 1.25 (s, 6H), 1.32 (s, 6H), 1.79 (s, 1H), 3.18 (t, J=6.8 Hz, 2H), 4.38 (t, J=6.8 Hz, 2H), 6.83 (m, 2H), 7.27 (m, 3H), 7.32 (m, 1H), 7.35 (s, 1H), 8.41 (m, 1H); MS ($DCI/NH_3$) m/z 352 $(M+H)^+$; Anal. calculated for $C_{22}H_{25}NOS$: C, 75.17; H, 7.17; N, 3.98. Found: C, 75.24; H, 7.40; N, 3.86.

EXAMPLE 17

{1-[2-(1-methylpyrrolidin-2-yl)ethyl]-1H-indol-3-yl}(2,2,3,3-tetramethylcyclopropyl)methanone p-toluenesulfonic acid

EXAMPLE 17A

Methanesulfonic acid 2-(1-methyl-pyrrolidin-2-yl)-ethyl ester

The 1-methyl-2-pyrrolidineethanol (Aldrich, 0.16 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 17B

{1-[2-(1-methylpyrrolidin-2-yl)ethyl]-1H-indol-3-yl}(2,2,3,3-tetramethylcyclopropyl)methanone The major product of Example 1B (0.15 g, 0.62 mmol), the product of Example 17A (1.2 mmol) and NaH (60% dispersion in mineral oil, 0.12 g, 3.1 mmol) in 8 mL DMF were processed as in Example 1D. Purification via column chromatography (SiO$_2$, 10% CH$_3$OH:90% CH$_2$Cl$_2$) gave 85 mg of the title compound (0.24 mmol, 39% yield). MS (DCI/NH$_3$) m/z 353 (M+H)$^+$.

EXAMPLE 17C

{1-[2-(1-methylpyrrolidin-2-yl)ethyl]-1H-indol-3-yl}(2,2,3,3-tetramethylcyclopropyl)methanone p-toluenesulfonic acid p-Toluenesulfonic acid monohydrate (45 mg, 0.23 mmol) and the product of Example 17B (80 mg, 0.23 mmol) were processed as in Example 1E. Recrystallization with CH$_3$OH, EtOAc and Et$_2$O provided 64 mg of the title compound (0.12 mmol, 54% yield). $^1$H NMR (MeOH-d$_4$, 300 MHz) δ 1.33 (m, 12H), 1.79 (m, 1H), 2.09 (m, 3H), 2.16 (s, 1H), 2.33 (m, 1H), 2.35 (s, 3H), 2.57 (m, 1H), 2.88 (s, 3H), 3.12 (m, 1H), 3.32 (m, 1H), 3.64 (m, 1H), 4.41 (t, J=7.8 Hz, 2H), 7.22 (br d, J=8.8 Hz, 2H), 7.23 (m, 1H), 7.30 (td, J=7.1, 1.4 Hz, 1H), 7.53 (br d, J=7.8 Hz, 1H), 7.70 (br d, J=8.1 Hz, 2H), 8.12 (s, 1H), 8.27 (br d, J=7.5 Hz, 1H); MS (DCI/NH$_3$) m/z 313 (M+H)$^+$; Anal. Calculated for C$_{23}$H$_{32}$N$_2$O.C$_7$H$_8$O$_3$S.0.2H$_2$O: C, 68.20; H, 7.71; N, 5.30. Found: C, 67.96; H, 7.83; N, 5.11.

EXAMPLE 18

[1-(tetrahydro-2H-pyran-4-ylmethyl)-1H-indol-3-yl](2,2,3,3-tetramethylcyclopropyl)methanone

EXAMPLE 18A tetrahydro-2H-pyran-4-ylmethyl methanesulfonate

The tetrahydropyran-4-methanol (Combi-Blocks, Inc., 0.15 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 18B

[1-(tetrahydro-2H-pyran-4-ylmethyl)-1H-indol-3-yl](2,2,3,3-tetramethylcyclopropyl)methanone The major product of Example 1B (0.15 g, 0.62 mmol), the product of Example 18A (1.2 mmol) and NaH (60% dispersion in mineral oil, 0.12 g, 3.1 mmol) in 8 mL DMF were processed as in Example 1D. Recrystallization with Et$_2$O and hexanes afforded 0.19 g of the title compound (0.56 mmol, 90% yield). $^1$H NMR (CDCl$_3$, 300 MHz) δ 1.31 (s, 6H), 1.35 (s, 6H), 1.46 (m, 4H), 1.94 (s, 1H), 2.16 (m, 1H), 3.33 (dt, J=11.5, 2.4 Hz, 2H), 3.98 (dd, J=10.5, 3.1 Hz, 2H), 4.04 (d, J=7.5 Hz, 2H), 7.27 (m, 2H), 7.33 (m, 1H), 7.61 (s, 1H), 8.40 (m, 1H); MS (DCI/NH$_3$) m/z 340 (M+H)$^+$; Anal. calculated for C$_{22}$H$_{29}$NO$_2$: C, 77.84; H, 8.61; N, 4.13. Found: C, 77.56; H, 8.84; N, 4.08.

EXAMPLE 19

[1-(2-pyridin-3-ylethyl)-1H-indol-3-yl](2,2,3,3-tetramethylcyclopropyl)methanone

EXAMPLE 19A 2-pyridin-3-ylethyl methanesulfonate

The 2-(3-pyridyl)ethan-1-ol (Maybridge, 0.15 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 19B

[1-(2-pyridin-3-ylethyl)-1H-indol-3-yl](2,2,3,3-tetramethylcyclopropyl)methanone The major product of Example 1B (0.15 g, 0.62 mmol), the product of Example 19A (1.2 mmol) and NaH (60% dispersion in mineral oil, 0.12 g, 3.1 mmol) in 8 mL DMF were processed as in Example 1D. Purification via column chromatography (SiO$_2$, 50% hexanes:50% EtOAc) gave 58 mg of the title compound (0.16 mmol, 25% yield). $^1$H NMR (CDCl$_3$, 300 MHz) δ 1.25 (s, 6H), 1.32 (s, 6H), 1.79 (s, 1H), 3.23 (t, J=6.8 Hz, 2H), 4.44 (t, J=6.8 Hz, 2H), 7.23 (m, 2H), 7.28 (m, 3H), 7.36 (s, 1H), 8.42 (m, 1H), 8.54 (m, 2H); MS (DCI/NH$_3$) m/z 347 (M+H)$^+$; Anal. Calculated for C$_{23}$H$_{26}$N$_2$O.0.2C$_6$H$_{14}$.0.3H$_2$O: C, 78.75; H, 8.03; N, 7.59. Found: C, 78.76; H, 8.31; N, 7.87.

EXAMPLE 20

{1-[2-(1H-pyrrol-1-yl)ethyl]-1H-indol-3-yl}(2,2,3,3-tetramethylcyclopropyl)methanone

EXAMPLE 20A 2-(1H-pyrrol-1-yl)ethyl methanesulfonate

The 1-(2-hydroxyethyl)pyrrole (TCI-US, 0.138 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 20B

{1-[2-(1H-pyrrol-1-yl)ethyl]-1H-indol-3-yl}(2,2,3,3-tetramethylcyclopropyl)methanone The major product of Example 1B (0.15 g, 0.62 mmol), the product of Example 20A (1.2 mmol) and NaH (60% dispersion in mineral oil, 0.12 g, 3.1 mmol) in 8 mL DMF were processed as in Example 1D. Purification via column chromatography (SiO$_2$, 80% hexanes:20% EtOAc) gave 25 mg of the title compound (0.075 mmol, 12% yield). $^1$H NMR (CDCl$_3$, 300 MHz) δ 1.24 (s, 6H), 1.31 (s, 6H), 1.71 (s, 1H), 4.25 (m, 2H), 4.44 (m, 2H), 6.13 (t, J=2.0 Hz, 2H), 6.41 (t, J=2.0 Hz, 2H), 6.92 (s, 1H), 7.28 (m, 3H), 8.42 (m, 1H); MS (DCI/NH$_3$) m/z 335 (M+H)$^+$; Anal. Calculated for C$_{22}$H$_{26}$N$_2$O.0.1C$_6$H$_{14}$.0.7H$_2$O: C, 77.09; H, 7.89; N, 7.62. Found: C, 76.94; H, 8.25; N, 7.91.

EXAMPLE 21

(1-{2-[4-(dimethylamino)phenyl]ethyl}-1H-indol-3-yl)(2,2,3,3-tetramethylcyclopropyl)methanone

EXAMPLE 21A

2-[4-(dimethylamino)phenyl]ethyl methanesulfonate

The (4-dimethylamino)-phenethyl alcohol (Aldrich, 0.205 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 21B (1-{2-[4-(dimethylamino)phenyl]ethyl}-1H-indol-3-yl)(2,2,3,3-tetramethylcyclopropyl)methanone The major product of Example 1B (0.15 g, 0.62 mmol), the product of Example 21A (1.2 mmol) and NaH (60% dispersion in mineral oil, 0.12 g, 3.1 mmol) in 8 mL DMF were processed as in Example 1D. Recrystallization with EtOAc and hexanes provided 0.15 g of the title compound (0.387 mmol, 62% yield). $^1$H NMR (CDCl$_3$, 300 MHz) δ 1.21 (s, 6H), 1.24 (s, 6H), 1.85 (s, 1H), 2.86 (s, 6H), 3.01 (t, 2H), 4.44 (t, J=6.5 Hz, 2H), 6.65 (m, 2H), 6.83 (m, 2H), 7.19 (dt, J=7.8, 1.4 Hz, 1H), 7.26 (dt, J=7.1, 1.4 Hz, 1H), 7.48 (m, 1H), 7.49 (s, 1H), 8.22 (m, 1H); MS (DCI/NH$_3$) m/z 389 (M+H)$^+$; Anal. calculated for C$_{26}$H$_{32}$N$_2$O: C, 80.37; H, 8.30; N, 7.21. Found: C, 79.99; H, 8.58; N, 7.08.

EXAMPLE 22

[1-(2-pyridin-4-ylethyl)-1H-indol-3-yl](2,2,3,3-tetramethylcyclopropyl)methanone

EXAMPLE 22A 2-pyridin-4-ylethyl methanesulfonate

The 4-(2-hydroxyethyl)pyridine (Lancaster, 0.153 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 22B

[1-(2-pyridin-4-ylethyl)-1H-indol-3-yl](2,2,3,3-tetramethylcyclopropyl)methanone The major product of Example 1B (0.15 g, 0.62 mmol), the product of Example 22A (1.2 mmol) and NaH (60% dispersion in mineral oil, 0.12 g, 3.1 mmol) in 8 mL DMF were processed as in Example 1D. Purification via column chromatography (SiO$_2$, 50% hexanes:50% EtOAc) afforded 42 mg of the title compound (0.12 mmol, 19% yield). $^1$H NMR (CDCl$_3$, 300 MHz) δ 1.25 (s, 6H), 1.31 (s, 6H), 1.78 (s, 1H), 3.20 (t, J=7.1 Hz, 2H), 4.44 (t, J=7.1 Hz, 2H), 7.03 (br d, J=5.4 Hz, 2H), 7.30 (m, 3H), 7.35 (s, 1H), 8.42 (m, 1H), 8.51 (br d, J=4.7 Hz, 2H); MS (DCI/NH$_3$) m/z 347 (M+H)$^+$; Anal. Calculated for C$_{23}$H$_{26}$N$_2$O.0.3H$_2$O: C, 78.51; H, 7.60; N, 7.96. Found: C, 78.50; H, 7.31; N, 7.95.

EXAMPLE 23

{1-[4-(benzyloxy)butyl]-1H-indol-3-yl}(2,2,3,3-tetramethylcyclopropyl)methanone

EXAMPLE 23A 4-(benzyloxy)butyl methanesulfonate

The 1-benzyloxy-1-butanol (Aldrich, 0.22 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 23B

{1-[4-(benzyloxy)butyl]-1H-indol-3-yl}(2,2,3,3-tetramethylcyclopropyl)methanone

The major product of Example 1B (0.15 g, 0.62 mmol), the product of Example 23A (1.2 mmol) and NaH (60% dispersion in mineral oil, 0.12 g, 3.1 mmol) in 8 mL DMF were processed as in Example 1D. Purification via column chromatography (SiO$_2$, 80% hexanes:20% EtOAc) gave 0.18 g of the title compound (0.45 mmol, 72% yield). $^1$H NMR (CDCl$_3$, 300 MHz) δ 1.29 (s, 6H), 1.34 (s, 6H), 1.66 (m, 2H), 1.93 (s, 1H), 2.01 (m, 2H), 3.50 (t, J=6.1 Hz, 2H), 4.19 (t, J=7.1 Hz, 2H), 4.49 (s, 2H), 7.25 (m, 2H), 7.32 (m, 6H), 7.66 (s, 1H), 8.39 (m, 1H); MS (DCI/NH$_3$) m/z 404 (M+H)$^+$; Anal. calculated for C$_{27}$H$_{33}$NO$_2$: C, 80.36; H, 8.24; N, 3.47. Found: C, 79.99; H, 8.46; N, 3.30.

EXAMPLE 24

[1-(4-hydroxybutyl)-1H-indol-3-yl](2,2,3,3-tetramethylcyclopropyl)methanone

EXAMPLE 24A

[1-(4-hydroxybutyl)-1H-indol-3-yl](2,2,3,3-tetramethylcyclopropyl)methanone

To the product of Example 23B (0.18 g, 0.45 mmol) in 40 mL ethanol (200 proof) was added 100 mg of Pd/C (10 wt % palladium on activated carbon, Aldrich). This mixture was stirred under 1 atm of H$_2$ (balloon) for 18 hours after which time the mixture was degassed three times with a N$_2$ backflush. The mixture was then filtered, concentrated under reduced pressure and purified via flash column chromatography (SiO$_2$, 50% ethyl acetate:hexanes) to give 85 mg of the title compound (0.27 mmol, 60% yield). $^1$H NMR (CDCl$_3$, 300 MHz) δ 1.31 (s, 6H), 1.35 (s, 6H), 1.62 (m, 2H), 1.95 (s, 1H), 2.01 (m, 2H), 3.69 (t, J=6.1 Hz, 2H), 4.22 (t, J=7.1 Hz, 2H), 7.26 (m, 2H), 7.34 (m, 1H), 7.67 (s, 1H), 8.40 (m, 1H); MS (DCI/NH$_3$) m/z 314 (M+H)$^+$; Anal. Calculated for C$_{20}$H$_{27}$NO$_2$.0.2H$_2$O: C, 75.77; H, 8.71; N, 4.42. Found: C, 75.66; H, 8.60; N, 4.16.

EXAMPLE 25

[1-(2-piperidin-1-ylethyl)-1H-indol-3-yl](2,2,3,3-tetramethylcyclopropyl)methanone

EXAMPLE 25A 2-piperidin-1-ylethyl methanesulfonate

The 1-piperidineethanol (Aldrich, 0.16 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 25B

[1-(2-piperidin-1-ylethyl)-1H-indol-3-yl](2,2,3,3-tetramethylcyclopropyl)methanone The major product of Example 1B (0.15 g, 0.62 mmol), the product of Example 25A (1.2 mmol) and NaH (60% dispersion in mineral oil, 0.12 g, 3.1 mmol) in 8 mL DMF were processed as in Example 1D. Purification via column chromatography (SiO$_2$, 50% EtOAc) afforded 0.21 g of the title compound (0.56 mmol, 91% yield). $^1$H NMR (CDCl$_3$, 300 MHz) δ 1.31 (s, 6H), 1.35 (s, 6H), 1.54 (m, 6H), 1.94 (s, 1H), 2.47 (m, 4H), 2.74 (m, 2H), 4.26 (m, 2H), 7.27 (m, 2H), 7.35 (m, 1H), 7.81 (br s, 1H), 8.41 (m, 1H); MS (DCI/NH$_3$) m/z 353 (M+H)$^+$; Anal. Calculated for C$_{23}$H$_{26}$N$_2$O.0.1C$_6$H$_{14}$.0.3H$_2$O: C, 76.58; H, 9.37; N, 7.57. Found: C, 76.48; H, 9.73; N, 7.82.

EXAMPLE 26

{1-[4-(methylthio)butyl]-1H-indol-3-yl}(2,2,3,3-tetramethylcyclopropyl)methanone

EXAMPLE 26A 4-(methylthio)butyl methanesulfonate

The 4-(methylthio)-1-butanol (Aldrich, 0.15 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 26B

{1-[4-(methylthio)butyl]-1H-indol-3-yl}(2,2,3,3-tetramethylcyclopropyl)methanone The major product of Example 1B (0.15 g, 0.62 mmol), the product of Example 26A (1.2 mmol) and NaH (60% dispersion in mineral oil, 0.12 g, 3.1 mmol) in 8 mL DMF were processed as in Example 1D. Purification via column chromatography (SiO$_2$, 80% hexanes:20% EtOAc) afforded 0.19 g of the title compound (0.55 mmol, 89% yield). $^1$H NMR (CDCl$_3$, 300 MHz) δ 1.31 (s, 6H), 1.35 (s, 6H), 1.66 (m, 2H), 1.95 (s, 1H), 2.03 (m, 2H), 2.06 (s, 3H), 2.53 (br t, J=6.8 Hz, 2H), 4.19 (t, J=7.1 Hz, 2H), 7.27 (m, 2H), 7.34 (m, 1H), 7.67 (s, 1H), 8.41 (m, 1H); MS (DCI/NH$_3$) m/z 344 (M+H)$^+$; Anal. calculated for C$_{23}$H$_{26}$N$_2$O: C, 73.42; H, 8.51; N, 4.08. Found: C, 73.36; H, 8.86; N, 4.00.

EXAMPLE 27

[1-(3-morpholin-4-ylpropyl)-1H-indol-3-yl](2,2,3,3-tetramethylcyclopropyl)methanone

EXAMPLE 27A 3-morpholin-4-ylpropyl methanesulfonate

The 4-(3-hydroxypropyl)morpholine (Aldrich, 0.18 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 27B

[1-(3-morpholin-4-ylpropyl)-1H-indol-3-yl](2,2,3,3-tetramethylcyclopropyl)methanone The major product of Example 1B (0.15 g, 0.62 mmol), the product of Example 27A (1.2 mmol) and NaH (60% dispersion in mineral oil, 0.12 g, 3.1 mmol) in 8 mL DMF were processed as in Example 1D. Purification via column chromatography (SiO$_2$, 20% hexanes:80% EtOAc) yielded 0.15 g of the title compound (0.41 mmol, 66% yield). $^1$H NMR (CDCl$_3$, 300 MHz) δ 1.30 (s, 6H), 1.35 (s, 6H), 1.93 (s, 1H), 2.05 (m, 2H), 2.29 (m, 2H), 2.42 (m, 4H), 3.75 (m, 4H), 4.28 (t, J=6.5 Hz, 2H), 7.26 (m, 2H), 7.38 (m, 1H), 7.71 (s, 1H), 8.40 (m, 1H); MS (DCI/NH$_3$) m/z 367 (M+H)$^+$; Anal. Calculated for C$_{23}$H$_{32}$N$_2$O$_2$: C, 74.96; H, 8.75; N, 7.60. Found: C, 74.85; H, 8.91; N, 7.43.

EXAMPLE 28

[1-(2-azepan-1-ylethyl)-1H-indol-3-yl](2,2,3,3-tetramethylcyclopropyl)methanone

EXAMPLE 28A 2-azepan-1-ylethyl methanesulfonate

The N-(2-hydroxyethyl)hexamethyleneimine (Lancaster, 0.18 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 28B

[1-(2-azepan-1-ylethyl)-1H-indol-3-yl](2,2,3,3-tetramethylcyclopropyl)methanone

The major product of Example 1B (0.15 g, 0.62 mmol), the product of Example 28A (1.2 mmol) and NaH (60% dispersion in mineral oil, 0.12 g, 3.1 mmol) in 8 mL DMF were processed as in Example 1D. Purification via column chromatography (SiO$_2$, 20% hexanes:80% EtOAc) gave 0.19 g of the title compound (0.50 mmol, 81% yield). $^1$H NMR (CDCl$_3$, 300 MHz) δ 1.30 (s, 6H), 1.35 (s, 6H), 1.62 (m, 8H), 1.95 (s, 1H), 2.70 (m, 4H), 2.94 (m, 2H), 4.22 (m, 2H), 7.27 (m, 2H), 7.34 (m, 1H), 7.84 (s, 1H), 8.42 (m, 1H); MS (DCI/NH$_3$) m/z 367 (M+H)$^+$; Anal. Calculated for C$_{23}$H$_{32}$N$_2$O$_2$.0.2H$_2$O: C, 77.50; H, 9.38; N, 7.53. Found: C, 77.39; H, 9.68; N, 7.50.

EXAMPLE 29

[1-(2-piperazin-1-ylethyl)-1H-indol-3-yl](2,2,3,3-tetramethylcyclopropyl)methanone tris-trifluoroacetic acid

EXAMPLE 29A tert-butyl 4-{2-[(methylsulfonyl)oxy]ethyl}piperazine-1-carboxylate A solution of tert-butyl-4-(2-hydroxyethyl)-piperazine-1-carboxylate (Maybridge, 0.29 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 29B tert-butyl 4-(2-{3-[(2,2,3,3-tetramethylcyclopropyl)carbonyl]-1H-indol-1-yl}ethyl)piperazine-1-carboxylate The major product of Example 1B (0.15 g, 0.62 mmol), the product of Example 29A (1.2 mmol) and NaH (60% dispersion in mineral oil, 0.12 g, 3.1 mmol) in 8 mL DMF were processed as in Example 1D. Purification via column chromatography (SiO$_2$, 50% hexanes:50% EtOAc) afforded 0.22 g of the title compound (0.48 mmol, 78% yield). MS (DCI/NH$_3$) m/z 454 (M+H)$^+$.

EXAMPLE 29C

[1-(2-piperazin-1-ylethyl)-1H-indol-3-yl](2,2,3,3-tetramethylcyclopropyl)methanone tris-trifluoroacetic acid To the product of Example 5B (0.42 g, 0.93 mmol) in 5 mL dichloromethane at 0° C. was added trifluoroacetic acid (TFA, 3 mL, excess). The ice-bath was removed and the mixture stirred at 23° C. for 20 min then the mixture was concentrated under reduced pressure. The residue was azeotroped three times with 7 mL toluene to remove any remaining TFA. The residue was then dissolved in ethyl acetate and concentrated under reduced pressure. After sitting under vacuum for 16 hours, the resulting solids were isolated to give 0.21 g of the title compound (0.30 mmol, 63% yield). $^1$H NMR (MeOH-d$_4$, 300 MHz) δ 1.34 (s, 12H), 2.01 and 2.15 (s, 1H, rotamers), 2.73 and 2.78 (m, 4H, rotamers), 2.92 and 3.00 (t, J=6.1 Hz, 2H, rotamers), 3.14 and 3.18 (m, 4H, rotamers), 4.40 and 4.59 (t, J=6.4 Hz, 2H, rotamers), 7.21 (dt, J=7.1, 1.4 Hz, 1H), 7.28 (dt, J=7.1, 1.4 Hz, 1H), 7.51 (m, 1H), 8.09 (s, 1H), 8.24 (m, 1H); MS (DCI/NH$_3$) m/z 354 (M+H)$^+$; Anal. Calculated for C$_{22}$H$_{31}$N$_3$O.3CF$_3$CO$_2$H.0.5H$_2$O: C, 47.73; H, 5.01; N, 5.96. Found: C, 47.65; H, 5.05; N, 5.83.

EXAMPLE 30

{1-[2-(4-methylpiperazin-1-yl)ethyl]-1H-indol-3-yl}(2,2,3,3-tetramethylcyclopropyl)methanone The product of Example 29C (0.19 g, 0.27 mmol), formaldehyde (36% aqueous solution, 10 mL), and NaBH(OAc)$_3$ (0.10 g, 0.47 mmol) were processed as in Example 7A. Purification via column chromatography (SiO$_2$, 1% NH$_4$OH:5% CH$_3$OH:94% CH$_2$Cl$_2$) provided 65 mg of the title compound (0.17 mmol, 63% yield). $^1$H NMR (MeOH-d$_4$, 300 MHz) δ 1.33 (s, 12H), 2.13 (s, 1H), 2.27 (s, 3H), 2.51 (br m, 8H), 2.80 (t, J=6.4 Hz, 2H), 4.37 (t, J=6.4 Hz, 2H), 7.20 (m, 1H), 7.25 (m, 1H), 7.48 (m, 1H), 8.10 (s, 1H), 8.24 (m, 1H); MS (DCI/NH$_3$) m/z 368 (M+H)$^+$; Anal. Calculated for C$_{23}$H$_{33}$N$_3$O.0.5CH$_3$OH: C, 73.59; H, 9.20; N, 10.96. Found: C, 73.35; H, 9.56; N, 10.98.

EXAMPLE 31

3-(2-{3-[(2,2,3,3-tetramethylcyclopropyl)carbonyl]-1H-indol-1-yl}ethyl)-1,3-oxazolidin-2-one

EXAMPLE 31A 2-(2-oxo-1,3-oxazolidin-3-yl)ethyl methanesulfonate

The 3-(2-hydroxyethyl)-2-oxazolidinone (Frinton Laboratories, 0.16 g, 1.2 mmol), triethylamine (0.56 mL, 4.1 mmol), and methanesulfonyl chloride (0.15 mL, 1.9 mmol) in 10 mL THF were processed as described in Example 1C to give the title compound which was used directly in the next reaction.

EXAMPLE 31B 3-(2-{3-[(2,2,3,3-tetramethylcyclopropyl)carbonyl]-1H-indol-1-yl}ethyl)-1,3-oxazolidin-2-one The major product of Example 1B (0.15 g, 0.62 mmol), the product of Example 31A (1.2 mmol) and NaH (60% dispersion in mineral oil, 0.12 g, 3.1 mmol) in 8 mL DMF were processed as in Example 1D. Purification via column chromatography (SiO$_2$, 20% hexanes:80% EtOAc) gave 0.10 g of the title compound (0.27 mmol, 44% yield). $^1$H NMR (MeOH-d$_4$, 300 MHz) δ 1.33 (s, 12H), 2.14 (s, 1H), 3.24 (m, 2H), 3.70 (t, J=6.1 Hz, 2H), 4.12 (m, 2H); 4.48 (t, J=6.1 Hz, 2H), 7.22 (m, 1H), 7.29 (dt, J=7.1, 1.4 Hz, 1H), 7.54 (m, 1H), 8.10 (s, 1H), 8.27 (m, 1H); MS (DCI/NH$_3$) m/z 355 (M+H)$^+$; Anal. Calculated for C$_{21}$H$_{26}$N$_2$O$_3$.0.9H$_2$O: C, 68.05; H, 7.56; N, 7.56. Found: C, 68.23; H, 7.33; N, 7.47.

EXAMPLE 32

[1-(tetrahydrofuran-3-ylmethyl)-1H-indol-3-yl](2,2,3,3-tetramethylcyclopropyl)methanone

EXAMPLE 32A tetrahydrofuran-3-ylmethyl methanesulfonate

The tetrahydro-3-furanmethanol (Aldrich, 0.13 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 32B

[1-(tetrahydrofuran-3-ylmethyl)-1H-indol-3-yl](2,2,3,3-tetramethylcyclopropyl)methanone The major product of Example 1B (0.15 g, 0.62 mmol), the product of Example 32A (1.2 mmol) and NaH (60% dispersion in mineral oil, 0.12 g, 3.1 mmol) in 8 mL DMF were processed as in Example 1D. Purification via column chromatography (SiO$_2$, 70% hexanes:30% EtOAc) afforded 0.16 g of the title compound (0.48 mmol, 77% yield). $^1$H NMR (CDCl$_3$, 300 MHz) δ 1.31 (s, 6H), 1.34 (s, 3H), 1.35 (s, 3H), 1.71 (m, 1H), 1.94 (s, 1H), 2.07 (m, 1H), 2.89 (m, 1H), 3.67 (m, 2H), 3.78 (m, 1H), 4.01 (m, 1H), 4.14 (d, J=7.8 Hz, 2H), 7.28 (m, 2H), 7.35 (m, 1H), 7.66 (s, 1H), 8.41 (m, 1H); MS (DCI/NH$_3$) m/z 326 (M+H)$^+$; Anal. Calculated for C$_{21}$H$_{27}$NO$_2$: C, 77.50; H, 8.36; N, 4.30. Found: C, 77.33; H, 8.47; N, 4.26.

EXAMPLE 33

(2,2,3,3-tetramethylcyclopropyl)[1-(4,4,4-trifluorobutyl)-1H-indol-3-yl]methanone

EXAMPLE 33A 4,4,4-trifluorobutyl methanesulfonate

The 4,4,4-trifluoro-1-butanol (Lancaster, 0.16 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 33B (2,2,3,3-tetramethylcyclopropyl)[1-(4,4,4-trifluorobutyl)-1H-indol-3-yl]methanone The major product of Example 1B (0.15 g, 0.62 mmol), the product of Example 33A (1.2 mmol) and NaH (60% dispersion in mineral oil, 0.12 g, 3.1 mmol) in 8 mL DMF were processed as in Example 1D. Purification via column chromatography (SiO$_2$, 70% hexanes:30% EtOAc) gave 0.19 g of the title compound (0.53 mmol, 86% yield). $^1$H NMR (CDCl$_3$, 300 MHz) δ 1.31 (s, 6H), 1.35 (s, 6H), 1.94 (s, 1H), 2.17 (m, 4H), 4.26 (br t, J=6.4 Hz, 2H), 7.30 (m, 3H), 7.64 (s, 1H), 8.41 (m, 1H); MS (DCI/NH$_3$) m/z 352 (M+H)$^+$; Anal. Calculated for C$_{20}$H$_{24}$F$_3$NO: C, 68.36; H, 6.88; N, 3.99. Found: C, 67.99; H, 7.18; N, 3.84.

EXAMPLE 34

{1-[2-(2,2-dimethyl-1,3-dioxolan-4-yl)ethyl]-1H-indol-3-yl}(2,2,3,3-tetramethylcyclopropyl)methanone

EXAMPLE 34A 2-(2,2-dimethyl-1,3-dioxolan-4-yl)ethyl methanesulfonate

The 4-(2-hydroxyethyl)-2,2-dimethyl-1,3-dioxolane (Aldrich, 0.19 g, 1.2 mmol), triethylamine (0.56 mL, 4.1 mmol), and methanesulfonyl chloride (0.15 mL, 1.9 mmol) in 10 mL THF were processed as described in Example 1C to give the title compound that was used directly in the next reaction.

EXAMPLE 34B

{1-[2-(2,2-dimethyl-1,3-dioxolan-4-yl)ethyl]-1H-indol-3-yl}(2,2,3,3-tetramethylcyclopropyl)methanone The major product of Example 1B (0.15 g, 0.62 mmol), the product of Example 34A (1.2 mmol) and NaH (60% dispersion in mineral oil, 0.12 g, 3.1 mmol) in 8 mL DMF were processed as in Example 1D. Purification via column chromatography (SiO$_2$, 80% hexanes:20% EtOAc) afforded 0.12 g of the title compound (0.32 mmol, 52% yield). $^1$H NMR (CDCl$_3$, 300 MHz) δ 1.30 (s, 6H), 1.34 (s, 3H), 1.36 (s, 6H), 1.48 (s, 3H), 1.93 (s, 1H), 2.08 (m, 2H), 3.52 (m 1H), 3.99 (m, 2H), 4.36 (m, 2H), 7.27 (m, 2H), 7.38 (m, 1H), 7.71 (s, 1H), 8.41 (m, 1H); MS (DCI/NH$_3$) m/z 370 (M+H)$^+$; Anal. Calculated for C$_{23}$H$_{31}$NO$_3$: C, 74.76; H, 8.46; N, 3.79. Found: C, 74.43; H, 8.36; N, 3.70.

EXAMPLE 35

[1-(3,4-dihydroxybutyl)-1H-indol-3-yl](2,2,3,3-tetramethylcyclopropyl)methanone

To the product of Example 34B (0.11 g, 0.30 mmol) in 2 mL of a 4:1 mixture of tetrahydropyran and water was added excess p-toluenesulfonic acid (p-TSA, 0.1 g, 5.3 mmol). This mixture stirred at ambient temperature for 24 h then was concentrated under reduced pressure. The residue was purified via flash column chromatography (SiO$_2$, 100% ethyl acetate) to give 35 mg of the title compound (0.10 mmol, 34% yield). $^1$H NMR (CDCl$_3$, 300 MHz) δ 1.31 (s, 6H), 1.35 (s, 6H), 1.67 (m, 2H), 1.95 (s, 1H), 1.97 (m, 2H), 3.46 (m, 1H), 3.63 (m, 2H), 4.39 (dd, J=8.1, 5.8 Hz, 2H), 7.27 (m, 2H), 7.39 (m, 1H), 7.72 (s, 1H), 8.39 (m, 1H); MS (DCI/NH$_3$) m/z 330 (M+H)$^+$; Anal. Calculated for C$_{20}$H$_{27}$NO$_3$.0.5H$_2$O: C, 70.98; H, 8.34; N, 4.14. Found: C, 70.68; H, 8.69; N, 3.86.

EXAMPLE 36

[1-(1,3-dioxolan-4-ylmethyl)-1H-indol-3-yl](2,2,3,3-tetramethylcyclopropyl)methanone

EXAMPLE 36A 1,3-dioxolan-4-ylmethyl methanesulfonate

The glycerol formal (Aldrich, 0.26 g, 2.5 mmol), triethylamine (1.1 mL, 8.3 mmol), and methanesulfonyl chloride (0.30 mL, 3.7 mmol) in 20 mL THF were processed as described in Example 1C to give the title compound that was used directly in the next reaction.

EXAMPLE 36B

[1-(1,3-dioxolan-4-ylmethyl)-1H-indol-3-yl](2,2,3,3-tetramethylcyclopropyl)methanone The major product of Example 1B (0.30 g, 1.2 mmol), the product of Example 36A (2.49 mmol) and NaH (60% dispersion in mineral oil, 0.248 g, 6.22 mmol) in 16 mL DMF were processed as in Example 1D. Purification via column chromatography (SiO$_2$, 70% hexanes:30% EtOAc) yielded 0.10 g of the title compound (0.305 mmol, 25% yield). $^1$H NMR (CDCl$_3$, 300 MHz) δ 1.31 (s, 6H), 1.34 (s, 3H), 1.35 (s, 3H), 1.95 (s, 1H), 3.71 (dd, J=8.5, 5.4 Hz, 1H), 3.99 (dd, J=8.8, 6.8 Hz, 1H), 4.28 (d, J=4.1 Hz, 1H), 4.30 (d, J=2.7 Hz, 1H), 4.46 (m, 1H), 4.89 (s, 1H), 5.09 (s, 1H), 7.28 (m, 2H), 7.34 (m, 1H), 7.74 (s, 1H), 8.42 (m, 1H); MS (DCI/NH$_3$) m/z 328 (M+H)$^+$; Anal. Calculated for C$_{20}$H$_{25}$NO$_3$: C, 73.37; H, 7.70; N, 4.28. Found: C, 72.94; H, 7.89; N, 4.13.

EXAMPLE 37

{1-[2-(benzyloxy)ethyl]-1H-indol-3-yl}(2,2,3,3-tetramethylcyclopropyl)methanone

EXAMPLE 37A 2-(benzyloxy)ethyl methanesulfonate

The 2-benzyloxyethanol (Aldrich, 0.25 g, 1.7 mmol), triethylamine (0.67 mL, 5.0 mmol), and methanesulfonyl chloride (0.19 mL, 2.5 mmol) in 20 mL THF were processed as described in Example 1C to give the title compound that was used directly in the next reaction.

EXAMPLE 37B

{1-[2-(benzyloxy)ethyl]-1H-indol-3-yl}(2,2,3,3-tetramethylcyclopropyl)methanone

The major product of Example 1B (0.20 g, 0.83 mmol), the product of Example 37A (1.66 mmol) and NaH (60% dispersion in mineral oil, 0.17 g, 4.1 mmol) in 10 mL DMF were processed as in Example 1D. Purification via column chromatography (SiO$_2$, 80% hexanes:20% EtOAc) afforded 0.20 g of the title compound (0.54 mmol, 65% yield). $^1$H NMR (CDCl$_3$, 300 MHz) δ 1.27 (s, 6H), 1.34 (s, 6H), 1.92 (s, 1H), 3.84 (t, J=5.4 Hz, 2H), 4.36 (t, J=5.1 Hz, 2H), 4.47 (s, 2H), 7.23 (m, 4H), 7.29 (m, 4H), 7.77 (s, 1H), 8.43 (m, 1H); MS (DCI/NH$_3$) m/z 376 (M+H)$^+$; Anal. Calculated for C$_{25}$H$_{29}$NO$_2$: C, 79.96; H, 7.78; N, 3.73. Found: C, 79.86; H, 7.63; N, 3.49.

EXAMPLE 38

[1-(2-hydroxyethyl)-1H-indol-3-yl](2,2,3,3-tetramethylcyclopropyl)methanone

To the product of Example 37B (0.19 g, 0.51 mmol) in 20 mL ethanol (200 proof) was added Pd/C (0.10 g, 10 wt % palladium on activated carbon, Aldrich). This mixture was stirred under 1 atm of H$_2$ (balloon) for 2 h after which time the reaction mixture was degassed three times with a N$_2$ back-flush. The mixture was then filtered, concentrated under reduced pressure and purified via flash column chromatography (SiO$_2$, 30% ethyl acetate:hexanes) to give 68 mg of the title compound (0.24 mmol, 47% yield). 1H NMR (CDCl$_3$, 300 MHz) δ 1.30 (s, 6H), 1.35 (s, 6H), 1.95 (s, 1H), 4.03 (m, 2H), 4.33 (t, J=5.1 Hz, 2H), 7.28 (m, 2H), 7.36 (m, 1H), 7.76 (s, 1H), 8.43 (m, 1H); MS (DCI/NH3) m/z 286 (M+H)$^+$; Anal. calculated for C$_{18}$H$_{23}$NO$_2$: C, 75.76; H, 8.12; N, 4.91. Found: C, 75.55; H, 7.82; N, 4.88.

EXAMPLE 39

{1-[3-(benzyloxy)propyl]-1H-indol-3-yl}(2,2,3,3-tetramethylcyclopropyl)methanone

EXAMPLE 39A 3-(benzyloxy)propyl methanesulfonate

The 3-benzyloxypropanol (Aldrich, 0.28 g, 1.7 mmol), triethylamine (0.67 mL, 5.0 mmol), and methanesulfonyl chloride (0.19 mL, 2.5 mmol) in 10 mL THF were processed as described in Example 1C to give the title compound that was used directly in the next reaction.

EXAMPLE 39B

{1-[3-(benzyloxy)propyl]-1H-indol-3-yl}(2,2,3,3-tetramethylcyclopropyl)methanone The major product of Example 1B (0.20 g, 0.83 mmol), the product of Example 39A (1.7 mmol) and NaH (60% dispersion in mineral oil, 0.17 g, 4.1 mmol) in 10 mL DMF were processed as in Example 1D. Purification via column chromatography (SiO$_2$, 80% hexanes:20% EtOAc) resulted in 0.27 g of the title compound (0.69 mmol, 84% yield). $^1$H NMR (CDCl$_3$, 300 MHz) δ 1.27 (s, 6H), 1.34 (s, 6H), 1.90 (s, 1H), 2.16 (m, 2H), 3.43 (t, J=5.4 Hz, 2H), 4.33 (t, J=6.8 Hz, 2H), 4.49 (s, 2H), 7.26 (m, 2H), 7.35 (m, 6H), 7.67 (s, 1H), 8.42 (m, 1H); MS (DCI/NH$_3$) m/z 390 (M+H)$^+$; Anal. calculated for C$_{26}$H$_{31}$NO$_2$: C, 80.17; H, 8.02; N, 3.60. Found: C, 79.91; H, 7.97; N, 3.36.

EXAMPLE 40

[1-(3-hydroxypropyl)-1H-indol-3-yl](2,2,3,3-tetramethylcyclopropyl)methanone

To the product of Example 39B (0.24 g, 0.62 mmol) in 40 mL ethanol (200 proof) was added 200 mg of Pd/C (10 wt % palladium on activated carbon, Aldrich). This mixture was stirred under 1 atm of H$_2$ (balloon) for 12 h after which time the reaction mixture was degassed three times with a N$_2$ back-flush. The mixture was then filtered, concentrated under reduced pressure and purified via flash column chromatography (SiO$_2$, 30% ethyl acetate:hexanes) to give 0.13 g of the title compound (0.43 mmol, 69% yield). 1H NMR (CDCl$_3$, 300 MHz) δ 1.30 (s, 6H), 1.35 (s, 6H), 1.94 (s, 1H), 2.12 (m, 2H), 3.67 (t, J=5.8 Hz, 2H), 4.34 (t, J=7.1 Hz, 2H), 7.26 (m, 2H), 7.38 (m, 1H), 7.71 (s, 1H), 8.41 (m, 1H); MS (DCI/NH$_3$) m/z 300 (M+H)$^+$; Anal. Calculated for C$_{19}$H$_{25}$NO$_2$.0.2H$_2$O: C, 75.31; H, 8.45; N, 4.62. Found: C, 75.60; H, 8.11; N, 4.25.

EXAMPLE 41

{1-[5-(benzyloxy)pentyl]-1H-indol-3-yl}(2,2,3,3-tetramethylcyclopropyl)methanone

EXAMPLE 41A 5-(benzyloxy)pentyl methanesulfonate

The 5-benzyloxypentanol (Aldrich, 0.32 g, 1.7 mmol), triethylamine (0.67 mL, 5.0 mmol), and methanesulfonyl chloride (0.19 mL, 2.5 mmol) in 10 mL THF were processed as described in Example 1C to give the title compound that was used directly in the next reaction.

EXAMPLE 41B

{1-[5-(benzyloxy)pentyl]-1H-indol-3-yl}(2,2,3,3-tetramethylcyclopropyl)methanone The major product of Example 1B (0.20 g, 0.83 mmol), the product of Example 41A (1.7 mmol) and NaH (60% dispersion in mineral oil, 0.17 g, 4.1 mmol) in 10 mL DMF were processed as in Example 1D. Purification via column chromatography (SiO$_2$, 80% hexanes:20% EtOAc) gave 0.30 g of the title compound (0.71 mmol, 86% yield). $^1$H NMR (CDCl$_3$, 300 MHz) δ 1.30 (s, 6H), 1.34 (s, 6H), 1.46 (m, 2H), 1.67 (m, 2H), 1.91 (m, 2H), 1.94 (s, 1H), 3.46 (t, J=6.1 Hz, 2H), 4.15 (t, J=7.1 Hz, 2H), 4.48 (s, 2H), 7.26 (m, 2H), 7.31 (m, 6H), 7.65 (s, 1H), 8.40 (m, 1H); MS (DCI/NH$_3$) m/z 418 (M+H)$^+$; Anal. Calculated for C$_{28}$H$_{35}$NO$_2$: C, 80.54; H, 8.45; N, 3.35. Found: C, 80.22; H, 8.67; N, 3.30.

EXAMPLE 42

[1-(5-hydroxypentyl)-1H-indol-3-yl](2,2,3,3-tetramethylcyclopropyl)methanone

To the product of Example 41B (0.29 g, 0.69 mmol) in 40 mL ethanol (200 proof) was added 200 mg of Pd/C (10 wt % palladium on activated carbon, Aldrich). This mixture was stirred under 1 atm of H$_2$ (balloon) for 16 h after which time the reaction mixture was degassed three times with a N$_2$ back-flush. The mixture was then filtered, concentrated under reduced pressure and purified via flash column chromatography (SiO$_2$, 50% ethyl acetate:hexanes) to give 0.16 g of the title compound (0.47 mmol, 68% yield). 1H NMR (CDCl$_3$, 300 MHz) 1.31 (s, 6H), 1.35 (s, 6H), 1.47 (m, 2H), 1.62 (m, 2H), 1.94 (m, 2H), 3.65 (t, J=6.4 Hz, 2H), 4.17 (t, J=7.1 Hz, 2H), 7.26 (m, 2H), 7.34 (m, 1H), 7.66 (s, 1H), 8.40 (m, 1H); MS (DCI/NH$_3$) m/z 328 (M+H)$^+$; Anal. Calculated for C$_{21}$H$_{29}$NO$_2$.0.5H$_2$O: C, 74.96; H, 8.99; N, 4.16. Found: C, 74.93; H, 9.06; N, 4.16.

EXAMPLE 44

[1-(3-methoxypropyl)-1H-indol-3-yl](2,2,3,3-tetramethylcyclopropyl)methanone

To a solution of the major product of Example 1B (0.15 g, 0.62 mmol) in 10 mL DMF at 0° C. was added NaH (60% dispersal in mineral oil, 0.10 g, 2.6 mmol). This mixture was warmed to ambient temperature and allowed to stir for 1 h. The solution was again cooled to 0° C. and 1-bromo-3-methoxypropane (Matrix Scientific, 0.19 mg, 1.2 mmol) was added. The reaction mixture was warmed to 45° C. at which temperature the reaction was allowed to stir for 4 h. The mixture was cooled to ambient temperature, quenched with 10 mL saturated, aqueous $NH_4Cl$ and ice. The layers were separated and the aqueous layer was extracted with 3×10 mL ethyl acetate. The combined organics were dried over anhydrous $Na_2SO_4$, filtered, concentrated and purified via flash column chromatography ($SiO_2$, 30% ethyl acetate:hexanes) to give 0.12 g of the title compound (0.38 mmol, 62% yield). $^1H$ NMR ($CDCl_3$, 300 MHz) δ 1.30 (s, 6H), 1.35 (s, 6H), 1.94 (s, 1H), 2.11 (m, 2H), 3.31 (t, J=5.8 Hz, 2H), 3.35 (s, 3H), 4.30 (t, J=6.8 Hz, 2H), 7.27 (m, 2H), 7.37 (m, 1H), 7.67 (s, 1H), 8.41 (m, 1H); MS ($DCI/NH_3$) m/z 314 $(M+H)^+$; Anal. Calculated for $C_{20}H_{27}NO_2$: C, 76.64; H, 8.68; N, 4.47. Found: C, 76.49; H, 8.57; N, 4.22.

EXAMPLE 51

[1-(tetrahydro-2H-pyran-4-ylacetyl)-1H-indol-3-yl] (2,2,3,3-tetramethylcyclopropyl)methanone

EXAMPLE 51A tetrahydro-2H-pyran-4-ylacetyl chloride

A solution of tetrahydropyran-4-yl acetic acid (Combi-Blocks, Inc., 0.18 g, 1.2 mmol) in thionyl chloride (7 mL, 96 mmol, excess) was refluxed for 1 h then was cooled to ambient temperature and concentrated under reduced pressure. The residue was azeotroped twice with 10 mL of benzene to remove any remaining thionyl chloride. The resulting acid chloride was used without further purification.

EXAMPLE 51B

[1-(tetrahydro-2H-pyran-4-ylacetyl)-1H-indol-3-yl] (2,2,3,3-tetramethylcyclopropyl)methanone The major product of Example 1B (0.15 g, 0.62 mmol), the product of Example 51A (1.2 mmol) and NaH (60% dispersion in mineral oil, 75 mg, 3.1 mmol) in 5 mL DMF were processed as in Example 1D. Recrystallization with EtOAc and hexanes resulted in 0.16 g of the title compound (0.44 mmol, 70% yield). $^1H$ NMR ($CDCl_3$, 300 MHz) δ 1.35 (s, 6H), 1.36 (s, 6H), 1.51 (m, 2H), 1.82 (m, 2H), 2.00 (m, 2H), 2.36 (m, 1H), 2.93 (m, 2H), 3.49 (dt, J=11.9, 2.0 Hz, 2H), 4.01 (dd, J=11.9, 4.1 Hz, 2H), 7.39 (m, 2H), 7.97 (s, 1H), 8.32 (m, 1H), 8.41 (m, 1H); MS ($DCI/NH_3$) m/z 368 $(M+H)^+$; Anal. Calculated for $C_{23}H_{29}NO_3$: C, 75.17; H, 7.95; N, 3.81. Found: C, 75.03; H, 8.06; N, 3.84.

EXAMPLE 52 methyl 4-({3-[(2,2,3,3-tetramethylcyclopropyl)carbonyl]-1H-indol-1-yl}methyl)cyclohexanecarboxylate

EXAMPLE 52A methyl 4-(hydroxymethyl)cyclohexanecarboxylate

To 4-hydroxymethylcyclohexanecarboxylic acid (TCI-JP, 0.50 g, 3.2 mmol) in 10 mL $CH_3OH$ was added 0.50 mL concentrated $H_2SO_4$. This mixture was warmed to reflux and allowed to stir for 2 h. The reaction mixture was then cooled and $NH_4OH$ was added until the solution tested basic using pH paper. The mixture was then extracted with 3×5 mL ethyl acetate. The combined organic extracts were washed with saturated, aqueous NaCl then were dried over anhydrous $Na_2SO_4$, filtered, and concentrated under reduced pressure to give 0.45 g of the title compound (0.26 mmol, 83% yield). MS ($DCI/NH_3$) m/z 190 $(M+NH_4)^+$.

EXAMPLE 52B methyl 4-{[(methylsulfonyl)oxy] methyl}cyclohexanecarboxylate

The product of Example 52A (0.214 g, 1.2 mmol), triethylamine (0.52 mL, 3.73 mmol), and methanesulfonyl chloride (0.144 mL, 1.9 mmol) in 10 mL THF were processed as described in Example 1C to give the title compound that was used directly in the next reaction.

EXAMPLE 52C methyl 4-({3-[(2,2,3,3-tetramethylcyclopropyl)carbonyl]-1H-indol-1-yl}methyl)cyclohexanecarboxylate The major product of Example 1B (0.15 g, 0.62 mmol), the product of Example 52B (1.2 mmol) and NaH (60% dispersion in mineral oil, 50 mg, 1.2 mmol) in 10 mL DMF were processed as in Example 1D. Purification via column chromatography ($SiO_2$, 80% hexanes:20% EtOAc) gave 88 mg of the title compound (0.22 mmol, 36% yield). $^1H$ NMR ($CDCl_3$, 300 MHz) δ 1.31 (s, 6H), 1.32 (m, 2H), 1.34 (s, 6H), 1.55 (m, 4H), 1.93 (s, 1H), 2.07 (m, 3H), 2.62 (m, 1H), 3.72 (s, 3H), 4.02 (d, J=7.5 Hz, 2H), 7.25 (m, 2H), 7.32 (m, 1H), 7.60 (s, 1H), 8.40 (m, 1H); MS ($DCI/NH_3$) m/z 396 $(M+H)^+$; Anal. Calculated for $C_{25}H_{33}NO_3$: C, 75.91; H, 8.41; N, 3.54. Found: C, 75.63; H, 8.70; N, 3.33.

EXAMPLE 53

3-{3-[(2,2,3,3-tetramethylcyclopropyl)carbonyl]-1H-indol-1-yl}propanamide

The major product of Example 1B (0.20 g, 0.83 mmol), 3-chloropropionamide (Aldrich, 0.18 g, 1.7 mmol) and NaH (60% dispersion in mineral oil, 0.10 g, 2.5 mmol) in 5 mL DMF were processed as in Example 1D. Purification via column chromatography ($SiO_2$, 5% $CH_3OH$:95% EtOAc) afforded 26 mg of the title compound (0.082 mmol, 10% yield). $^1H$ NMR ($CDCl_3$, 300 MHz) δ 1.30 (s, 6H), 1.33 (s, 6H), 1.92 (s, 1H), 2.75 (t, J=6.4 Hz, 2H), 4.55 (t, J=6.4 Hz, 2H), 5.27 (br s, 2H), 7.27 (m, 2H), 7.33 (m, 1H), 7.75 (s, 1H), 8.43 (m, 1H); MS ($DCI/NH_3$) m/z 313 $(M+H)^+$; Anal. Calculated for $C_{19}H_{24}N_2O_2 \cdot 0.25H_2O$: C, 72.01; H, 7.79; N, 8.84. Found: C, 71.86; H, 7.41; N, 8.68.

EXAMPLE 54

6-{3-[(2,2,3,3-tetramethylcyclopropyl)carbonyl]-1H-indol-1-yl}hexan-2-one

The major product of Example 1B (0.20 g, 0.83 mmol), 2-chloro-2-hexanone (Aldrich, 0.22 g, 1.7 mmol) and NaH (60% dispersion in mineral oil, 0.10 g, 2.5 mmol) in 5 mL DMF were processed as in Example 1D. Purification via column chromatography ($SiO_2$, 50% hexanes:50% EtOAc) resulted in 43 mg of the title compound (0.13 mmol, 15% yield). $^1$H NMR ($CDCl_3$, 300 MHz) δ 1.31 (s, 6H), 1.35 (s, 6H), 1.65 (m, 4H), 1.89 (m, 2H), 1.95 (s, 1H), 2.11 (s, 3H), 2.46 (t, J=7.1 Hz, 2H), 4.17 (t, J=7.1 Hz, 2H), 7.27 (m, 2H), 7.33 (m, 1H), 7.67 (s, 1H), 8.40 (m, 1H); MS ($DCI/NH_3$) m/z 34 $(M+H)^+$; Anal. Calculated for $C_{22}H_{29}NO_2$: C, 77.84; H, 8.61; N, 4.13. Found: C, 77.57; H, 8.97; N, 3.84.

EXAMPLE 55

{1-[(2R)-2,3-dihydroxypropyl]-1H-indol-3-yl}(2,2,3,3-tetramethylcyclopropyl)methanone

EXAMPLE 55A

[(4S)-2,2-dimethyl-1,3-dioxolan-4-yl]methyl methanesulfonate

The (R)-(−)-2,2-dimethyl-1,3-dioxolane-4-methanol (Aldrich, 0.38 mL, 3.1 mmol), triethylamine (0.85 mL, 6.1 mmol), and methanesulfonyl chloride (0.31 mL, 4.1 mmol) in 10 mL THF were processed as described in Example 1C to give the title compound that was used directly in the next reaction.

EXAMPLE 55B

(1-{[(4R)-2,2-dimethyl-1,3-dioxolan-4-yl]methyl}-1H-indol-3-yl)(2,2,3,3-tetramethylcyclopropyl)methanone The major product of Example 1B (0.49 g, 2.0 mmol), the product of Example 55A (3.05 mmol) and NaH (60% dispersion in mineral oil, 0.24 g, 6.1 mmol) in 15 mL DMF were processed as in Example 1D to give 0.65 g of a 4.4:1 inseparable mixture of the title compound and the major product of Example 1B. This mixture was used without further purification. The mixture was isolated via column chromatography ($SiO_2$, 50% hexanes:50% EtOAc). Title compound: MS ($DCI/NH_3$) m/z 356 $(M+H)^+$; major product of Example 1B: MS ($DCI/NH_3$) m/z 242 $(M+H)^+$.

EXAMPLE 55C

{1-[(2R)-2,3-dihydroxypropyl]-1H-indol-3-yl}(2,2,3,3-tetramethylcyclopropyl)methanone To the mixture obtained from Example 55B in 10 mL THF was added 5 mL $H_2O$ followed by 1.7 g of p-toluenesulfonic acid monohydrate (9.1 mmol). This mixture was stirred at ambient temperature for 16 hours then was concentrated under reduced pressure. The residue was purified via column chromatography ($SiO_2$, 90% ethyl acetate:hexanes) to give 0.30 g of the title compound (0.95 mmol, 47% two-step yield). $^1$H NMR ($CDCl_3$, 300 MHz) δ 1.30 (s, 6H), 1.34 (s, 3H), 1.35 (s, 3H), 1.93 (s, 1H), 3.59 (dd, J=11.2, 5.4 Hz, 1H), 3.77 (dd, J=11.2, 3.7 Hz, 1H), 4.24 (m, 3H), 7.27 (m, 2H), 7.38 (m, 1H), 7.75 (s, 1H), 8.41 (m, 1H); MS ($DCI/NH_3$) m/z 316 $(M+H)^+$; Anal. Calculated for $C_{22}H_{29}NO_2 \cdot 0.1H_2O$: C, 71.94; H, 8.01; N, 4.42. Found: C, 71.65; H, 8.03; N, 4.10.

EXAMPLE 57

[2-methyl-1-(2-morpholin-4-ylethyl)-1H-indol-3-yl](2,2,3,3-tetramethylcyclopropyl)methanone hydrochloride

EXAMPLE 57A

(2-Methyl-1H-indol-3-yl)-(2,2,3,3-tetramethyl-cyclopropyl)-methanone

A mixture of 2-methylindole (0.75 g, 5.7 mmol), ethylmagnesium bromide (1.0 M solution in THF, 6.6 mL, 6.6 mmol), zinc chloride (1.0 M solution in $Et_2O$, 6.6 mL, 6.6 mmol) and the product of Example 1A (6.3 mmol) in 15 mL of dichloromethane was processed as described in Example 1B to provide the title compound (0.76 g, 3.0 mmol, 52% yield). MS ($DCI/NH_3$) m/z 256 $(M+H)^+$.

EXAMPLE 57B

[2-methyl-1-(2-morpholin-4-ylethyl)-1H-indol-3-yl](2,2,3,3-tetramethylcyclopropyl)methanone hydrochloride The product of Example 57A (0.22 g, 0.87 mmol), the product of Example 2A (1.8 mmol), and NaH (60% dispersion in mineral oil, 0.18 g, 4.4 mmol) in 8 mL of DMF were processed as described in Example 1D to provide the corresponding free base of the title compound (0.25 g, 0.68 mmol, 78% yield), which was then treated with 4 N HCl in dioxane (0.68 mmol, 0.17 mL) to afford the title compound (0.15 g, 0.36 mmol, 53% yield). $^1$H NMR (MeOH-$d_4$, 300 MHz) δ ppm 1.36 (s, 6H), 1.38 (s, 6H), 2.22 (s, 1H), 2.72 (s, 3H), 3.14-3.37 (m, 2H), 3.44-3.53 (m, 3H), 3.53-3.64 (m, 1H), 3.80-3.96 (m, 2H), 4.01-4.15 (m, 2H), 4.63-4.71 (m, 2H), 7.23 (dt, J=7.5, 1.4 Hz, 1H), 7.29 (dt, J=7.6, 1.4 Hz, 1H), 7.51-7.58 (m, 1H), 7.86-7.93 (m, 1H); MS ($DCI/NH_3$) m/z 369 $(M+H)^+$; Anal. Calculated for $C_{22}H_{29}NO_2 \cdot 1.25$ HCl: C, 66.71; H, 8.09; N, 6.76. Found: C, 66.68; H, 8.20; N, 6.71.

EXAMPLE 58

[4-amino-1-(2-morpholin-4-ylethyl)-1H-indol-3-yl](2,2,3,3-tetramethylcyclopropyl)methanone

EXAMPLE 58A

(4-Nitro-1H-indol-3-yl)-(2,2,3,3-tetramethyl-cyclopropyl)-methanone

A mixture of 4-nitroindole (1.0 g, 6.2 mmol), ethylmagnesium bromide (1.0 M in THF, 6.8 mL, 6.8 mmol), zinc chloride (1.0 M solution in $Et_2O$, 6.8 mL, 6.8 mmol) and the product of Example 1A (6.8 mmol) in 15 mL of dichloromethane was processed as described in Example 1B to provide the title compound (0.15 g, 0.53 mmol, 8% yield). MS ($DCI/NH_3$) m/z 287 $(M+H)^+$.

EXAMPLE 58B

[1-(2-morpholin-4-ylethyl)-4-nitro-1H-indol-3-yl](2,2,3,3-tetramethylcyclopropyl)methanone The product of Example 58A (0.15 g, 0.53 mmol), the product of Example 2A (0.79 mmol) and NaH (60% dispersion in mineral oil, 63 mg, 1.6 mmol) in 10 mL of DMF 10 mL were processed as described in Example 1D to provide the title compound (0.14 g, 0.35 mmol, 66% yield). $^1$H NMR (CDCl$_3$, 300 MHz) δ ppm 1.28 (s, 6H), 1.35 (s, 6H), 1.79 (s, 1H), 2.44-2.55 (m, 4H), 2.78 (t, J=5.9 Hz, 2H), 3.63-3.77 (m, 4H), 4.29 (t, J=6.1 Hz, 2H), 7.33 (t, J=8.0 Hz, 1H), 7.56-7.64 (m, 1H), 7.73 (d, J=7.8 Hz, 1H), 7.77 (s, 1H); MS (DCI/NH$_3$) m/z 400 (M+H)$^+$; Anal. Calculated for C$_{22}$H$_{29}$N$_3$O$_4$: C, 66.14; H, 7.32; N, 10.52. Found: C, 65.80; H, 7.34; N, 10.49.

EXAMPLE 59

[4-amino-1-(2-morpholin-4-ylethyl)-1H-indol-3-yl](2,2,3,3-tetramethylcyclopropyl)methanone A mixture of the product of Example 58B (0.11 g, 0.28 mmol) and 20 mg of Pd/C (10 weight % palladium on activated carbon) in 10 mL of EtOH was stirred under 1 atmosphere of H$_2$ (balloon) for 4 hours. The system was purged with an inert nitrogen atmosphere. The mixture was filtered, concentrated under reduced pressure and purified via column chromatography (SiO$_2$, 10% methanol in dichloromethane containing 1% NH$_4$OH) to afford a quantitative yield of the title compound. $^1$H NMR (CDCl$_3$, 300 MHz) δ ppm 11.30 (s, 12H), 1.93 (s, 1H), 2.49-2.66 (m, 4H), 2.75-2.95 (m, 2H), 3.69-3.83 (m, 4H), 4.17-4.40 (m, 2H), 6.40 (d, J=7.1 Hz, 1H), 6.59 (d, J=7.8 Hz, 1H), 7.06 (t, J=8.0 Hz, 1H), 7.74 (s, 1H); MS (DCI/NH$_3$) m/z 370 (M+H)$^+$; Anal. Calculated for C$_{22}$H$_{31}$N$_3$O$_2$: C, 71.51; H, 8.46; N, 11.37. Found: C, 71.49; H, 8.77; N, 11.14.

EXAMPLE 60 cycloheptyl[1-(2-morpholin-4-ylethyl)-1H-indol-3-yl]methanone

EXAMPLE 60A cycloheptyl-(1H-indol-3-yl)-methanone

Cycloheptane carboxylic acid (1.5 g, 10 mmol) in 5 mL of thionyl chloride was processed as described in Example 1A to provide the corresponding acid chloride. The freshly prepared acid chloride (10 mmol), indole (1.2 g, 10 mmol), ethylmagnesium bromide (1.0 M solution in THF, 11 mL, 11 mmol), and zinc chloride (1.0 M solution in Et$_2$O, 11 mL, 11 mmol) in 20 mL of dichloromethane were processed as described in Example 1B to provide the title compound (0.36 g, 1.5 mmol, 15% yield). MS (DCI/NH$_3$) m/z 242 (M+H)$^+$.

EXAMPLE 60B cycloheptyl[1-(2-morpholin-4-ylethyl)-1H-indol-3-yl]methanone

The product of Example 60A (0.10 g, 0.42 mmol), NaH (60% dispersion in mineral oil, 50 mg, 1.2 mmol) and the product of Example 2A (0.17 g, 0.83 mmol) in 8 mL of DMF were processed as described in Example 1D to provide the title compound (78 mg, 0.22 mmol, 52% yield). $^1$H NMR (CDCl$_3$, 300 MHz) δ ppm 1.58-1.70 (m, 6H), 1.75-1.91 (m, 4H), 1.92-2.05 (m, 2H), 2.45-2.57 (m, 4H), 2.73-2.84 (m, 2H), 3.13-3.25 (m, 1H), 3.66-3.75 (m, 4H), 4.21-4.31 (m, 2H), 7.27-7.41 (m, 3H), 7.86 (s, 1H), 8.37-8.45 (m, 1H); MS (DCI/NH$_3$) m/z 355 (M+H)$^+$; Anal. Calculated for C$_{22}$H$_{30}$N$_2$O$_2$.0.2H$_2$O: C, 73.79; H, 8.56; N, 7.82. Found: C, 73.76; H, 8.68; N, 7.77.

EXAMPLE 61

(2,2,3,3-tetrafluoro-1-methylcyclobutyl)[1-(tetrahydro-2H-pyran-4-ylmethyl)-1H-indol-3-yl]methanone

EXAMPLE 61A (1H-Indol-3-yl)-(2,2,3,3-tetrafluoro-1-methylcyclobutyl)methanone A mixture of 2,2,3,3-tetrafluoro-1-(methyl)-cyclobutanecarbonyl chloride (ABCR, 1.0 g, 4.9 mmol), indole (0.57 g, 4.9 mmol), ethylmagnesium bromide (1.0 M solution in THF, 5.4 ml, 5.4 mmol) and zinc chloride (1.0 M solution in Et$_2$O, 5.4 mL, 5.4 mmol) in 50 mL of dichloromethane was processed as described in Example 1B to provide the title compound (0.40 g, 1.4 mmol, 29% yield). MS (DCI/NH$_3$) m/z 286 (M+H)$^+$.

EXAMPLE 61B (2,2,3,3-tetrafluoro-1-methylcyclobutyl)[1-(tetrahydro-2H-pyran-4-ylmethyl)-1H-indol-3-yl]methanone The product of Example 61A (0.15 g, 0.53 mmol), the product of Example 18A (1.1 mmol), and NaH (60% dispersion in mineral oil, 84 mg, 2.1 mmol) in 10 mL of DMF were processed as described in Example 1D to provide the title compound (35 mg, 0.09 mmol, 17% yield). $^1$H NMR (CDCl$_3$, 300 MHz) δ ppm 1.35-1.59 (m, 5H), 1.71 (s, 3H), 2.06-2.23 (m, 1H), 2.27-2.44 (m, 1H), 3.25-3.42 (m, 2H), 3.93-4.03 (m, 2H), 4.05-4.19 (m, 2H), 7.31-7.41 (m, 3H), 7.67 (d, J=1.7 Hz, 1H), 8.37-8.49 (m, 1H); MS (DCI/NH$_3$) m/z 384 (M+H)$^+$; Anal. Calculated for C$_{20}$H$_{21}$FNO$_2$: C, 62.66; H, 5.52; N, 3.65. Found: C, 63.00; H, 5.83; N, 3.66.

EXAMPLE 62 cyclopentyl[1-(tetrahydro-2H-pyran-4-ylmethyl)-1H-indol-3-yl]methanone

EXAMPLE 62A cyclopentyl-(1H-indol-3-yl)-methanone

Cyclopentane carboxylic acid (1.1 g, 10 mmol) in 5 mL of thionyl chloride was processed as described in Example 1A to provide the corresponding acid chloride. The freshly prepared acid chloride (10 mmol), indole (1.2 g, 10 mmol), ethylmagnesium bromide (1.0 M solution in THF, 11 mL, 11 mmol), and zinc chloride (1.0 M solution in Et$_2$O, 11 mL, 11 mmol) in 30 mL of dichloromethane were processed as described in Example 1B to provide the title compound (0.51 g, 2.4 mmol, 24% yield). MS (DCI/NH$_3$) m/z 214 (M+H)$^+$.

EXAMPLE 62B cyclopentyl[1-(tetrahydro-2H-pyran-4-ylmethyl)-1H-indol-3-yl]methanone The product of Example 62A (0.10 g, 0.47 mmol), the product of Example 18A (0.94 mmol), and NaH (60% dispersion in mineral oil, 57 mg, 1.4 mmol) in 10 mL of DMF were processed as described in Example 1D to provide the title compound (45 mg, 0.14 mmol, 31% yield). $^1$H NMR (CDCl$_3$, 300 MHz) δ ppm 1.34-1.48 (m, 2H), 1.48-1.53 (m, 2H), 1.62-1.72 (m, 2H), 1.73-1.85 (m, 2H), 1.87-2.07 (m, 4H), 2.08-2.22 (m, 1H), 3.33 (dt, J=11.6, 2.5 Hz, 2H), 3.45-3.61 (m, 1H), 3.92-4.03 (m, 2H), 4.05 (d, J=7.1 Hz, 2H), 7.27-7.39 (m, 3H), 7.72 (s, 1H), 8.40-8.47 (m, 1H); MS (DCI/NH$_3$) m/z 312 (M+H)$^+$; Anal. Calculated for C$_{20}$H$_{25}$NO$_2$.0.2H$_2$O: C, 76.25; H, 8.13; N, 4.45. Found: C, 76.29; H, 8.09; N, 4.56.

EXAMPLE 63 cyclopentyl[1-(2-morpholin-4-ylethyl)-1H-indol-3-yl]methanone

The product of Example 62A (0.10 g, 0.47 mmol), NaH (60% dispersion in mineral oil, 57 mg, 1.4 mmol) and the product of Example 2A (0.94 mmol) in 10 mL of DMF were processed as described in Example 1D to provide the title compound (15 mg, 0.04 mmol, 4% yield). $^1$H NMR (CDCl$_3$, 300 MHz) δ ppm 1.61-1.72 (m, 2H), 1.72-1.84 (m, 2H), 1.86-2.08 (m, 4H), 2.41-2.57 (m, 4H), 2.73-2.85 (m, 2H), 3.45-3.61 (m, 1H), 3.62-3.79 (m, 4H), 4.18-4.36 (m, 2H), 7.27-7.43 (m, 3H), 8.02 (s, 1H), 8.38-8.49 (m, 1H); MS (DCI/NH$_3$) m/z 327 (M+H)$^+$; Anal. Calculated for C$_{20}$H$_{26}$N$_2$O$_2$.0.2H$_2$O: C, 72.78; H, 8.06; N, 8.49. Found: C, 72.78; H, 7.95; N, 8.54.

EXAMPLE 64

4-{3-[(2,2,3,3-tetramethylcyclopropyl)carbonyl]-1H-indol-1-yl}butyl acetate

To a solution of the product of Example 24A (0.11 g, 0.35 mmol) in 2 mL of THF at ambient temperature was added pyridine (57 μL, 0.70 mmol) followed by acetic anhydride (50 μL, 0.53 mmol). The mixture was stirred at ambient temperature for 16 hours then was quenched with 2 mL H$_2$O. The mixture was diluted with 5 mL of EtOAc and the layers were separated. The aqueous layer was extracted 3×3 mL of EtOAc and the combined organic extracts were dried over anhydrous Na$_2$SO$_4$, filtered, concentrated under reduced pressure and purified via column chromatography (SiO$_2$, 70% hexanes in EtOAc) to provide the title compound (85 mg, 0.24 mmol, 68% yield). $^1$H NMR (CDCl$_3$, 300 MHz) δ ppm 1.31 (s, 6H), 1.35 (s, 6H), 1.62-1.76 (m, 2H), 1.92-2.01 (m, 2H), 1.95 (s, 1H), 2.04 (s, 3H), 4.10 (t, J=6.4 Hz, 2H), 4.20 (t, J=7.1 Hz, 2H), 7.24-7.37 (m, 3H), 7.66 (s, 1H), 8.37-8.43 (m, 1H); MS (DCI/NH$_3$) m/z 356 (M+H)$^+$; Anal. Calculated for C$_{22}$H$_{29}$NO$_2$.0.1C$_6$H$_{14}$.0.15C$_4$H$_8$O$_2$: C, 73.85; H, 8.44; N, 3.71. Found: C, 73.58; H, 8.70; N, 3.61.

EXAMPLE 65

(2E)-4-oxo-4-(4-{3-[(2,2,3,3-tetramethylcyclopropyl)carbonyl]-1H-indol-1-yl}butoxy)but-2-enoic acid To a solution of the product of Example 24A (0.71 g, 2.3 mmol) in 140 mL Et$_2$O at ambient temperature was added triethylamine (0.32 mL, 2.3 mL) followed by fumaryl chloride (0.26 mL, 2.4 mmol). The mixture was stirred at ambient temperature for 30 minutes and then filtered. The filtrate was concentrated under reduced pressure. The residue was dissolved in 10 mL of EtOAc and washed 4×3 mL of H$_2$O and 1×3 mL of brine and the organic layer was dried over anhydrous Na$_2$SO$_4$, filtered, concentrated under reduced pressure and purified via column chromatography (9% CH$_3$OH:1% AcOH:90% EtOAc) to provide the title compound (0.42 g, 1.0 mmol, 44% yield). $^1$H NMR (CDCl$_3$, 300 MHz) δ ppm 1.31 (s, 6H), 1.35 (s, 6H), 1.69-1.82 (m, 2H), 1.96 (s, 1H), 1.97-2.07 (m, 2H), 4.16-4.32 (m, 4H), 6.88 (d, J=6.4 Hz, 2H), 7.25-7.38 (m, 3H), 7.67 (s, 1H), 8.33-8.43 (m, 1H); MS (DCI/NH$_3$) m/z 412 (M+H)$^+$; Anal. Calculated for C$_{24}$H$_{29}$NO$_5$: C, 70.05; H, 7.10; N, 3.40. Found: C, 69.80; H, 7.40; N, 3.25.

EXAMPLE 66

[6-chloro-1-(tetrahydro-2H-pyran-4-ylmethyl)-1H-indol-3-yl](2,2,3,3-tetramethylcyclopropyl)methanone

EXAMPLE 66A (6-chloro-1H-indol-3-yl)-(2,2,3,3-tetramethyl-cyclopropyl)-methanone A mixture of 6-chloroindole (0.38 g, 2.5 mmol), ethylmagnesium bromide (1.0 M solution in THF, 3.0 mL, 3.0 mmol), zinc chloride (1.0 M solution in Et$_2$O, 3.0 mL, 3.0 mmol) and the product of Example 1A (3.0 mmol) in 10 mL of dichloromethane was processed as described in Example 1B to provide the title compound (0.23 g, 0.83 mmol, 34% yield). MS (DCI/NH$_3$) m/z 276 (M+H)$^+$.

EXAMPLE 66B

[6-chloro-1-(tetrahydro-2H-pyran-4-ylmethyl)-1H-indol-3-yl](2,2,3,3-tetramethylcyclopropyl)methanone The product of Example 66A (0.23 g, 0.83 mmol), the product of Example 18A (1.4 mmol), and NaH (60% dispersion in mineral oil, 0.10 g, 2.5 mmol) in 10 mL of DMF were processed as described in Example 1D to provide the title compound (85 mg, 0.22 mmol, 27% yield). $^1$H NMR (CDCl$_3$, 300 MHz) δ ppm 1.30 (s, 6H), 1.34 (s, 6H), 1.38-1.61 (m, 4H), 1.89 (s, 1H), 2.06-2.22 (m, 1H), 3.35 (dt, J=11.6, 2.5 Hz, 2H), 3.94-4.03 (m, 4H), 7.22 (dd, J=8.6, 1.9 Hz, 1H), 7.31 (d, J=1.7 Hz, 1H), 7.58 (s, 1H), 8.33 (d, J=8.8 Hz, 1H); MS (DCI/NH$_3$) m/z 374 (M+H)$^+$; Anal. Calculated for C$_{22}$H$_{28}$ClNO$_2$.0.2H$_2$O.0.2C$_6$H$_{14}$: C, 70.59; H, 7.97; N, 3.55. Found: C, 70.48; H, 8.35; N, 3.79.

EXAMPLE 67

4-({3-[(2,2,3,3-tetramethylcyclopropyl)carbonyl]-1H-indol-1-yl}methyl)phenyl acetate The major product of Example 1B (0.50 g, 2.1 mmol), 4-(chloromethyl)phenyl acetate (0.35 mL, 2.3 mmol) and NaH (60% dispersion in mineral oil, 0.17 g, 4.1 mmol) in 10 mL of DMF were processed as described in Example 1D to provide the title compound (67 mg, 0.17 mmol, 8% yield) and the product of Example 68 (0.22 g, 0.60 mmol, 31% yield). $^1$H NMR (CDCl$_3$, 300 MHz) δ ppm 1.28 (s, 6H), 1.35 (s, 6H), 1.93 (s, 1H), 2.29 (s, 3H), 5.36 (s, 2H), 7.02-7.10 (m, 2H), 7.11-7.19 (m, 2H), 7.22-7.33 (m, 3H), 7.68 (s, 1H), 8.39-8.47 (m, 1H); MS (DCI/NH$_3$) m/z 390 (M+H)$^+$; Anal. Calculated for C$_{25}$H$_{27}$NO$_3$: C, 77.09; H, 6.99; N, 3.60. Found: C, 76.87; H, 7.20; N, 3.35.

EXAMPLE 68

[1-(4-hydroxybenzyl)-1H-indol-3-yl](2,2,3,3-tetramethylcyclopropyl)methanone

The title compound was obtained by the method described in Example 67. $^1$H NMR (CDCl$_3$, 300 MHz) δ ppm 1.27 (s, 6H), 1.34 (s, 6H), 1.92 (s, 1H), 5.27 (s, 2H), 6.75-6.84 (m, 2H), 7.01-7.10 (m, 2H), 7.18-7.33 (m, 3H), 7.66 (s, 1H), 8.36-8.45 (m, 1H); MS (DCI/NH$_3$) m/z 348 (M+H)$^+$; Anal. Calculated for C$_{23}$H$_{25}$NO$_2$: C, 79.51; H, 7.25; N, 4.03. Found: C, 79.43; H, 7.40; N, 3.81.

EXAMPLE 69

[6-(benzyloxy)-1-(tetrahydro-2H-pyran-4-ylmethyl)-1H-indol-3-yl](2,2,3,3-tetramethylcyclopropyl) methanone

EXAMPLE 69A (6-Benzyloxy-1H-indol-3-yl)-(2,2,3,3-tetramethylcyclopropyl)-methanone A mixture of 6-benzyloxyindole (Lancaster, 2.0 g, 9.0 mmol), ethylmagnesium bromide (1.0 M solution in THF, 11 mL, 11 mmol), zinc chloride (1.0 M solution in Et$_2$O, 11 mL, 11 mmol) and the product of Example 1A (13.4 mmol) in 30 mL of dichloromethane was processed as described in Example 1B to provide the title compound (2.0 g, 5.8 mmol, 64% yield). MS (DCI/NH$_3$) m/z 348 (M+H)$^+$.

EXAMPLE 69B

[6-(benzyloxy)-1-(tetrahydro-2H-pyran-4-ylmethyl)-1H-indol-3-yl](2,2,3,3-tetramethylcyclopropyl) methanone The product of Example 69A (0.90 g, 2.6 mmol), the product of Example 18A (4.4 mmol), and NaH (60% dispersion in mineral oil, 0.31 g, 7.8 mmol) in 15 mL of DMF were processed as described in Example 1D to provide the title compound (0.87 g, 2.0 mmol, 75% yield). $^1$H NMR (CDCl$_3$, 300 MHz) δ ppm 1.29 (s, 6H), 1.34 (s, 6H), 1.34-1.51 (m, 4H), 1.90 (s, 1H), 1.98-2.12 (m, 1H), 3.30 (dt, J=11.7, 2.4 Hz, 2H), 3.91-4.00 (m, 2H), 3.93 (d, J=7.1 Hz, 2H), 5.15 (s, 2H), 6.81 (d, J=2.4 Hz, 1H), 7.01 (dd, J=8.8, 2.0 Hz, 1H), 7.29-7.43 (m, 3H), 7.43-7.49 (m, 2H), 7.50 (s, 1H), 8.28 (d, J=8.8 Hz, 1H); MS (DCI/NH$_3$) m/z 446 (M+H)$^+$; Anal. Calculated for C$_{29}$H$_{35}$NO$_3$: C, 78.17; H, 7.92; N, 3.14. Found: C, 78.03; H, 8.07; N, 3.16.

EXAMPLE 70

[6-hydroxy-1-(tetrahydro-2H-pyran-4-ylmethyl)-1H-indol-3-yl](2,2,3,3-tetramethylcyclopropyl)methanone The product of Example 69B (0.64 g, 1.4 mmol) and Pd/C (10 wt % palladium on activated carbon, 100 mg) in 20 mL of EtOH and 10 mL of EtOAc was stirred under 1 atmosphere of H$_2$ (balloon) for 16 hours. The system was purged with an inert nitrogen atmosphere. The mixture was filtered, concentrated under reduced pressure and purified via column chromatography (SiO$_2$, 50% hexanes in EtOAc) to provide the title compound (0.48 g, 1.35 mmol, 94% yield). $^1$H NMR (CDCl$_3$, 300 MHz) δ ppm 1.29 (s, 6H), 1.34 (s, 6H), 1.38-1.58 (m, 4H), 1.89 (s, 1H), 2.06-2.21 (m, 1H), 3.33 (dt, J=11.8, 2.2 Hz, 2H), 3.95 (d, J=7.1 Hz, 2H), 3.97-4.04 (m, 2H), 4.67 (s, 1H), 6.76-6.81 (m, 2H), 7.50 (s, 1H), 8.25 (d, J=9.2 Hz, 1H); MS (DCI/NH$_3$) m/z 356 (M+H)$^+$; Anal. Calculated for C$_{22}$H$_{29}$NO$_3$: C, 74.33; H, 8.22; N, 3.94. Found: C, 74.38; H, 7.96; N, 3.86.

EXAMPLE 71

(2E)-4-oxo-4-({1-(tetrahydro-2H-pyran-4-ylmethyl)-3-[(2,2,3,3-tetramethylcyclopropyl)carbonyl]-1H-indol-6-yl}oxy)but-2-enoic acid The product of Example 70 (0.33 g, 0.93 mmol), furmaryl chloride (0.11 mL, 0.98 mmol) and triethylamine (0.13 mL, 0.93 mmol) in 60 mL Et$_2$O and 15 mL of THF were processed as described in Example 65 to provide the title compound (0.36 g, 0.78 mmol, 84% yield). $^1$H NMR (CDCl$_3$, 300 MHz) δ ppm 1.31 (s, 6H), 1.34 (s, 6H), 1.37-1.60 (m, 4H), 1.92 (s, 1H), 2.08-2.22 (m, 1H), 3.35 (dt, J=11.6, 2.2 Hz, 2H), 3.94-4.05 (m, 2H), 4.01 (d, J=7.1 Hz, 2H), 7.02-7.08 (m, 1H), 7.12 (d, J=14.2 Hz, 2H), 7.17-7.20 (m, 1H), 7.63 (s, 1H), 8.42 (d, J=8.5 Hz, 1H); MS (DCI/NH$_3$) m/z 454 (M+H)$^+$; Anal. Calculated for C$_{26}$H$_{31}$NO$_6$: C, 68.86; H, 6.89; N, 3.09. Found: C, 68.70; H, 6.66; N, 3.33.

EXAMPLE 72

[6-methoxy-1-(tetrahydro-2H-pyran-4-ylmethyl)-1H-indol-3-yl](2,2,3,3-tetramethylcyclopropyl) methanone To a solution of the product of Example 70 (0.15 g, 0.42 mmol) in 10 mL of THF was added NaH (60% dispersion in mineral oil, 51 mg, 1.3 mmol) followed by CH$_3$I (39 μL, 0.63 mmol). The mixture was stirred at ambient temperature for 18 hours then was quenched with 3 mL of saturated aqueous NH$_4$Cl. The mixture was diluted with 10 mL of EtOAc, the layers were separated and the aqueous layer was extracted with 3×3 mL of EtOAc. The combined organic extracts were dried over anhydrous Na$_2$SO$_4$, filtered, concentrated under reduced pressure and purified via column chromatography (SiO$_2$, 30% hexanes in EtOAc) to provide the title compound (86 mg, 0.23 mmol, 55% yield). $^1$H NMR (CDCl$_3$, 300 MHz) δ ppm 1.30 (s, 6H), 1.34 (s, 6H), 1.34-1.63 (m, 4H), 1.90 (s, 1H), 2.05-2.24 (m, 1H), 3.34 (dt, J=11.7, 2.4 Hz, 2H), 3.88 (s, 3H), 3.94-4.02 (m, 2H), 3.97 (d, J=7.5 Hz, 2H), 6.77 (d, J=2.4 Hz, 1H), 6.92 (dd, J=8.8, 2.0 Hz, 1H), 7.51 (s, 1H), 8.28 (d, J=8.8 Hz, 1H); MS (DCI/NH$_3$) m/z 370 (M+H)$^+$; Anal. Calculated for C$_{23}$H$_{31}$NO$_3$: C, 74.76; H, 8.46; N, 3.79. Found: C, 74.53; H, 8.44; N, 3.49.

EXAMPLE 73

{1-[(2R)-tetrahydrofuran-2-ylmethyl]-1H-indol-3-yl}(2,2,3,3-tetramethylcyclopropyl)methanone (R)-(−)-Tetrahydrofurfuryl alcohol (Lancaster, 0.33 mL, 3.4 mmol), methanesulfonyl chloride (0.35 mL, 4.5 mmol), and triethylamine (0.78 mL, 5.6 mmol) in 10 mL of THF were processed as described in Example 1C to provide the corresponding mesylate. The major product of Example 1B (0.27 g, 1.1 mmol), the freshly prepared mesylate (3.4 mmol) and NaH (60% dispersion in mineral oil, 0.13 g, 3.4 mmol) in 10 mL of DMF were processed as described in Example 1D to provide the title compound (0.28 g, 0.86 mmol, 77% yield). $^1$H NMR (CDCl$_3$, 300 MHz) δ ppm 1.30 (s, 6H), 1.33 (s, 3H), 1.35 (s, 3H), 1.46-1.62 (m, 1H), 1.69-1.92 (m, 2H), 1.93-2.07 (m, 1H), 1.95 (s, 1H), 3.72-3.91 (m, 2H), 4.13-4.34 (m, 3H), 7.22-7.29 (m, 2H), 7.32-7.39 (m, 1H), 7.78 (s, 1H), 8.38-8.45 (m, 1H); MS (DCI/NH$_3$) m/z 326 (M+H)$^+$; Anal. Calculated for C$_{21}$H$_{27}$NO$_2$.0.1H$_2$O: C, 77.50; H, 8.36; N, 4.30. Found: C, 77.21; H, 8.34; N, 4.18.

EXAMPLE 74

[5-(benzyloxy)-1-(tetrahydro-2H-pyran-4-ylmethyl)-1H-indol-3-yl](2,2,3,3-tetramethylcyclopropyl) methanone

EXAMPLE 74A (5-Benzyloxy-1H-indol-3-yl)-(2,2,3,3-tetramethyl-cyclopropyl)-methanone A mixture of 5-benzyloxyindole (1.2 g, 5.6 mmol), ethylmagnesium bromide (1.0 M solution in THF, 6.1 mL, 6.1 mmol), zinc chloride (1.0 M solution in Et$_2$O, 6.1 mL, 6.1 mmol) and the product of Example 1A (5.6 mmol) in 25 mL of dichloromethane was processed as described in Example 1B to provide the title compound (0.53 g, 1.5 mmol, 27% yield). MS (DCI/NH$_3$) m/z 348 (M+H)$^+$.

EXAMPLE 74B

[5-(benzyloxy)-1-(tetrahydro-2H-pyran-4-ylmethyl)-1H-indol-3-yl](2,2,3,3-tetramethylcyclopropyl) methanone The product of Example 74A (0.52 g, 1.5 mmol), the product of Example 18A (2.6 mmol), and NaH (60% dispersion in mineral oil, 0.18 g, 4.5 mmol) in 12 mL of DMF were processed as described in Example 1D to provide the title compound (0.45 g, 1.0 mmol, 67% yield). $^1$H NMR (MeOH-d$_4$, 300 MHz) δ ppm 1.31-1.31 (m, 6H), 1.33 (s, 6H), 1.34-1.52 (m, 4H), 2.10(s, 1H), 2.13-2.27(m, 1H), 3.34-3.48(m, 2H), 3.88-3.99(m, 2H), 4.12 (d, J=7.5 Hz, 2H), 5.12 (s, 2H), 6.97 (dd, J=8.8, 2.4 Hz, 1H), 7.28-7.43 (m, 4H), 7.44-7.51 (m, 2H), 7.92 (d, J=2.4 Hz, 1H), 8.01 (s, 1H); MS (DCI/NH$_3$) m/z 446 (M+H)$^+$; Anal. Calculated for C$_{29}$H$_{35}$NO$_3$.0.8H$_2$O: C, 75.72; Hp 8.02; N, 3.04. Found: C, 75.90; H, 7.78; N, 2.85.

EXAMPLE 75

(1-benzyl-1H-indol-3-yl)(2,2,3,3-tetramethylcyclopropyl)methanone

The major product of Example 1B (0.15 g, 0.62 mmol), benzyl bromide (0.15 mL, 1.2 mmol) and NaH (60% dispersion in mineral oil, 0.12 g, 3.1 mmol) in 12 mL of DMF were processed as described in Example 1D to provide the title compound (0.19 g, 0.56 mmol, 90% yield). $^1$H NMR (MeOH-d$_4$, 300 MHz) δ ppm 1.31 (s, 6H), 1.32 (s, 6H), 2.13 (s, 1H), 5.47 (s, 2H), 7.15-7.24 (m, 3H), 7.25-7.40 (m, 5H), 8.12 (s, 1H), 8.21-8.31 (m, 1H); MS (DCI/NH$_3$) m/z 332 (M+H)$^+$; Anal. Calculated for C$_{23}$H$_{25}$NO: C, 83.34; H, 7.60; N, 4.23. Found: C, 83.22; H, 7.65; N, 4.02.

EXAMPLE 76

[7-(benzyloxy)-1-(tetrahydro-2H-pyran-4-ylmethyl)-1H-indol-3-yl](2,2,3,3-tetramethylcyclopropyl) methanone

EXAMPLE 76A (7-Benzyloxy-1H-indol-3-yl)-(2,2,3,3-tetramethyl-cyclopropyl)-methanone A mixture of 7-benzyloxyindole (Matrix Scientific, 2.0 g, 9.0 mmol), ethylmagnesium bromide (1.0 M solution in THF, 11 mL, 11 mmol), zinc chloride (1.0 M solution in Et$_2$O, 11 mL, 11 mmol) and the product of Example 1A (13.4 mmol) in 30 mL of dichloromethane was processed as described in Example 1B to provide the title compound (1.3 g, 3.6 mmol, 40% yield). MS (DCI/NH$_3$) m/z 348 (M+H)$^+$.

EXAMPLE 76B

[7-(benzyloxy)-1-(tetrahydro-2H-pyran-4-ylmethyl)-1H-indol-3-yl](2,2,3,3-tetramethylcyclopropyl) methanone The product of Example 76A (1.3 g, 3.6 mmol), the product of Example 18A (6.1 mmol), and NaH (60% dispersion in mineral oil, 0.43 g, 11 mmol) in 20 mL of DMF were processed as described in Example 1D to provide the title compound (1.2 g, 2.7 mmol, 75% yield). $^1$H NMR (CDCl$_3$, 300 MHz) δ ppm 1.02-1.23 (m, 4H), 1.29 (s, 6H), 1.33 (s, 6H), 1.89 (s, 1H), 1.93-2.09 (m, 1H), 3.13 (dt, J=11.6, 2.5 Hz, 2H), 3.77-3.88 (m, 2H), 4.09 (d, J=7.1 Hz, 2H), 5.13 (s, 2H), 6.82 (d, J=7.8 Hz, 1H), 7.16 (t, J=7.8 Hz, 1H), 7.34-7.50 (m, 5H), 7.44 (s, 1H), 8.03 (dd, J=8.0, 0.8 Hz, 1H); MS (DCI/NH$_3$) m/z 446 (M+H)$^+$; Anal. Calculated for C$_{29}$H$_{35}$NO$_3$.0.2H$_2$O: C, 77.54; H, 7.94; N, 3.12. Found: C, 77.44; H, 7.81; N, 3.04.

EXAMPLE 77

[1-(4-methoxybenzyl)-1H-indol-3-yl](2,2,3,3-tetramethylcyclopropyl)methanone

The product of Example 68 (0.11 g, 0.32 mmol), NaH (60% dispersion in mineral oil, 38 mg, 0.95 mmol) and iodomethane (50 μL, 0.79 mmol) in 3 mL of THF were processed as described in Example 72 to provide the title compound (70 mg, 0.19 mmol, 61% yield). $^1$H NMR (CDCl$_3$, 300 MHz) δ ppm 1.27 (s, 6H), 1.34 (s, 6H), 1.92 (s, 1H), 3.79 (s, 3H), 5.29 (s, 2H), 6.81-6.92 (m, 2H), 7.07-7.15 (m, 2H), 7.18-7.33 (m, 3H), 7.66 (s, 1H), 8.37-8.45 (m, 1H); MS (DCI/NH$_3$) m/z 362 (M+H)$^+$; Anal. Calculated for C$_{24}$H$_{27}$NO$_2$: C, 79.74; H, 7.53; N, 3.87. Found: C, 79.40; H, 7.27; N, 3.87.

EXAMPLE 78

[1-(3-methoxybenzyl)-1H-indol-3-yl](2,2,3,3-tetramethylcyclopropyl)methanone

The major product of Example 1B (0.15 g, 0.62 mmol), 1-chloromethyl-3-methoxybenzene (0.17 mL, 1.2 mmol) and NaH (60% dispersion in mineral oil, 0.12 g, 3.1 mmol) in 10 mL of DMF were processed as described in Example 1D to provide the title compound (0.11 g, 0.30 mmol, 49% yield). $^1$H NMR (MeOH-d$_4$, 300 MHz) δ ppm 1.31 (s, 6H), 1.32 (s, 6H), 2.13 (s, 1H), 3.72 (s, 3H), 5.44 (s, 2H), 6.72-6.79 (m, 2H), 6.80-6.87 (m, 1H), 7.16-7.28 (m, 3H), 7.32-7.42 (m, 1H), 8.12 (s, 1H), 8.21-8.30 (m, 1H); MS (DCI/NH$_3$) m/z 362 (M+H)$^+$; Anal. Calculated for C$_{24}$H$_{27}$NO$_2$: C, 79.74; H, 7.53; N, 3.87. Found: C, 80.02; H, 7.50; N, 3.70.

EXAMPLE 79

[5-hydroxy-1-(tetrahydro-2H-pyran-4-ylmethyl)-1H-indol-3-yl](2,2,3,3-tetramethylcyclopropyl)methanone A mixture of the product of Example 74B (0.38 g, 0.85 mmol) and Pd/C (10 wt % palladium on activated carbon, 160 mg) in 30 mL EtOH and 10 mL of EtOAc was processed as described in Example 70 to provide the title compound (0.27 g, 0.75 mmol, 89% yield). $^1$H NMR (MeOH-d$_4$, 300 MHz) δ ppm 1.31 (s, 12H), 1.33-1.54 (m, 4H), 2.08 (s, 1H), 2.10-2.25 (m, 1H), 3.37 (dt, J=11.5, 2.7 Hz, 2H), 3.88-3.98 (m, 2H), 4.09 (d, J=7.5 Hz, 2H), 6.79 (dd, J=8.8, 2.4 Hz, 1H), 7.31 (d, J=8.8 Hz, 1H), 7.66 (d, J=2.0 Hz, 1H), 7.95 (s, 1H); MS (DCI/NH$_3$) m/z 356 (M+H)$^+$; Anal. Calculated for C$_{22}$H$_{29}$NO$_3$: C, 74.33; H, 8.22; N, 3.94. Found: C, 74.14; H, 8.21; N, 3.97.

EXAMPLE 80

[1-(1,3-benzodioxol-5-ylmethyl)-1H-indol-3-yl](2,2,3,3-tetramethylcyclopropyl)methanone A mixture of piperonyl alcohol (0.16 g, 1.1 mmol), methanesulfonyl chloride (0.11 mL, 1.4 mmol), and triethylamine (0.29 mL, 2.1 mmol) in 10 mL of THF was processed as described in Example 1C to provide the corresponding mesylate. The major product of Example 1B (0.15 g, 0.62 mmol), the freshly prepared mesylate (1.1 mmol) and NaH (60% dispersion in mineral oil, 75 mg, 1.9 mmol) in 10 mL of DMF were processed as described in Example 1D to provide the title compound (0.11 g, 0.30 mmol, 49% yield). $^1$H NMR (MeOH-d$_4$, 300 MHz) δ ppm 1.31 (s, 6H), 1.32 (s, 6H), 2.13 (s, 1H), 5.36 (s, 2H), 5.91 (s, 2H), 6.69-6.79 (m, 3H), 7.15-7.22 (m, 2H), 7.36-7.43 (m, 1H), 8.11 (s, 1H), 8.21-8.29 (m, 1H); MS (DCI/NH$_3$) m/z 376 (M+H)$^+$; Anal. Calculated for C$_{24}$H$_{25}$NO$_3$: C, 76.77; H, 6.71; N, 3.73. Found: C, 76.51; H, 6.70; N, 3.79.

EXAMPLE 81

[7-hydroxy-1-(tetrahydro-2H-pyran-4-ylmethyl)-1H-indol-3-yl](2,2,3,3-tetramethylcyclopropyl)methanone The product of Example 76B (1.1 g, 2.5 mmol) and Pd/C (10 wt % palladium on activated carbon, 113 mg) in 50 mL of EtOH and 50 mL of EtOAc were processed as described in Example 70 to provide the title compound (0.79 g, 2.2 mmol, 87% yield). $^1$H NMR (CDCl$_3$, 300 MHz) δ ppm 1.30 (s, 6H), 1.33 (s, 6H), 1.38-1.58 (m, 4H), 1.91 (s, 1H), 2.13-2.27 (m, 1H), 3.33 (dt, J=11.4, 2.2 Hz, 2H), 3.92-4.03 (m, 2H), 4.31 (d, J=7.1 Hz, 2H), 6.63 (dd, J=7.8, 0.7 Hz, 1H), 7.04 (t, J=7.8 Hz, 1H), 7.51 (s, 1H), 7.95 (dd, J=8.1, 1.0 Hz, 1H); MS (DCI/NH$_3$) m/z 356 (M+H)$^+$; Anal. Calculated for C$_{22}$H$_{29}$NO$_3$: C, 74.33; H, 8.22; N, 3.94. Found: C, 74.43; H, 8.30; N, 3.98.

EXAMPLE 82

[1-(2,3-dihydro-1,4-benzodioxin-6-ylmethyl)-1H-indol-3-yl](2,2,3,3-tetramethylcyclopropyl)methanone A mixture of 2,3-dihydro-1,4-benzodioxin-6-ylmethanol (Acros, 0.18 g, 1.1 mmol), methanesulfonyl chloride (0.11 mL, 1.4 mmol), and triethylamine (0.29 mL, 2.1 mmol) in 10 mL of THF was processed as described in Example 1C to provide the corresponding mesylate. The major product of Example 1B (0.15 g, 0.62 mmol), the freshly prepared mesylate (1.1 mmol) and NaH (60% dispersion in mineral oil, 75 mg, 1.9 mmol) in 10 mL of DMF were processed as described in Example 1D to provide the title compound (0.14 g, 0.36 mmol, 58% yield). $^1$H NMR (MeOH-d$_4$, 300 MHz) δ ppm 1.31 (d, J=1.7 Hz, 6H), 1.32 (s, 6H), 2.12 (s, 1H), 4.19 (s, 4H), 5.33 (s, 2H), 6.68-6.75 (m, 2H), 6.75-6.81 (m, 1H), 7.15-7.24 (m, 2H), 7.35-7.41 (m, 1H), 8.09 (s, 1H), 8.21-8.29 (m, 1H); MS (DCI/NH$_3$) m/z 390 (M+H)$^+$; Anal. Calculated for C$_{25}$H$_{27}$NO$_3$: C, 77.09; H, 6.99; N, 3.60. Found: C, 76.87; H, 7.00; N, 3.61.

EXAMPLE 83

(2E)-4-oxo-4-({1-(tetrahydro-2H-pyran-4-ylmethyl)-3-[(2,2,3,3-tetramethylcyclopropyl)carbonyl]-1H-indol-7-yl}oxy)but-2-enoic acid The product of Example 81 (0.20 g, 0.56 mmol), furmaryl chloride (68 µL, 0.59 mmol) and triethylamine (78 µL, 0.56 mmol) in 60 mL Et$_2$O were processed as described in Example 65 to provide the title compound (0.11 g, 0.24 mmol, 42% yield). $^1$H NMR (CDCl$_3$, 300 MHz) δ ppm 1.31 (s, 6H), 1.34 (s, 6H), 1.34-1.46 (m, 4H), 1.90 (s, 1H), 1.97-2.11 (m, 1H), 3.31 (dt, J=10.9, 4.1 Hz, 2H), 3.94-4.03 (m, 2H), 4.07 (d, J=7.5 Hz, 2H), 7.06 (d, J=7.1 Hz, 1H), 7.16 (d, J=3.7 Hz, 2H), 7.26 (t, J=7.8 Hz, 1H), 7.53 (s, 1H), 8.35 (d, J=8.8 Hz, 1H); MS (DCI/NH$_3$) m/z 454 (M+H)$^+$; Anal. Calculated for C$_{26}$H$_{31}$NO$_6$.0.2H$_2$O: C, 68.31; H, 6.92; N, 3.06. Found: C, 68.05; H, 6.83; N, 2.94.

EXAMPLE 84

[7-methoxy-1-(tetrahydro-2H-pyran-4-ylmethyl)-1H-indol-3-yl](2,2,3,3-tetramethylcyclopropyl)methanone The product of Example 81 (0.14 g, 0.39 mmol), NaH (60% dispersion in mineral oil, 47 mg, 1.2 mmol) and iodomethane (61 µL, 0.98 mmol) in 3 mL of THF were processed as described in Example 72 to provide the title compound (88 mg, 0.24 mmol, 61% yield). $^1$H NMR (CDCl$_3$, 300 MHz) δ ppm 1.30 (s, 6H), 1.33 (s, 6H), 1.34-1.52 (m, 4H), 1.90 (s, 1H), 2.04-2.20 (m, 1H), 3.32 (dt, J=11.4, 2.5 Hz, 2H), 3.94 (s, 3H), 3.95-4.02 (m, 2H), 4.28 (d, J=7.1 Hz, 2H), 6.71 (d, J=7.5 Hz, 1H), 7.15 (t, J=8.0 Hz, 1H), 7.48 (s, 1H), 8.00 (dd, J=8.0, 0.8 Hz, 1H); MS (DCI/NH$_3$) m/z 370 (M+H)$^+$; Anal. Calculated for C$_{23}$H$_{31}$NO$_3$.0.2H$_2$O: C, 74.04; H, 8.48; N, 3.75. Found: C, 74.10; H, 8.39; N, 3.72.

EXAMPLE 85 methyl 1-(tetrahydro-2H-pyran-4-ylmethyl)-3-[(2,2,3,3-tetramethylcyclopropyl)carbonyl]-1H-indole-6-carboxylate

EXAMPLE 85A 3-(2,2,3,3-Tetramethyl-cyclopropanecarbonyl)-1H-indole-6-carboxylic acid methyl ester A mixture of methyl-indole-6-carboxylate (2.0 g, 11.4 mmol), ethylmagnesium bromide (1.0 M solution in THF, 14 mL, 14 mmol), zinc chloride (1.0 M solution in Et$_2$O, 14 mL, 14 mmol) and the product of Example 1A (17 mmol) in 30 mL of dichloromethane was processed as described in Example 1B to provide the title compound (1.35 g, 4.5 mmol, 40% yield). MS (DCI/NH$_3$) m/z 300 (M+H)$^+$.

EXAMPLE 85B methyl 1-(tetrahydro-2H-pyran-4-ylmethyl)-3-[(2,2,3,3-tetramethylcyclopropyl)carbonyl]-1H-indole-6-carboxylate The product of Example 85A (1.4 g, 4.5 mmol), the product of Example 18A (9.0 mmol), and NaH (60% dispersion in mineral oil, 0.54 g, 14 mmol) in 30 mL of DMF were processed as described in Example 1D to provide the title compounds (0.43 g, 1.1 mmol, 24% yield) and the product of Example 86 (0.37 g, 0.97 mmol, 21% yield). $^1$H NMR (CDCl$_3$, 300 MHz) δ ppm 1.32 (s, 6H), 1.35 (s, 6H), 1.40-1.54 (m, 4H), 1.93 (s, 1H), 2.10-2.24 (m, 1H), 3.34 (dt, J=11.4, 2.5 Hz, 2H), 3.96 (s, 3H), 3.97-4.03 (m, 2H), 4.10 (d, J=7.5 Hz, 2H), 7.73 (s, 1H), 7.94 (dd, J=8.5, 1.0 Hz, 1H), 8.09 (s, 1H), 8.44 (d, J=8.5 Hz, 1H); MS (DCI/NH$_3$) m/z 398 (M+H)$^+$; Anal. Calculated for C$_{24}$H$_{31}$NO$_4$·0.1H$_2$O: C, 72.19; H, 7.88; N, 3.51. Found: C, 71.88; H, 7.79; N, 3.45.

EXAMPLE 86

1-(tetrahydro-2H-pyran-4-ylmethyl)-3-[(2,2,3,3-tetramethylcyclopropyl)carbonyl]-1H-indole-6-carboxylic acid The title compound was obtained by the methods described in Example 85: $^1$H NMR (CDCl$_3$, 300 MHz) δ ppm 1.32 (s, 6H), 1.35 (s, 6H), 1.41-1.61 (m, 4H), 1.93 (s, 1H), 2.14-2.24 (m, 1H), 3.35 (dt, J=11.6, 2.5 Hz, 2H), 3.95-4.04 (m, 2H), 4.12 (d, J=7.5 Hz, 2H), 7.76 (s, 1H), 7.99 (dd, J=8.3, 1.5 Hz, 1H), 8.14 (s, 1H), 8.46 (d, J=7.8 Hz, 1H); MS (DCI/NH$_3$) m/z 384 (M+H)$^+$; Anal. Calculated for C$_{23}$H$_{29}$NO$_4$·0.4H$_2$O: C, 70.71; H, 7.69; N, 3.59. Found: C, 70.54; H, 7.54; N, 3.60.

EXAMPLE 87

{1-[(5-chloro-1,2,4-thiadiazol-3-yl)methyl]-1H-indol-3-yl}(2,2,3,3-tetramethylcyclopropyl)methanone The major product of Example 1B (0.15 g, 0.62 mmol), 5-chloro-3-(chloromethyl)-1,2,4-thiadiazole (Maybridge, 0.21 g, 1.2 mmol) and NaH (60% dispersion in mineral oil, 0.12 g, 3.1 mmol) in 10 mL of DMF were processed as described in Example 1D to provide the title compound (50 mg, 0.13 mmol, 22% yield). $^1$H NMR (CDCl$_3$, 300 MHz) δ ppm 1.36 (s, 6H), 1.37 (s, 6H), 2.07 (s, 1H), 4.79 (s, 2H), 7.43 (dt, J=7.5, 1.2 Hz, 1H), 7.50 (dt, J=7.7, 1.5 Hz, 1H), 7.85-7.92 (m, 1H), 8.34 (s, 1H), 8.47-8.54 (m, 1H); MS (DCI/NH$_3$) m/z 374 (M+H)$^+$; Anal. Calculated for C$_{19}$H$_{20}$ClN$_3$OS·0.4H$_2$O: C, 59.88; H, 5.50; N, 11.03. Found: C, 59.71; H, 5.07; N, 111.12.

EXAMPLE 88

(2E)-4-oxo-4-({1-(tetrahydro-2H-pyran-4-ylmethyl)-3-[(2,2,3,3-tetramethylcyclopropyl)carbonyl]-1H-indol-5-yl}oxy)but-2-enoic acid The product of Example 79 (77 mg, 0.22 mmol), furmaryl chloride (25 µL, 0.23 mmol) and triethylamine (30 µL, 0.22 mmol) in 20 mL Et$_2$O and 4 mL of THF were processed as described in Example 65 to provide the title compound (51 mg, 0.11 mmol, 51% yield). $^1$H NMR (MeOH-d$_4$, 300 MHz) δ ppm 1.31 (s, 6H), 1.32 (s, 6H), 1.38-1.55 (m, 4H), 2.13 (s, 1H), 2.16-2.28 (m, 1H), 3.37 (dt, J=10.9, 2.4 Hz, 2H), 3.89-3.99 (m, 2H), 4.18 (d, J=7.5 Hz, 2H), 7.00 (d, J=1.7 Hz, 2H), 7.07 (dd, J=8.8, 2.4 Hz, 1H), 7.55 (d, J=8.8 Hz, 1H), 8.03 (d, J=2.4 Hz, 1H), 8.14 (s, 1H); MS (DCI/NH$_3$) m/z 454 (M+H)$^+$; Anal. Calculated for C$_{26}$H$_{31}$NO$_6$: C, 68.86; H, 6.89; N, 3.09. Found: C, 68.77; H, 6.72; N, 3.06.

EXAMPLE 89

[1-(1,3-benzothiazol-2-ylmethyl)-1H-indol-3-yl](2,2,3,3-tetramethylcyclopropyl)methanone The 2-hydroxymethylbenzothiazole (Acros, 0.18 g, 1.1 mmol), methanesulfonyl chloride (0.11 mL, 1.4 mmol), and triethylamine (0.29 mL, 2.1 mmol) in 10 mL of THF were processed as described in Example 1C to provide the corresponding mesylate. The major product of Example 1B (0.15 g, 0.62 mmol), the freshly prepared mesylate (1.1 mmol) and NaH (60% dispersion in mineral oil, 75 mg, 1.9 mmol) in 10 mL of DMF were processed as described in Example 1D to provide the title compound (55 mg, 0.14 mmol, 23% yield). $^1$H NMR (CDCl$_3$, 300 MHz) δ ppm 1.31 (s, 6H), 1.36 (s, 6H), 1.97 (s, 1H), 5.76 (s, 2H), 7.26-7.32 (m, 2H), 7.35-7.45 (m, 2H), 7.51 (ddd, J=8.3, 7.3, 1.4 Hz, 1H), 7.76-7.82 (m, 1H), 7.84 (s, 1H), 8.05 (d, J=8.1 Hz, 1H), 8.39-8.49 (m, 1H); MS (DCI/NH$_3$) m/z 389 (M+H)$^+$; Anal. Calculated for C$_{24}$H$_{24}$N$_2$OS: C, 74.19; H, 6.23; N, 7.21. Found: C, 74.06; H, 6.25; N, 7.04.

EXAMPLE 90 ethyl N-({1-(tetrahydro-2H-pyran-4-ylmethyl)-3-[(2,2,3,3-tetramethylcyclopropyl)carbonyl]-1H-indol-6-yl}carbonyl)-beta-alaninate To a solution of the product of Example 86 (0.26 g, 0.68 mmol) in 5 mL of EtOAc was added 1,1'-carbonyldiimidazole (0.13 g, 0.81 mmol). The mixture was stirred at ambient temperature for 3 hours then β-alanine ethyl ester hydrochloride (0.13 g, 0.81 mmol) in 1 mL H$_2$O was added. The reaction mixture was stirred at ambient temperature for 1 hour then warmed to reflux and allowed to stir for 16 h. The mixture was cooled to ambient temperature, quenched with 5 mL of saturated aqueous NaHCO$_3$ and the layers were separated. The aqueous layer was extracted 3×3 mL of EtOAc and the combined organic extracts were dried over anhydrous Na$_2$SO$_4$, filtered, concentrated under reduced pressure and purified via column chromatography (50% hexanes in EtOAc) to provide the title compound (55 mg, 0.11 mmol, 17% yield). $^1$H NMR (CDCl$_3$, 300 MHz) δ ppm 1.28 (t, J=7.1 Hz, 3H), 1.32 (s, 6H), 1.35 (s, 6H), 1.39-1.55 (m, 4H), 1.92 (s, 1H), 2.13-2.23 (m, 1H), 2.68 (dd, J=5.8 Hz, 2H), 3.33 (dt, J=11.6, 2.5 Hz, 2H), 3.78 (q, J=6.0 Hz, 2H), 3.92-4.02 (m, 2H), 4.10 (d, J=7.5 Hz, 2H), 4.19 (q, J=7.1 Hz, 2H), 6.90-6.98 (m, 1H), 7.49 (dd, J=8.5, 1.7 Hz, 1H), 7.70 (s, 1H), 8.01 (d, J=0.7 Hz, 1H), 8.42 (d, J=8.5 Hz, 1H); MS (DCI/NH$_3$) m/z 483 (M+H)$^+$; Anal. Calculated for C$_{28}$H$_{38}$N$_2$O$_5$: C, 69.68; H, 7.94; N, 5.80. Found: C, 69.00; H, 7.71; N, 5.79.

EXAMPLE 91

[5-methoxy-1-(tetrahydro-2H-pyran-4-ylmethyl)-1H-indol-3-yl](2,2,3,3-tetramethylcyclopropyl)methanone The product of Example 79 (0.11 g, 0.30 mmol), NaH (60% dispersion in mineral oil, 48 mg, 1.2 mmol) and iodomethane (76 μL, 0.90 mmol) in 10 mL of THF were processed as described in Example 72 to provide the title compound (59 mg, 0.16 mmol, 53% yield). $^1$H NMR(CDCl$_3$, 300 MHz) δ ppm 1.30 (s, 6H), 1.35 (s, 6H), 1.37-1.53 (m, 4H), 1.89 (s, 1H), 2.04-2.21 (m, 1H), 3.33 (dt, J=11.6, 2.5 Hz, 2H), 3.89 (s, 3H), 3.94-4.00 (m, 2H), 4.00 (d, J=7.5 Hz, 2H), 6.92 (dd, J=9.0, 2.5 Hz, 1H), 7.21 (d, J=9.2 Hz, 1H), 7.56 (s, 1H), 7.92 (d, J=2.7 Hz, 1H); MS (DCI/NH$_3$) m/z 370 (M+H)$^+$; Anal. Calculated for C$_{23}$H$_{31}$NO$_3$.0.2H$_2$O: C, 74.04; H, 8.48; N, 3.75. Found: C, 73.92; H, 8.31; N, 3.66.

EXAMPLE 92

[4-(benzyloxy)-1-(tetrahydro-2H-pyran-4-ylmethyl)-1H-indol-3-yl](2,2,3,3-tetramethylcyclopropyl)methanone

EXAMPLE 92A (4-Benzyloxy-1H-indol-3-yl)-(2,2,3,3-tetramethyl-cyclopropyl)-methanone A mixture of 4-benzyloxyindole (1.1 g, 4.8 mmol), ethylmagnesium bromide (1.0 M solution in THF, 5.2 mL, 5.2 mmol), zinc chloride (1.0 M solution in Et$_2$O, 5.2 mL, 5.2 mmol) and the product of Example 1A (4.8 mmol) in 25 mL of dichloromethane was processed as described in Example 1B to provide the title compound (0.56 g, 1.6 mmol, 34% yield). MS (DCI/NH$_3$) m/z 348 (M+H)$^+$.

EXAMPLE 92B

[4-(benzyloxy)-1-(tetrahydro-2H-pyran-4-ylmethyl)-1H-indol-3-yl](2,2,3,3-tetramethylcyclopropyl)methanone The product of Example 92A (0.56 g, 1.6 mmol), the product of Example 18A (2.7 mmol), and NaH (60% dispersion in mineral oil, 0.19 g, 4.8 mmol) in 12 mL of DMF were processed as described in Example 1D to provide the title compound (0.49 g, 1.1 mmol, 68% yield). $^1$H NMR (CDCl$_3$, 300 MHz) δ ppm 1.14 (s, 6H), 1.31 (s, 6H), 1.34-1.53 (m, 4H), 2.05 (s, 1H), 2.06-2.20 (m, 1H), 3.32 (dt, J=11.6, 2.2 Hz, 2H), 3.92-3.98 (m, 2H), 3.97 (d, J=7.1 Hz, 2H), 5.29 (s, 2H), 6.66 (d, J=8.1 Hz, 1H), 6.95 (d, J=7.8 Hz, 1H), 7.13 (t, J=8.0 Hz, 1H), 7.27-7.39 (m, 3H), 7.44-7.54 (m, 3H); MS (DCI/NH$_3$) m/z 446 (M+H)$^+$; Anal. Calculated for C$_{29}$H$_{35}$NO$_3$: C, 78.17; H, 7.92; N, 3.14. Found: C, 78.25; H, 7.79; N, 3.18.

EXAMPLE 93

1-(tetrahydro-2H-pyran-4-ylmethyl)-3-[(2,2,3,3-tetramethylcyclopropyl)carbonyl]-1H-indole-6-carboxamide To a solution of the product of Example 86 (0.10 g, 0.27 mmol) in 5 mL of EtOAc was added 1,1'-carbonyldiimidazole (57 mg, 0.35 mmol). The mixture was stirred at ambient temperature for 3 hour then 1 mL of concentrated aqueous ammonium hydroxide was added (15 mmol). The reaction mixture was stirred at 35° C. for 16 hours then was cooled to ambient temperature, quenched with 5 mL of saturated aqueous NaHCO$_3$ and the layers were separated. The aqueous layer was extracted 3×3 mL of EtOAc and the combined organic extracts were dried over anhydrous Na$_2$SO$_4$, filtered, concentrated under reduced pressure and purified via column chromatography (10% CH$_3$OH in EtOAc) to provide the title compound (52 mg, 0.14 mmol, 50% yield). $^1$H NMR (MeOH-d$_4$, 300 MHz) δ ppm 1.33 (s, 6H), 1.33 (s, 6H), 1.40-1.54 (m, 4H), 2.16 (s, 1H), 2.20-2.31 (m, 1H), 3.38 (dt, J=11.2, 3.1 Hz, 2H), 3.89-3.98 (m, 2H), 4.22 (d, J=7.5 Hz, 2H), 7.74 (dd, J=8.5, 1.7 Hz, 1H), 8.10 (d, J=1.0 Hz, 1H), 8.22 (s, 1H), 8.30-8.35 (m, 1H); MS (DCI/NH$_3$) m/z 383 (M+H)$^+$; Anal. Calculated for C$_{23}$H$_{30}$N$_2$O$_3$.0.5C$_2$H$_4$O$_2$ (acetic acid): C, 69.88; H, 7.82; N, 6.79. Found: C, 69.70; H, 7.42; N, 6.79.

EXAMPLE 94

1-(2-morpholin-4-ylethyl)-3-[(2,2,3,3-tetramethylcyclopropyl)carbonyl]-1H-indole-7-carboxylic acid The title compound was obtained by the methods described in Example 95. $^1$H NMR (CDCl$_3$, 300 MHz) δ ppm 1.32 (s, 6H), 1.36 (s, 6H), 1.98 (s, 1H), 2.56-2.75 (m, 4H), 2.78-2.91 (m, 2H), 3.76-3.91 (m, 4H), 4.48-4.62 (m, 2H), 7.32 (t, J=7.6 Hz, 1H), 7.85 (s, 1H), 7.95 (d, J=7.5 Hz, 1H), 8.69 (d, J=7.8 Hz, 1H); MS (DCI/NH$_3$) m/z 399 (M+H)$^+$; Anal. Calculated for C$_{23}$H$_{30}$N$_2$O$_4$: C, 68.32; H, 7.59; N, 7.03. Found: C, 68.92; H, 7.57; N, 6.93.

EXAMPLE 95

2-morpholin-4-ylethyl 1-(2-morpholin-4-ylethyl)-3-[(2,2,3,3-tetramethylcyclopropyl)carbonyl]-1H-indole-7-carboxylate dihydrochloride

EXAMPLE 95A 3-(2,2,3,3-Tetramethyl-cyclopropanecarbonyl)-1H-indole-7-carboxylic acid methyl ester A mixture of methyl-indole-7-carboxylate (Maybridge, 1.0 g, 5.7 mmol), ethylmagnesium bromide (1.0 M solution in THF, 6.9 mL, 6.9 mmol), zinc chloride (1.0 M solution in Et$_2$O, 6.9 mL, 6.9 mmol) and the product of Example 1A (7.4 mmol) in 25 mL of dichloromethane was processed as described in Example 1B to provide the title compound (1.1 g, 3.6 mmol, 63% yield). MS (DCI/NH$_3$) m/z 300 (M+H)$^+$.

EXAMPLE 95B 2-morpholin-4-ylethyl 1-(2-morpholin-4-ylethyl)-3-[(2,2,3,3-tetramethylcyclopropyl)carbonyl]-1H-indole-7-carboxylate dihydrochloride The product of Example 95A (0.47 g, 2.1 mmol), the product of Example 2A (3.1 mmol) and NaH (60% dispersion in mineral oil, 0.16 g, 4.1 mmol) in 10 mL of DMF were processed as described in Example 1D to provide the title compound of Example 94 (0.13 g, 0.33 mmol, 16% yield) and the free base of the morpholinylethyl ester (30 mg, 0.06 mmol, 2% yield), which was treated with 4 N HCl in dioxane (0.12 mmol, 60 μL) to provide the title compound (25 mg, 0.04 mmol, 67% yield). $^1$H NMR (MeOH-d$_4$, 300 MHz) δ ppm 1.34 (s, 6H), 1.35 (s, 6H), 2.19 (s, 1H), 3.12-3.29 (m, 4H), 3.32-3.47 (m, 4H), 3.70-3.78 (m, 4H), 3.86-4.09 (m, 8H), 4.80-4.84 (m, 2H), 4.88-4.97 (m, 2H), 7.33 (t, J=7.8 Hz, 1H), 8.00 (dd, J=7.5, 0.7 Hz, 1H), 8.28 (s, 1H), 8.69 (dd, J=8.1, 1.4 Hz, 1H); MS (DCI/NH$_3$) m/z 512 (M+H)$^+$; Anal. Calculated for C$_{22}$H$_{29}$NO$_2$.2HCl: C, 59.58; H, 7.41; N, 7.19. Found: C, 59.71; H, 7.45; N, 7.11.

EXAMPLE 96

[4-hydroxy-1-(tetrahydro-2H-pyran-4-ylmethyl)-1H-indol-3-yl](2,2,3,3-tetramethylcyclopropyl)methanone The product of Example 92B (0.44 g, 0.98 mmol) and Pd/C (10 wt % palladium on activated carbon, 200 mg) in 60 mL EtOH were processed as described in Example 70 to provide the title compound (0.23 g, 0.65 mmol, 67% yield). $^1$H NMR (CDCl$_3$, 300 MHz) δ ppm 1.31 (s, 6H), 1.33 (s, 6H), 1.38-1.58 (m, 4H), 1.90 (s, 1H), 2.08-2.25 (m, 1H), 3.34 (dt, J=11.7, 2.4 Hz, 2H), 3.95-4.03 (m, 2H), 3.99 (d, J=7.5 Hz, 2H), 6.69 (d, J=7.8 Hz, 1H), 6.75 (d, J=8.1 Hz, 1H), 7.18 (t, J=8.0 Hz, 1H), 7.53 (s, 1H), 12.04 (s, 1H); MS (DCI/NH$_3$) m/z 356 (M+H)$^+$; Anal. Calculated for C$_{22}$H$_{29}$NO$_3$: 74.33; H, 8.22; N, 3.94. Found: C, 74.08; H, 8.16; N, 3.86.

EXAMPLE 97

[4-methoxy-1-(tetrahydro-2H-pyran-4-ylmethyl)-1H-indol-3-yl](2,2,3,3-tetramethylcyclopropyl)methanone The product of Example 96 (63 mg, 0.18 mmol), NaH (60% dispersion in mineral oil, 28 mg, 0.71 mmol) and iodomethane (45 µL, 0.53 mmol) in 5 mL of THF were processed as described in Example 72 to provide the title compound (53 mg, 0.14 mmol, 81% yield). $^1$H NMR (CDCl$_3$, 300 MHz) δ ppm 1.28 (s, 6H), 1.35 (s, 6H), 1.37-1.52 (m, 4H), 2.02-2.17 (m, 1H), 2.53 (s, 1H), 3.31 (dt, J=11.6, 2.2 Hz, 2H), 3.93-4.00 (m, 4H), 3.95 (s, 3H), 6.67 (d, J=7.8 Hz, 1H), 6.95 (d, J=7.8 Hz, 1H), 7.20 (t, J=8.0 Hz, 1H), 7.47 (s, 1H); MS (DCI/NH$_3$) m/z 370 (M+H)$^+$; Anal. Calculated for C$_{23}$H$_{31}$NO$_3$: C, 74.76; H, 8.46; N, 3.79. Found: C, 74.76; H, 8.63; N, 3.79.

EXAMPLE 98

[6-methyl-1-(tetrahydro-2H-pyran-4-ylmethyl)-1H-indol-3-yl](2,2,3,3-tetramethylcyclopropyl)methanone

EXAMPLE 98A (6-Methyl-1H-indol-3-yl)-(2,2,3,3-tetramethylcyclopropyl)methanone A mixture of 6-methylindole (1.0 g, 7.6 mmol), ethylmagnesium bromide (1.0 M solution in THF, 9.1 mL, 9.1 mmol), zinc chloride (1.0 M solution in Et$_2$O, 9.1 mL, 9.1 mmol) and the product of Example 1A (11 mmol) in 25 mL of dichloromethane was processed as described in Example 1B to provide the title compound (1.3 g, 5.0 mmol, 65% yield). MS (DCI/NH$_3$) m/z 256 (M+H)$^+$.

EXAMPLE 98B

[6-methyl-1-(tetrahydro-2H-pyran-4-ylmethyl)-1H-indol-3-yl](2,2,3,3-tetramethylcyclopropyl)methanone The product of Example 98A (0.38 g, 1.5 mmol), the product of Example 18A (3.0 mmol), and NaH (60% dispersion in mineral oil, 0.18 g, 4.5 mmol) in 10 mL of DMF were processed as described in Example 1D to provide the title compound (0.17 g, 0.48 mmol, 32% yield). $^1$H NMR (CDCl$_3$, 300 MHz) δ ppm 1.30 (s, 6H), 1.34 (s, 6H), 1.38-1.63 (m, 4H), 1.93 (s, 1H), 2.07-2.23 (m, 1H), 2.49 (s, 3H), 3.34 (dt, J=11.7, 2.4 Hz, 2H), 3.93-4.04 (m, 2H), 4.00 (d, J=7.1 Hz, 2H), 7.06-7.13 (m, 1H), 7.11 (s, 1H), 7.55 (s, 1H), 8.25 (d, J=8.8 Hz, 1H); MS (DCI/NH$_3$) m/z 354 (M+H)$^+$; Anal. Calculated for C$_{23}$H$_{31}$NO$_2$: C, 78.15; H, 8.84; N, 3.96. Found: C, 78.03; H, 8.64; N, 3.92.

EXAMPLE 99

[6-(benzyloxy)-1-(2-morpholin-4-ylethyl)-1H-indol-3-yl](2,2,3,3-tetramethylcyclopropyl)methanone The product of Example 69A (0.96 g, 2.8 mmol), the product of Example 2A (4.1 mmol), and NaH (60% dispersion in mineral oil, 0.33 g, 8.3 mmol) in 20 mL of DMF were processed as described in Example 1D to provide the title compound (1.2 g, 2.7 mmol, 96% yield). $^1$H NMR (CDCl$_3$, 300 MHz) δ ppm 1.30 (s, 6H), 1.34 (s, 6H), 1.90 (s, 1H), 2.42-2.54 (m, 4H), 2.73 (t, J=6.6 Hz, 2H), 3.65-3.77 (m, 4H), 4.17 (t, J=6.3 Hz, 2H), 5.14 (s, 2H), 6.86 (s, 1H), 7.00 (dd, J=8.6, 2.2 Hz, 1H), 7.31-7.44 (m, 3H), 7.43-7.50 (m, 2H), 7.65 (s, 1H), 8.29 (d, J=8.8 Hz, 1H); MS (DCI/NH$_3$) m/z 461 (M+H)$^+$; Anal. Calculated for C$_{23}$H$_{31}$NO$_2$: C, 75.62; H, 7.88; N, 6.08. Found: C, 75.31; H, 7.81; N, 6.04.

EXAMPLE 100

[6-hydroxy-1-(2-morpholin-4-ylethyl)-1H-indol-3-yl](2,2,3,3-tetramethylcyclopropyl)methanone The product of Example 99 (1.0 g, 2.2 mmol) and Pd/C (10 wt % palladium on activated carbon, 100 mg) in 20 mL EtOH and 10 mL of EtOAc were processed as described in Example 70 to provide the title compound (0.75 g, 2.0 mmol, 90% yield). $^1$H NMR (CDCl$_3$, 300 MHz) δ ppm 1.30 (s, 6H), 1.34 (s, 6H), 1.89 (s, 1H), 2.45-2.64 (m, 4H), 2.74-2.89 (m, 2H), 3.67-3.80 (m, 4H), 4.14-4.30 (m, 2H), 6.79 (dd, J=8.5, 2.4 Hz, 1H), 6.81-6.85 (m, 1H), 7.65 (s, 1H), 8.24 (d, J=8.5 Hz, 1H); MS (DCI/NH$_3$) m/z 371 (M+H)$^+$; Anal. Calculated for C$_{22}$H$_{30}$N$_2$O$_3$: C, 71.32; H, 8.16; N, 7.56. Found: C, 71.18; H, 8.33; N, 7.52.

EXAMPLE 101

[6-methoxy-1-(2-morpholin-4-ylethyl)-1H-indol-3-yl](2,2,3,3-tetramethylcyclopropyl)methanone The product of Example 100 (0.20 g, 0.54 mmol), NaH (60% dispersion in mineral oil, 65 mg, 1.6 mmol) and iodomethane (84 µL, 1.4 mmol) in 5 mL of THF were processed as described in Example 72 to provide the title compound (70 mg, 0.18 mmol, 34% yield). $^1$H NMR (CDCl$_3$, 300 MHz) δ ppm 1.30 (s, 6H), 1.34 (s, 6H), 1.90 (s, 1H), 2.51 (t, 4H), 2.78 (t, J=6.4 Hz, 2H), 3.66-3.75 (m, 4H), 3.84-3.92 (m, 3H), 4.20 (t, J=6.6 Hz, 2H), 6.80 (s, 1H), 6.91 (dd, J=8.8, 2.0 Hz, 1H), 7.66 (s, 1H), 8.28 (d, J=8.8 Hz, 1H); MS (DCI/NH$_3$) m/z 385 (M+H)$^+$; Anal. Calculated for C$_{23}$H$_{32}$N$_2$O$_2$: C, 71.84; H, 8.39; N, 7.29. Found: C, 71.73; H, 8.42; N, 7.12.

EXAMPLE 102

4-oxo-4-({1-(tetrahydro-2H-pyran-4-ylmethyl)-3-[(2,2,3,3-tetramethylcyclopropyl)carbonyl]-1H-indol-5-yl}oxy)butanoic acid The product of Example 79 (0.13 g, 0.37 mmol) and succinic anhydride (0.11 g, 1.1 mmol) were combined in 5 mL pyridine. This mixture was warmed to reflux and allowed to stir for 18 h. The mixture was cooled to ambient temperature and poured into ~10 mL of ice and water. This mixture was extracted with 3×5 mL of EtOAc. The combined organic extracts were dried over anhydrous $Na_2SO_4$, filtered, concentrated under reduced pressure and purified via column chromatography ($SiO_2$, 9:1:0.1 EtOAc:$CH_3$OH:AcOH) to provide the title compound (90 mg, 0.20 mmol, 54% yield). $^1$H NMR (MeOH-$d_4$, 300 MHz) δ ppm 1.31 (s, 6H), 1.32 (s, 6H), 1.37-1.54 (m, 4H), 2.12 (s, 1H), 2.13-2.27 (m, 1H), 2.71 (t, J=6.4 Hz, 2H), 2.85-2.92 (m, 2H), 3.32-3.43 (m, 2H), 3.89-3.99 (m, 2H), 4.16 (d, J=7.5 Hz, 2H), 7.01 (dd, J=8.8, 2.4 Hz, 1H), 7.51 (d, J=8.8 Hz, 1H), 7.97 (d, J=2.0 Hz, 1H), 8.10 (s, 1H); MS (DCI/$NH_3$) m/z 456 (M+H)$^+$; Anal. Calculated for $C_{26}H_{33}NO_6$: C, 68.55; H, 7.30; N, 3.07. Found: C, 68.15; H, 7.40; N, 2.99.

EXAMPLE 103

(2,2-dichloro-1-methylcyclopropyl)[1-(tetrahydro-2H-pyran-4-ylmethyl)-1H-indol-3-yl]methanone

EXAMPLE 103A (2,2-Dichloro-1-methyl-cyclopropyl)-(1H-indol-3-yl)methanone

A mixture of 2,2-dichloro-1-methylcyclopropane carboxylic acid (1.0 g, 5.9 mmol) in 5 mL of thionyl chloride was processed as described in Example 1A to provide the corresponding acid chloride. The freshly prepared acid chloride (5.9 mmol), indole (0.69 g, 5.9 mmol), ethylmagnesium bromide (1.0 M solution in THF, 6.5 mL, 6.5 mmol), and zinc chloride (1.0 M solution in $Et_2O$, 6.5 mL, 6.5 mmol) in 30 mL of dichloromethane were processed as described in Example 1B to provide the title compound (0.36 g, 1.3 mmol, 23% yield). MS (DCI/$NH_3$) m/z 268 (M+H)$^+$.

EXAMPLE 103B (2,2-dichloro-1-methylcyclopropyl)[1-(tetrahydro-2H-pyran-4-ylmethyl)-1H-indol-3-yl]methanone The product of Example 103A (0.18 g, 0.68 mmol), the product of Example 18A (1.2 mmol), and NaH (60% dispersion in mineral oil, 82 mg, 2.0 mmol) in 10 mL of DMF were processed as described in Example 1D to provide the title compound (80 mg, 0.22 mmol, 32% yield). $^1$H NMR (CDCl$_3$, 300 MHz) δ ppm 1.40-1.62 (m, 5H), 1.76 (s, 3H), 2.09-2.22 (m, 1H), 2.25 (d, J=7.5 Hz, 1H), 3.34 (dq, J=11.6, 6.2, 2.5 Hz, 2H), 3.93-4.04 (m, 2H), 4.03-4.22 (m, 2H), 7.30-7.43 (m, 3H), 7.73 (s, 1H), 9.31-8.40 (m, 1H); MS (DCI/$NH_3$) m/z 366 (M+H)$^+$; Anal. Calculated for $C_{19}H_{21}Cl_2NO_2$·$0.1C_6H_{14}$: C, 62.79; H, 6.02; N, 3.74. Found: C, 63.09; H, 5.77; N, 3.40.

EXAMPLE 104

[1-(4-azidobutyl)-1H-indol-3-yl](2,2,3,3-tetramethylcyclopropyl)methanone

To a solution of the product of Example 24A (0.29 g, 0.93 mmol) in 10 mL of THF at 0° C. was added triethylamine (0.39 mL, 2.8 mmol) followed by methanesulfonyl chloride (0.14 mL, 1.9 mmol). The ice bath was removed and the mixture was stirred at ambient temperature for 2 h. The mixture was filtered and the filtrate was concentrated under reduced pressure to afford the corresponding mesylate. To a solution of the freshly prepared mesylate (0.93 mmol) in 5 mL of DMF was added sodium azide (0.18 g, 2.8 mmol). The mixture was warmed to 80° C. and was stirred for 4 h. The mixture was then cooled to ambient temperature, diluted with 5 mL of dichloromethane, and quenched with 3 mL of saturated aqueous $NaHCO_3$. The layers were separated and the aqueous layer was extracted with 3×5 mL of dichloromethane. The combined organic extracts were dried over anhydrous $Na_2SO_4$, filtered, concentrated under reduced pressure and purified via column chromatography ($SiO_2$, 50% hexanes in EtOAc) to provide the title compound (0.30 g, 0.89 mmol, 95% yield). $^1$H NMR (CDCl$_3$, 300 MHz) δ ppm 1.31 (s, 6H), 1.35 (s, 6H), 1.59-1.72 (m, 2H), 1.95 (s, 1H), 1.96-2.06 (m, 2H), 3.33 (t, J=6.6 Hz, 2H), 4.21 (t, J=7.1 Hz, 2H), 7.26-7.38 (m, 3H), 7.65 (s, 1H), 8.37-8.44 (m, 1H); MS (DCI/$NH_3$) m/z 339 (M+H)$^+$; Anal. Calculated for $C_{20}H_{26}N_4O$: C, 70.98; H, 7.74; N, 16.55. Found: C, 70.67; H, 7.89; N, 14.14.

EXAMPLE 105

[1-(2-azidoethyl)-1H-indol-3-yl](2,2,3,3-tetramethylcyclopropyl)methanone

The product of Example 38 (0.46 g, 1.6 mmol), methanesulfonyl chloride (0.27 mL, 3.6 mmol), triethylamine (0.74 mL, 5.3 mmol) and $NaN_3$ (0.31 g, 4.8 mmol) were processed as described in Example 104 to provide the title compound (0.32 g, 0.10 mmol, 65% yield). $^1$H NMR (CDCl$_3$, 300 MHz) δ ppm 1.31 (s, 6H), 1.35 (s, 6H), 1.95 (s, 1H), 3.74 (t, J=5.8 Hz, 2H), 4.32 (t, J=5.9 Hz, 2H), 7.28-7.35 (m, 3H), 7.70 (s, 1H), 8.39-8.47 (m, 1H); MS (DCI/$NH_3$) m/z 311 (M+H)$^+$; Anal. Calculated for $C_{18}H_{22}N_4O$: C, 69.65; H, 7.14; N, 18.05. Found: C, 69.30; H, 7.03; N, 17.83.

EXAMPLE 106

N-(4-{3-[(2,2,3,3-tetramethylcyclopropyl)carbonyl]-1H-indol-1-yl}butyl)methanesulfonamide

EXAMPLE 106A

[1-(4-Amino-butyl)-1H-indol-3-yl]-(2,2,3,3-tetramethyl-cyclopropyl)-methanone

To a solution of the product of Example 104 (0.28 g, 0.82 mmol) in 7 mL of THF and 3.5 mL $H_2O$ was added triphenylphosphine (0.24 g, 0.91 mmol). The mixture was stirred at ambient temperature for 72 hours then diluted with 5 mL of EtOAc. The layers were separated and the aqueous layer was extracted with 3×3 mL of EtOAc. The combined organic extracts were dried over anhydrous $Na_2SO_4$, filtered, concentrated under reduced pressure and purified via column chromatography ($SiO_2$, 9:1:0.1 $CH_2Cl_2$:$CH_3$OH:$NH_4$OH) to provide the title compound (0.23 g, 0.73 mmol, 89% yield). MS (DCI/$NH_3$) m/z 313 (M+H)$^+$.

EXAMPLE 106B

N-(4-{3-[(2,2,3,3-tetramethylcyclopropyl)carbonyl]-1H-indol-1-yl}butyl)methanesulfonamide To a solution of the product of Example 106A (0.21 g, 0.67 mmol) in 5 mL of THF at 0° C. was added triethylamine (0.19 mL, 1.3 mmol) followed by methanesulfonyl chloride (57 μL, 0.74 mmol). The ice bath was removed and the mixture was stirred at ambient temperature for 6 h. The mixture was filtered and the filtrate was concentrated under reduced pressure. The residue was purified via column chromatography (SiO$_2$, 20% hexanes in EtOAc) to provide the title compound (0.19 g, 0.49 mmol, 73% yield). $^1$H NMR (CDCl$_3$, 300 MHz) δ ppm 1.32 (s, 6H), 1.35 (s, 6H), 1.57-1.67 (m, 2H), 1.94-2.06 (m, 2H), 1.96 (s, 1H), 2.91 (s, 3H), 3.08-3.20 (m, 2H), 4.09-4.18 (m, 1H), 4.22 (t, J=6.8 Hz, 2H), 7.26-7.36 (m, 3H), 7.67 (s, 1H), 8.38-8.45 (m, 1H); MS (DCI/NH$_3$) m/z 391 (M+H)$^+$; Anal. Calculated for C$_{21}$H$_{30}$N$_2$O$_3$S: C, 64.58; H, 7.74; N, 7.17. Found: C, 64.35; H, 7.69; N, 7.00.

EXAMPLE 107 ethyl 4-({1-(tetrahydro-2H-pyran-4-ylmethyl)-3-[(2,2,3,3-tetramethylcyclopropyl)carbonyl]-1H-indol-5-yl}oxy)butanoate To a solution of the product of Example 79 (0.21 g, 0.59 mmol) in 5 mL of DMF was added Cs$_2$CO$_3$ (0.58 g, 1.8 mmol) followed by ethyl 4-bromobutyrate (0.13 mL, 0.89 mmol). This mixture was warmed to 90° C. and was stirred for 90 minutes. The mixture was then cooled to ambient temperature, quenched with 3 mL of saturated aqueous NH$_4$Cl and diluted with 5 mL of EtOAc. The layers were separated, the aqueous layer was extracted 3×3 mL of EtOAc and the combined organic extracts were dried over anhydrous Na$_2$SO$_4$, filtered, concentrated under reduced pressure and purified via column chromatography (SiO$_2$, 50% hexanes in EtOAc) to provide the title compound (0.26 g, 0.55 mmol, 94% yield). $^1$H NMR (CDCl$_3$, 300 MHz) δ ppm 1.26 (t, J=7.3 Hz, 3H), 1.30 (s, 6H), 1.34 (s, 6H), 1.37-1.60 (m, 4H), 1.88 (s, 1H), 2.07-2.18 (m, 2H), 2.52 (t, J=7.3 Hz, 2H), 3.33 (dt, J=11.7, 2.4 Hz, 2H), 3.93-4.02 (m, 2H), 3.99 (d, J=7.1 Hz, 2H), 4.05-4.20 (m, 5H), 6.91 (dd, J=8.8, 2.4 Hz, 1H), 7.20 (d, J=8.8 Hz, 1H), 7.55 (s, 1H), 7.90 (d, J=2.4 Hz, 1H); MS (DCI/NH$_3$) m/z 470 (M+H)$^+$; Anal. Calculated for C$_{28}$H$_{32}$NO$_5$: C, 71.61; H, 8.37; N, 2.98. Found: C, 71.64; H, 8.49; N, 2.92.

EXAMPLE 108

[1-(3-azidopropyl)-1H-indol-3-yl](2,2,3,3-tetramethylcyclopropyl)methanone

The product of Example 40 (0.41 g, 1.4 mmol), methanesulfonyl chloride (0.23 mL, 3.0 mmol), triethylamine (0.63 mL, 4.5 mmol) and sodium azide (0.27 g, 4.1 mmol) were processed according to the methods described in Example 104 to afford the title compound (0.31 g, 0.95 mmol, 70% yield). $^1$H NMR (CDCl$_3$, 300 MHz) δ ppm 1.31 (s, 6H), 1.35 (s, 6H), 1.94 (s, 1H), 2.07-2.20 (m, 2H), 3.32 (t, J=6.1 Hz, 2H), 4.30 (t, J=6.6 Hz, 2H), 7.27-7.38 (m, 3H), 7.66 (s, 1H), 8.37-8.45 (m, 1H); MS (DCI/NH$_3$) m/z 325 (M+H)$^+$; Anal. Calculated for C$_{19}$H$_{24}$N$_4$O.0.1H$_2$O: C, 69.95; H, 7.48; N, 17.17. Found: C, 69.87; H, 7.39; N, 17.13.

EXAMPLE 109

{1-[(2S)-tetrahydrofuran-2-ylmethyl]-1H-indol-3-yl}(2,2,3,3-tetramethylcyclopropyl)methanone

EXAMPLE 109A (S)-(tetrahydro-furan-2-yl)methanol

To a flask containing 60 mL of THF at 0° C. was added lithium aluminum hydride (0.98 g, 26 mmol). The mixture was stirred at 0° C. for 5 minutes then (S)-(−)-tetrahydro-2-furoic acid (1.0 g, 8.6 mmol) in 5 mL of THF was added dropwise via syringe. This mixture was warmed to reflux and was allowed to stir for 18 h. The mixture was then cooled to 0° C. and quenched by the slow addition of Na$_2$SO$_4$.10H$_2$O (excess). The mixture was filtered and the filtrate was concentrated under reduced pressure to afford the title compound. MS (DCI/NH$_3$) m/z 103 (M+H)$^+$.

EXAMPLE 109B

{1-[(2S)-tetrahydrofuran-2-ylmethyl]-1H-indol-3-yl}(2,2,3,3-tetramethylcyclopropyl)methanone The product of Example 109A (0.38 g, 3.7 mmol), methanesulfonyl chloride (0.34 mL, 4.4 mmol), and triethylamine (0.70 mL, 5.0 mmol) in 15 mL of THF were processed as described in Example 1C to provide the corresponding mesylate. The major product of Example 1B (0.30 g, 1.2 mmol), the freshly prepared mesylate (3.7 mmol) and NaH (60% dispersion in mineral oil, 0.15 g, 3.7 mmol) in 12 mL of DMF were processed as described in Example 1D to provide the title compound (0.23 g, 0.70 mmol, 56% yield). $^1$H NMR (CDCl$_3$, 300 MHz) δ ppm 1.30 (s, 6H), 1.34 (s, 3H), 1.35 (s, 3H), 1.50-1.64 (m, 1H), 1.70-1.92 (m, 2H), 1.95 (s, 1H), 1.96-2.08 (m, 1H), 3.72-3.92 (m, 2H), 4.10-4.36 (m, 3H), 7.24-7.29 (m, 2H), 7.32-7.39 (m, 1H), 7.79 (s, 1H), 8.38-8.45 (m, 1H); MS (DCI/NH$_3$) m/z 326 (M+H)$^+$; Anal. Calculated for C$_{21}$H$_{27}$NO$_2$: C, 77.50; H, 8.36; N, 4.30. Found: C, 77.25; H, 8.68; N, 4.33.

EXAMPLE 110

[5-(4-hydroxybutoxy)-1-(tetrahydro-2H-pyran-4-ylmethyl)-1H-indol-3-yl](2,2,3,3-tetramethylcyclopropyl)methanone The product of Example 79 (0.57 g, 1.6 mmol), 4-bromo-1-butanol (TCI-America, 0.37 g, 2.4 mmol) and Cs$_2$CO$_3$ (1.6 g, 4.8 mmol) in 10 mL of DMF were processed as described in Example 107 to provide the title compound (75 mg, 0.18 mmol, 11% yield) and the product of Example 111 (0.24 g, 0.50 mmol, 31% yield). $^1$H NMR (CDCl$_3$, 300 MHz) δ ppm 1.30 (s, 6H), 1.34(s, 6H), 1.38-1.59(m, 4H), 1.74-1.82(m, 3H), 1.85-1.95(m, 2H), 1.88 (s, 1H), 2.08-2.20 (m, 1H), 3.33 (dt, J=11.5, 2.4 Hz, 2H), 3.74 (t, J=6.3 Hz, 2H), 3.93-4.03 (m, 2H), 4.00 (d, J=7.1 Hz, 2H), 4.11 (t, J=7.0 Hz, 2H), 6.92 (dd, J=9.0, 2.5 Hz, 1H), 7.21 (d, J=8.8 Hz, 1H), 7.56 (s, 1H), 7.93 (d, J=2.4 Hz, 1H); MS (DCI/NH$_3$) m/z 428 (M+H)$^+$; Anal. Calculated for C$_{26}$H$_{37}$NO$_4$: C, 73.03; H, 8.72; N, 3.28. Found: C, 72.68; H, 8.43; N, 3.12.

EXAMPLE 111

[5-(4-bromobutoxy)-1-(tetrahydro-2H-pyran-4-ylmethyl)-1H-indol-3-yl](2,2,3,3-tetramethylcyclopropyl)methanone The title compound was obtained using the method described in Example 110: $^1$H NMR (CDCl$_3$, 300 MHz) δ ppm 1.30 (s, 6H), 1.34 (s, 6H), 1.39-1.70 (m, 5H), 1.88 (s, 1H), 1.92-2.00 (m, 2H), 2.06-2.15 (m, 2H), 3.33 (dt, J=11.6, 2.2 Hz, 2H), 3.41-3.46 (m, 1H), 3.50 (t, J=6.6 Hz, 2H), 3.94-4.02 (m, 2H), 4.00 (d, J=7.1 Hz, 2H), 4.09 (t, J=5.8 Hz, 2H), 6.91 (dd, J=8.8, 2.4 Hz, 1H), 7.21 (d, J=8.8 Hz, 1H), 7.56 (s, 1H), 7.92 (d, J=2.4 Hz, 1H); MS (DCI/NH$_3$) m/z 490, 492 (M+H)$^+$; Anal. Calculated for C$_{26}$H$_{36}$BrNO$_3$: C, 63.67; H, 7.40; N, 2.86. Found: C, 64.04; H, 7.60; N, 2.67.

EXAMPLE 112

[1-(6-azidohexyl)-1H-indol-3-yl](2,2,3,3-tetramethylcyclopropyl)methanone

The product of Example 42 (0.54 g, 1.7 mmol), methanesulfonyl chloride (0.28 mL, 3.6 mmol), triethylamine (0.76 mL, 5.5 mmol) and sodium azide (0.32 g, 5.0 mmol) were processed as in Example 104 to afford the title compound (0.37 g, 1.0 mmol, 63% yield). $^1$H NMR (CDCl$_3$, 300 MHz) δ ppm 1.31 (s, 6H), 1.35 (s, 6H), 1.40-1.51 (m, 2H), 1.58-1.69 (m, 2H), 1.87-1.99 (m, 2H), 1.95 (s, 1H), 3.28 (t, J=6.8 Hz, 2H), 4.18 (t, J=7.1 Hz, 2H), 7.26-7.36 (m, 3H), 7.65 (s, 1H), 8.37-8.44 (m, 1H); MS (DCI/NH$_3$) m/z 353 (M+H)$^+$; Anal. Calculated for C$_{21}$H$_{28}$N$_4$O.0.1H$_2$O: C, 71.20; H, 8.02; N, 15.81. Found: C, 70.95; H, 7.97; N, 15.70.

EXAMPLE 113

N-(2-{3-[(2,2,3,3-tetramethylcyclopropyl)carbonyl]-1H-indol-1-yl}ethyl)methanesulfonamide

EXAMPLE 113A

[1-(2-Amino-ethyl)-1H-indol-3-yl]-(2,2,3,3-tetramethyl-cyclopropyl)-methanone

The product of Example 105 (0.28 g, 0.90 mmol) and triphenylphospine (0.26 g, 0.99 mmol) in 9.5 mL of THF and 0.5 mL H$_2$O were processed as described in Example 106A to provide the title compound (0.17 g, 0.60 mmol, 66% yield). MS (DCI/NH$_3$) m/z 285 (M+H)$^+$.

EXAMPLE 113B

N-(2-{3-[(2,2,3,3-tetramethylcyclopropyl)carbonyl]-1H-indol-1-yl}ethyl)methanesulfonamide The product of Example 113A (0.16 g, 0.55 mmol), methanesulfonyl chloride (64 µL, 0.83 mmol) and triethylamine (0.23 mL, 1.7 mmol) in 10 mL of THF were processed as described in Example 106B to provide the title compound (0.16 g, 0.44 mmol, 80% yield). $^1$H NMR (CDCl$_3$, 300 MHz) δ ppm 1.31 (s, 6H), 1.35 (s, 6H), 1.94 (s, 1H), 2.83 (s, 3H), 3.57 (q, J=6.1 Hz, 2H), 4.39 (t, J=5.8 Hz, 2H), 4.40-4.47 (m, 1H), 7.26-7.41 (m, 3H), 7.73 (s, 1H), 8.38-8.46 (m, 1H); MS (DCI/NH$_3$) m/z 363 (M+H)$^+$; Anal. Calculated for C$_{19}$H$_{26}$N$_2$O$_3$S.0.2H$_2$O: C, 62.34; H, 7.27; N, 7.65. Found: C, 62.58; H, 7.10; N, 7.32.

EXAMPLE 114 methyl 1-(tetrahydro-2H-pyran-4-ylmethyl)-3-[(2,2,3,3-tetramethylcyclopropyl)carbonyl]-1H-indole-5-carboxylate

EXAMPLE 114A 3-(2,2,3,3-Tetramethyl-cyclopropanecarbonyl)-1H-indole-5-carboxylic acid methyl ester Methyl-indole-5-carboxylate (Lancaster, 3.0 g, 17 mmol), ethylmagnesium bromide (1.0 M solution in THF, 21 mL, 21 mmol), zinc chloride (1.0 M solution in Et$_2$O, 21 mL, 21 mmol) and the product of Example 1A (26 mmol) in 50 mL of dichloromethane were processed as described in Example 1B to provide the title compound (3.4 g, 11 mmol, 66% yield). MS (DCI/NH$_3$) m/z 300 (M+H)$^+$.

EXAMPLE 114B methyl 1-(tetrahydro-2H-pyran-4-ylmethyl)-3-[(2,2,3,3-tetramethylcyclopropyl)carbonyl]-1H-indole-5-carboxylate The product of Example 114A (1.5 g, 5.1 mmol), the product of Example 18A (10 mmol), and NaH (60% dispersion in mineral oil, 0.61 g, 15 mmol) in 40 mL of DMF were processed as described in Example 1D to provide the title compound (0.89 g, 2.2 mmol, 44% yield) and 1-(tetrahydro-2H-pyran-4-ylmethyl)-3-[(2,2,3,3-tetramethylcyclopropyl)carbonyl]-1H-indole-5-carboxylic acid as a minor product (0.21 g, 0.55 mmol, 11% yield, MS (DCI/NH$_3$) m/z 384 (M+H)$^+$ for the carboxylic acid). Data for Example 114B (major product): $^1$H NMR (CDCl$_3$, 300 MHz) δ ppm 1.33 (s, 6H), 1.36 (s, 6H), 1.40-1.58 (m, 4H), 1.95 (s, 1H), 2.06-2.24 (m, 1H), 3.34 (dt, J=11.6, 2.5 Hz, 2H), 3.92 (s, 3H), 3.94-4.01 (m, 2H), 4.06 (d, J=7.1 Hz, 2H), 7.36 (d, J=8.8 Hz, 1H), 7.66 (s, 1H), 8.00 (dd, J=8.5, 1.7 Hz, 1H), 9.12 (dd, J=1.7, 0.7 Hz, 1H); MS (DCI/NH$_3$) m/z 398 (M+H)$^+$; Anal. Calculated for C$_{24}$H$_{31}$NO$_4$: C, 72.52; H, 7.86; N, 3.52. Found: C, 72.53; H, 7.90; N, 3.48.

EXAMPLE 115

N-(3-{3-[(2,2,3,3-tetramethylcyclopropyl)carbonyl]-1H-indol-1-yl}propyl)methanesulfonamide

EXAMPLE 115A

[1-(3-Amino-propyl)-1H-indol-3-yl]-(2,2,3,3-tetramethyl-cyclopropyl)-methanone

The product of Example 108 (0.28 g, 0.88 mmol) and triphenylphospine (0.25 g, 0.96 mmol) in 9.5 mL of THF and 0.5 mL of H$_2$O were processed as described in Example 106A to provide the title compound (0.20 g, 0.66 mmol, 76% yield). MS (DCI/NH$_3$) m/z 299 (M+H)$^+$.

EXAMPLE 115B

N-(3-{3-[(2,2,3,3-tetramethylcyclopropyl)carbonyl]-1H-indol-1-yl}propyl)methanesulfonamide The product of Example 115A (0.19 g, 0.64 mmol), methanesulfonyl chloride (74 µL, 0.96 mmol) and triethylamine (0.27 mL, 1.9 mmol) in 10 mL of THF were processed as described in Example 106B to provide the title compound (60 mg, 0.16 mmol, 25% yield). $^1$H NMR (CDCl$_3$, 300 MHz) δ ppm 1.31 (s, 6H), 1.35 (s, 6H), 1.99 (s, 1H), 2.09-2.23 (m, 2H), 2.94 (s, 3H), 3.09-3.21 (m, 2H), 4.28-4.32 (m, 1H), 4.33 (t, J=6.6 Hz, 2H), 7.28-7.37 (m, 3H), 7.78 (s, 1H), 8.38-8.45 (m, 1H); MS (DCI/NH$_3$) m/z 377 (M+H)$^+$; Anal. Calculated for C$_{20}$H$_{28}$N$_2$O$_3$S: C, 63.80; H, 7.50; N, 7.44. Found: C, 63.44; H, 7.29; N, 7.67.

EXAMPLE 116

N-(5-{3-[(2,2,3,3-tetramethylcyclopropyl)carbonyl]-1H-indol-1-yl}pentyl)methanesulfonamide

EXAMPLE 116A

[1-(5-Amino-pentyl)-1H-indol-3-yl]-(2,2,3,3-tetramethyl-cyclopropyl)-methanone

The product of Example 112 (0.33 g, 0.95 mmol) and triphenylphospine (0.27 g, 1.0 mmol) in 9.5 mL of THF and 0.5 mL of H$_2$O were processed as described in Example 106A to provide the title compound (0.27 g, 0.82 mmol, 87% yield). MS (DCI/NH$_3$) m/z 327 (M+H)$^+$.

EXAMPLE 116B

N-(5-{3-[(2,2,3,3-tetramethylcyclopropyl)carbonyl]-1H-indol-1-yl}pentyl)methanesulfonamide The product of Example 116A (0.26 g, 0.80 mmol), methanesulfonyl chloride (93 µL, 1.2 mmol) and triethylamine (0.34 mL, 2.4 mmol) in 15 mL of THF were processed as described in Example 106B to provide the title compound (24 g, 0.59 mmol, 74% yield). $^1$H NMR (CDCl$_3$, 300 MHz) δ ppm 1.31 (s, 6H), 1.35 (s, 6H), 1.36-1.49 (m, 2H), 1.55-1.65 (m, 2H), 1.86-1.99(m, 2H), 1.96(s, 1H), 2.91 (s, 3H), 3.11 (q, J=6.8 Hz, 2H), 4.12-4.19 (m, 1H), 4.18 (t, J=7.0 Hz, 2H), 7.26-7.38 (m, 3H), 7.66 (s, 1H), 8.36-8.45 (m, 1H); MS (DCI/NH$_3$) m/z 405 (M+H)$^+$; Anal. Calculated for C$_{22}$H$_{32}$N$_2$O$_3$S.0.3H$_2$O: C, 64.45; H, 8.01; N, 6.83. Found: C, 64.14; H, 7.66; N, 6.78.

EXAMPLE 117

[5-(4-aminobutoxy)-1-(tetrahydro-2H-pyran-4-ylmethyl)-1H-indol-3-yl](2,2,3,3-tetramethylcyclopropyl)methanone

EXAMPLE 117A

[5-(4-Azido-butoxy)-1-(tetrahydro-pyran-4-ylmethyl)-1H-indol-3-yl]-(2,2,3,3-tetramethyl-cyclopropyl)-methanone A mixture of the product of Example 111 (0.20 g, 0.42 mmol) and sodium azide (81 mg, 1.2 mmol) in 5 mL of DMF was warmed to 80° C. and stirred for 2 h. The mixture was cooled to ambient temperature, quenched with 3 mL of H$_2$O and diluted with 5 mL of EtOAc. The layers were separated, the aqueous layer was extracted 3×3 mL of EtOAc and the combined organic extracts were dried over anhydrous Na$_2$SO$_4$, filtered, and concentrated under reduced pressure to provide the title compound (0.19 g, 0.42 mmol, 100% yield). MS (DCI/NH$_3$) m/z 453 (M+H)$^+$.

EXAMPLE 117B

[5-(4-aminobutoxy)-1-(tetrahydro-2H-pyran-4-ylmethyl)-1H-indol-3-yl](2,2,3,3-tetramethylcyclopropyl)methanone The product of Example 117A (0.19 g, 0.42 mmol) and triphenylphosphine (0.12 g, 0.46 mmol) in 4 mL of THF and 2 mL of H$_2$O were processed as described in Example 106A to provide the title compound (0.17 g, 0.40 mmol, 95% yield). $^1$H NMR (CDCl$_3$, 300 MHz) δ ppm 1.28 (s, 6H), 1.33 (s, 6H), 1.39-1.60 (m, 4H), 1.59-1.78 (m, 2H), 1.80-2.02 (m, 4H), 1.89 (s, 1H), 2.05-2.22 (m, 1H), 3.10 (t, J=6.8 Hz, 2H), 3.22-3.37 (m, 2H), 3.86-4.11 (m, 4H), 6.92 (dd, J=9.0, 2.2 Hz, 1H), 7.20 (d, J=9.2 Hz, 1H), 7.59 (s, 1H), 7.87 (d, J=2.4 Hz, 1H); MS (DCI/NH$_3$) m/z 427 (M+H)$^+$; Anal. Calculated for C$_{26}$H$_{38}$N$_2$O$_3$.1H$_2$O: C, 70.24; H, 9.07; N, 6.30. Found: C, 69.94; H, 9.05; N, 6.21.

EXAMPLE 118

[5-hydroxy-1-(2-morpholin-4-ylethyl)-1H-indol-3-yl](2,2,3,3-tetramethylcyclopropyl)methanone

EXAMPLE 118A

[5-Benzyloxy-1-(2-morpholin-4-yl-ethyl)-1H-indol-3-yl]-(2,2,3,3-tetramethyl-cyclopropyl)-methanone The product of Example 74A (1.1 g, 3.0 mmol), the product of Example 2A (5.1 mmol), and NaH (60% dispersion in mineral oil, 0.36 g, 9.1 mmol) in 25 mL of DMF were processed as described in Example 1D to provide the title compound (1.2 g, 2.6 mmol, 86% yield). MS (DCI/NH$_3$) m/z 461 (M+H)$^+$.

EXAMPLE 118B

[5-hydroxy-1-(2-morpholin-4-ylethyl)-1H-indol-3-yl](2,2,3,3-tetramethylcyclopropyl)methanone The product of Example 118A (1.2 g, 2.5 mmol) and Pd/C (10 wt % palladium on activated carbon, 120 mg) in 50 mL of EtOH were processed as described in Example 70 to provide the title compound (0.85 g, 2.3 mmol, 92% yield). $^1$H NMR (CDCl$_3$, 300 MHz) δ ppm 1.30 (s, 6H), 1.34 (s, 6H), 1.87 (s, 1H), 2.41-2.58 (m, 4H), 2.70-2.84 (m, 2H), 3.66-3.81 (m, 4H), 4.16-4.28 (m, 2H), 4.84-4.98 (m, 1H), 6.87 (dd, J=8.8, 2.4 Hz, 1H), 7.21 (d, J=8.8 Hz, 1H), 7.73 (s, 1H), 7.88 (d, J=2.7 Hz, 1H); MS (DCI/NH$_3$) m/z 371 (M+H)$^+$; Anal. Calculated for C$_{22}$H$_{30}$N$_2$O$_3$: C, 71.32; H, 8.16; N, 7.56. Found: C, 71.08; H, 7.94; N, 7.36.

EXAMPLE 119

(2E)-4-({1-(2-morpholin-4-ylethyl)-3-[(2,2,3,3-tetramethylcyclopropyl)carbonyl]-1H-indol-5-yl}oxy)-4-oxobut-2-enoic acid The product of Example 118B (0.15 g, 0.41 mmol), fumaryl chloride (46 µL, 0.43 mmol) and triethylamine (57 µL, 0.41 mmol) in 40 mL of Et$_2$O and 20 mL of THF were processed as described in Example 65 to provide the title compound (60 mg, 0.13 mmol, 32% yield). $^1$H NMR (MeOH-d$_4$, 300 MHz) δ ppm 1.32 (s, 6H), 1.33 (s, 6H), 2.01 (s, 1H), 2.56-2.63 (m, 4H), 2.88 (t, J=6.4 Hz, 2H), 3.66-3.72 (m, 4H), 4.42 (t, J=6.4 Hz, 2H), 7.00 (s, 2H), 7.08 (dd, J=8.8, 2.4 Hz, 1H), 7.55 (d, J=8.8 Hz, 1H), 8.03 (d, J=2.4 Hz, 1H), 8.19 (s, 1H); MS (DCI/NH$_3$) m/z 469 (M+H)$^+$; Anal. Calculated for C$_{26}$H$_{32}$N$_2$O$_6$: C, 65.64; H, 6.35; N, 5.89. Found: C, 65.45; H, 6.63; N, 5.64.

EXAMPLE 120

[5-methoxy-1-(2-morpholin-4-ylethyl)-1H-indol-3-yl](2,2,3,3-tetramethylcyclopropyl)methanone The product of Example 118B (0.15 g, 0.41 mmol), Cs$_2$CO$_3$ (0.4 g, 1.2 mmol) and CH$_3$I (51 µL, 0.61 mmol) in 5 mL of DMF combined and stirred at ambient temperature for 72 h. The mixture was quenched with 3 mL NH$_4$Cl and diluted with 5 mL of EtOAc. The layers were separated and the aqueous layer was extracted 3×3 mL of EtOAc. The combined organic extracts were washed with 1×5 mL of saturated aqueous NaCl, dried over anhydrous Na$_2$SO$_4$, filtered, concentrated under reduced pressure and recrystallized with 4:1 hexanes:EtOAc to provide the title compound (75 mg, 0.20 mmol, 48% yield). $^1$H NMR (MeOH-d$_4$, 300 MHz) δ ppm 1.33 (s, 12H), 2.10 (s, 1H), 2.47-2.53 (m, 4H), 2.77 (t, J=6.4 Hz, 2H), 3.63-3.69 (m, 4H), 3.84 (s, 3H), 4.33 (t, J=6.4 Hz, 2H), 6.89 (dd, J=8.8, 2.7 Hz, 1H), 7.38 (d, J=8.8 Hz, 1H), 7.81 (d, J=2.4 Hz, 1H), 8.06 (s, 1H); MS (DCI/NH$_3$) m/z 385 (M+H)$^+$; Anal. Calculated for C$_{23}$H$_{32}$N$_2$O$_3$: C, 71.84; H, 8.39; N, 7.29. Found: C, 71.65; H, 8.46; N, 7.08.

EXAMPLE 121

N-[4-({1-(tetrahydro-2H-pyran-4-ylmethyl)-3-[(2,2, 3,3-tetramethylcyclopropyl)carbonyl]-1H-indol-5-yl}oxy)butyl]methanesulfonamide The product of Example 117B (75 mg, 0.18 mmol), methanesulfonyl chloride (20 μL, 0.26 mmol) and triethylamine (74 μL, 0.53 mmol) in 2 mL of THF were processed as described in Example 106B to provide the title compound (60 mg, 0.12 mmol, 66% yield). $^1$H NMR (CDCl$_3$, 300 MHz) δ ppm 1.30 (s, 6H), 1.34 (s, 6H), 1.36-1.63 (m, 4H), 1.88 (s, 4H), 1.88 (s, 1H), 2.06-2.20 (m, 1H), 2.97 (s, 3H), 3.21-3.28 (m, 2H), 3.33 (dt, J=11.7, 2.4 Hz, 2H), 3.41-3.54 (m, 1H), 3.93-4.03 (m, 2H), 4.00 (d, J=7.1 Hz, 2H), 4.05-4.15 (m, 2H), 6.92 (dd, J=8.8, 2.7 Hz, 1H), 7.22 (d, J=8.8 Hz, 1H), 7.57 (s, 1H), 7.92 (d, J=2.4 Hz, 1H); MS (DCI/NH$_3$) m/z 505 (M+H)$^+$; Anal. Calculated for C$_{27}$H$_{40}$N$_2$O$_5$S: C, 64.26; H, 7.99; N, 5.55. Found: C, 64.22; H, 7.93; N, 5.43.

EXAMPLE 122

1-(tetrahydro-2H-pyran-4-ylmethyl)-3-[(2,2,3,3-tetramethylcyclopropyl)carbonyl]-1H-indole-5-carboxamide A mixture 1-(tetrahydro-2H-pyran-4-ylmethyl)-3-[(2,2,3, 3-tetramethylcyclopropyl)carbonyl]-1H-indole-5-carboxylic acid (0.10 g, 0.26 mmol, the minor product of Example 114B), 1,1'-carbonyldimidazole (55 mg, 0.34 mmol) and concentrated aqueous NH$_4$OH (2 mL) in 5 mL of EtOAc and 3 mL of THF was processed as described in Example 93 to provide the title compound (20 mg, 0.052 mmol, 20% yield). $^1$H NMR (CDCl$_3$, 300 MHz) δ ppm 1.32 (s, 6H), 1.36 (s, 6H), 1.39-1.58 (m, 4H), 1.92 (s, 1H), 2.08-2.23 (m, 1H), 3.34 (dt, J=11.4, 2.5 Hz, 2H), 3.94-4.04 (m, 2H), 4.08 (d, J=7.1 Hz, 2H), 7.41 (d, J=8.5 Hz, 1H), 7.67 (s, 1H), 7.98 (dd, J=8.5, 1.4 Hz, 1H), 8.84 (d, J=1.0 Hz, 1H); MS (DCI/NH$_3$) m/z 383 (M+H)$^+$; Anal. Calculated for C$_{23}$H$_{30}$N$_2$O$_3$.0.4H$_2$O: C, 70.89; H, 7.97; N, 7.19. Found: C, 70.77; H, 7.91; N, 7.32.

EXAMPLE 123

N-(2-hydroxyethyl)-1-(tetrahydro-2H-pyran-4-ylmethyl)-3-[(2,2,3,3-tetramethylcyclopropyl)carbonyl]-1H-indole-5-carboxamide A mixture 1-(tetrahydro-2H-pyran-4-ylmethyl)-3-[(2,2,3, 3-tetramethylcyclopropyl)carbonyl]-1H-indole-5-carboxylic acid (0.10 g, 0.26 mmol, the minor product of Example 114B), 1,1'-carbonyldimidazole (55 mg, 0.34 mmol) and ethanolamine (21 μL, 0.34 mmol) in 4 mL of EtOAc and 3 mL of THF was processed as described in Example 93 to provide the title compound (51 mg, 0.12 mmol, 46% yield). $^1$H NMR (DMSO-d$_6$, 300 MHz) δ ppm 1.27 (s, 12H), 1.30-1.45 (m, 4H), 2.05-2.19 (m, 1H), 2.23 (s, 1H), 3.22 (dt, J=11.1, 3.2 Hz, 2H), 3.31-3.39 (m, 2H), 3.52 (q, J=6.0 Hz, 2H), 3.83 (d, 2H), 4.17 (d, J=7.1 Hz, 2H), 4.70 (t, J=5.6 Hz, 1H), 7.66 (d, J=8.1 Hz, 1H), 7.74 (dd, J=8.5, 1.7 Hz, 1H), 8.35 (t, J=5.8 Hz, 1H), 8.38 (s, 1H), 8.74 (d, J=1.4 Hz, 1H); MS (DCI/NH$_3$) m/z 427 (M+H)$^+$; Anal. Calculated for C$_{25}$H$_{34}$N$_2$O$_4$.0.3H$_2$O: C, 69.51; H, 8.07; N, 6.49. Found: C, 69.36; H, 7.88; N, 6.27.

EXAMPLE 124

N-methyl-1-(tetrahydro-2H-pyran-4-ylmethyl)-3-[(2, 2,3,3-tetramethylcyclopropyl)carbonyl]-1H-indole-5-carboxamide A mixture 1-(tetrahydro-2H-pyran-4-ylmethyl)-3-[(2,2,3, 3-tetramethylcyclopropyl)carbonyl]-1H-indole-5-carboxylic acid (0.10 g, 0.26 mmol, the minor product of Example 114B), 1,1'-carbonyldimidazole (55 mg, 0.34 mmol) and methylamine (2 M solution in THF, 0.2 mL, 0.4 mmol) in 4 mL of EtOAc and 3 mL of THF was processed as described in Example 93 to provide the title compound (14 mg, 0.035 mmol, 14% yield). $^1$H NMR (DMSO-d$_6$, 300 MHz) δ ppm 1.27 (s, 12H), 1.30-1.46 (m, 4H), 2.03-2.17 (m, 1H), 2.22 (s, 1H), 2.79 (d, J=4.7 Hz, 3H), 3.22 (dt, J=11.4, 3.1 Hz, 2H), 3.80-3.88 (m, 2H), 4.17 (d, J=7.5 Hz, 2H), 7.63-7.77 (m, 2H), 8.32-8.37 (m, 1H), 8.38 (s, 1H), 8.74 (d, J=1.4 Hz, 1H); MS (DCI/NH$_3$) m/z 397 (M+H)$^+$; Anal. Calculated for C$_{24}$H$_{32}$N$_2$O$_2$.0.3H$_2$O: C, 71.72; H, 8.18; N, 6.97. Found: C, 71.96; H, 8.19; N, 6.69.

EXAMPLE 125

1-(tetrahydro-2H-pyran-4-ylmethyl)-3-[(2,2,3,3-tetramethylcyclopropyl)carbonyl]-1H-indole-5-carbonitrile

EXAMPLE 125A 3-(2,2,3,3-Tetramethyl-cyclopropanecarbonyl)-1H-indole-5-carbonitrile A mixture of 5-cyanoindole (1.42 g, 10 mmol), ethylmagnesium bromide (1.0 M solution in THF, 11 mL, 11 mmol), zinc chloride (1.0 M solution in Et$_2$O, 11 mL, 11 mmol) and the product of Example 1A (10 mmol) in 30 mL of dichloromethane was processed as described in Example 1B to provide the title compound (0.45 g, 1.7 mmol, 17% yield). MS (DCI/NH$_3$) m/z 267 (M+H)$^+$.

EXAMPLE 125B 1-(tetrahydro-2H-pyran-4-ylmethyl)-3-[(2,2,3,3-tetramethylcyclopropyl)carbonyl]-1H-indole-5-carbonitrile The product of Example 125A (0.45 g, 1.7 mmol), the product of Example 18A (2.9 mmol), and NaH (60% dispersion in mineral oil, 0.20 g, 5.1 mmol) in DMF (10 mL) were processed as described in Example 1D to provide the title compound (0.41 g, 1.1 mmol, 66% yield). $^1$H NMR (CDCl$_3$, 300 MHz) δ ppm 1.32 (s, 6H), 1.35 (s, 6H), 1.39-1.55 (m, 4H), 1.89 (s, 1H), 2.05-2.21 (m, 1H), 3.34 (dt, J=11.5, 2.7 Hz, 2H), 3.94-4.03 (m, 2H), 4.07 (d, J=7.5 Hz, 2H), 7.39 (d, J=8.5 Hz, 1H), 7.52 (dd, J=11.8, 1.7 Hz, 1H), 7.69 (s, 1H), 8.83 (d, J=1.7 Hz, 1H); MS (DCI/NH$_3$) m/z 365 (M+H)$^+$; Anal. Calculated for C$_{23}$H$_{28}$N$_2$O$_2$: C, 75.79; H, 7.74; N, 7.69. Found: C, 75.54; H, 7.85; N, 7.78.

EXAMPLE 126

[5-(benzyloxy)-6-methoxy-1-(tetrahydro-2H-pyran-4-ylmethyl)-1H-indol-3-yl](2,2,3,3-tetramethylcyclopropyl)methanone

EXAMPLE 126A (5-Benzyloxy-6-methoxy-1H-indol-3-yl)-(2,2,3,3-tetramethyl-cyclopropyl)-methanone A mixture of 5-benzyloxy-6-methoxyindole (Sigma, 2.0 g, 7.9 mmol), ethylmagnesium bromide (1.0 M solution in THF, 9.5 mL, 9.5 mmol), zinc chloride (1.0 M solution in $Et_2O$, 9.5 mL, 9.5 mmol) and the product of Example 1A (12 mmol) was processed as described in Example 1B to provide the title compound (2.0 g, 5.2 mmol, 66% yield). MS ($DCI/NH_3$) m/z 378 $(M+H)^+$.

EXAMPLE 126B

[5-(benzyloxy)-6-methoxy-1-(tetrahydro-2H-pyran-4-ylmethyl)-1H-indol-3-yl](2,2,3,3-tetramethylcyclopropyl)methanone The product of Example 126A (0.98 g, 2.6 mmol), the product of Example 18A (4.4 mmol), and NaH (60% dispersion in mineral oil, 0.31 g, 7.8 mmol) in DMF (20 mL) were processed as described in Example 1D to provide the title compound (1.2 g, 2.5 mmol, 96% yield). $^1$H NMR ($CDCl_3$, 300 MHz) δ ppm 1.29 (s, 6H), 1.34 (s, 6H), 1.37-1.51 (m, 4H), 1.85-1.90 (m, 1H), 2.07-2.20 (m, 1H), 3.35 (dt, J=11.6, 2.2 Hz, 2H), 3.94 (s, 3H), 3.96-4.03 (m, 2H), 3.98 (d, J=7.5 Hz, 2H), 5.19 (s, 2H), 6.79 (s, 1H), 7.28-7.41 (m, 3H), 7.48 (s, 1H), 7.50-7.54 (m, 2H), 8.04 (s, 1H); MS ($DCI/NH_3$) m/z 476 $(M+H)^+$; Anal. Calculated for $C_{30}H_{37}NO_4$: C, 75.76; H, 7.84; N, 2.94. Found: C, 75.56; H, 7.92; N, 2.94.

EXAMPLE 127

N,N-dimethyl-1-(tetrahydro-2H-pyran-4-ylmethyl)-3-[(2,2,3,3-tetramethylcyclopropyl)carbonyl]-1H-indole-5-carboxamide A mixture 1-(tetrahydro-2H-pyran-4-ylmethyl)-3-[(2,2,3,3-tetramethylcyclopropyl)carbonyl]-1H-indole-5-carboxylic acid (0.10 g, 0.26 mmol, the minor product of Example 114B), 1,1'-carbonyldimidazole (55 mg, 0.34 mmol) and dimethylamine (2 M solution in THF, 0.17 mL, 0.34 mmol) in 4 mL of EtOAc and 3 mL of THF was processed as described in Example 93 to provide the title compound (38 mg, 0.093 mmol, 35% yield). $^1$H NMR ($DMSO-d_6$, 300 MHz) δ ppm 1.25 (s, 6H), 1.27 (s, 6H), 1.29-1.48 (m, 4H), 2.03-2.18 (m, 1H), 2.20 (s, 1H), 2.97 (s, 3H), 3.23 (dt, J=11.3, 2.9 Hz, 2H), 3.78-3.89 (m, 2H), 4.17 (d, J=7.1 Hz, 2H), 7.27 (dd, J=8.5, 1.7 Hz, 1H), 7.66 (d, J=9.2 Hz, 1H), 8.27 (d, J=1.4 Hz, 1H), 8.37 (s, 1H); MS ($DCI/NH_3$) m/z 411 $(M+H)^+$; Anal. Calculated for $C_{25}H_{34}N_2O_3 \cdot 0.2H_2O$: C, 72.50; H, 8.37; N, 6.76. Found: C, 72.51; H, 8.29; N, 6.66.

EXAMPLE 128

N-heptyl-1-(tetrahydro-2H-pyran-4-ylmethyl)-3-[(2,2,3,3-tetramethylcyclopropyl)carbonyl]-1H-indole-5-carboxamide A mixture 1-(tetrahydro-2H-pyran-4-ylmethyl)-3-[(2,2,3,3-tetramethylcyclopropyl)carbonyl]-1H-indole-5-carboxylic acid (0.10 g, 0.26 mmol, the minor product of Example 114B), 1,1'-carbonyldimidazole (55 mg, 0.34 mmol) and heptylamine (50 μL, 0.34 mmol) in 4 mL of EtOAc and 3 mL of THF was processed as described in Example 93 to provide the title compound (25 mg, 0.052 mmol, 20% yield). $^1$H NMR ($MeOH-d_4$, 300 MHz) δ ppm 0.87-0.95 (m, 3H), 1.34 (s, 12H), 1.37-1.43 (m, 7H), 1.43-1.51 (m, 6H), 1.58-1.71 (m, 2H), 2.13-2.27 (m, 1H), 2.18 (s, 1H), 3.32-3.37 (m, 2H), 3.40 (t, J=7.1 Hz, 2H), 3.87-3.97 (m, 2H), 4.19 (d, J=7.1 Hz, 2H), 7.58 (d, J=8.8 Hz, 1H), 7.75 (dd, J=8.6, 1.9 Hz, 1H), 8.16 (s, 1H), 8.77 (d, J=1.7 Hz, 1H); MS ($DCI/NH_3$) m/z 481 $(M+H)^+$; Anal. Calculated for $C_{30}H_{44}N_2O_3 \cdot 0.2H_2O$: C, 74.40; H, 9.24; N, 5.78. Found: C, 74.43; H, 9.00; N, 5.81.

EXAMPLE 129

[5-hydroxy-6-methoxy-1-(tetrahydro-2H-pyran-4-ylmethyl)-1H-indol-3-yl](2,2,3,3-tetramethylcyclopropyl)methanone The product of Example 126B (1.0 g, 2.2 mmol) and Pd/C (10 wt % palladium on activated carbon, 100 mg) in 20 mL EtOH and 5 mL of EtOAc were processed as described in Example 70 to provide the title compound (0.86 g, 2.2 mmol, 100% yield). $^1$H NMR ($MeOH-d_4$, 300 MHz) δ ppm 1.31 (s, 12H), 1.34-1.57 (m, 4H), 2.07 (s, 1H), 2.11-2.24 (m, 1H), 3.37 (dt, J=11.5, 2.7 Hz, 2H), 3.89-3.97 (m, 2H), 3.93 (s, 3H), 4.09 (d, J=7.1 Hz, 2H), 7.01 (s, 1H), 7.67 (s, 1H), 7.84 (s, 1H); MS ($DCI/NH_3$) m/z 386 $(M+H)^+$; Anal. Calculated for $C_{23}H_{31}NO_4 \cdot 0.1H_2O$: C, 71.33; H, 8.12; N, 3.62. Found: C, 71.15; H, 7.87; N, 3.53.

EXAMPLE 130

(2E)-4-({6-methoxy-1-(tetrahydro-2H-pyran-4-ylmethyl)-3-[(2,2,3,3-tetramethylcyclopropyl)carbonyl]-1H-indol-5-yl}oxy)-4-oxobut-2-enoic acid The product of Example 129 (0.23 g, 0.60 mmol), furmaryl chloride (68 μL, 0.63 mmol) and triethylamine (83 μL, 0.60 mmol) in 60 mL $Et_2O$ and 5 mL of THF were processed as described in Example 65 to provide the title compound (0.13 mg, 0.26 mmol, 44% yield). $^1$H NMR ($MeOH-d_4$, 300 MHz) δ ppm 1.31 (s, 6H), 1.31 (s, 6H), 1.40-1.56 (m, 4H), 2.11 (s, 1H), 2.14-2.25 (m, 1H), 3.38 (dt, J=11.5, 3.1 Hz, 2H), 3.89 (s, 3H), 3.90-3.98 (m, 2H), 4.16 (d, J=7.5 Hz, 2H), 6.99 (d, J=4.7 Hz, 2H), 7.17 (s, 1H), 7.94 (s, 1H), 8.00 (s, 1H); MS ($DCI/NH_3$) m/z 484 $(M+H)^+$; Anal. Calculated for $C_{27}H_{33}NO_7$: C, 67.06; H, 6.88; N, 2.90. Found: C, 66.91; H, 6.81; N, 2.80.

EXAMPLE 131

{5-(benzyloxy)-1-[(2R)-tetrahydrofuran-2-ylmethyl]-1H-indol-3-yl}(2,2,3,3-tetramethylcyclopropyl)methanone The product of Example 74A (0.61 g, 1.8 mmol), the mesylate of (R)-(−)-tetrahydrofurfuryl alcohol (Lancaster, 0.33 g, 3.1 mmol), and NaH (60% dispersion in mineral oil, 0.22 g, 5.5 mmol) in 10 mL of DMF were processed as described in Example 1D to provide the title compound (0.70 g, 1.6 mmol, 88% yield). $^1$H NMR ($CDCl_3$, 300 MHz) δ ppm 1.30 (s, 6H), 1.34 (s, 3H), 1.36 (s, 3H), 1.51-1.63 (m, 1H), 1.70-1.89 (m, 2H), 1.91 (s, 1H), 1.93-2.07 (m, 1H), 3.73-3.89 (m, 2H), 4.11-4.32 (m, 3H), 5.14 (s, 2H), 6.99 (dd, J=9.0, 2.5 Hz, 1H), 7.26 (t, J=4.4 Hz, 1H), 7.30-7.43 (m, 3H), 7.45-7.51 (m, 2H), 7.74 (s, 1H), 8.07 (d, J=2.4 Hz, 1H); MS ($DCI/NH_3$) m/z 432

(M+H)$^+$; Anal. Calculated for $C_{28}H_{33}NO_3$: C, 77.93; H, 7.71; N, 3.25. Found: C, 77.82; H, 7.72; N, 3.22.

EXAMPLE 132

[5-(aminomethyl)-1-(tetrahydro-2H-pyran-4-ylmethyl)-1H-indol-3-yl](2,2,3,3-tetramethylcyclopropyl)methanone The product of Example 125B (0.34 g, 0.93 mmol) and Raney-Nickel (RaNi 2800 slurry in water, 100 mg) in 2 mL of a 20% NH$_3$ in MeOH were placed under 60 psi of hydrogen. The mixture was shaken at ambient temperature for 16 hours and then filtered. The resulting material was concentrated under reduced pressure and purified via flash column chromatography (SiO$_2$, 9:1:0.1 CH$_2$Cl$_2$:CH$_3$OH:NH$_4$OH) to provide the title compound (0.17 g, 0.46 mmol, 50% yield). $^1$H NMR (CDCl$_3$, 300 MHz) δ ppm 1.29 (s, 6H), 1.32 (s, 6H), 1.35-1.55 (m, 4H), 1.91 (s, 1H), 2.05-2.19 (m, 1H), 3.32 (dt, J=11.5, 2.0 Hz, 2H), 3.92-4.06 (m, 4H), 7.29-7.41 (m, 2H), 7.61 (s, 1H), 8.34 (s, 1H); MS (DCI/NH$_3$) m/z 369 (M+H)$^+$; Anal. Calculated for $C_{23}H_{32}N_2O_2 \cdot 0.4H_2O$: C, 73.53; H, 8.80; N, 7.46. Found: C, 73.41; H, 8.61; N, 7.44.

EXAMPLE 133

{5-hydroxy-1-[(2R)-tetrahydrofuran-2-ylmethyl]-1H-indol-3-yl}(2,2,3,3-tetramethylcyclopropyl)methanone The product of Example 131 (0.70 g, 1.6 mmol) and Pd/C (10 wt % palladium on activated carbon, 350 mg) in 30 mL EtOH were processed as described in Example 70 to provide the title compound (0.35 g, 1.0 mmol, 64% yield). $^1$H NMR (MeOH-d$_4$, 300 MHz) δ ppm 1.30 (s, 3H), 1.31 (s, 9H), 1.57-1.70 (m, 1H), 1.73-1.92 (m, 2H), 1.99-2.09 (m, 1H), 2.05 (s, 1H), 3.69-3.88 (m, 2H), 4.16-4.36 (m, 3H), 6.78 (dd, J=8.8, 2.7 Hz, 1H), 7.33 (dd, J=8.8, 0.7 Hz, 1H), 7.65 (d, J=2.0 Hz, 1H), 7.96 (s, 1H); MS (DCI/NH$_3$) m/z 342 (M+H)$^+$; Anal. Calculated for $C_{21}H_{27}NO_3 \cdot 0.2H_2O$: C, 73.10; H, 8.00; N, 4.06. Found: C, 73.32; H, 8.11; N, 4.01.

EXAMPLE 134

N-({1-(tetrahydro-2H-pyran-4-ylmethyl)-3-[(2,2,3,3-tetramethylcyclopropyl)carbonyl]-1H-indol-5-yl}methyl)methanesulfonamide The product of Example 132 (0.16 g, 0.45 mmol), methanesulfonyl chloride (52 µL, 0.67 mmol) and triethylamine (0.19 mL, 1.3 mmol) in 10 mL of THF were processed as described in Example 106B to provide the title compound (0.16 g, 0.35 mmol, 78% yield). $^1$H NMR (MeOH-d$_4$, 300 MHz) δ ppm 1.33 (s, 12H), 1.36-1.55 (m, 4H), 2.14 (s, 1H), 2.15-2.26 (m, 1H), 2.83 (s, 3H), 3.32-3.40 (m, 2H), 3.88-3.97 (m, 2H), 4.15 (d, J=7.5 Hz, 2H), 4.35 (s, 2H), 7.32 (dd, J=8.5, 1.7 Hz, 1H), 7.51 (d, J=8.5 Hz, 1H), 8.07 (s, 1H), 8.28 (d, J=1.4 Hz, 1H); MS (DCI/NH$_3$) m/z 447 (M+H)$^+$; Anal. Calculated for $C_{24}H_{34}N_2O_4S \cdot 0.1H_2O$: C, 64.29; H, 7.69; N, 6.25. Found: C, 64.12; H, 7.73; N, 6.19.

EXAMPLE 135

{5-(benzyloxy)-1-[4-(benzyloxy)butyl]-1H-indol-3-yl}(2,2,3,3-tetramethylcyclopropyl)methanone The product of Example 74A (0.71 g, 2.0 mmol), product of Example 23A (3.5 mmol), and NaH (60% dispersion in mineral oil, 0.12 g, 3.1 mmol) in 12 mL of DMF were processed as described in Example 1D to provide the title compound (0.37 g, 0.73 mmol, 36% yield). $^1$H NMR (CDCl$_3$, 300 MHz) δ ppm 1.29 (s, 6H), 1.35 (s, 6H), 1.60-1.73 (m, 2H), 1.88 (s, 1H), 1.94-2.07 (m, 2H), 3.50 (t, J=6.1 Hz, 2H), 4.16 (t, J=7.1 Hz, 2H), 4.49 (s, 2H), 5.14 (s, 2H), 6.98 (dd, J=8.8, 2.7 Hz, 1H), 7.21 (d, J=8.8 Hz, 1H), 7.28-7.43 (m, 8H), 7.45-7.51 (m, 2H), 7.62 (s, 1H), 8.06 (d, J=2.4 Hz, 1H); MS (DCI/NH$_3$) m/z 510 (M+H)$^+$; Anal. Calculated for $C_{34}H_{39}NO_3$: C, 80.12; H, 7.71; N, 2.75. Found: C, 79.77; H, 7.58; N, 2.70.

EXAMPLE 136

[6-(methylsulfonyl)-1-(tetrahydro-2H-pyran-4-ylmethyl)-1H-indol-3-yl](2,2,3,3-tetramethylcyclopropyl)methanone

EXAMPLE 136A (6-Methanesulfonyl-1H-indol-3-yl)-(2,2,3,3-tetramethyl-cyclopropyl)-methanone The 6-(methylsulfonyl)-1H-indole (Apollo Scientific, 1.0 g, 5.1 mmol), ethylmagnesium bromide (1.0 M solution in THF, 6.1 mL, 6.1 mmol), zinc chloride (1.0 M solution in Et$_2$O, 6.1 mL, 6.1 mmol) and the product of Example 1A (7.7 mmol) were processed as described in Example 1B to provide the title compound (0.21 g, 0.66 mmol, 13% yield). MS (DCI/NH$_3$) m/z 378 (M+H)$^+$.

EXAMPLE 136B

[6-(methylsulfonyl)-1-(tetrahydro-2H-pyran-4-ylmethyl)-1H-indol-3-yl](2,2,3,3-tetramethylcyclopropyl)methanone The product of Example 136A (0.21 g, 0.66 mmol), the product of Example 18A (1.3 mmol), and NaH (60% dispersion in mineral oil, 79 mg, 2.0 mmol) in DMF (10 mL) were processed as described in Example 1D to provide the title compound (0.18 g, 0.43 mmol, 65% yield). $^1$H NMR (CDCl$_3$, 300 MHz) δ ppm 1.32 (s, 6H), 1.35 (s, 6H), 1.37-1.55 (m, 4H), 1.92 (s, 1H), 2.09-2.27 (m, 1H), 3.11 (s, 3H), 3.35 (dt, J=11.5, 2.7 Hz, 2H), 3.93-4.04 (m, 2H), 4.12 (d, J=7.5 Hz, 2H), 7.77 (dd, J=8.5, 1.7 Hz, 1H), 7.79 (s, 1H), 7.99 (d, J=1.4 Hz, 1H), 8.61 (d, J=8.5 Hz, 1H); MS (DCI/NH$_3$) m/z 418 (M+H)$^+$; Anal. Calculated for $C_{23}H_{31}NO_4S$: C, 66.16; H, 7.48; N, 3.35. Found: C, 65.77; H, 7.23; N, 3.35.

EXAMPLE 137

[5-hydroxy-1-(4-hydroxybutyl)-1H-indol-3-yl](2,2,3,3-tetramethylcyclopropyl)methanone The product of Example 135 (0.36 g, 0.71 mmol) and Pd/C (10 wt % palladium on activated carbon, 360 mg) in 50 mL EtOH were processed as described in Example 70 to provide the title compound (0.16 g, 0.48 mmol, 68% yield). $^1$H NMR (MeOH-d$_4$, 300 MHz) δ ppm 1.31 (s, 12H), 1.47-1.61 (m, 2H), 1.87-2.01 (m, 2H), 2.08 (s, 1H), 3.57 (t, J=6.4 Hz, 2H), 4.23 (t, J=7.1 Hz, 2H), 6.79 (dd, J=8.8, 2.7 Hz, 1H), 7.30 (d, J=8.8 Hz, 1H), 7.66 (d, J=2.4 Hz, 1H), 7.97 (s, 1H); MS (DCI/NH$_3$) m/z 330 (M+H)$^+$; Anal. Calculated for C$_{20}$H$_{27}$NO$_3$: C, 72.92; H, 8.26; N, 4.25. Found: C, 72.76; H, 8.21; N, 4.19.

EXAMPLE 138

1-(tetrahydro-2H-pyran-4-ylmethyl)-3-[(2,2,3,3-tetramethylcyclopropyl)carbonyl]-1H-indole-6-carbonitrile

EXAMPLE 138A

3-(2,2,3,3-Tetramethyl-cyclopropanecarbonyl)-1H-indole-6-carbonitrile

A mixture of 6-cyanoindole (Lancaster, 1.0 g, 7.0 mmol), ethylmagnesium bromide (1.0 M solution in THF, 8.4 mL, 8.4 mmol), zinc chloride (1.0 M solution in Et$_2$O, 8.4 mL, 8.4 mmol) and the product of Example 1A (11 mmol) was processed as described in Example 1B to provide the title compound (0.91 g, 3.4 mmol, 49% yield). MS (DCI/NH$_3$) m/z 267 (M+H)$^+$.

EXAMPLE 138B

1-(tetrahydro-2H-pyran-4-ylmethyl)-3-[(2,2,3,3-tetramethylcyclopropyl)carbonyl]-1H-indole-6-carbonitrile The product of Example 138A (0.91 g, 3.4 mmol), the product of Example 18A (5.8 mmol), and NaH (60% dispersion in mineral oil, 0.37 g, 9.1 mmol) in DMF (20 mL) were processed as described in Example 1D to provide the title compound (0.87 g, 2.4 mmol, 70% yield). $^1$H NMR (CDCl$_3$, 300 MHz) δ ppm 1.32 (s, 6H), 1.34 (s, 6H), 1.39-1.57 (m, 4H), 1.90 (s, 1H), 2.06-2.22 (m, 1H), 3.36 (dt, J=11.5, 2.7 Hz, 2H), 3.96-4.04 (m, 2H), 4.07 (d, J=7.5 Hz, 2H), 7.49 (dd, J=8.5, 1.4 Hz, 1H), 7.67 (d, J=0.7 Hz, 1H), 7.75 (s, 1H), 8.51 (d, J=8.1 Hz, 1H); MS (DCI/NH$_3$) m/z 365 (M+H)$^+$; Anal. Calculated for C$_{23}$H$_{28}$N$_2$O$_2$: C, 75.79; H, 7.74; N, 7.69. Found: C, 75.64; H, 7.61; N, 7.36.

EXAMPLE 139

[1-(tetrahydro-2H-pyran-4-ylmethyl)-6-(trifluoromethyl)-1H-indol-3-yl](2,2,3,3-tetramethylcyclopropyl)methanone

EXAMPLE 139A

(2,2,3,3-Tetramethyl-cyclopropyl)-(6-trifluoromethyl-1H-indol-3-yl)methanone A mixture of 6-(trifluoromethyl)indole (Lancaster, 1.0 g, 5.4 mmol), ethylmagnesium bromide (1.0 M solution in THF, 6.6 mL, 6.6 mmol), zinc chloride (1.0 M solution in Et$_2$O, 6.6 mL, 6.6 mmol) and the product of Example 1A (8.1 mmol) in 40 mL of dichloromethane was processed as described in Example 1B to provide the title compound (0.17 g, 0.53 mmol, 10% yield). MS (DCI/NH$_3$) m/z 310 (M+H)$^+$.

EXAMPLE 139B

[1-(tetrahydro-2H-pyran-4-ylmethyl)-6-(trifluoromethyl)-1H-indol-3-yl](2,2,3,3-tetramethylcyclopropyl)methanone The product of Example 139A (0.16 g, 0.52 mmol), the product of Example 18A (0.89 mmol), and NaH (60% dispersion in mineral oil, 63 mg, 1.6 mmol) in DMF (10 mL) were processed as described in Example 1D to provide the title compound (70 mg, 0.17 mmol, 33% yield). $^1$H NMR (CDCl$_3$, 300 MHz) δ ppm 1.32 (s, 6H), 1.35 (s, 6H), 1.37-1.58 (m, 4H), 1.92 (s, 1H), 2.09-2.24 (m, 1H), 3.36 (dt, J=11.5, 2.7 Hz, 2H), 3.95-4.04 (m, 2H), 4.09 (d, J=7.1 Hz, 2H), 7.50 (dd, J=8.6, 1.2 Hz, 1H), 7.58 (d, J=0.7 Hz, 1H), 7.69-7.77 (m, 1H), 8.51 (d, J=8.5 Hz, 1H); MS (DCI/NH$_3$) m/z 408 (M+H)$^+$; Anal. Calculated for C$_{23}$H$_{28}$F$_3$NO$_2$.0.1H$_2$O: C, 67.50; H, 6.94; N, 3.42. Found: C, 67.20; H, 6.88; N, 3.42.

EXAMPLE 140

[6-(aminomethyl)-1-(tetrahydro-2H-pyran-4-ylmethyl)-1H-indol-3-yl](2,2,3,3-tetramethylcyclopropyl)methanone The product of Example 138B (0.75 g, 2.1 mmol), Raney-Nickel (RaNi 2800 slurry in water, 225 mg) and H$_2$ (60 psi) in 4 mL of a 20% NH$_3$ in MeOH solution were processed as described in Example 132 to provide the title compound (0.75 g, 2.0 mmol, 99% yield). $^1$H NMR (MeOH-d$_4$, 300 MHz) δ ppm 1.32 (s, 12H), 1.37-1.55 (m, 4H), 2.13 (s, 1H), 2.16-2.31 (m, 1H), 3.37 (dt, J=11.2, 3.1 Hz, 2H), 3.89-3.97 (m, 2H), 3.95 (s, 2H), 4.16 (d, J=7.5 Hz, 2H), 7.20 (dd, J=8.1, 1.4 Hz, 1H), 7.50 (d, J=0.7 Hz, 1H), 8.04 (s, 1H), 8.22 (d, J=8.5 Hz, 1H); MS (DCI/NH$_3$) m/z 369 (M+H)$^+$; Anal. Calculated for C$_{23}$H$_{32}$N$_2$O$_2$.0.3H$_2$O: C, 73.88; H, 8.79; N, 7.49. Found: C, 73.69; H, 8.52; N, 7.41.

EXAMPLE 141

N-({1-(tetrahydro-2H-pyran-4-ylmethyl)-3-[(2,2,3,3-tetramethylcyclopropyl)carbonyl]-1H-indol-6-yl}methyl)methanesulfonamide The product of Example 140 (0.73 g, 2.0 mmol), methanesulfonyl chloride (0.24 mL, 3.1 mmol) and triethylamine (0.86 mL, 6.2 mmol) in 30 mL of THF were processed as described in Example 106B to provide the title compound (0.52 g, 1.2 mmol, 58% yield). $^1$H NMR (CDCl$_3$, 300 MHz) δ ppm 1.31 (s, 6H), 1.35 (s, 6H), 1.39-1.59 (m, 4H), 1.92 (s, 1H), 2.07-2.22 (m, 1H), 2.85 (s, 3H), 3.35 (dt, J=11.6, 2.5 Hz, 2H), 3.94-4.02 (m, 2H), 4.05 (d, J=7.5 Hz, 2H), 4.45 (s, 2H), 4.63 (s, 1H), 7.21 (dd, J=8.3, 1.5 Hz, 1H), 7.35 (s, 1H), 7.63 (s, 1H), 8.40 (d, J=8.5 Hz, 1H); MS (DCI/NH$_3$) m/z 447 (M+H)$^+$; Anal. Calculated for C$_{24}$H$_{34}$N$_2$O$_4$S: C, 64.54; H, 7.67; N, 6.27. Found: C, 64.23; H, 7.64; N, 6.13.

EXAMPLE 142

[5,6-dihydroxy-1-(tetrahydro-2H-pyran-4-ylmethyl)-1H-indol-3-yl](2,2,3,3-tetramethylcyclopropyl)methanone

EXAMPLE 142A

(5,6-Bis-benzyloxy-1H-indol-3-yl)-(2,2,3,3-tetramethyl-cyclopropyl)-methanone The 5,6-dibenzyloxyindole (Sigma, 0.60 g, 1.8 mmol), ethylmagnesium bromide (1.0 M solution in THF, 2.2 mL, 2.2 mmol), zinc chloride (1.0 M solution in Et$_2$O, 2.2 mL, 2.2 mmol) and the product of Example 1A (2.7 mmol) in 20 mL of dichloromethane were processed as described in Example 1B to provide the title compound (0.45 g, 0.99 mmol, 55% yield). MS (DCI/NH$_3$) m/z 454 (M+H)$^+$.

EXAMPLE 142B

[5,6-Bis-benzyloxy-1-(tetrahydro-pyran-4-ylmethyl)-1H-indol-3-yl]-(2,2,3,3-tetramethyl-cyclopropyl)-methanone The product of Example 142A (0.45 g, 0.99 mmol), the product of Example 18A (2.0 mmol), and NaH (60% dispersion in mineral oil, 0.12 g, 3.0 mmol) in DMF (15 mL) were processed as described in Example 1D to provide the title compound (0.45 g, 0.82 mmol, 82% yield). MS (DCI/NH$_3$) m/z 552 (M+H)$^+$.

EXAMPLE 142C

[5,6-dihydroxy-1-(tetrahydro-2H-pyran-4-ylmethyl)-1H-indol-3-yl](2,2,3,3-tetramethylcyclopropyl) methanone The product of Example 142B (0.45 g, 0.82 mmol) and Pd/C (10 wt % palladium on activated carbon, 450 mg) in 8 mL EtOH were processed as described in Example 70 to provide the title compound (0.12 g, 0.32 mmol, 39% yield). $^1$H NMR (CDCl$_3$, 300 MHz) δ ppm 1.29 (s, 6H), 1.32 (s, 6H), 1.36-1.57 (m, 4H), 1.86 (s, 1H), 2.07-2.17 (m, 1H), 3.33 (dt, J=11.6, 2.2 Hz, 2H), 3.93 (d, J=7.5 Hz, 2H), 3.94-4.01 (m, 2H), 6.86 (s, 1H), 7.47 (s, 1H), 7.95 (s, 1H); MS (DCI/NH$_3$) m/z 372 (M+H)$^+$; Anal. Calculated for C$_{22}$H$_{29}$NO$_4$·0.1H$_2$O: C, 70.79; H, 7.88; N, 3.75. Found: C, 70.70; H, 7.86; N, 3.68.

EXAMPLE 143 tetrahydro-2H-pyran-4-yl{3-[(2,2,3,3-tetramethylcyclopropyl)carbonyl]-1H-indol-1-yl}acetic acid

EXAMPLE 143A (tetrahydro-pyran-4-ylidene)-acetic acid ethyl ester

To a solution of tetrahydro-4H-pyran-4-one (5.0 g, 50 mmol) in 150 mL toluene at ambient temperature was added carbethoxymethylenetriphenyl phosphorane (17.4 g, 50 mmoL). The mixture was warmed to 50° C. and allowed to stir for 16 h. The mixture was cooled to ambient temperature, concentrated under reduced pressure and purified by column chromatography (Si$_2$O, 50% hexanes in EtOAc) to provide the title compound (2.2 g, 13 mmol, 26% yield). MS (DCI/NH$_3$) m/z 171 (M+H)$^+$.

EXAMPLE 143B (tetrahydro-pyran-4-yl)-acetic acid ethyl ester

The product of Example 143A (2.2 g, 13 mmol) and Pd/C (10 wt % palladium on activated carbon, 220 mg) in 30 mL EtOH were processed as described in Example 70 to provide the title compound (2.0 g, 12 mmol, 91% yield). MS (DCI/NH$_3$) m/z 173 (M+H)$^+$.

EXAMPLE 143C bromo-(tetrahydro-pyran-4-yl)-acetic acid ethyl ester

To a solution of lithium diisopropylamide (1.8 M in THF/heptane/ethylbenzene, 3.6 mL, 6.4 mmol) in 10 mL of THF at −78° C. was added trimethylsilyl chloride (1.4 mL, 11 mmol) dropwise via syringe pump. The product of Example 143B (1.0 g, 5.8 mmol) in 5 mL of THF was then added to the mixture dropwise via syringe pump. The mixture was stirred at −78° C. for 2 hours then N-bromosuccinimide (NBS, 1.1 g, 6.0 mmol) in 10 mL of THF was added dropwise via syringe pump. The reaction mixture was allowed to warm slowly to ambient temperature and was stirred for 16 h. The mixture was then concentrated under reduced pressure and the residue was dissolved in 20 mL of EtOAc, washed 1×5 mL of H$_2$O. The aqueous layer was extracted 3×5 mL of EtOAc and the combined organic extracts were dried over anhydrous Na$_2$SO$_4$, filtered, concentrated under reduced pressure and purified via column chromatography (SiO$_2$, 70% hexanes in EtOAc) to provide the title compound (0.70 g, 2.8 mmol, 48% yield). MS (DCI/NH$_3$) m/z 268 (M+NH$_4$)$^+$.

EXAMPLE 143D tetrahydro-2H-pyran-4-yl{3-[(2,2,3,3-tetramethylcyclopropyl)carbonyl]-1H-indol-1-yl}acetic The major product of Example 1B (0.56 g, 2.3 mmol), the product of Example 143C (0.70 g, 2.8 mmol), and NaH (60% dispersion in mineral oil, 0.28 g, 7.0 mmol) in DMF (10 mL) were processed as described in Example 1D to provide the title compound (0.43 g, 1.0 mmol, 45% yield). $^1$H NMR (MeOH-d$_4$, 300 MHz) δ ppm 1.06-1.16 (m, 1H), 1.30 (s, 3H), 1.30-1.36 (m, 1H), 1.33 (s, 6H), 1.34 (s, 3H), 1.56 (ddd, J=24.8, 11.8, 4.7 Hz, 1H), 1.84-1.93 (m, 1H), 1.99 (s, 1H), 2.58-2.76 (m, 1H), 3.37 (dt, J=12.0, 2.5 Hz, 1H), 3.49 (dt, J=11.8, 2.2 Hz, 1H), 3.81-3.90 (m, 1H), 3.95-4.04 (m, 1H), 4.97 (d, J=10.2 Hz, 1H), 7.18-7.31 (m, 2H), 7.54-7.59 (m, 1H), 8.23 (s, 1H), 8.27 (ddd, J=7.5, 1.4, 0.7 Hz, 1H); MS (DCI/NH$_3$) m/z 384 (M+H)$^+$; Anal. Calculated for C$_{23}$H$_{29}$NO$_4$·0.1H$_2$O: C, 71.70; H, 7.64; N, 3.64. Found: C, 71.56; H, 7.56; N, 3.61

EXAMPLE 144 ethyl tetrahydro-2H-pyran-4-yl{3-[(2,2,3,3-tetramethylcyclopropyl)carbonyl]-1H-indol-1-yl}acetate To a solution of the product of Example 143D (0.19 g, 0.50 mmol) in 10 mL EtOH at ambient temperature was added 0.5 mL concentrated H$_2$SO$_4$ (8 mmol). This mixture was warmed to reflux and stirred for 6 h. The mixture was cooled to ambient temperature and then quenched with excess NaHCO$_3$. This mixture was concentrated under reduced pressure and the residue was diluted with 20 mL of EtOAc and 20 mL H$_2$O. The layers were separated and the organic extracts was washed 1×5 mL H$_2$O. The combined aqueous layers were extracted 3×5 mL of EtOAc and the combined organic extracts were dried over anhydrous Na$_2$SO$_4$, filtered, concentrated under reduced pressure and purified via column chromatography (SiO$_2$, 50% hexanes in EtOAc) to provide the title compound (40 mg, 0.097 mmol, 19% yield). $^1$H NMR (CDCl$_3$, 300 MHz) δ ppm 1.09-1.19(m, 1H), 1.27(t, J=7.1 Hz, 3H), 1.32 (s, 3H), 1.32 (s, 6H), 1.35 (s, 3H), 1.50-1.64 (m, 2H), 1.68-1.79 (m, 1H), 1.97 (s, 1H), 2.46-2.62 (m, 1H), 3.33 (dt, J=11.8, 2.2 Hz, 1H), 3.46 (dt, J=11.7, 2.4 Hz, 1H), 3.83-3.92 (m, 1H), 3.99-4.09 (m, 1H), 4.13-4.31 (m, 2H), 4.74 (d, J=10.5 Hz, 1H), 7.25-7.34 (m, 2H), 7.37-7.43 (m, 1H), 7.96 (s, 1H), 8.38-8.43 (m, 1H); MS (DCI/NH$_3$) m/z 412 (M+H)$^+$;

EXAMPLE 145 tert-butyl 1-(tetrahydro-2H-pyran-4-ylmethyl)-3-[(2,2,3,3-tetramethylcyclopropyl)carbonyl]-1H-indol-5-ylcarbamate

EXAMPLE 145A (1H-indol-5-yl)-carbamic acid tert-butyl ester

To a solution 5-aminoindole (1.0 g, 7.6 mmol) in 100 mL of EtOAc was added di-tert-butyldicarbonate (4.1 g. 19 mmol). The mixture was stirred at ambient temperature for 24 hours and then was quenched with 20 mL $H_2O$. The layers were separated and the aqueous layer was extracted 3×10 mL of EtOAc. The combined organic extracts were dried over anhydrous $Na_2SO_4$, filtered, concentrated under reduced pressure and purified via flash column chromatography ($SiO_2$, 50% hexanes in EtOAc) to provide the title compound (1.8 g, 7.7 mmol, >100% yield). MS ($DCI/NH_3$) m/z 233 $(M+H)^+$.

EXAMPLE 145B

[3-(2,2,3,3-Tetramethyl-cyclopropanecarbonyl)-1H-indol-5-yl]-carbamic acid tert-butyl ester The product of Example 145A (1.7 g. 7.3 mmol), ethylmagnesium bromide (1.0 M solution in THF, 9.4 mL, 9.4 mmol), zinc chloride (1.0 M solution in $Et_2O$, 9.4 mL, 9.4 mmol) and the product of Example 1A (12 mmol) in 30 mL of dichloromethane were processed as described in Example 1B to provide the title compound (1.6 g, 4.6 mmol, 60% yield). MS ($DCI/NH_3$) m/z 357 $(M+H)^+$.

EXAMPLE 145C tert-butyl 1-(tetrahydro-2H-pyran-4-ylmethyl)-3-[(2,2,3,3-tetramethylcyclopropyl)carbonyl]-1H-indol-5-ylcarbamate The product of Example 145B (1.6 g, 4.6 mmol), the product of Example 18A (7.8 mmol), and NaH (60% dispersion in mineral oil, 0.55 g, 14 mmol) in DMF (25 mL) were processed as described in Example 1D to provide the title compound (0.55 g, 1.2 mmol, 26% yield). $^1$H NMR ($CDCl_3$, 300 MHz) δ ppm 1.30 (s, 6H), 1.33 (s, 6H), 1.37-1.50 (m, 4H), 1.52 (s, 9H), 1.89 (s, 1H), 2.06-2.22 (m, 1H), 3.32 (dt, J=11.6, 2.5 Hz, 2H), 3.92-3.98 (m, 2H), 4.01 (d, J=7.1 Hz, 2H), 6.50 (s, 1H), 7.22-7.30 (m, 1H), 7.57 (s, 1H), 7.60-7.67 (m, 1H), 8.11 (d, J=2.0 Hz, 1H); MS ($DCI/NH_3$) m/z 455 $(M+H)^+$; Anal. Calculated for $C_{27}H_{38}N_2O_4$: C, 71.34; H, 8.43; N, 6.16. Found: C, 71.27; H, 8.32; N, 6.04.

EXAMPLE 146

[5-amino-1-(tetrahydro-2H-pyran-4-ylmethyl)-1H-indol-3-yl](2,2,3,3-tetramethylcyclopropyl)methanone trifluoroacetic acid To a solution of the product of Example 145C (0.50 g, 1.1 mmol) in 35 mL of dichloromethane was added 5 mL trifluoroacetic acid (67 mmol). The mixture was stirred at ambient temperature for 1 hour then was concentrated under reduced pressure and 5 mL toluene was added. The mixture was again concentrated under reduced pressure and the addition of toluene followed by concentration was repeated. The residue was stirred in 8 mL of EtOAc at ambient temperature for 2 hours and the resulting solids were isolated via filtration to provide the title compound (0.40 g, 0.85 mmol, 77% yield). $^1$H NMR (MeOH-$d_4$, 300 MHz) δ ppm 1.33 (s, 12H), 1.38-1.51 (m, 4H), 2.12-2.29 (m, 1H), 2.17 (s, 1H), 3.32-3.41 (m, 2H), 3.88-3.98 (m, 2H), 4.21 (d, J=7.5 Hz, 2H), 7.25 (dd, J=8.6, 2.2 Hz, 1H), 7.70 (dd, J=8.8, 0.7 Hz, 1H), 8.26 (s, 1H), 8.32-8.35 (m, 1H); MS ($DCI/NH_3$) m/z 355 $(M+H)^+$; Anal. Calculated for $C_{22}H_{30}N_2O_2.CF_3CO_2H.0.4H_2O$: C, 60.59; H, 6.74; N, 5.89. Found: C, 60.38; H, 6.53; N, 6.17.

EXAMPLE 147

[4,5,6,7-tetrafluoro-1-(tetrahydro-2H-pyran-4-ylmethyl)-1H-indol-3-yl](2,2,3,3-tetramethylcyclopropyl)methanone

EXAMPLE 147A (4,5,6,7-tetrafluoro-1H-indol-3-yl)-(2,2,3,3-tetramethyl-cyclopropyl)-methanone A mixture of 4,5,6,7-tetrafluoroindole (Matrix Scientific, 1.0 g. 5.3 mmol), ethylmagnesium bromide (1.0 M solution in THF, 6.4 mL, 6.4 mmol), zinc chloride (1.0 M solution in $Et_2O$, 6.4 mL, 6.4 mmol) and the product of Example 1A (7.9 mmol) in 40 mL of dichloromethane was processed as described in Example 1B to provide the title compound (0.19 g, 0.61 mmol, 12% yield). MS ($DCI/NH_3$) m/z 314 $(M+H)^+$.

EXAMPLE 147B

[4,5,6,7-tetrafluoro-1-(tetrahydro-2H-pyran-4-ylmethyl)-1H-indol-3-yl](2,2,3,3-tetramethylcyclopropyl)methanone The product of Example 147A (91 mg, 0.29 mmol), the product of Example 18A (0.49 mmol), and NaH (60% dispersion in mineral oil, 38 mg, 0.96 mmol) in DMF (6 mL) were processed as described in Example 1D to provide the title compound (11 mg, 0.027 mmol, 9% yield). $^1$H NMR (MeOH-$d_4$, 300 MHz) δ ppm 1.33 (s, 12H), 1.40-1.58 (m, 4H), 2.05-2.18 (m, 1H), 2.08 (s, 1H), 3.41 (dt, J=11.2, 2.4 Hz, 2H), 3.95-4.04 (m, 2H), 4.22 (d, J=7.1 Hz, 2H), 7.78 (s, 1H); MS ($DCI/NH_3$) m/z 412 $(M+H)^+$; Anal. Calculated for $C_{22}H_{25}F_4NO_2$: C, 64.22; H, 6.12; N, 3.40. Found: C, 63.88; H, 6.17; N, 3.41.

EXAMPLE 148

N-{1-(tetrahydro-2H-pyran-4-ylmethyl)-3-[(2,2,3,3-tetramethylcyclopropyl)carbonyl]-1H-indol-5-yl}methanesulfonamide The product of Example 146 (0.20 g, 0.46 mmol), methanesulfonyl chloride (50 μL, 0.63 mmol) and triethylamine (0.26 mL, 1.9 mmol) in 10 mL of THF were processed as described in Example 106B to provide the title compound (0.12 g, 0.28 mmol, 60% yield). $^1$H NMR ($CDCl_3$, 300 MHz) δ ppm 1.31 (s, 6H), 1.34 (s, 6H), 1.38-1.57 (m, 4H), 1.89 (s, 1H), 2.07-2.25 (m, 1H), 2.97 (s, 3H), 3.34 (dt, J=111.6, 2.5 Hz, 2H), 3.95-4.02 (m, 2H), 4.04 (d, J=7.5 Hz, 2H), 6.28 (s, 1H), 7.33 (d, J=8.8 Hz, 1H), 7.42 (dd, J=8.8, 2.0 Hz, 1H), 7.64 (s, 1H), 8.20 (d, J=2.0 Hz, 1H); MS ($DCI/NH_3$) m/z 433 $(M+H)^+$; Anal. Calculated for $C_{23}H_{32}N_2C_4S$: C, 63.86; H, 7.46; N, 6.48. Found: C, 63.48; H, 7.19; N, 6.23.

EXAMPLE 149

[5-(hydroxymethyl)-1-(tetrahydro-2H-pyran-4-ylmethyl)-1H-indol-3-yl](2,2,3,3-tetramethylcyclopropyl)methanone

EXAMPLE 149A 5-(tert-Butyl-dimethyl-silanyloxymethyl)-1H-indole

To a solution of indole-1-methanol (Combi-Blocks, 1.0 g, 6.8 mmol) in 50 mL of dichloromethane was added imidazole (0.56 g, 8.2 mmol) followed by tert-butyldimethylsilyl chloride (1.1 g, 7.0 mmol). The mixture was stirred at ambient temperature for 17 hours then 10 mL $H_2O$ was added and the layers were separated. The aqueous layer was extracted 3×5 mL of dichloromethane and the combined organic extracts were dried over anhydrous $Na_2SO_4$, filtered, concentrated under reduced pressure and purified via flash column chromatography ($SiO_2$, 80% hexanes in EtOAc) to provide the title compound (1.6 g, 6.2 mmol, 91% yield). MS (DCI/$NH_3$) m/z 262 (M+H)$^+$.

EXAMPLE 149B

[5-(tert-Butyl-dimethyl-silanyloxymethyl)-1H-indol-3-yl]-(2,2,3,3-tetramethyl-cyclopropyl)-methanone The product of Example 149A (1.6 g. 6.2 mmol), ethylmagnesium bromide (1.0 M solution in THF, 7.5 mL, 7.5 mmol), zinc chloride (1.0 M solution in $Et_2O$, 7.5 mL, 7.5 mmol) and the product of Example 1A (9.4 mmol) in 30 mL of dichloromethane were processed as described in Example 1B to provide the title compound (0.90 g, 2.3 mmol, 38% yield). MS (DCI/$NH_3$) m/z 386 (M+H)$^+$.

EXAMPLE 149C

[5-(hydroxymethyl)-1-(tetrahydro-2H-pyran-4-ylmethyl)-1H-indol-3-yl](2,2,3,3-tetramethylcyclopropyl)methanone The product of Example 149B (0.88 g, 2.3 mmol), the product of Example 18A (3.9 mmol), and NaH (60% dispersion in mineral oil, 0.28 g, 6.9 mmol) in DMF (12 mL) were processed as described in Example 1D to provide the title compound (0.20 g, 0.54 mmol, 24% yield, major product) as well as the corresponding tert-butyldimethylsilyl ether (0.17 g, 0.35 mmol, 15% yield). $^1$H NMR (CDCl$_3$, 300 MHz) δ ppm 1.31 (s, 6H), 1.35 (s, 6H), 1.38-1.62 (m, 4H), 1.92 (s, 1H), 2.09-2.22 (m, 1H), 2.55-2.74 (m, 1H), 3.25-3.46 (m, 2H), 3.93-4.02 (m, 2H), 4.04 (d, J=7.5 Hz, 2H), 4.79 (s, 2H), 7.32-7.37 (m, 2H), 7.62 (s, 1H), 8.41 (s, 1H); MS (DCI/NH$_3$) m/z 370 (M+H)$^+$; Anal. Calculated for C$_{23}$H$_{31}$NO$_3$.0.9H$_2$O: C, 71.62; H, 8.57; N, 3.63. Found: C, 71.57; H, 8.29; N, 3.70.

EXAMPLE 150

[5-(methoxymethyl)-1-(tetrahydro-2H-pyran-4-ylmethyl)-1H-indol-3-yl](2,2,3,3-tetramethylcyclopropyl)methanone The major product of Example 149C (0.10 g, 0.28 mmol), NaH (60% dispersion in mineral oil, 45 mg, 1.1 mmol) and CH$_3$I (71 μL, 0.84 mmol) in 10 mL of THF were processed as described in Example 72 to provide the title compound (60 mg, 0.16 mmol, 56% yield). $^1$H NMR (CDCl$_3$, 300 MHz) δ ppm 1.31 (s, 6H), 1.35 (s, 6H), 1.38-1.56 (m, 4H), 1.92 (s, 1H), 2.09-2.22 (m, 1H), 3.32 (dt, J=11.5, 2.7 Hz, 2H), 3.37 (s, 3H), 3.93-4.02 (m, 2H), 4.04 (d, J=7.5 Hz, 2H), 4.57 (s, 2H), 7.33 (d, J=1.4 Hz, 2H), 7.61 (s, 1H), 8.38 (s, 1H); MS (DCI/NH$_3$) m/z 384 (M+H)$^+$; Anal. Calculated for C$_{24}$H$_{33}$NO$_3$.0.2H$_2$O: C, 74.46; H, 8.70; N, 3.62. Found: C, 74.25; H, 8.20; N, 3.54.

EXAMPLE 151

3-(2-{5-hydroxy-3-[(2,2,3,3-tetramethylcyclopropyl)carbonyl]-1H-indol-1-yl}ethyl)-1,3-oxazolidin-2-one The product of Example 152 (0.50 g, 1.1 mmol) and Pd/C (10 wt % palladium on activated carbon, 110 mg) in 20 mL EtOH were processed as described in Example 70 to provide the title compound (0.26 g, 0.69 mmol, 64% yield). $^1$H NMR (CDCl$_3$, 300 MHz) δ ppm 1.30 (s, 6H), 1.34 (s, 6H), 1.87 (s, 1H), 2.92 (dd, J=8.1 Hz, 8.1 Hz, 2H), 3.66 (t, J=5.8 Hz, 2H), 4.08 (dd, J=7.5 Hz, 7.5 Hz, 2H), 4.39 (t, J=5.8 Hz, 2H), 6.90 (dd, J=8.8, 2.4 Hz, 1H), 7.25 (d, J=8.8 Hz, 1H), 7.64 (s, 1H), 7.90 (d, J=2.4 Hz, 1H); MS (DCI/NH$_3$) m/z 371 (M+H)$^+$; Anal. Calculated for C$_{21}$H$_{26}$N$_2$O$_4$.0.1H$_2$O: C, 67.94; H, 6.84; N, 7.55. Found: C, 67.84; H, 7.05; N, 7.35.

EXAMPLE 152

3-(2-{5-(benzyloxy)-3-[(2,2,3,3-tetramethylcyclopropyl)carbonyl]-1H-indol-1-yl}ethyl)-1,3-oxazolidin-2-one The product of Example 74A (0.60 g, 1.7 mmol), the product of Example 31A (3.5 mmol), and NaH (60% dispersion in mineral oil, 0.21 g, 5.2 mmol) in 20 mL of DMF were processed as described in Example 1D to provide the title compound (0.55 g, 1.2 mmol, 70% yield). $^1$H NMR (CDCl$_3$, 300 MHz) δ ppm 1.31 (s, 6H), 1.36 (s, 6H), 1.90 (s, 1H), 2.90-2.96 (m, 2H), 3.67 (t, J=5.8 Hz, 2H), 4.08 (dd, J=8.6, 7.3 Hz, 2H), 4.40 (t, J=5.9 Hz, 2H), 5.14 (s, 2H), 7.03 (dd, J=9.0, 2.5 Hz, 1H), 7.27-7.45 (m, 4H), 7.45-7.52 (m, 2H), 7.65 (s, 1H), 8.08 (d, J=2.7 Hz, 1H); MS (DCI/NH$_3$) m/z 461 (M+H)$^+$; Anal. Calculated for C$_{28}$H$_{32}$N$_2$O$_4$.0.2H$_2$O: C, 72.45; H, 7.04; N, 6.04. Found: C, 72.43; H, 7.00; N, 6.13.

EXAMPLE 153

N-methyl-1-(tetrahydro-2H-pyran-4-ylmethyl)-3-[(2,2,3,3-tetramethylcyclopropyl)carbonyl]-1H-indole-6-carboxamide To a solution of the product of Example 86 (0.24 g, 0.63 mmol), methylamine (2.0 M solution in THF, 0.38 mL, 0.75 mmol) and diisopropylethyl amine (0.27 mL, 1.6 mmol) in 5 mL of THF was added o-(7-azabenzotriazol-1-yl)-N,N,N',N'-tetramethyluronium hexafluorophosphate (HATU, 0.25 g, 0.66 mmol). The mixture was stirred at ambient temperature for 16 hours and then was quenched with 5 mL $H_2O$ and diluted with 10 mL of EtOAc. The layers were separated, the aqueous layer was extracted 2×5 mL of EtOAc and the combined organic extracts were dried over Na$_2$SO$_4$, filtered, concentrated under reduced pressure. The residue was purified via column chromatography (SiO$_2$, 10% CH$_3$OH in EtOAc) to provide the title compound (80 mg, 0.20 mmol, 32% yield). $^1$H NMR (MeOH-d$_4$, 300 MHz) δ ppm 1.33 (d, J=1.4 Hz, 6H), 1.33 (s, 6H), 1.40-1.54 (m, 4H), 2.16 (s, 1H), 2.18-2.32 (m, 1H), 2.96 (s, 3H), 3.33-3.43 (m, 2H), 3.90-3.98 (m, 2H), 4.21 (d, J=7.5 Hz, 2H), 7.67 (dd, J=8.3, 1.5 Hz, 1H), 8.02 (dd, J=1.4, 0.7 Hz, 1H), 8.21 (s, 1H), 8.31 (dd, J=8.5, 0.7 Hz, 1H); MS (DCI/NH$_3$) m/z 397 (M+H)$^+$; Anal. Calculated for C$_{24}$H$_{32}$N$_2$O$_3$: C, 72.70; H, 8.13; N, 7.06. Found: C, 72.52; H, 8.40; N, 7.05.

EXAMPLE 154

N,N-dimethyl-1-(tetrahydro-2H-pyran-4-ylmethyl)-3-[(2,2,3,3-tetramethylcyclopropyl)carbonyl]-1H-indole-6-carboxamide To a solution of the product of Example 86 (0.15 g, 0.39 mmol), dimethylamine (40 wt % in water, 19 µL, 0.38 mmol), i-Pr$_2$NEt (0.20 mL, 1.2 mmol) and o-(7-azabenzotriazol-1-yl)-N,N,N',N'-tetramethyluronium hexafluorophosphate (HATU, 0.15 g, 0.40 mmol) in 10 mL of THF were processed as described in Example 153 to provide the title compound (50 mg, 0.12 mmol, 31% yield). $^1$H NMR (AcOH-d$_4$, 300 MHz) δ ppm 1.30-1.32 (m, 6H), 1.33 (s, 6H), 1.44-1.59 (m, 4H), 2.12 (s, 1H), 2.17-2.29 (m, 1H), 3.08 (s, 3H), 3.16 (s, 3H), 3.40 (dt, J=11.6, 2.1 Hz, 2H), 4.01-4.08 (m, 2H), 4.16 (d, J=7.3 Hz, 2H), 7.33 (dd, J=8.4, 0.8 Hz, 1H), 7.75 (s, 1H), 8.05 (s, 1H), 8.36 (d, J=8.2 Hz, 1H); MS (DCI/NH$_3$) m/z 411 (M+H)$^+$; Anal. Calculated for C$_{25}$H$_{34}$N$_2$O$_3$: C, 73.14; H, 8.35; N, 6.82. Found: C, 72.93; H, 8.18; N, 6.74.

EXAMPLE 155

N-ethyl-1-(tetrahydro-2H-pyran-4-ylmethyl)-3-[(2,2,3,3-tetramethylcyclopropyl)carbonyl]-1H-indole-6-carboxamide To a solution of the product of Example 86 (0.15 g, 0.39 mmol), ethylamine (2.0 M solution in THF, 0.38 mL, 0.76 mmol), i-Pr$_2$NEt (0.20 mL, 1.2 mmol) and o-(7-azabenzotriazol-1-yl)-N,N,N',N'-tetramethyluronium hexafluorophosphate (HATU, 0.15 g, 0.40 mmol) in 10 mL of THF were processed as described in Example 153 to provide the title compound (60 mg, 0.15 mmol, 38% yield). $^1$H NMR (CDCl$_3$, 300 MHz) δ ppm 1.29 (t, J=7.1 Hz, 3H), 1.32 (s, 6H), 1.35 (s, 6H), 1.39-1.57 (m, 4H), 1.92 (s, 1H), 2.12-2.26 (m, 1H), 3.33 (dt, J=11.4, 2.2 Hz, 2H), 3.50-3.62 (m, 2H), 3.92-4.02 (m, 2H), 4.10 (d, J=7.5 Hz, 2H), 6.20-6.29 (m, 1H), 7.47 (d, J=8.5 Hz, 1H), 7.70 (s, 1H), 8.04 (s, 1H), 8.43 (d, J=8.1 Hz, 1H); MS (DCI/NH$_3$) m/z 411 (M+H)$^+$; Anal. Calculated for C$_{25}$H$_{34}$N$_2$O$_3$.0.7H$_2$O: C, 70.96; H, 8.43; N, 6.62. Found: C, 70.81; H, 8.12; N, 6.76.

EXAMPLE 156

[1-(pyridin-3-ylmethyl)-1H-indol-3-yl](2,2,3,3-tetramethylcyclopropyl)methanone

The 3-pyridylcarbinol (0.21 mL, 2.1 mmol), methanesulfonyl chloride (0.33 mL, 4.2 mmol), and triethylamine (0.93 mL, 6.7 mmol) in 20 mL of THF were processed as described in Example 1C to provide the corresponding mesylate. The major product of Example 1B (0.30 g, 1.2 mmol), the freshly prepared mesylate (2.1 mmol) and NaH (60% dispersion in mineral oil, 0.23 g, 5.8 mmol) in 25 mL of DMF were processed as described in Example 1D to provide the title compound (0.31 g, 0.94 mmol, 79% yield). $^1$H NMR (CDCl$_3$, 300 MHz) δ ppm 1.29 (s, 6H), 1.35 (s, 6H), 1.94 (s, 1H), 5.44 (s, 2H), 7.18-7.31 (m, 3H), 7.33-7.41 (m, 1H), 7.45-7.53 (m, 1H), 7.71 (s, 1H), 8.39-8.47 (m, 1H), 8.53-8.68 (m, 2H); MS (DCI/NH$_3$) m/z 333 (M+H)$^+$; Anal. Calculated for C$_{22}$H$_{24}$N$_2$O.0.2H$_2$O: C, 78.63; H, 7.32; N, 8.34. Found: C, 78.48; H, 7.20; N, 8.17.

EXAMPLE 157

[1-(pyridin-4-ylmethyl)-1H-indol-3-yl](2,2,3,3-tetramethylcyclopropyl)methanone

The 4-pyridylcarbinol (0.24 g, 2.1 mmol), methanesulfonyl chloride (0.33 mL, 4.2 mmol), and triethylamine (0.93 mL, 6.7 mmol) in 20 mL of THF were processed as described in Example 1C to provide the corresponding mesylate. The major product of Example 1B (0.30 g, 1.2 mmol), the freshly prepared mesylate (2.1 mmol) and NaH (60% dispersion in mineral oil, 0.23 g, 5.8 mmol) in 25 mL of DMF were processed as described in Example 1D to provide the title compound (0.31 g, 0.94 mmol, 79% yield). $^1$H NMR (CDCl$_3$, 300 MHz) δ ppm 1.30 (s, 6H), 1.36 (s, 6H), 1.95 (s, 1H), 5.43 (s, 2H), 7.04-7.09 (m, 2H), 7.11-7.16 (m, 1H), 7.20-7.34 (m, 2H), 7.71 (s, 1H), 8.42-8.49 (m, 1H), 8.53-8.65 (m, 2H); MS (DCI/NH$_3$) m/z 333 (M+H)$^+$; Anal. Calculated for C$_{22}$H$_{24}$N$_2$O: C, 79.48; H, 7.28; N, 8.43. Found: C, 79.42; H, 7.33; N, 8.43.

EXAMPLE 158

[5-bromo-1-(tetrahydro-2H-pyran-4-ylmethyl)-1H-indol-3-yl](2,2,3,3-tetramethylcyclopropyl)methanone

EXAMPLE 158A (5-Bromo-1H-indol-3-yl)-(2,2,3,3-tetramethyl-cyclopropyl)-methanone A mixture of 5-bromoindole (5.0 g. 26 mmol), ethylmagnesium bromide (1.0 M solution in THF, 31 mL, 31 mmol), zinc chloride (1.0 M solution in Et$_2$O, 31 mL, 31 mmol) and the product of Example 1A (38 mmol) in 100 mL of dichloromethane was processed as described in Example 1B to provide the title compound (3.1 g, 9.8 mmol, 38% yield). MS (DCI/NH$_3$) m/z 321, 322 (M+H)$^+$.

EXAMPLE 158B

[5-bromo-1-(tetrahydro-2H-pyran-4-ylmethyl)-1H-indol-3-yl](2,2,3,3-tetramethylcyclopropyl)methanone The product of Example 158A (3.1 g, 9.8 mmol), the product of Example 18A (17 mmol), and NaH (60% dispersion in mineral oil, 1.8 g, 46 mmol) in DMF (30 mL) were processed as described in Example 1D to provide the title compound (3.4 g, 8.2 mmol, 83% yield). $^1$H NMR (CDCl$_3$, 300 MHz) δ ppm 1.31 (s, 6H), 1.34 (s, 6H), 1.37-1.56 (m, 4H), 1.88 (s, 1H), 2.05-2.21 (m, 1H), 3.33 (dt, J=11.6, 2.5 Hz, 2H), 3.93-4.00 (m, 2H), 4.01 (d, J=7.5 Hz, 2H), 7.20 (d, J=8.8 Hz, 1H), 7.37 (dd, J=8.6, 1.9 Hz, 1H), 7.59 (s, 1H), 8.61 (d, J=1.7 Hz, 1H); MS (DCI/NH$_3$) m/z 418, 420 (M+H)$^+$; Anal. Calculated for C$_{22}$H$_{28}$BrNO$_2$: C, 63.16; H, 6.75; N, 3.35. Found: C, 62.92; H, 6.79; N, 3.24.

EXAMPLE 159

[5-(2-methoxyphenyl)-1-(tetrahydro-2H-pyran-4-ylmethyl)-1H-indol-3-yl](2,2,3,3-tetramethylcyclopropyl)methanone The product of Example 158B (0.20 g, 0.48 mmol), 2-methoxyphenylboronic acid (0.15 g, 0.96 mmol), tris (dibenzylideneacetone)dipalladium (0) (Pd$_2$dba$_3$, Strem, 17 mg, 0.019 mmol), 1,3-bis(2,6-di-i-propylphenyl)imidazolium chloride (Strem, 20 mg, 0.048 mmol) and 3 mL of 2 N aqueous Na$_2$CO$_3$ were combined in 20 mL toluene. The system was degassed under vacuum and the flask refilled with N$_2$. This was repeated three times then the mixture was warmed to 85° C. and stirred for 48 h. The mixture was cooled to ambient temperature, the layers separated and the organic layer was dried over anhydrous Na$_2$SO$_4$, filtered, concentrated under reduced pressure and purified via flash column chromatography (SiO$_2$, 50% hexanes in EtOAc) to provide the title compound (0.17 g, 0.37 mmol, 77% yield). $^1$H NMR (CDCl$_3$, 300 MHz) δ ppm 1.30 (s, 6H), 1.33 (s, 6H), 1.37-1.53 (m, 4H), 1.97 (s, 1H), 2.11-2.26 (m, 1H), 3.35 (dt, J=11.7, 2.4 Hz, 2H), 3.81 (s, 3H), 3.95-4.03 (m, 2H), 4.05 (d, J=7.5 Hz, 2H), 6.95-7.07 (m, 2H), 7.26-7.33 (m, 1H), 7.35 (dd, J=8.5, 0.7 Hz, 1H), 7.41 (dd, J=7.5, 1.7 Hz, 1H), 7.50 (dd, J=8.5, 1.7 Hz, 1H), 7.62 (s, 1H), 8.51 (d, J=1.7 Hz, 1H); MS (DCI/NH$_3$) m/z 446 (M+H)$^+$; Anal. Calculated for C$_{29}$H$_{35}$NO$_3$.0.1H$_2$O: C, 77.85; H, 7.93; N, 3.13. Found: C, 77.74; H, 7.92; N, 3.11.

EXAMPLE 160

[5-phenyl-1-(tetrahydro-2H-pyran-4-ylmethyl)-1H-indol-3-yl](2,2,3,3-tetramethylcyclopropyl)methanone The product of Example 158B (0.20 g, 0.48 mmol), phenylboronic acid (0.12 g, 0.96 mmol), tris(dibenzylideneacetone)dipalladium (0) (Pd$_2$dba$_3$, Strem, 17 mg, 0.019 mmol), 1,3-bis(2,6-di-i-propylphenyl)imidazolium chloride (Strem, 20 mg, 0.048 mmol) and 3 mL of 2 N aqueous Na$_2$CO$_3$ in 20 mL toluene were processed as described in Example 159 to provide the title compound (47 mg, 0.11 mmol, 24% yield). $^1$H NMR (CDCl$_3$, 300 MHz) δ ppm 1.32 (s, 6H), 1.36 (s, 6H), 1.40-1.57 (m, 4H), 1.95 (s, 1H), 2.11-2.27 (m, 1H), 3.35 (dt, J=11.7, 2.4 Hz, 2H), 3.95-4.04 (m, 2H), 4.07 (d, J=7.5 Hz, 2H), 7.27-7.34 (m, 1H), 7.36-7.47 (m, 3H), 7.55 (dd, J=8.5, 1.7 Hz, 1H), 7.64 (s, 1H), 7.67-7.73 (m, 2H), 8.67 (d, J=1.7 Hz, 1H); MS (DCI/NH$_3$) m/z 416 (M+H)$^+$, Anal. Calculated for C$_{28}$H$_{33}$NO$_2$.0.1H$_2$O: C, 80.58; H, 8.02; N, 3.36. Found: C, 80.36; H, 7.90; N, 3.48.

EXAMPLE 162

[5-(3-methoxyphenyl)-1-(tetrahydro-2H-pyran-4-ylmethyl)-1H-indol-3-yl](2,2,3,3-tetramethylcyclopropyl)methanone The product of Example 158B (0.20 g, 0.48 mmol), 3-methoxyphenylboronic acid (0.15 g, 0.96 mmol), tris(dibenzylideneacetone)dipalladium (0) (Pd$_2$dba$_3$, Strem, 17 mg, 0.019 mmol), 1,3-bis(2,6-di-i-propylphenyl)imidazolium chloride (Strem, 20 mg, 0.048 mmol) and 3 mL of 2 N aqueous Na$_2$CO$_3$ in 20 mL toluene were processed as described in Example 159 to provide the title compound (12 mg, 0.026 mmol, 5% yield). $^1$H NMR (CDCl$_3$, 300 MHz) δ ppm 1.32 (s, 6H), 1.35 (s, 6H), 1.37-1.62 (m, 4H), 1.95 (s, 1H), 2.10-2.23 (m, 1H), 3.35 (dt, J=11.6, 2.2 Hz, 2H), 3.87 (s, 3H), 3.94-4.03 (m, 2H), 4.06 (d, J=7.1 Hz, 2H), 6.87 (ddd, J=7.9, 2.5, 1.2 Hz, 1H), 7.19-7.23 (m, 1H), 7.27-7.41 (m, 3H), 7.53 (dd, J=8.6, 1.9 Hz, 1H), 7.64 (s, 1H), 8.65 (d, J=1.4 Hz, 1H); MS (DCI/NH$_3$) m/z 446 (M+H)$^+$; Anal. Calculated for C$_{29}$H$_{35}$NO$_3$.0.6H$_2$O: C, 76.32; H, 7.99; N, 3.07. Found: C, 76.11; H, 7.60; N, 2.89.

EXAMPLE 164

[5-chloro-1-(tetrahydro-2H-pyran-4-ylmethyl)-1H-indol-3-yl](2,2,3,3-tetramethylcyclopropyl)methanone

EXAMPLE 164A (5-Chloro-1H-indol-3-yl)-(2,2,3,3-tetramethyl-cyclopropyl)-methanone A mixture of 5-chloroindole (0.30 g. 2.0 mmol), ethylmagnesium bromide (1.0 M solution in THF, 2.4 mL, 2.4 mmol), zinc chloride (1.0 M solution in Et$_2$O, 2.4 mL, 2.4 mmol) and the product of Example 1A (3.0 mmol) in 15 mL of dichloromethane was processed as described in Example 1B to provide the title compound (0.23 g, 0.85 mmol, 43% yield). MS (DCI/NH$_3$) m/z 276 (M+H)$^+$.

EXAMPLE 164B

[5-chloro-1-(tetrahydro-2H-pyran-4-ylmethyl)-1H-indol-3-yl](2,2,3,3-tetramethylcyclopropyl)methanone The product of Example 164A (85 mg, 0.31 mmol), the product of Example 18A (1.4 mmol), and NaH (60% dispersion in mineral oil, 58 mg, 1.5 mmol) in DMF (5 mL) were processed as described in Example 1D to provide the title compound (56 mg, 0.15 mmol, 48% yield). $^1$H NMR (CDCl$_3$, 300 MHz) δ ppm 1.31 (s, 6H), 1.34 (s, 6H), 1.37-1.55 (m, 4H), 1.88 (s, 1H), 2.07-2.20 (m, 1H), 3.33 (dt, J=11.6, 2.5 Hz, 2H), 3.94-4.00 (m, 2H), 4.02 (d, J=7.1 Hz, 2H), 7.23-7.27 (m, 2H), 7.61 (s, 1H), 8.44 (t, J=1.4 Hz, 1H); MS (DCI/NH$_3$) m/z 374 (M+H)$^+$; Anal. Calculated for C$_{22}$H$_{28}$ClNO$_2$.0.1H$_2$O: C, 70.33; H, 7.57; N, 3.73. Found: C, 70.25; H, 7.58; N, 3.71.

EXAMPLE 165

[6-bromo-1-(tetrahydro-2H-pyran-4-ylmethyl)-1H-indol-3-yl](2,2,3,3-tetramethylcyclopropyl)methanone

EXAMPLE 165A (6-Bromo-1H-indol-3-yl-(2,2,3,3-tetramethyl-cyclopropyl)-methanone A mixture of 6-bromoindole (2.0 g. 10 mmol), ethylmagnesium bromide (1.0 M solution in THF, 12 mL, 12 mmol), zinc chloride (1.0 M solution in Et$_2$O, 12 mL, 12 mmol) and the product of Example 1A (15 mmol) in 50 mL of dichloromethane was processed as described in Example 1B to provide the title compound (1.4 g, 4.4 mmol, 44% yield). MS (DCI/NH$_3$) m/z 320, 322 (M+H)$^+$.

EXAMPLE 165B

[6-bromo-1-(tetrahydro-2H-pyran-4-ylmethyl)-1H-indol-3-yl](2,2,3,3-tetramethylcyclopropyl)methanone The product of Example 165A (1.3 g, 4.0 mmol), the product of Example 18A (6.8 mmol), and NaH (60% dispersion in mineral oil, 0.75 g, 19 mmol) in DMF (15 mL) were processed as described in Example 1D to provide the title compound (0.64 g, 1.5 mmol, 39% yield). $^1$H NMR (CDCl$_3$, 300 MHz) δ ppm 1.30 (s, 6H), 1.34 (s, 6H), 1.39-1.57 (m, 4H), 1.89 (s, 1H, 2.03-2.23 (m, 1H), 3.35 (dt, J=11.7, 2.4 Hz, 2H), 3.94-4.05 (m, 2H), 3.99 (d, J=7.5 Hz, 2H), 7.36 (dd, J=8.5, 1.7 Hz, 1H), 7.47 (d, J=1.7 Hz, 1H), 7.56 (s, 1H), 8.28 (d, J=8.5 Hz, 1H); MS (DCI/NH$_3$) m/z 418, 420 (M+H)$^+$; Anal. Calculated for C$_{22}$H$_2$BrNO$_2$: C, 63.16; H, 6.75; N, 3.35. Found: C, 63.02; H, 6.49; N, 3.31.

EXAMPLE 166

[6-(2-methoxyphenyl)-1-(tetrahydro-2H-pyran-4-ylmethyl)-1H-indol-3-yl](2,2,3,3-tetramethylcyclopropyl)methanone The product of Example 165B (0.15 g, 0.36 mmol), 2-methoxyphenylboronic acid (0.12 g, 0.72 mmol), tris (dibenzylideneacetone)dipalladium (0) (Pd$_2$dba$_3$, Strem, 13 mg, 0.014 mmol), 1,3-bis(2,6-di-i-propylphenyl)imidazolium chloride (Strem, 15 mg, 0.036 mmol) and 3 mL of 2N aqueous Na$_2$CO$_3$ in 20 mL toluene were processed as described in Example 159 to provide the title compound (0.12 g, 0.27 mmol, 76% yield). $^1$H NMR (CDCl$_3$, 300 MHz) δ ppm 1.32 (s, 6H), 1.35 (s, 6H), 1.37-1.60 (m, 4H), 1.97 (s, 1H), 2.09-2.28 (m, 1H), 3.32 (dt, J=11.6, 2.2 Hz, 2H), 3.82 (s, 3H), 3.93-4.02 (m, 2H), 4.05 (d, J=7.5 Hz, 2H), 6.98-7.10 (m, 2H), 7.30-7.53 (m, 4H), 7.63 (s, 1H), 8.38 (d, J=8.5 Hz, 1H); MS (DCI/NH$_3$) m/z 446 (M+H)$^+$; Anal. Calculated for C$_{29}$H$_{35}$NO$_3$: C, 78.17; H, 7.92; N, 3.14. Found: C, 77.83; H, 7.94; N, 2.97.

EXAMPLE 167

[6-phenyl-1-(tetrahydro-2H-pyran-4-ylmethyl)-1H-indol-3-yl](2,2,3,3-tetramethylcyclopropyl)methanone The product of Example 165B (0.15 g, 0.36 mmol), phenylboronic acid (88 mg, 0.72 mmol), tris(dibenzylideneacetone)dipalladium (0) (Pd$_2$dba$_3$, Strem, 13 mg, 0.014 mmol), 1,3-bis(2,6-di-i-propylphenyl)imidazolium chloride (Strem, 15 mg, 0.036 mmol) and 3 mL of 2N aqueous Na$_2$CO$_3$ in 20 mL toluene were processed as described in Example 159 to provide the title compound (0.10 g, 0.25 mmol, 69% yield). $^1$H NMR (CDCl$_3$, 300 MHz) δ ppm 1.32 (s, 6H), 1.36 (s, 6H), 1.40-1.52 (m, 4H), 1.96 (s, 1H), 2.10-2.26 (m, 1H), 3.34 (dt, J=11.7, 2.4 Hz, 2H), 3.93-4.03 (m, 2H), 4.09 (d, J=7.1 Hz, 2H), 7.31-7.40 (m, 1H), 7.42-7.56 (m, 4H), 7.61-7.69 (m, 3H), 8.44 (d, J=9.2 Hz, 1H); MS (DCI/NH$_3$) m/z 416 (M+H)$^+$; Anal. Calculated for C$_{28}$H$_{33}$NO$_2$: C, 80.93; H, 8.00; N, 3.37. Found: C, 80.67; H, 8.04; N, 3.39.

EXAMPLE 168

[5-fluoro-1-(tetrahydro-2H-pyran-4-ylmethyl)-1H-indol-3-yl](2,2,3,3-tetramethylcyclopropyl)methanone

EXAMPLE 168A (5-fluoro-1H-indol-3-yl)-(2,2,3,3-tetramethyl-cyclopropyl)-methanone A mixture of 5-fluoroindole (0.34 g. 2.5 mmol), ethylmagnesium bromide (1.0 M solution in THF, 3.0 mL, 3.0 mmol), zinc chloride (1.0 M solution in Et$_2$O, 3.0 mL, 3.0 mmol) and the product of Example 1A (3.7 mmol) in 25 mL of dichloromethane was processed as described in Example 1B to provide the title compound (0.26 g, 1.0 mmol, 40% yield). MS (DCI/NH$_3$) m/z 260 (M+H)$^+$.

EXAMPLE 168B

[5-fluoro-1-(tetrahydro-2H-pyran-4-ylmethyl)-1H-indol-3-yl](2,2,3,3-tetramethylcyclopropyl)methanone The product of Example 168A (0.26 g, 1.0 mmol), the product of Example 18A (1.7 mmol), and NaH (60% dispersion in mineral oil, 0.19 g, 4.7 mmol) in DMF (10 mL) were processed as described in Example 1D to provide the title compound (80 mg, 0.22 mmol, 22% yield). $^1$H NMR (CDCl$_3$, 300 MHz) δ ppm 1.31 (s, 6H), 1.34 (s, 6H), 1.38-1.53 (m, 4H), 1.88 (s, 1H), 2.06-2.20 (m, 1H), 3.34 (dt, J=11.6, 2.5 Hz, 2H), 3.95-4.01 (m, 2H), 4.02 (d, J=7.1 Hz, 2H), 7.02 (dt, J=8.9, 2.5 Hz, 1H), 7.21-7.25 (m, 1H), 7.63 (s, 1H), 8.10 (dd, J=10.0, 2.5 Hz, 1H); MS (DCI/NH$_3$) m/z 358 (M+H)$^+$; Anal. Calculated for C$_{22}$H$_{28}$FNO$_2$: C, 73.92; H, 7.90; N, 3.92. Found: C, 73.87; H, 7.97; N, 3.93.

In Vitro Methods

Human CB$_2$ Radioligand Binding Assays:

HEK293 cells stably expressing human CB$_2$ receptors were grown until a confluent monolayer was formed. Briefly, the cells were harvested and homogenized in TE buffer (50 mM Tris-HCl, 1 mM MgCl$_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM MgCl$_2$, and 1 mM EDTA and 10% sucrose) and frozen at −78° C. until used. Saturation binding reactions were initiated by the addition of membrane preparation (protein concentration of 5 µg/well for human CB$_2$) into wells of a deep well plate containing ([$^3$H] CP-55,940 (120 Ci/mmol, a nonselective CB agonist commercially available from Tocris) in assay buffer (50 mM Tris, 2.5 mM EDTA, 5 mM MgCl$_2$, and 0.5 mg/mL fatty acid free BSA, pH 7.4). After 90 min incubation at 30° C., binding reaction was terminated by the addition of 300 µl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations (1 mM to 10 µM) of displacing ligands. The addition of 10 µM unlabeled CP-55,940 (Tocris, Ellisville, Mo.) was used to assess non-specific binding.

The compounds of the present invention bound (Ki) to CB$_2$ receptors less than about 10,000 nM. In a more preferred embodiment, compounds of the present invention bound to CB$_2$ receptors less than about 200 nM.

Human CB$_1$ Radioligand Binding Assay:

HEK293 human CB$_1$ membranes were purchased from Perkin Elmer. Binding was initiated by the addition of membranes (8-12 µg per well) into wells (Scienceware 96-well DeepWell plate, VWR, West Chester, Pa.) containing [$^3$H] CP-55,940 (120 Ci/mmol, Perkin Elmer, Boston, Mass.) and a sufficient volume of assay buffer (50 mM Tris, 2.5 mM EDTA, 5 mM MgCl$_2$, and 0.5 mg/mL fatty acid free BSA, pH 7.4) to bring the total volume to 250 µL. After incubation (30° C. for 90 minutes), binding was terminated by the addition of 300 µL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 μM) of displacing ligands. The addition of 10 μM unlabeled CP-55,940 (Tocris, Ellisville, Mo.) was used to assess nonspecific binding.

The $CB_1$ and $CB_2$ radioligand binding assays described herein can be utilized to ascertain the selectivity of compounds of the present invention for binding to $CB_2$ relative to $CB_1$ receptors.

In Vivo Methods:

Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under halothane anesthesia (4% to induce, 2% to maintain), and the incision sites were sterilized using a 10% povidone-iodine solution prior to and after surgeries.

Complete Freund's Adjuvant (CFA) Model of Inflammatory Pain

Chronic inflammatory thermal hyperalgesia was induced by injection of 150 μl of a 50% solution of CFA in phosphate buffered saline (PBS) into the plantar surface of the right hind paw in rats; control animals received only PBS treatment. Thermal hyperalgesia was assessed 48 hours post CFA injection. Thermal hyperalgesia was determined using a commercially available thermal paw stimulator (University Anesthesiology Research and Development Group (UARDG), University of California, San Diego, Calif.) described by Hargreaves et al. (Hargreaves, et. al., 1988, Pain 32, 77). Rats were placed into individual plastic cubicles mounted on a glass surface maintained at 30° C., and allowed a 20 min habituation period. A thermal stimulus, in the form of radiant heat emitted from a focused projection bulb, was then applied to the plantar surface of each hind paw. The stimulus current was maintained at 4.50±0.05 amp, and the maximum time of exposure was set at 20.48 sec to limit possible tissue damage. The elapsed time until a brisk withdrawal of the hind paw from the thermal stimulus was recorded automatically using photodiode motion sensors. The right and left hind paw of each rat was tested in three sequential trials at approximately 5-minute intervals. Paw withdrawal latency (PWL) was calculated as the mean of the two shortest latencies.

Representative compounds of the present invention showed efficacy at less than about 300 micromoles/kg in the Complete Freund's Adjuvant (CFA) model of inflammatory pain. In a more preferred embodiment, compounds of the present invention showed efficacy at less than about 50 micromoles/kg in the Complete Freund's Adjuvant (CFA) model of inflammatory pain.

Spinal Nerve Ligation Model of Neuropathic Pain

A model of spinal nerve ligation-induced (SNL model) neuropathic pain was produced using the procedure originally described by Kim and Chung (Kim, S. H. and J. M. Chung, 1992, An experimental model for peripheral neuropathy produced by segmental spinal nerve ligation in the rat, Pain 50, 355). The left L5 and L6 spinal nerves of the rat were isolated adjacent to the vertebral column and tightly ligated with a 5-0 silk suture distal to the DRG, and care was taken to avoid injury of the L4 spinal nerve. Sham rats underwent the same procedure, but without nerve ligation. All animals were allowed to recover for at least one week and not more than three weeks prior to assessment of tactile allodynia.

Tactile allodynia was measured using calibrated von Frey filaments (Stoelting, Wood Dale, Ill.) as previously described (Chaplan, S. R., F. W. Bach, J. W. Pogrel, J. M. Chung and T. L. Yaksh, 1994, Quantitative assessment of tactile allodynia in the rat paw, J. Neurosci. Methods 53, 55). Rats were placed into inverted individual plastic containers (20×12.5×20 cm) on top of a suspended wire mesh grid, and acclimated to the test chambers for 20 minutes. The von Frey filaments were presented perpendicularly to the plantar surface of the selected hind paw, and then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol. 20, 441). Only rats with a baseline threshold score of less that 4.25 g were used in this study, and animals demonstrating motor deficit were excluded. Tactile allodynia thresholds were also assessed in several control groups, including naive, sham-operated, and saline infused animals a well as in the contralateral paws of nerve-injured rats.

Representative compounds of the present invention showed efficacy at less than about 300 micromoles/kg in the spinal nerve ligation model of neuropathic pain. In a more preferred embodiment, compounds of the present invention showed efficacy at less than about 100 micromoles/kg in the spinal nerve ligation model of neuropathic pain.

The data contained herein demonstrates that compounds of the present invention bind to the $CB_2$ receptor. Certain compounds of the present invention were shown to have an analgesic effect in two types of animal pain models relating to neuropathic and nociceptive pain.

In addition to the data contained herein, several lines of evidence support the assertion that $CB_2$ receptors play a role in analgesia. For example, Zimmer et al. have reported that the nonselective cannabinoid agonist $\Delta^9$-THC retains some analgesic efficacy in $CB_1$ receptor knockout mice (Zimmer, A., et al., Proc. Nat. Acad. Sci., 1999, 96, 5780-5785). HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabinoid ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260). The analgesic effects induced by these $CB_2$-selective ligands are blocked by $CB_2$ and not by $CB_1$ receptor antagonists. Furthermore, at fully efficacious doses, AM-1241 and GW405833 are devoid of typical $CB_1$ receptor-mediated CNS side effects, providing evidence that modulation of $CB_2$ receptors can produce broad-spectrum pain relief with reduced side-effect liability.

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators are useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. They are quiescent and resting having a ramified morphology as long as the CNS is healthy. Microglia express a variety of receptors enabling them to survey the CNS and respond to pathological events. Insult or injury to the CNS leads to microglial cell activation, which is characterized by various morphological changes allowing response to the lesion. Ramifications are retracted and microglia are transformed into amoeboid-like cells with phagocytic function. They can proliferate, rapidly migrate to the site of injury, and produce and release cytokines, chemokines and complement components (Watkins L. R., et al., Trends in Neuroscience, 2001, 24(8), 450; Kreutzberg, G. W., Trends Neurosci., 1996, 19, 312-318). $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. It is conceivable that $CB_2$ receptors may be more susceptible to pharmacological effects during neuroinflammation (Walter, L., Stella, N., Br. J. Pharmacol. 2004, 141, 775-785). Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands may be clinically useful for the treatment of neuroinflammation.

$CB_2$ receptor expression has been detected in perivascular microglial cells within normal, healthy human cerebellum (Nunez, E., et al., Synapse, 2004, 58, 208-213). Perivascular cells are immunoregulatory cells located adjacent to CNS blood vessels and, along with parenchymal microglia and astrocytes, they play a pivotal role in maintaining CNS homeostasis and blood-brain barrier functionality (Williams, K., et al., Glia, 2001, 36, 156-164). $CB_2$ receptor expression has also been detected on cerebromicrovascular endothelial cells, which represent a main component of the blood-brain barrier (Golech, S. A., et al., Mol. Brain Res., 2004, 132, 87-92). A recent report demonstrated that $CB_2$ receptor expression is up-regulated in the brains of macaques with simian immunodeficiency virus-induced encephalitis (Benito, C., et al., J. Neurosci. 2005, 25(10), 2530-2536). Thus, compounds that affect $CB_2$ signaling may protect the blood-brain barrier and be clinically useful in the treatment of neuroinflammation and a variety of neuroinflammatory disorders including retroviral encephalitis, which occurs with human immunodeficiency virus (HIV) infection in the CNS.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A., et al., J. Neurosci., 2003, 23(7), 2511-2516), which are critical features in the development of multiple sclerosis. Thus, $CB_2$ receptor modulators provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL -8, are upregulated in inflammatory bowel disease (Warhurst, A. C., et al., Gut, 1998, 42, 208-213). Thus, administration of $CB_2$ receptor modulators represents a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators represents a unique approach for the treatment of liver fibrosis.

$CB_2$ receptors are involved in the neuroprotective and anti-inflammatory mechanisms induced by the interleukin-1 receptor antagonist (IL-1ra) (Molina-Holgado, F., et al., J. Neurosci., 2003, 23(16), 6470-6474). IL-1ra is an important anti-inflammatory cytokine that protects against ischemic, excitotoxic, and traumatic brain insults. $CB_2$ receptors play a role in mediating these neuroprotective effects indicating that $CB_2$ ligands are useful in the treatment of traumatic brain injury, stroke, and in mitigating brain damage.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators have utility as antitussive agents for the treatment pulmonary inflammation, chronic cough, and a variety of airway inflammatory diseases including but not limited to asthma, chronic obstructive pulmonary disease, and pulmonary fibrosis.

Osteoporosis is a disease characterized by reduced bone mass, which leads to deterioration of bone microstructure and increased susceptibility to fracture. Age is associated with bone loss and it is estimated that 50% of all Caucasian women will have osteoporosis by the age of 80 (Ralston, S. H., Curr. Opin. Pharmacol., 2003, 3, 286-290). There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators are useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor are clinically useful for the treatment of atheroscelorsis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators have utility for the treatment or prophylaxis of cardiovascular disease and the development of myocardial infarction.

The present invention also provides pharmaceutical compositions that comprise compounds of the present invention. The pharmaceutical compositions comprise compounds of the present invention formulated together with one or more non-toxic pharmaceutically acceptable carriers.

The pharmaceutical compositions of this invention can be administered to humans and other mammals orally, rectally, parenterally, intracisternally, intravaginally, topically (as by powders, ointments or drops), bucally or as an oral or nasal spray. The term "parenterally," as used herein, refers to modes of administration that include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable carrier or excipient, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants, which may be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "pharmaceutically acceptable salt," as used herein, means salts derived from inorganic or organic acids. The salts can be prepared in situ during the final isolation and purification of compounds of Formula (I) or separately by reacting the free base of a compound of Formula (I) with an inorganic or organic acid. Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, fumarate, methanesulfonate, nicotinate, 2-naphthalenesulfonate, oxalate, pamoate, pectinate, persulfate, 3-phenylpropionate, picrate, pivalate, propionate, succinate, sulfate, (L) tartrate, (D) tartrate, (DL) tartrate, thiocyanate, phosphate, glutamate, bicarbonate, p-toluenesulfonate, and undecanoate.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the like. Prodrugs of the present invention may be rapidly transformed in vivo to compounds of Formula (I), for example, by hydrolysis in blood.

The present invention contemplates compounds of Formula (I) formed by synthetic means or formed by in vivo biotransformation.

The compounds of the invention can exist in unsolvated as well as solvated forms, including hydrated forms, such as hemi-hydrates. In general, the solvated forms, with pharmaceutically acceptable solvents such as water and ethanol among others, are equivalent to the unsolvated forms for the purposes of the invention.

The total daily dose of the compounds of this invention administered to a human or lower animal may range from about 0.003 to about 30 mg/kg/day. For purposes of oral administration, more preferable doses can be in the range of from about 0.01 to about 10 mg/kg/day. If desired, the effective daily dose can be divided into multiple doses for purposes of administration; consequently, single dose compositions may contain such amounts or submultiples thereof to make up the daily dose.

What is claimed is:

1. A compound of Formula (I)

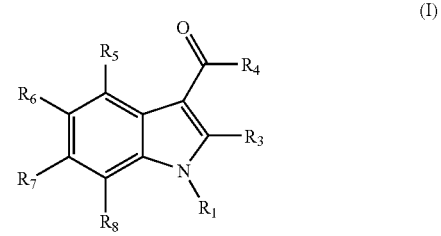

or a pharmaceutically acceptable salt thereof, wherein $R_1$ is selected from the group consisting of alkoxyalkyl, alkylcarbonyl, alkylcarbonylalkyl, alkylthioalkyl, arylalkyl, arylalkylcarbonyl, azidoalkyl, cycloalkylalkyl, cycloalkylalkylcarbonyl, haloalkyl, heteroarylalkyl, heteroarylalkylcarbonyl, heterocyclealkyl, heterocyclealkylcarbonyl, hydroxyalkyl, mercaptoalkyl, $(NR_AR_B)$carbonylalkyl, $(NR_AR_B)$sulfonylalkyl, $(NR_C R_D)$alkyl, -$LOR_2$, -$LSR_2$, -$LS(O)R_2$, and -$LS(O)_2R_2$;

L is alkylene;

$R_2$ is selected from the group consisting of alkyl, alkylcarbonyl, aryl, arylalkyl, carboxyalkenylcarbonyl, carboxyalkyl, carboxyalkylcarbonyl, cycloalkyl, cycloalkylalkyl, haloalkyl, heteroaryl, heteroarylalkyl, heterocycle, heterocyclealkyl, $(NR_AR_B)$carbonylalkenylcarbonyl, $(NR_AR_B)$carbonylalkyl, and $(NR_AR_B)$carbonylalkylcarbonyl;

$R_3$ is selected from the group consisting of hydrogen, alkoxyalkyl, alkyl, and haloalkyl;

$R_4$ is selected from the group consisting of cyclopropyl, cyclobutyl, cyclopentyl, cycloheptyl, and cyclooctyl, wherein the cyclopropyl, cyclobutyl, and cyclopentyl are substituted with 1, 2, 3, 4, 5, or 6 substituents selected from the group consisting of alkenyl, alkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, haloalkoxy, haloalkyl, halogen, hydroxy, hydroxyalkyl, mercapto, mercaptoalkyl, oxo, —$NR_ER_F$, $(NR_ER_F)$alkyl, $(NR_GR_H)$carbonyl, $(NR_GR_H)$carbonylalkyl, $(NR_GR_H)$sulfonyl, and $(NR_GR_H)$sulfonylalkyl, wherein the cycloheptyl and cyclooctyl are optionally substituted with 1, 2, 3, 4, 5, or 6 substituents selected from the group consisting of alkenyl, alkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, haloalkoxy, haloalkyl, halogen, hydroxy, hydroxyalkyl, mercapto, mercaptoalkyl, oxo, —$NR_ER_F$, $(NR_ER_F)$alkyl, $(NR_GR_H)$carbonyl, $(NR_GR_H)$carbonylalkyl, $(NR_GR_H)$sulfonyl, and $(NR_GR_H)$sulfonylalkyl;

$R_5$, $R_6$, $R_7$, and $R_8$ are independently selected from the group consisting of hydrogen, alkenyl, alkoxy, alkoxyalkyl, alkoxycarbonyl, alkoxycarbonylalkoxy, alkoxycarbonylalkyl, alkoxysulfonyl, alkyl, alkylcarbonyl, alkylcarbonylalkyl, alkylcarbonyloxy, alkylsulfinyl, alkylsulfinylalkyl, alkylsulfonyl, alkylsulfonylalkyl, alkylsulfonyloxy, alkylthio, alkylthioalkyl, alkynyl, aryl, arylalkoxy, arylalkyl, arylalkylthio, arylcarbonyl, aryloxy, aryloxyalkyl, arylthio, arylthioalkyl, carboxy, carboxyalkenyl, carboxyalkenylcarbonyl, carboxyalkenylcarbonyloxy, carboxy, carboxyalkyl, carboxyalkylcarbonyl, carboxyalkylcarbonyloxy, cyano, cyanoalkyl, cycloalkyl, cycloalkylalkoxy, cycloalkylalkyl, cycloalkylcarbonyl, cycloalkyloxy, cycloalkyloxyalkyl, haloalkoxy, haloalkyl, halogen, heteroaryl, heteroarylalkoxy, heteroarylalkyl, heteroaryloxy, heteroaryloxyalkyl, heterocycle, heterocyclealkoxy, heterocyclealkoxycarbonyl, heterocyclealkyl, heterocycleoxy, heterocycleoxyalkyl, hydroxy, hydroxyalkoxy, hydroxyalkyl, mercapto, mercaptoalkyl, nitro, —$NR_JR_K$, $(NR_JR_K)$alkoxy, $(NR_JR_K)$alkyl, $(NR_MR_N)$carbonyl, $(NR_MR_N)$carbonylalkyl, $(NR_MR_N)$sulfonyl, and $(NR_MR_N)$sulfonylalkyl;

$R_A$, $R_B$, $R_G$, $R_H$, $R_M$, and $R_N$ are independently selected from the group consisting of hydrogen, alkenyl, alkoxyalkyl, alkoxycarbonylalkyl, alkyl, alkynyl, aryl, arylalkyl, cycloalkyl, cycloalkylalkyl, heteroaryl, heteroarylalkyl, heterocycle, heterocyclealkyl, and hydroxyalkyl; and $R_C$, $R_D$, $R_E$, $R_F$, $R_J$, $R_K$, are independently selected from the group consisting of hydrogen, alkenyl, alkoxyalkyl, alkoxycarbonyl, alkoxycarbonylalkyl, alkyl, alkylcarbonyl, alkylsulfonyl, alkynyl, aryl, arylalkyl, arylsulfonyl, arylalkylsulfonyl, cycloalkyl, cycloalkylalkyl, cycloalkylsulfonyl, cycloalkylalkylsulfonyl, heteroaryl, heteroarylalkyl, heteroarylsulfonyl, heteroarylalkylsulfonyl, heterocycle, heterocyclealkyl, heterocyclesulfonyl, and heterocyclealkylsulfonyl.

2. A compound according to claim 1 wherein
$R_1$ is selected from the group consisting of alkoxyalkyl, alkylcarbonylalkyl, alkylthioalkyl, arylalkyl, azidoalkyl, cycloalkylalkyl, haloalkyl, heteroarylalkyl, heterocyclealkyl, heterocyclealkylcarbonyl, hydroxyalkyl, mercaptoalkyl, $(NR_AR_B)$carbonylalkyl, $(NR_AR_B)$sulfonylalkyl, $(NR_CR_D)$alkyl, and -$LOR_2$;
L is alkylene;
$R_2$ is selected from the group consisting of alkylcarbonyl, arylalkyl, and carboxyalkenylcarbonyl;
$R_3$ is selected from the group consisting of hydrogen and alkyl wherein the alkyl is methyl;
$R_4$ is selected from the group consisting of cyclopropyl, cyclobutyl, cyclopentyl, and cycloheptyl, wherein the cyclopropyl, cyclobutyl, and cyclopentyl are substituted with 1, 2, 3, 4, 5, or 6 substituents selected from the group consisting of alkyl and halogen;
$R_5$, $R_6$, $R_7$, and $R_8$ are independently selected from the group consisting of hydrogen, alkoxy, alkoxyalkyl, alkoxycarbonyl, alkoxycarbonylalkoxy, alkyl, alkylsulfonyl, arylalkoxy, carboxy, carboxyalkenylcarbonyloxy, carboxy, carboxyalkylcarbonyloxy, cyano, haloalkoxy, haloalkyl, halogen, heterocyclealkoxycarbonyl, hydroxy, hydroxyalkoxy, hydroxyalkyl, nitro, —$NR_JR_K$, $(NR_JR_K)$alkoxy, $(NR_JR_K)$alkyl, and $(NR_MR_N)$carbonyl;
$R_A$, $R_B$, $R_M$, and $R_N$ are independently selected from the group consisting of hydrogen, alkoxycarbonylalkyl, alkyl, and hydroxyalkyl; and
$R_C$, $R_D$, $R_J$, $R_K$, are independently selected from the group consisting of hydrogen, alkoxycarbonyl, alkyl, and alkylsulfonyl.

3. A compound according to claim 1 wherein
$R_3$ is selected from the group consisting of hydrogen and alkyl wherein the alkyl is methyl; and
$R_4$ is 2,2,3,3-tetramethylcyclopropyl.

4. A compound according to claim 1 wherein
$R_1$ is heterocyclealkyl;
$R_3$ is selected from the group consisting of hydrogen and alkyl wherein the alkyl is methyl; and
$R_4$ is 2,2,3,3-tetramethylcyclopropyl.

5. A compound according to claim 1 wherein
$R_1$ is heteroarylalkyl;
$R_3$ is selected from the group consisting of hydrogen and alkyl wherein the alkyl is methyl; and
$R_4$ is 2,2,3,3-tetramethylcyclopropyl.

6. A compound according to claim 1 wherein
$R_1$ is arylalkyl;
$R_3$ is selected from the group consisting of hydrogen and alkyl wherein the alkyl is methyl; and
$R_4$ is 2,2,3,3-tetramethylcyclopropyl.

7. A compound according to claim 1 wherein
$R_1$ is selected from the group consisting of alkoxyalkyl, alkylcarbonylalkyl, alkylthioalkyl, azidoalkyl, cycloalkylalkyl, haloalkyl, heterocyclealkylcarbonyl, mercaptoalkyl, $(NR_AR_B)$carbonylalkyl, $(NR_AR_B)$sulfonylalkyl, $(NR_AR_B)$sulfonylalkyl, and $(NR_CR_D)$alkyl;
$R_3$ is selected from the group consisting of hydrogen and alkyl wherein the alkyl is methyl;
$R_4$ is 2,2,3,3-tetramethylcyclopropyl;
$R_A$ and $R_B$ are independently selected from the group consisting of hydrogen, alkoxycarbonylalkyl, alkyl, and hydroxyalkyl; and
$R_C$ and $R_D$ are independently selected from the group consisting of hydrogen, alkoxycarbonyl, alkyl, and alkylsulfonyl.

8. A compound according to claim 1 wherein
$R_1$ is -$LOR_2$;
$R_2$ is selected from the group consisting of alkylcarbonyl, arylalkyl, and carboxyalkenylcarbonyl;
$R_3$ is selected from the group consisting of hydrogen and alkyl wherein the alkyl is methyl;
$R_4$ is 2,2,3,3-tetramethylcyclopropyl; and
L is alkylene.

9. A compound according to claim 1 wherein
$R_1$ is hydroxyalkyl;
$R_3$ is selected from the group consisting of hydrogen and alkyl wherein the alkyl is methyl; and
$R_4$ is 2,2,3,3-tetramethylcyclopropyl.

10. A compound according to claim 1 wherein
$R_1$ is alkylthioalkyl;
$R_3$ is selected from the group consisting of hydrogen and alkyl wherein the alkyl is methyl; and
$R_4$ is 2,2,3,3-tetramethylcyclopropyl.

11. A compound according to claim 1 wherein
$R_1$ is heterocyclealkyl;
$R_3$ is selected from the group consisting of hydrogen and alkyl wherein the alkyl is methyl; and
$R_4$ is 2,2,3,3-tetrafluoro-1-methylcyclobutyl.

12. A compound according to claim 1 wherein
$R_1$ is heterocyclealkyl;
$R_3$ is selected from the group consisting of hydrogen and alkyl wherein the alkyl is methyl; and
$R_4$ is cycloheptyl.

13. A compound selected from the group consisting of
{1-[(1-methylpiperidin-2-yl)methyl]-1H-indol-3-yl}(2,2,3,3-tetramethylcyclopropyl)methanone;
[1-(2-morpholin-4-ylethyl)-1H-indol-3-yl](2,2,3,3-tetramethylcyclopropyl)methanone p-toluenesulfonic acid;
[1-(2-pyridin-2-ylethyl)-1H-indol-3-yl](2,2,3,3-tetramethylcyclopropyl)methanone p-toluenesulfonic acid;
{1-[(1-methyl-1H-imidazol-2-yl)methyl]-1H-indol-3-yl}(2,2,3,3-tetramethylcyclopropyl)methanone p-toluenesulfonic acid;
tert-butyl 4-(2-{3-[(2,2,3,3-tetramethylcyclopropyl)carbonyl]-1H-indol-1-yl}ethyl)piperidine-1-carboxylate;
[1-(2-Piperidin-4-yl-ethyl)-1H-indol-3-yl]-(2,2,3,3-tetramethyl-cyclopropyl)-methanone p-toluenesulfonic acid;
{1-[2-(1-methylpiperidin-4-yl)ethyl]-1H-indol-3-yl}(2,2,3,3-tetramethylcyclopropyl)methanone p-toluenesulfonic acid;
[1-(2-tetrahydro-2H-pyran-4-ylethyl)-1H-indol-3-yl](2,2,3,3-tetramethylcyclopropyl)methanone;
[1-(2-pyrrolidin-1-ylethyl)-1H-indol-3-yl](2,2,3,3-tetramethylcyclopropyl)methanone p-toluenesulfonic acid;
(2,2,3,3-tetramethylcyclopropyl)[1-(2-thien-2-ylethyl)-1H-indol-3-yl]methanone;
[1-(2-methoxyethyl)-1H-indol-3-yl](2,2,3,3-tetramethylcyclopropyl)methanone;
1-(2-{3-[(2,2,3,3-tetramethylcyclopropyl)carbonyl]-1H-indol-1-yl}ethyl)pyrrolidin-2-one;
1-(2-{3-[(2,2,3,3-tetramethylcyclopropyl)carbonyl]-1H-indol-1-yl}ethyl)pyrrolidine-2,5-dione;
{1-[2-(4-methyl-1,3-thiazol-5-yl)ethyl]-1H-indol-3-yl}(2,2,3,3-tetramethylcyclopropyl)methanone;
{1-[2-(dimethylamino)ethyl]-1H-indol-3-yl}(2,2,3,3-tetramethylcyclopropyl)methanone;
(2,2,3,3-tetramethylcyclopropyl)[1-(2-thien-3-ylethyl)-1H-indol-3-yl]methanone;
{1-[2-(1-methylpyrrolidin-2-yl)ethyl]-1H-indol-3-yl}(2,2,3,3-tetramethylcyclopropyl)methanone p-toluenesulfonic acid;
[1-(tetrahydro-2H-pyran-4-ylmethyl)-1H-indol-3-yl](2,2,3,3-tetramethylcyclopropyl)methanone;
[1-(2-pyridin-3-ylethyl)-1H-indol-3-yl](2,2,3,3-tetramethylcyclopropyl)methanone;
{1-[2-(1H-pyrrol-1-yl)ethyl]-1H-indol-3-yl}(2,2,3,3-tetramethylcyclopropyl)methanone;
(1-{2-[4-(dimethylamino)phenyl]ethyl}-1H-indol-3-yl)(2,2,3,3-tetramethylcyclopropyl)methanone;
[1-(2-pyridin-4-ylethyl)-1H-indol-3-yl](2,2,3,3-tetramethylcyclopropyl)methanone;
{1-[4-(benzyloxy)butyl]-1H-indol-3-yl}(2,2,3,3-tetramethylcyclopropyl)methanone;
[1-(4-hydroxybutyl)-1H-indol-3-yl](2,2,3,3-tetramethylcyclopropyl)methanone;
[1-(2-piperidin-1-ylethyl)-1H-indol-3-yl](2,2,3,3-tetramethylcyclopropyl)methanone;
{1-[4-(methylthio)butyl]-1H-indol-3-yl}(2,2,3,3-tetramethylcyclopropyl)methanone;
[1-(3-morpholin-4-ylpropyl)-1H-indol-3-yl](2,2,3,3-tetramethylcyclopropyl)methanone;
[1-(2-azepan-1-ylethyl)-1H-indol-3-yl](2,2,3,3-tetramethylcyclopropyl)methanone;
[1-(2-piperazin-1-ylethyl)-1H-indol-3-yl](2,2,3,3-tetramethylcyclopropyl)methanone tris-trifluoroacetic acid;
{1-[2-(4-methylpiperazin-1-yl)ethyl]-1H-indol-3-yl}(2,2,3,3-tetramethylcyclopropyl)methanone;
3-(2-{3-[(2,2,3,3-tetramethylcyclopropyl)carbonyl]-1H-indol-1-yl}ethyl)-1,3-oxazolidin-2-one;
[1-(tetrahydrofuran-3-ylmethyl)-1H-indol-3-yl](2,2,3,3-tetramethylcyclopropyl)methanone;
(2,2,3,3-tetramethylcyclopropyl)[1-(4,4,4-trifluorobutyl)-1H-indol-3-yl]methanone;
{1-[2-(2,2-dimethyl-1,3-dioxolan-4-yl)ethyl]-1H-indol-3-yl}(2,2,3,3-tetramethylcyclopropyl)methanone;
[1-(3,4-dihydroxybutyl)-1H-indol-3-yl](2,2,3,3-tetramethylcyclopropyl)methanone;
[1-(1,3-dioxolan-4-ylmethyl)-1H-indol-3-yl](2,2,3,3-tetramethylcyclopropyl)methanone;
{1-[2-(benzyloxy)ethyl]-1H-indol-3-yl}(2,2,3,3-tetramethylcyclopropyl)methanone;
[1-(2-hydroxyethyl)-1H-indol-3-yl](2,2,3,3-tetramethylcyclopropyl)methanone;
{1-[3-(benzyloxy)propyl]-1H-indol-3-yl}(2,2,3,3-tetramethylcyclopropyl)methanone;
[1-(3-hydroxypropyl)-1H-indol-3-yl](2,2,3,3-tetramethylcyclopropyl)methanone;
{1-[5-(benzyloxy)pentyl]-1H-indol-3-yl}(2,2,3,3-tetramethylcyclopropyl)methanone;
[1-(5-hydroxypentyl)-1H-indol-3-yl](2,2,3,3-tetramethylcyclopropyl)methanone;
[1-(3-methoxypropyl)-1H-indol-3-yl](2,2,3,3-tetramethylcyclopropyl)methanone;
[1-(tetrahydro-2H-pyran-4-ylacetyl)-1H-indol-3-yl](2,2,3,3-tetramethylcyclopropyl)methanone;
methyl 4-({3-[(2,2,3,3-tetramethylcyclopropyl)carbonyl]-1H-indol-1-yl}methyl)cyclohexanecarboxylate;
3-{3-[(2,2,3,3-tetramethylcyclopropyl)carbonyl]-1H-indol-1-yl}propanamide;
6-{3-[(2,2,3,3-tetramethylcyclopropyl)carbonyl]-1H-indol-1-yl}hexan-2-one;
{1-[(2R)-2,3-dihydroxypropyl]-1H-indol-3-yl}(2,2,3,3-tetramethylcyclopropyl)methanone;
[2-methyl-1-(2-morpholin-4-ylethyl)-1H-indol-3-yl](2,2,3,3-tetramethylcyclopropyl)methanone;
[1-(2-morpholin-4-ylethyl)-4-nitro-1H-indol-3-yl](2,2,3,3-tetramethylcyclopropyl)methanone;
[4-amino-1-(2-morpholin-4-ylethyl)-1H-indol-3-yl](2,2,3,3-tetramethylcyclopropyl)methanone;
cycloheptyl[1-(2-morpholin-4-ylethyl)-1H-indol-3-yl]methanone;
(2,2,3,3-tetrafluoro-1-methylcyclobutyl)[1-(tetrahydro-2H-pyran-4-ylmethyl)-1H-indol-3-yl]methanone;
4-{3-[(2,2,3,3-tetramethylcyclopropyl)carbonyl]-1H-indol-1-yl}butyl acetate;
4-oxo-4-(4-{3-[(2,2,3,3-tetramethylcyclopropyl)carbonyl]-1H-indol-1-yl}butoxy)but-2-enoic acid;
[6-chloro-1-(tetrahydro-2H-pyran-4-ylmethyl)-1H-indol-3-yl](2,2,3,3-tetramethylcyclopropyl)methanone;
4-({3-[(2,2,3,3-tetramethylcyclopropyl)carbonyl]-1H-indol-1-yl}methyl)phenyl acetate;
[1-(4-hydroxybenzyl)-1H-indol-3-yl](2,2,3,3-tetramethylcyclopropyl)methanone;
[6-(benzyloxy)-1-(tetrahydro-2H-pyran-4-ylmethyl)-1H-indol-3-yl](2,2,3,3-tetramethylcyclopropyl)methanone;
[6-hydroxy-1-(tetrahydro-2H-pyran-4-ylmethyl)-1H-indol-3-yl](2,2,3,3-tetramethylcyclopropyl)methanone;
4-oxo-4-({1-(tetrahydro-2H-pyran-4-ylmethyl)-3-[(2,2,3,3-tetramethylcyclopropyl)carbonyl]-1H-indol-6-yl}oxy)but-2-enoic acid;
[6-methoxy-1-(tetrahydro-2H-pyran-4-ylmethyl)-1H-indol-3-yl](2,2,3,3-tetramethylcyclopropyl)methanone;

{1-[(2R)-tetrahydrofuran-2-ylmethyl]-1H-indol-3-yl}(2,2,3,3-tetramethylcyclopropyl)methanone;
[5-(benzyloxy)-1-(tetrahydro-2H-pyran-4-ylmethyl)-1H-indol-3-yl](2,2,3,3-tetramethylcyclopropyl)methanone;
(1-benzyl-1H-indol-3-yl)(2,2,3,3-tetramethylcyclopropyl)methanone;
[7-(benzyloxy)-1-(tetrahydro-2H-pyran-4-ylmethyl)-1H-indol-3-yl](2,2,3,3-tetramethylcyclopropyl)methanone;
[1-(4-methoxybenzyl)-1H-indol-3-yl](2,2,3,3-tetramethylcyclopropyl)methanone;
[1-(3-methoxybenzyl)-1H-indol-3-yl](2,2,3,3-tetramethylcyclopropyl)methanone;
[5-hydroxy-1-(tetrahydro-2H-pyran-4-ylmethyl)-1H-indol-3-yl](2,2,3,3-tetramethylcyclopropyl)methanone;
[1-(1,3-benzodioxol-5-ylmethyl)-1H-indol-3-yl](2,2,3,3-tetramethylcyclopropyl)methanone;
[7-hydroxy-1-(tetrahydro-2H-pyran-4-ylmethyl)-1H-indol-3-yl](2,2,3,3-tetramethylcyclopropyl)methanone;
[1-(2,3-dihydro-1,4-benzodioxin-6-ylmethyl)-1H-indol-3-yl](2,2,3,3-tetramethylcyclopropyl)methanone;
4-oxo-4-({1-(tetrahydro-2H-pyran-4-ylmethyl)-3-[(2,2,3,3-tetramethylcyclopropyl)carbonyl]-1H-indol-7-yl}oxy)but-2-enoic acid;
[7-methoxy-1-(tetrahydro-2H-pyran-4-ylmethyl)-1H-indol-3-yl](2,2,3,3-tetramethylcyclopropyl)methanone;
methyl 1-(tetrahydro-2H-pyran-4-ylmethyl)-3-[(2,2,3,3-tetramethylcyclopropyl)carbonyl]-1H-indole-6-carboxylate;
1-(tetrahydro-2H-pyran-4-ylmethyl)-3-[(2,2,3,3-tetramethylcyclopropyl)carbonyl]-1H-indole-6-carboxylic acid;
{1-[(5-chloro-1,2,4-thiadiazol-3-yl)methyl]-1H-indol-3-yl}(2,2,3,3-tetramethylcyclopropyl)methanone;
4-oxo-4-({1-(tetrahydro-2H-pyran-4-ylmethyl)-3-[(2,2,3,3-tetramethylcyclopropyl)carbonyl]-1H-indol-5-yl}oxy)but-2-enoic acid;
[1-(1,3-benzothiazol-2-ylmethyl)-1H-indol-3-yl](2,2,3,3-tetramethylcyclopropyl)methanone;
ethyl 3-[({1-(tetrahydro-2H-pyran-4-ylmethyl)-3-[(2,2,3,3-tetramethylcyclopropyl)carbonyl]-1H-indol-6-yl}carbonyl)amino]propanoate;
[5-methoxy-1-(tetrahydro-2H-pyran-4-ylmethyl)-1H-indol-3-yl](2,2,3,3-tetramethylcyclopropyl)methanone;
[4-(benzyloxy)-1-(tetrahydro-2H-pyran-4-ylmethyl)-1H-indol-3-yl](2,2,3,3-tetramethylcyclopropyl)methanone;
1-(tetrahydro-2H-pyran-4-ylmethyl)-3-[(2,2,3,3-tetramethylcyclopropyl)carbonyl]-1H-indole-6-carboxamide;
1-(2-morpholin-4-ylethyl)-3-[(2,2,3,3-tetramethylcyclopropyl)carbonyl]-1H-indole-7-carboxylic acid;
2-morpholin-4-ylethyl 1-(2-morpholin-4-ylethyl)-3-[(2,2,3,3-tetramethylcyclopropyl)carbonyl]-1H-indole-7-carboxylate;
[4-hydroxy-1-(tetrahydro-2H-pyran-4-ylmethyl)-1H-indol-3-yl](2,2,3,3-tetramethylcyclopropyl)methanone;
[4-methoxy-1-(tetrahydro-2H-pyran-4-ylmethyl)-1H-indol-3-yl](2,2,3,3-tetramethylcyclopropyl)methanone;
[6-methyl-1-(tetrahydro-2H-pyran-4-ylmethyl)-1H-indol-3-yl](2,2,3,3-tetramethylcyclopropyl)methanone;
[6-(benzyloxy)-1-(2-morpholin-4-ylethyl)-1H-indol-3-yl](2,2,3,3-tetramethylcyclopropyl)methanone;
[6-hydroxy-1-(2-morpholin-4-ylethyl)-1H-indol-3-yl](2,2,3,3-tetramethylcyclopropyl)methanone;
[6-methoxy-1-(2-morpholin-4-ylethyl)-1H-indol-3-yl](2,2,3,3-tetramethylcyclopropyl)methanone;
4-oxo-4-({1-(tetrahydro-2H-pyran-4-ylmethyl)-3-[(2,2,3,3-tetramethylcyclopropyl)carbonyl]-1H-indol-5-yl}oxy)butanoic acid;
(2,2-dichloro-1-methylcyclopropyl)[1-(tetrahydro-2H-pyran-4-ylmethyl)-1H-indol-3-yl]methanone;
[1-(4-azidobutyl)-1H-indol-3-yl](2,2,3,3-tetramethylcyclopropyl)methanone;
[1-(2-azidoethyl)-1H-indol-3-yl](2,2,3,3-tetramethylcyclopropyl)methanone;
N-(4-{3-[(2,2,3,3-tetramethylcyclopropyl)carbonyl]-1H-indol-1-yl}butyl)methanesulfonamide;
ethyl 4-({1-(tetrahydro-2H-pyran-4-ylmethyl)-3-[(2,2,3,3-tetramethylcyclopropyl)carbonyl]-1H-indol-5-yl}oxy)butanoate;
[1-(3-azidopropyl)-1H-indol-3-yl](2,2,3,3-tetramethylcyclopropyl)methanone;
{1-[(2S)-tetrahydrofuran-2-ylmethyl]-1H-indol-3-yl}(2,2,3,3-tetramethylcyclopropyl)methanone;
[5-(4-hydroxybutoxy)-1-(tetrahydro-2H-pyran-4-ylmethyl)-1H-indol-3-yl](2,2,3,3-tetramethylcyclopropyl)methanone;
[5-(4-bromobutoxy)-1-(tetrahydro-2H-pyran-4-ylmethyl)-1H-indol-3-yl](2,2,3,3-tetramethylcyclopropyl)methanone;
[1-(5-azidopentyl)-1H-indol-3-yl](2,2,3,3-tetramethylcyclopropyl)methanone;
N-(2-{3-[(2,2,3,3-tetramethylcyclopropyl)carbonyl]-1H-indol-1-yl}ethyl)methanesulfonamide;
methyl 1-(tetrahydro-2H-pyran-4-ylmethyl)-3-[(2,2,3,3-tetramethylcyclopropyl)carbonyl]-1H-indole-5-carboxylate;
N-(3-{3-[(2,2,3,3-tetramethylcyclopropyl)carbonyl]-1H-indol-1-yl}propyl)methanesulfonamide;
N-(5-{3-[(2,2,3,3-tetramethylcyclopropyl)carbonyl]-1H-indol-1-yl}pentyl)methanesulfonamide;
[5-(4-aminobutoxy)-1-(tetrahydro-2H-pyran-4-ylmethyl)-1H-indol-3-yl](2,2,3,3-tetramethylcyclopropyl)methanone;
[5-hydroxy-1-(2-morpholin-4-ylethyl)-1H-indol-3-yl](2,2,3,3-tetramethylcyclopropyl)methanone;
(2E)-4-({1-(2-morpholin-4-ylethyl)-3-[(2,2,3,3-tetramethylcyclopropyl)carbonyl]-1H-indol-5-yl}oxy)-4-oxobut-2-enoic acid;
[5-methoxy-1-(2-morpholin-4-ylethyl)-1H-indol-3-yl](2,2,3,3-tetramethylcyclopropyl)methanone;
N-[4-({1-(tetrahydro-2H-pyran-4-ylmethyl)-3-[(2,2,3,3-tetramethylcyclopropyl)carbonyl]-1H-indol-5-yl}oxy)butyl]methanesulfonamide;
1-(tetrahydro-2H-pyran-4-ylmethyl)-3-[(2,2,3,3-tetramethylcyclopropyl)carbonyl]-1H-indole-5-carboxamide;
N-(2-hydroxyethyl)-1-(tetrahydro-2H-pyran-4-ylmethyl)-3-[(2,2,3,3-tetramethylcyclopropyl)carbonyl]-1H-indole-5-carboxamide;
N-methyl-1-(tetrahydro-2H-pyran-4-ylmethyl)-3-[(2,2,3,3-tetramethylcyclopropyl)carbonyl]-1H-indole-5-carboxamide;
1-(tetrahydro-2H-pyran-4-ylmethyl)-3-[(2,2,3,3-tetramethylcyclopropyl)carbonyl]-1H-indole-5-carbonitrile;
[5-(benzyloxy)-6-methoxy-1-(tetrahydro-2H-pyran-4-ylmethyl)-1H-indol-3-yl](2,2,3,3-tetramethylcyclopropyl)methanone;
N,N-dimethyl-1-(tetrahydro-2H-pyran-4-ylmethyl)-3-[(2,2,3,3-tetramethylcyclopropyl)carbonyl]-1H-indole-5-carboxamide;
N-heptyl-1-(tetrahydro-2H-pyran-4-ylmethyl)-3-[(2,2,3,3-tetramethylcyclopropyl)carbonyl]-1H-indole-5-carboxamide;

[5-hydroxy-6-methoxy-1-(tetrahydro-2H-pyran-4-ylmethyl)-1H-indol-3-yl](2,2,3,3-tetramethylcyclopropyl)methanone;
(2E)-4-({6-methoxy-1-(tetrahydro-2H-pyran-4-ylmethyl)-3-[(2,2,3,3-tetramethylcyclopropyl)carbonyl]-1H-indol-5-yl}oxy)-4-oxobut-2-enoic acid;
{5-(benzyloxy)-1-[(2R)-tetrahydrofuran-2-ylmethyl]-1H-indol-3-yl}(2,2,3,3-tetramethylcyclopropyl)methanone;
[5-(aminomethyl)-1-(tetrahydro-2H-pyran-4-ylmethyl)-1H-indol-3-yl](2,2,3,3-tetramethylcyclopropyl)methanone;
{5-hydroxy-1-[(2R)-tetrahydrofuran-2-ylmethyl]-1H-indol-3-yl}(2,2,3,3-tetramethylcyclopropyl)methanone;
N-({1-(tetrahydro-2H-pyran-4-ylmethyl)-3-[(2,2,3,3-tetramethylcyclopropyl)carbonyl]-1H-indol-5-yl}methyl)methanesulfonamide;
{5-(benzyloxy)-1-[4-(benzyloxy)butyl]-1H-indol-3-yl}(2,2,3,3-tetramethylcyclopropyl)methanone;
[6-(methylsulfonyl)-1-(tetrahydro-2H-pyran-4-ylmethyl)-1H-indol-3-yl](2,2,3,3-tetramethylcyclopropyl)methanone;
[5-hydroxy-1-(4-hydroxybutyl)-1H-indol-3-yl](2,2,3,3-tetramethylcyclopropyl)methanone;
1-(tetrahydro-2H-pyran-4-ylmethyl)-3-[(2,2,3,3-tetramethylcyclopropyl)carbonyl]-1H-indole-6-carbonitrile;
[1-(tetrahydro-2H-pyran-4-ylmethyl)-6-(trifluoromethyl)-1H-indol-3-yl](2,2,3,3-tetramethylcyclopropyl)methanone;
[6-(aminomethyl)-1-(tetrahydro-2H-pyran-4-ylmethyl)-1H-indol-3-yl](2,2,3,3-tetramethylcyclopropyl)methanone;
N-({1-(tetrahydro-2H-pyran-4-ylmethyl)-3-[(2,2,3,3-tetramethylcyclopropyl)carbonyl]-1H-indol-6-yl}methyl)methanesulfonamide;
[5,6-dihydroxy-1-(tetrahydro-2H-pyran-4-ylmethyl)-1H-indol-3-yl](2,2,3,3-tetramethylcyclopropyl)methanone;
tetrahydro-2H-pyran-4-yl {3-[(2,2,3,3-tetramethylcyclopropyl)carbonyl]-1H-indol-1-yl}acetic acid;
ethyl tetrahydro-2H-pyran-4-yl{3-[(2,2,3,3-tetramethylcyclopropyl)carbonyl]-1H-indol-1-yl}acetate;
tert-butyl 1-(tetrahydro-2H-pyran-4-ylmethyl)-3-[(2,2,3,3-tetramethylcyclopropyl)carbonyl]-1H-indol-5-ylcarbamate;
[5-amino-1-(tetrahydro-2H-pyran-4-ylmethyl)-1H-indol-3-yl](2,2,3,3-tetramethylcyclopropyl)methanonel;
[4,5,6,7-tetrafluoro-1-(tetrahydro-2H-pyran-4-ylmethyl)-1H-indol-3-yl](2,2,3,3-tetramethylcyclopropyl)methanone;
N-{1-(tetrahydro-2H-pyran-4-ylmethyl)-3-[(2,2,3,3-tetramethylcyclopropyl)carbonyl]-1H-indol-5-yl}methanesulfonamide;
[5-(hydroxymethyl)-1-(tetrahydro-2H-pyran-4-ylmethyl)-1H-indol-3-yl](2,2,3,3-tetramethylcyclopropyl)methanone;
[5-(methoxymethyl)-1-(tetrahydro-2H-pyran-4-ylmethyl)-1H-indol-3-yl](2,2,3,3-tetramethylcyclopropyl)methanone;
3-(2-{5-hydroxy-3-[(2,2,3,3-tetramethylcyclopropyl)carbonyl]-1H-indol-1-yl}ethyl)-1,3-oxazolidin-2-one;
3-(2-{5-(benzyloxy)-3-[(2,2,3,3-tetramethylcyclopropyl)carbonyl]-1H-indol-1-yl}ethyl)-1,3-oxazolidin-2-one;
N-methyl-1-(tetrahydro-2H-pyran-4-ylmethyl)-3-[(2,2,3,3-tetramethylcyclopropyl)carbonyl]-1H-indole-6-carboxamide;
N,N-dimethyl-1-(tetrahydro-2H-pyran-4-ylmethyl)-3-[(2,2,3,3-tetramethylcyclopropyl)carbonyl]-1H-indole-6-carboxamide;
N-ethyl-1-(tetrahydro-2H-pyran-4-ylmethyl)-3-[(2,2,3,3-tetramethylcyclopropyl)carbonyl]-1H-indole-6-carboxamide;
[1-(pyridin-3-ylmethyl)-1H-indol-3-yl](2,2,3,3-tetramethylcyclopropyl)methanone;
[1-(pyridin-4-ylmethyl)-1H-indol-3-yl](2,2,3,3-tetramethylcyclopropyl)methanone;
[5-bromo-1-(tetrahydro-2H-pyran-4-ylmethyl)-1H-indol-3-yl](2,2,3,3-tetramethylcyclopropyl)methanone;
[5-(2-methoxyphenyl)-1-(tetrahydro-2H-pyran-4-ylmethyl)-1H-indol-3-yl](2,2,3,3-tetramethylcyclopropyl)methanone;
[5-phenyl-1-(tetrahydro-2H-pyran-4-ylmethyl)-1H-indol-3-yl](2,2,3,3-tetramethylcyclopropyl)methanone;
[5-(3-methoxyphenyl)-1-(tetrahydro-2H-pyran-4-ylmethyl)-1H-indol-3-yl](2,2,3,3-tetramethylcyclopropyl)methanone;
[5-chloro-1-(tetrahydro-2H-pyran-4-ylmethyl)-1H-indol-3-yl](2,2,3,3-tetramethylcyclopropyl)methanone;
[6-bromo-1-(tetrahydro-2H-pyran-4-ylmethyl)-1H-indol-3-yl](2,2,3,3-tetramethylcyclopropyl)methanone;
[6-(2-methoxyphenyl)-1-(tetrahydro-2H-pyran-4-ylmethyl)-1H-indol-3-yl](2,2,3,3-tetramethylcyclopropyl)methanone;
[6-phenyl-1-(tetrahydro-2H-pyran-4-ylmethyl)-1H-indol-3-yl](2,2,3,3-tetramethylcyclopropyl)methanone;
[5-fluoro-1-(tetrahydro-2H-pyran-4-ylmethyl)-1H-indol-3-yl](2,2,3,3-tetramethylcyclopropyl)methanone; and
2-oxatricyclo[3.3.1.1~3,7~]dec-1-yl[1-(tetrahydro-2H-pyran-4-ylmethyl)-1H-indol-3-yl]methanone.

14. A pharmaceutical composition comprising a therapeutically effective amount of a compound of Formula (I) of claim 1 or a pharmaceutically acceptable salt thereof in combination with a pharmaceutically acceptable carrier.

* * * * *

UNITED STATES PATENT AND TRADEMARK OFFICE
CERTIFICATE OF CORRECTION

PATENT NO. : 7,560,481 B2
APPLICATION NO. : 11/315862
DATED : July 14, 2009
INVENTOR(S) : Frost et al.

It is certified that error appears in the above-identified patent and that said Letters Patent is hereby corrected as shown below:

Column 107, line 5, claim 13: "methanone   p-toluenesulfonic" to read as --methanone p-toluenesulfonic--

Column 107, line 10, claim 13: "methanone   p-toluenesulfonic" to read as --methanone p-toluenesulfonic--

Column 107, line 12, claim 13: "tert-butyl   4" to read as --tert-butyl 4--

Column 107, line 17, claim 13: "methanone   p-toluenesulfonic" to read as --methanone p-toluenesulfonic--

Column 107, line 20, claim 13: "methanone   p-toluenesulfonic" to read as --methanone p-toluenesulfonic--

Column 107, line 25, claim 13: "methanone   p-toluenesulfonic" to read as --methanone p-toluenesulfonic--

Column 109, line 30, claim 13: "methyl  1" to read as --methyl 1--

Column 109, line 41, claim 13: "ethyl  3" to read as --ethyl 3--

Column 110, line 12, claim 13: "ethyl   4" to read as --ethyl 4--

Column 110, line 29, claim 13: "methyl  1" to read as --methyl 1--

Column 111, line 39, claim 13: "4-yl   {3" to read as --4-yl {3--

Column 111, line 41, claim 13: "ethyl   tetrahydro" to read as --ethyl tetrahydro--

Signed and Sealed this
Fifteenth Day of March, 2011

David J. Kappos
*Director of the United States Patent and Trademark Office*

CERTIFICATE OF CORRECTION (continued)
U.S. Pat. No. 7,560,481 B2

Column 111, line 43, claim 13: "tert-butyl  1" to read as --tert-butyl 1--

Column 111, line 47, claim 13: "methanonel" to read as --methanone--